US012195551B2

(12) United States Patent
Maussang-Detaille et al.

(10) Patent No.: US 12,195,551 B2
(45) Date of Patent: Jan. 14, 2025

(54) COMBINATION OF AN ErbB-2/ErbB-3 BISPECIFIC ANTIBODY WITH ENDOCRINE THERAPY FOR BREAST CANCER

(71) Applicant: Merus N.V., Utrecht (NL)

(72) Inventors: David Andre Baptiste Maussang-Detaille, Utrecht (NL); Cecilia Anna Wilhelmina Geuijen, Utrecht (NL)

(73) Assignee: Merus N.V., Utrecht (NL)

( * ) Notice: Subject to any disclaimer, the term of this patent is extended or adjusted under 35 U.S.C. 154(b) by 0 days.

(21) Appl. No.: 16/614,237

(22) PCT Filed: May 17, 2018

(86) PCT No.: PCT/NL2018/050329
§ 371 (c)(1),
(2) Date: Nov. 15, 2019

(87) PCT Pub. No.: WO2018/212656
PCT Pub. Date: Nov. 22, 2018

(65) Prior Publication Data
US 2021/0054096 A1 Feb. 25, 2021

Related U.S. Application Data

(60) Provisional application No. 62/507,675, filed on May 17, 2017.

(51) Int. Cl.
| C07K 16/32 | (2006.01) |
| A61K 31/138 | (2006.01) |
| A61K 31/4196 | (2006.01) |
| A61K 31/567 | (2006.01) |
| A61K 39/00 | (2006.01) |
| A61K 39/395 | (2006.01) |
| A61K 45/06 | (2006.01) |
| A61P 35/00 | (2006.01) |

(52) U.S. Cl.
CPC ............ *C07K 16/32* (2013.01); *A61K 31/138* (2013.01); *A61K 31/4196* (2013.01); *A61K 31/567* (2013.01); *A61K 39/001106* (2018.08); *A61K 39/39558* (2013.01); *A61K 45/06* (2013.01); *A61P 35/00* (2018.01); *A61K 2039/505* (2013.01); *A61K 2039/54* (2013.01); *A61K 2039/545* (2013.01); *C07K 2317/31* (2013.01); *C07K 2317/732* (2013.01)

(58) Field of Classification Search
CPC .. C07K 16/32; A61K 31/138; A61K 31/4196; A61K 39/39558
See application file for complete search history.

(56) References Cited

U.S. PATENT DOCUMENTS

| 4,801,687 A | 1/1989 | Ngo |
| 4,816,567 A | 3/1989 | Cabilly et al. |
| 5,151,504 A | 9/1992 | Croze |
| 5,731,168 A | 3/1998 | Carter et al. |
| 7,642,228 B2 | 1/2010 | Carter et al. |
| 7,705,103 B2 | 4/2010 | Sherman et al. |
| 8,349,574 B2 | 1/2013 | Bates et al. |
| 8,592,562 B2 | 11/2013 | Kannan et al. |
| 8,628,774 B2 | 1/2014 | Gurney et al. |
| 9,220,775 B2 | 12/2015 | Chowdhury et al. |
| 9,248,181 B2 | 2/2016 | De Kruif et al. |
| 9,248,182 B2 | 2/2016 | De Kruif et al. |
| 9,358,286 B2 | 6/2016 | De Kruif et al. |
| 9,551,208 B2 | 1/2017 | Ma et al. |
| 9,758,805 B2 | 9/2017 | De Kruif et al. |
| 9,914,777 B2 | 3/2018 | Bakker et al. |
| 10,358,492 B2 | 7/2019 | Bakker et al. |
| 10,416,162 B2 | 9/2019 | Huang et al. |
| 11,279,770 B2 * | 3/2022 | Geuijen ............... A61K 31/519 |
| 2003/0078385 A1 | 4/2003 | Arathoon et al. |
| 2004/0071696 A1 | 4/2004 | Adams et al. |
| 2004/0197328 A1 * | 10/2004 | Young .................... C07K 16/00 424/155.1 |
| 2006/0212956 A1 | 9/2006 | Crocker et al. |
| 2009/0181022 A1 | 7/2009 | Nielsen et al. |

(Continued)

FOREIGN PATENT DOCUMENTS

| AU | 2014212081 A1 | 8/2015 |
| EP | 0120694 A2 | 10/1984 |

(Continued)

OTHER PUBLICATIONS

Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Chames et al., Therapeutic antibodies: successes, limitations and hopes for the future, British J. of Pharmacology, 2009, 157, 220-233 (Year: 2009).*

(Continued)

*Primary Examiner* — Peter J Reddig
*Assistant Examiner* — Cheng Lu
(74) *Attorney, Agent, or Firm* — Sterne, Kessler, Goldstein & Fox P.L.L.C.

(57) ABSTRACT

The invention relates to methods of treating of subject that has breast cancer or is at risk of having said cancer, comprising administering to the subject in need thereof a combination of a therapeutically effective amount of an ErbB-2/ErbB-3 bispecific antibody and a therapeutically effective amount of an endocrine therapy drug, wherein the bispecific antibody has an antigen binding site that can bind an extra-cellular part of ErbB-2 and an antigen binding site that can bind an extra-cellular part of ErbB-3; and to means for said method.

9 Claims, 31 Drawing Sheets

Specification includes a Sequence Listing.

(56) References Cited

U.S. PATENT DOCUMENTS

| | | |
|---|---|---|
| 2009/0182127 A1 | 7/2009 | Kjaergaard et al. |
| 2009/0191559 A1 | 7/2009 | Huang et al. |
| 2010/0015133 A1 | 1/2010 | Igawa et al. |
| 2010/0183615 A1 | 7/2010 | Kufer et al. |
| 2010/0286374 A1 | 11/2010 | Kannan et al. |
| 2011/0077163 A1 | 3/2011 | Doranz |
| 2011/0195454 A1 | 8/2011 | McWhirter et al. |
| 2012/0107234 A1 | 5/2012 | Pedersen et al. |
| 2012/0107306 A1 | 5/2012 | Elis et al. |
| 2012/0270801 A1 | 10/2012 | Frejd et al. |
| 2012/0328623 A1 | 12/2012 | Takahashi |
| 2013/0071859 A1 | 3/2013 | Bates et al. |
| 2013/0084297 A1 | 4/2013 | Daly et al. |
| 2013/0115208 A1 | 5/2013 | Ho et al. |
| 2013/0156779 A1 | 6/2013 | Clarke et al. |
| 2013/0185821 A1 | 7/2013 | Babb et al. |
| 2013/0251703 A1 | 9/2013 | Elis et al. |
| 2013/0259867 A1 | 10/2013 | Amler et al. |
| 2013/0336885 A1 | 12/2013 | Hongo et al. |
| 2013/0336981 A1 | 12/2013 | De Kruif et al. |
| 2013/0344093 A1 | 12/2013 | Daly et al. |
| 2014/0056898 A1* | 2/2014 | Zhang .................. A61K 31/517 435/375 |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0141019 A1 | 5/2014 | Kharrat et al. |
| 2014/0378664 A1 | 12/2014 | Suh et al. |
| 2015/0013996 A1 | 1/2015 | Davies et al. |
| 2015/0139996 A1 | 5/2015 | De Kruif et al. |
| 2015/0196637 A1 | 7/2015 | De Kruif et al. |
| 2016/0031984 A1 | 2/2016 | Reyes et al. |
| 2016/0229920 A1 | 8/2016 | Ward et al. |
| 2016/0367699 A1 | 12/2016 | Jackson et al. |
| 2017/0037145 A1 | 2/2017 | Geuijen et al. |
| 2017/0166653 A1 | 6/2017 | Garner et al. |
| 2020/0102393 A1 | 4/2020 | Throsby et al. |
| 2020/0291130 A1 | 9/2020 | Throsby et al. |

FOREIGN PATENT DOCUMENTS

| | | |
|---|---|---|
| EP | 0314161 A1 | 5/1989 |
| EP | 0481790 A2 | 4/1992 |
| EP | 0523949 A1 | 1/1993 |
| EP | 0870459 A2 | 10/1998 |
| EP | 2604625 A1 | 6/2013 |
| EP | 17164292 | 3/2017 |
| EP | 17164382 | 3/2017 |
| JP | H11500915 A | 1/1999 |
| JP | 2008531557 A | 8/2008 |
| JP | 2011508604 A | 3/2011 |
| JP | 2012509259 A | 4/2012 |
| JP | 2014508782 A | 4/2014 |
| JP | 2014511383 A | 5/2014 |
| JP | 2017507944 A | 3/2017 |
| WO | WO-9627011 A1 | 9/1996 |
| WO | WO-9850431 A2 | 11/1998 |
| WO | WO-0063403 A2 | 10/2000 |
| WO | WO-0120694 A1 | 3/2001 |
| WO | WO-03004704 A2 | 1/2003 |
| WO | WO-03107218 A1 | 12/2003 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006044908 A2 | 4/2006 |
| WO | WO-2006091209 A2 | 8/2006 |
| WO | WO-2006106905 A1 | 10/2006 |
| WO | WO-2007110205 A2 | 10/2007 |
| WO | WO-2007147901 A1 | 12/2007 |
| WO | WO-2008027236 A2 | 3/2008 |
| WO | WO-2008100624 A2 | 8/2008 |
| WO | WO-2008119353 A1 | 10/2008 |
| WO | WO-2008140493 A2 | 11/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010022736 A2 | 3/2010 |
| WO | WO-2010059315 A1 | 5/2010 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011022727 A2 | 2/2011 |
| WO | WO-2011028952 A1 | 3/2011 |
| WO | WO-2011028953 A1 | 3/2011 |
| WO | WO-2011143545 A1 | 11/2011 |
| WO | WO-2012023053 A2 | 2/2012 |
| WO | WO-2012058768 A1 | 5/2012 |
| WO | WO 2012116317 A2 | 8/2012 |
| WO | WO 2012125573 A2 | 9/2012 |
| WO | WO-2012125864 A2 | 9/2012 |
| WO | WO-2012131555 A2 | 10/2012 |
| WO | WO-2013048883 A2 | 4/2013 |
| WO | WO-2013084151 A2 | 6/2013 |
| WO | WO-2013107218 A1 | 7/2013 |
| WO | WO-2013134686 A1 | 9/2013 |
| WO | WO-2013149159 A1 | 10/2013 |
| WO | WO-2013157953 A1 | 10/2013 |
| WO | WO-2013157954 A1 | 10/2013 |
| WO | WO-2014051433 A1 | 4/2014 |
| WO | WO-2014060365 A1 | 4/2014 |
| WO | WO-2014081954 A1 | 5/2014 |
| WO | WO-2014159580 A1 | 10/2014 |
| WO | WO-2014165855 A1 | 10/2014 |
| WO | WO-2014182970 A1 | 11/2014 |
| WO | WO-2015077891 A1 | 6/2015 |
| WO | WO-2015130172 A1 | 9/2015 |
| WO | WO-2015130173 A1 * | 9/2015 ........... A61K 31/185 |
| WO | WO-2016077734 A2 | 5/2016 |
| WO | WO-2016090024 A2 | 6/2016 |
| WO | WO-2017069628 A2 | 4/2017 |
| WO | WO-2018182422 A1 | 10/2018 |

OTHER PUBLICATIONS

McDonagh et al., Antitumor Activity of a Novel Bispecific Antibody That Targets the ErbB2/ErbB3 Oncogenic Unit and Inhibits Heregulin-Induced Activation of ErbB3, Mol Cancer Ther, 11(3) with Supp. (Year: 2012).*

Kumler et al., A systematic review of dual targeting in HER2-positive breast cancer, Cancer Treatment Reviews, 40: 259-270 (Year: 2014).*

Zhang et al., Combination of MM-111, an ErbB2/ErbB3 bispecific antibody, with endocrine therapies as an effective strategy for treatment of ER+/HER2+ breast cancer, Cancer Research 71 (8):655-655 (Year: 2011).*

Brown et al., Tolerance to Single, but Not Multiple, Amino Acid Replacements in Antibody V, CDR2, J. of Immunogy, 156:3285-3291, Publication Year: 1996 (Year: 1996).*

Huang et al., Bispecific antibodies targeting dual tumor-associated antigens in cancer therapy, Journal of Cancer Research and Clinical Oncology (2020) 146: 3111-3122, Publication Date: Sep. 28, 2020 (Year: 2020).*

McDonagh et al., Antitumor Activity of a Novel Bispecific Antibody That Targets the ErbB2/ErbB3 Oncogenic Unit and Inhibits Heregulin-induced Activation of ErbB3, Mol Cancer Ther, 11(3) with Supp., Publication Date: Mar. 2012 (Year: 2012).*

Chandra A., "The Role of ErbB3 Inhibitors as Cancer Therapeutics," Boston University, 1-78 (May 2015).

Conforti F., et al., "Dissecting Breast Cancer Complexity: Specific Biological Features and Vulnerabilities of Triple Positive Breast Cancer Tumors," Clinics in Oncology 2:1288, Remedy Publications, LLC., United States (2017).

(56) References Cited

OTHER PUBLICATIONS

Corona S.P., et al., "CDK4/6 Inhibitors in HER2-positive Breast Cancer," *Critical Reviews in Oncology/Hematology* 118:208-214, Elsevier Ireland Ltd., Netherlands (2017).
Curley M.D., et al., "Seribantumab. An Anti-ERBB3 Antibody. Delays the Onset of Resistance and Restores Sensitivity to Letrozole in an Estrogen Receptor Positive Breast Cancer Model," *Molecular Cancer Therapeutics* 14(11): 2642-2652, American Association for Cancer Research Inc., United States (2015).
Ewer, M.S., et al., "Cardiotoxicity of Anticancer Treatments: What the Cardiologist Needs to Know," *Nature Reviews Cardiology* 7(10):564-575, Nature Publishing Group, United Kingdom (2010).
GenBank Accession No. NC_000017.10, *Homo sapiens* Chromosome 17, GRCh37.p13 Primary Assembly, 2013, 2 Pages.
GenBank Accession No. NC_018923.2, *Homo sapiens* Chromosome 12, Alternate Assembly CHM1_1.1, Whole Genome Shotgun Sequence, 2016.
GenBank Accession No. NC_018928.2, *Homo sapiens* Chromosome 17, Alternate Assembly CHM1_1.1, Whole Genome Shotgun Sequence, 2016.
GenBank Accession No. NP_001005862.1, Receptor Tyrosine-Protein Kinase erbB-2 Isoform b [*Homo sapiens*], 2018.
GenBank Accession No. NP_001005915.1, Receptor Tyrosine-Protein Kinase ErbB-3 isoform s Precursor [*Homo sapiens*], 2018.
GenBank Accession No. NP_001973.2, Receptor Tyrosine-Protein Kinase ErbB-3 isoform 1 precursor [*Homo sapiens*], 2018.
GenBank Accession No. NP_004439.2, Receptor Tyrosine-Protein Kinase ErbB-2 isoform a Precursor [*Homo sapiens*], 2018.
GenBank Accession No. NT_010783.15, *Homo sapiens* Chromosome 17 Genomic Scaffold, GRCh38.p12 Primary Assembly HSCHR17_CTG4, 2018.
GenBank Accession No. NT_029419.12, *Homo sapiens* Chromosome 12 Genomic Contig, GRCh37.p13 Primary Assembly, 2013.
Genbank, "*Homo sapiens* chromosome 12, GRCh37 .p13 Primary Assembly," Accession No. NC_000012.11 accessed at https:http://www.ncbi.nlm.nih.gov/nuccore/NC000012.11, 2013, 3 pages.
Hammond, M.E.H., et al., "American Society of Clinical Oncology/College Of American Pathologists Guideline Recommendations for Immunohistochemical Testing of Estrogen and Progesterone Receptors in Breast Cancer," *Journal of Clinical Oncology* 28(16):2784-2795, American Society of Clinical Oncology, United States (2010).
Huang, W., et al., "Comparison of Central HER2 Testing With Quantitative Total HER2 Expression and HER2 Homodimer Measurements Using a Novel Proximity-Based Assay," *American Journal of Clinical Pathology* 134(2):303-311, Oxford University Press, United Kingdom (2010).
International Search Report and Written Opinion for Application No. PCT/NL2018/050329, mailed on Sep. 17, 2018, 10 pages.
Jain, K.K., et al., "A Prospective Randomized Comparison of Epirubicin and Doxorubicin in Patients With Advanced Breast Cancer," *Journal of Clinical Oncology* 3(6):818-826, American Society of Clinical Oncology, United States (1985).
Junttila, T.T., et al., "Superior in Vivo Efficacy of Afucosylated Trastuzumab in the Treatment of HER2-amplified Breast Cancer," *Cancer Research* 70(11):4481-4489, American Association for Cancer Research, United States (2010).
Landgraf R., "HER2 Therapy. HER2 (ERBB2): Functional Diversity From Structurally Conserved Building Blocks," *Breast Cancer Research* 9(1):202, BioMed Central Ltd., United Kingdom (2007).
Lazrek Y., et al., "Anti-HER3 Domain 1 and 3 Antibodies Reduce TumorGrowth by Hindering HER2/HER3Dimerization and AKT-InducedMDM2. XIAP, and Fox01 Phosphorylation," *Neoplasia* 15(3):335-347, Neoplasia Press, Netherlands (2013).
Lumachi, F., et al., "Endocrine Therapy of Breast Cancer," *Current Medicinal Chemistry* 18(4):513-522, Bentham Science Publishers B.V., United Arab Emirates (2011).
Merchant, A.M., et al., "An Efficient Route to Human Bispecific IgG," *Nature Biotechnology* 16(7):677-681, Nature Publishing Group, United Kingdom (1998).

Morrison, M.M., et al., "ErbB3 Downregulation Enhances Luminal Breast Tumor Response to Antiestrogens," *The Journal of Clinical Investigation* 123(10):4329-4343, American Society for Clinical Investigation, United States (2013).
Nissim, A., et al., "Antibody Fragments From a 'single Pot' Phage Display Library as Immunochemical Reagents," *The EMBO Journal*, 13(3):692-698, Wiley-VCH Verlag GmbH & Co. KGaA, Germany (1994).
Osborne K.C., et al., "Mechanisms of Endocrine Resistance in Breast Cancer," *Annual Review of Medicine* 62:233-247, Annual Reviews Inc, United States (2011).
Pedersen M.W., et al., "Targeting Three Distinct HER2 Domains with a Recombinant Antibody Mixture Overcomes Trastuzumab Resistance," *Molecular Cancer Therapeutics* 14(3):669-680, American Association for Cancer Research, United States (2015).
Schaefer G., et al., "A Two-In-One Antibody Against HER3 and EGFR Has Superior Inhibitory Activity Compared With Monospecific Antibodies," *Cancer Cell* 20(4):472-486, Cell Press, United States (2011).
Wadhwa, D., et al., "Trastuzumab Mediated Cardiotoxicity in the Setting of Adjuvant Chemotherapy for Breast Cancer: A Retrospective Study," *Breast Cancer Research and Treatment* 117(2):357-364, Springer New York, Netherlands (2009).
Wolff, A.C., et al., "Recommendations for Human Epidermal Growth Factor Receptor 2 Testing in Breast Cancer: American Society of Clinical Oncology/College of American Pathologists Clinical Practice Guideline Update," *Journal of Clinical Oncology* 31(31):3997-4013, American Society of Clinical Oncology, United States (2013).
Zhang, B., et al., "Abstract 655: Combination of MM-111, an ErbB2/ErbB3 Bispecific Antibody, With Endocrine Therapies as an Effective Strategy for Treatment of ER+/HER2+ Breast Cancer," *Cancer Research* 71(8):655-655, American Association for Cancer Research Inc., United States (2011).
Co-pending U.S. Appl. No. 15/476,260, inventors Throsby, M., et al., filed Mar. 31, 2017 (Not Published).
125084 Erbitux Pharmacology Review Part 2—FDA.
Adelaide, J., et al., "A Recurrent Chromosome Translocation Breakpoint in Breast and Pancreatic Cancer Cell Lines Targets the Neuregulin/NRG1 Gene," *Genes Chromosome Cancer*, 37(4), 333-345, Wiley-Liss, Inc, United States (2003).
Agus, D.B., et al., "Targeting ligand-activated ErbB2 signaling inhibits breast and prostate tumor growth," *Cancer Cell*, 2(2): 127-137, Cell Press, United States (2002).
Ahmed M. et al. Lack of in Vivo Antibody Dependent Cellular Cytotoxicity with Antibody containing gold particles/ Bioconjugate chemistry (2015): 26 812-816.
Alexandra, H., et al., "MM-111, an ErbB2/ErbB3 Bispecific Antibody with Potent Activity in ErbB2-Overexpressing Cells, Positively Combines with Trastuzumab to Inhibit Growth of Breast Cancer Cells Driven by the ErbB2/ErbB3 Oncogenic Unit", American Association for Cancer Research, Proceedings of the Annual Meeting 51:845-846, American Association for Cancer Research, US (Apr. 2010).
Almagro, J.C. and Fransson, J., "Humanization of Antibodies," *Frontiers in Bioscience* 13:1619-1633, Frontiers In Bioscience Publications, United States (Jan. 2008).
Almagro J.C., et al., "Humanization of antibodies," *Frontiers in bioscience* 13:1619-1633, Frontiers in Bioscience Publications, United states (Jan. 2008).
Appella, E , and It Weber, F Blasi., "Structure and Functionof Epidermal Growth Factor-Like Regions In Proteins, " *FEBS Letters* 231(1):1-4, John Wiley & Sons Ltd, England (Apr. 1988).
Ardeshirpour, Y.,et al., "In vivo assessment of HER2 receptor density in HER2-positive tumors by near-infrared imaging, using repeated injections of the fluorescent probe," *Technology In Cancer Research & Treatment*, 13(5):427-434, SAGE, United States (Oct. 2014).
Armour, K.L., et al., "Differential Binding to Human FcgammaRIIa and FcgammaRIIb Receptors by Human IgG Wildtype and Mutant Antibodies," *Molecular Immunology* 40(9):585-593, Pergamon Press, England (2003).

(56) References Cited

OTHER PUBLICATIONS

Arteaga, C.L., et al., "Treatment of Her2-positive Breast Cancer: Current Status and Future Perspectives," Nature Reviews Clinical Oncology 9(1):16-32, Nature Publishing Group, England (Nov. 2011).

Atwell, S., et al., "Stable Heterodimers from Remodeling the Domain Interface of a Homodimer Using a Phage Display Library," Journal of Molecular Biology 270(1):26-35, Elsevier, England (1997).

Baeuerle, P.A., et al, "Multiple Myeloma and Monoclonal Gammopathy of Undetermined Significance: Importance of Whole-body Versus Spinal Mr Imaging," Cancer Research 252(2):477-485, Radiology (Aug. 2009).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Balko, J.M., et al., "Profiling of residual breast cancers after neoadjuvant chemotherapy identifies DUSP4 deficiency as a mechanism of drug resistance," Nature Medicine ., 18(7):1052-1059, Nature Publishing Company, United States (Jul. 2012).

Balko, J.M., et al., "The Receptor Tyrosine Kinase Erbb3 Maintains the Balance Between Luminal and Basal Breast Epithelium," Proceedings of the National Academy of Sciences of the United States of America 109(1):221-226, National Academy of Sciences, United States (Jan. 2012).

Bardelli, A et al., "Amplification of the MET receptor drives resistance to anti-EGFR therapies in colorectal cancer, " Cancer Discovery 3(6):658-673, American Association for Cancer Research, United States(Jun. 2013) doi: 10.1158/2159-8290.CD-12-0558).

Bargou, R., et al., "Tumor Regression in Cancer Patients by Very Low Doses of a T Cell-engaging Antibody," Science 321(5891):974-977, American Association for the Advancement of Science, United States (Aug. 2008).

Barthelemy P.A., et al., "Comprehensive Analysis of the Factors Contributing to the Stability and Solubility of Autonomous Human VH Domains," The Journal of Biological Chemistry283, 3639-3654, American Society for Biochemistry and Molecular Biology (Feb. 2008).

Baselga, J., et al., "Pertuzumab Plus Trastuzumab Plus Docetaxel for Metastatic Breast Cancer," The New England Journal of Medicine 366(2):109-119, Massachusetts Medical Society, United States (Jan. 2012).

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, England (Feb. 2000).

Bendig, M.M., et al., "The Production of Foreign Proteins in Mammalian Cells," Genetic Engineering 7:91-127, Academic Press, England (1988).

Berglund, L., et al., "The Epitope Space of the Human Proteome," Protein Science 17(4):606-613, Cold Spring Harbor Laboratory Press, United States (Apr. 2008).

Bernard et al. (Human Immunol. 1986; 17: 388-405).

Bettler., et al., "Binding site For Ige Of The Human Lymphocyte Low-Affinity Fc Epsilon Receptor (Fc Epsilon RII/CD23) is Confined to the Domain Homologous With Animal Lectins," Proceedings of the National Academy of Sciences of the United States of America 86(18):7118-7122, National Academy of Sciences, United States (Sep. 1989).

Birchmeier C., et al., "Met, Metastasis, Motility and More," Nature Reviews Molecular Cell Biology 4(12): 915-925, Nature Publishing Group, England (Dec. 2003).

Birnbaum, D., et al., "Chromosome arm 8p and cancer: a fragile hypothesis," The Lancet Oncology, 4: 639-642, Elsevier, Netherlands (2003).

Blomquist, M.C., et al., "Vaccinia Virus 19-KilodaltonProtein: Relationship to Several Mammalian Proteins, Including Two GrowthFactors,"Proceedings of the National Academy of Sciences of the United Statesof America 81(23):7363-7367, National Academy of Sciences, United States(Dec. 1984).

Bluemel, C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy 59(8):1197-1209, Springer Verlag, Germany (Aug. 2010).

Bogan, A., et al., "Anatomy of Hot Spots in Protein Interfaces," Journal of Molecular Biology, vol. 280, pp. 1-9 (1998).

Bostrom, J., et al., "Variants of the Antibody Herceptin that Interact with HER2 and VEGF at the Antigen Binding Site," Science 323(5921):1610-1614, American Association for the Advancement of Science, United States (Mar. 2009).

Boyer,C.M et al., "Relative Cytotoxic Activity of Immunotoxins Reactive With Different Epitopes on the Extracellular Domain of the C☐Erbb☐2 (Her☐2/Neu) Gene Product P185," International Journal of Cancer, 82(4): 525-531, John Wiley & Sons, Inc (Aug. 1999).

Buday, L and Downward, J., "Epidermal Growth Factor Regulates P21ras Through the Formation of a Complex of Receptor, Grb2 Adapter Protein, and Sos Nucleotide Exchange Factor," Cell 73(3):611-620, Cell Press, United States (May 1993).

Buday, L. et al., "Epidermal Growth Factor Regulates the Exchange Rate of Guanine Nucleotides on p21ras in Fibroblasts," Molecular and Cellular Biology, vol. 13{3}:1903-1910 {1993}.

Caldas, C., et al., "Humanization of the Anti-Cd18 Antibody 6.7: An Unexpected Effect of a Framework Residue in Binding to Antigen," Molecular Immunology 39(15):941-952, Pergamon Press, England (May 2003).

Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).

Carmon, K.S., et al., "R-Spondins Function as Ligands of the Orphan Receptors LGR4 and LGR5 to Regulate Wnt/β-Catenin Signaling," Proceedings of the National Academy of Sciences 108(28):11452-11457, National Academy of Sciences, United States (2011).

Carter, P., "Bispecific Human IgG by Design," Journal of Immunological Methods 248(1-2):7-15, Elsevier, Netherlands (2001).

Carter, P., et al., "Toward the Production of Bispecific Antibody Fragments for Clinical Applications," Journal of Hematotherapy, vol. 4, pp. 463-470 (1995).

Cartron, G., et al., "Therapeutic Activity of Humanized Anti-cd20 Monoclonal Antibody and Polymorphism in IgG Fc Receptor FcgammaRIIIa Gene," Blood 99(3):754-758, American Society of Hematology, United States (2002).

Casset, F., et al., "A Peptide Mimetic of an Anti-CD4 Monoclonal Antibody By Rational Design," Biochemical and Biophysical Research Communications 307(1):198-205, Academic Press, United States (Jul. 2003).

Castoldi, R., et al., "A Novel Bispecific EGFR/Met Antibody Blocks Tumor-promoting Phenotypic Effects Induced by Resistance to EGFR Inhibition and Has Potent Antitumor Activity," Oncogene, 32(50):5593-5601, Nature Publishing Group, England (Jul. 1, 2013).

Chames, P. and Baty, D., "Bispecific Antibodies for Cancer Therapy: The Light at the End of the Tunnel?," MAbs 1(6):539-547, Taylor & Francis, United States (Nov.-Dec. 2009).

Chang et al. (Structure. Jan. 7, 2014; 22 (1 ): 9-21).

Chatenoud, L., et al., "In Vivo Cell Activation Following OKT3 Administration. Systemic Cytokine Release and Modulation by Corticosteroids," Transplantation 49(4):697-702, Lippincott Williams & Wilkins, United States (Apr. 1990).

Chen, C.H., et al., "Effect of Duration of Osmotherapy on Blood-brain Barrier Disruption and Regional Cerebral Edema After Experimental Stroke," Journal of Cerebral Blood Flow and Metabolism 26(7):951-958, SAGE Publications, United States (Jul. 2006).

Chen, C.T et al., "MET activation mediates resistance to lapatinib inhibition of HER2-amplified gastric cancer cells," Molecular Cancer Therapeutics 11(3):650-669, American Association for Cancer Research, Inc, United States (Mar. 2012).

(56) References Cited

OTHER PUBLICATIONS

Chernomordik, V., et al., "Quantitative Analysis of Her2 Receptor Expression in Vivo By Near-Infrared Optical Imaging," Molecular imaging, 9(4):192-200, SAGE Publications, United States (Aug. 2010).
Chien, N.C., et al., "Significant Structural and Functional Change of an Antigen-Binding Site by a Distant Amino Acid Substitution: Proposal of a Structural Mechanism," Proceedings of the National Academy of Sciences USA 86(14):5532-5536, National Academy of Sciences, United States (1989).
Choi Y, and Deane C.M., "Predicting Antibody Complementarity Determining Region Structures Without Classification," Molecular BioSystems 7:3327-3334, The royal society of chemistry (Sep. 2011).
Chua, Y.L., et al., "The NRG1 gene is frequently silenced by methylation in breast cancers and is a strong candidate for the 8p tumor suppressor gene," Oncogene, 28(46): 4041-4052, Macmillan Publishers Limited, Germany (2009).
Chuan, Weng Peng et al. "A molecular triad governing adult stem cells activation: crystallographic studies of LGR5 R-spondin 1 and E3 ligase ZNRF3" https:/ I dspace.li bra ry .u u .n 1/bitstrea m/ha nd le/187 4/308080/peng. pdf?sequence=1.
Clarke, M.F., et al., "Cancer stem cells—perspectives on current status and future directions: AACR Workshop on cancer stem cells," Cancer Research 66(19):9339-9344, American Association for Cancer Research, United States (2006).
Cochran J.R., et al., "Domain-level Antibody Epitope Mapping Through Yeast Surface Display of Epidermal Growth Factor Receptor Fragments," Journal of Immunology Methods 287(1-2):147-158, Elsevier, Netherland (Apr. 2004).
Coligan, J.E., "Commonly Used Detergents," Current Protocols in Protein Science, Appendix 1, 2001.
Cooke, S.L., et al., High-resolution array CGH clarifies events occurring on 8p in carcinogenesis, BMC Cancer, 8(288): 1-15, BioMed Central Ltd., London (2008).
Corada, M., et al., "Monoclonal Antibodies Directed To Different Regions of Vascular Endothelial Cadherin Extracellular Domain Affect Adhesion and Clustering of the Protein and Modulate Endothelial Permeability," Blood 97(6):1679-1684, American Society of Hematology (Mar. 2001).
Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).
Davidson E and Doranz BJ, "A high-throughput shotgun mutagenesis approach to mapping B-cell antibody epitopes." Immunology. Sep. 2014;143{1):13-20 {2014).
Davies, J. and Riechmann, L., "Antibody VH Domains as Small Recognition Units," Biotechnology 13(5):475-479, Nature Publishing Group, United States (1995).
Davis, C G., "The Many Faces of Epidermal Growth Factor-Repeats," New biologist 2(5):410-419, W.B. Saunders, United States (May 1990).
Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies.," Protein Engineering, Design & Selection 23(4):195-202, Oxford University Press, England (2010).
De Kruif, J. et al., "Human immunoglobulin repertoires against Tetanus toxoid contain a large and diverse fraction of high-affinity VH genes" J. Mol. Biol., vol. 387 ,(2009) p. No. (548-558).
De Genst, E., et al., "Antibody Repertoire Development in Camelids," Developmental and Comparative Immunology 30(1-2):187-198, Elsevier Science, United States (2006).
De Goeij, B.E., et al., "Efficient Payload Delivery by a Bispecific Antibody-Drug Conjugate Targeting HER2 and CD63," Molecular Cancer Therapeutics 5(11):2688-2697, American Association for Cancer Research, United States (Nov. 2016).
De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).
De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, England (Apr. 1995).
De Kruif, J., et al., "Generation of Stable Cell Clones Expressing Mixtures of Human Antibodies," Biotechnology and Bioengineering 106(5):741-750, Wiley, United States (Aug. 2010).
De Lau, W., et al., "Lgr5 Homologues Associate with Wnt Receptors and Mediate R-spondin Signalling," Nature 476(7360):293-297, Macmillan Publishers Limited, England (2011) (D14 as cited in Opposition of EP 2173379).
De Lau, W., et al., "The R-spondin/Lgr5/Rnf43 Module: Regulator of Wnt Signal Strength," Genes and Development 28(4):305-316, Cold Spring Harbor Laboratory Press, United States (2014) (D31 as cited in Opposition of EP 2173379.
De Lau, W., et al., "The R-spondin/Lgr5/Rnf43 module: regulator of Wnt signal strength," Genes Dev, vol. 28:305-316 (2014).
De Lau, W., et al., "Lgr5 Homologues Associate With Wnt Receptors and Mediate R-spondin Signalling," Nature 476: 293-298 (2011).
De Nardis, C., et al., "A new approach for generation bispecific antibodies based on a common light chain format and the stable architecture of human immunoglobulin G1," Journal of Biological Chemistry, 292(35): 14706-14717, The American Society for Biochemistry and Molecular Biology, Inc., United States (2017).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
De Vries, S.J., et al., "The HADDOCK Web Server for Data-driven Biomolecular Docking," Nature Protocols 5(5):883-897, Nature Publishing Group, England (May 2010).
De Wildt, et al., Analysis of Heavy and Light Chain Pairings Indicates that Receptor Editing Shapes the Human Antibody Repertoire, Journal of Molecular Biology, 285(3):895-901, Elsevier,England(1999).
Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).
Deisenhofer, J., "Crystallographic refinement and atomic models of a human Fe fragment and its complex withragmen! B of protein A from *Staphylococcus aureus* at 2.9- and 2.8-A resolution," Biochemistry, vol. 20{9): 2361-2370 (1981).
Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007 ).
Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).
Desmyter, A., et al., "Antigen Specificity and High Affinity Binding Provided by One Single Loop of a Camel Single-domain Antibody," The Journal of Biological Chemistry 276(28):26285-26290, American Society for Biochemistry and Molecular Biology, United States (Jul. 2001).
Devash, Y., et al., "Vertical Transmission of Human Immunodeficiency Virus Is Correlated With the Absence of High-affinity/avidity Maternal Antibodies to the Gp120 Principal Neutralizing Domain," Proceedings of the National Academy of Sciences of the United States of America 87(9):3445-3449, National Academy of Sciences, United States (May 1990).
Dhanasekaran SM et al., "Transcriptome meta-analysis of lung cancer reveals recurrent aberrations in NRG1 and Hippo pathway genes," Nat. Commun. Dec. 22, 2014;5:5893.

(56) References Cited

OTHER PUBLICATIONS

Di et al., "Ultra high content image analysis and phenotype profiling of 3D cultured microtissues," PLoS One. Oct. 7, 2014;9{10}:e109688 {2011}.
Dijoseph, J.F., et al., "Antibody-targeted Chemotherapy with CMC-544: A CD22-targeted Immunoconjugate of Calicheamicin for the Treatment of B-lymphoid Malignancies," Blood 103(5):1807-1814, American Society of Hematology, United States (2004).
Doolittle, R.F., et al., "Computer-Based Characterization ofEpidermal Growth Factor Precursor," Nature 307(5951):558-560, Nature PublishingGroup, England (Feb. 1984).
Dreier, T., et al., "Extremely Potent, Rapid and Costimulation-Independent Cytotoxic T-Cell Response against Lymphoma Cells Catalyzed By a Single-Chain Bispecific Antibody," International Journal of Cancer 100(6):690-697, Wiley-Liss, United States (2002).
Duruisseaux, M., et al., "NRG1 fusion in a French cohort of invasive mucinous lung adenocarcinoma," Cancer Medicine, 5(12): 3579-3585, John Wiley & Sons Ltd., United States (2016).
Edwards, B.M., et al., "The Remarkable Flexibility of the Human Antibody Repertoire; Isolation of Over One Thousand Different Antibodies to a Single Protein, BLyS," Journal of Molecular Biology, 334(1):103-118, Elsevier, England (Nov. 2003).
Ellerson, J.R., et al., "Structure and Function of Immunoglobulin Domains. III. Isolation and Characterization of a Fragment Corresponding to the Cgamma2 Homology Region of Human Immunoglobin G1," Journal of Immunology 116(2):510-517, American Association of Immunologists, United States (Feb. 1976).
Elliot, B.E et al. "The Role of Hepatocyte Growth Factor (Scatter Factor) InEpithelial-Mesenchymal Transition and Breast Cancer," Canadian Journal of Physiology and Pharmacology 80(2), 91-102, Canadian Science Publishing, Canada (Feb. 2002).
Falls, D.L., "Neuregulins: functions, form, and signaling strategies," Exp. Cell Res, 284: 14-30, Elsevier, Netherlands (2003).
Farnan, D. and Moreno, G.T., "Multiproduct High-resolution Monoclonal Antibody Charge Variant Separations by pH Gradient Ion-exchange Chromatography," Analytical Chemistry 81(21):8846-8857, American Chemical Society, United States (2009).
Ferguson, K.M., "Structure-based View of Epidermal Growth Factor Receptor Regulation," AnnualReview of Biophysics 37:353-373,AnnualReviews, United States (2008).
Fernandez-Cuesta, L., et al., "CD74-NRG1 Fusions in Lung Adenocarcinoma," Cancer Discovery, 4(4): 415-422, American Association for Cancer Research, United States (2014).
Fernandez-Cuesta, L., et al., "Molecular Pathways: Targeting NRG1 Fusions in Lung Cancer," Clinical Cancer Research, 21 (9): 1989-1994, American Association for Cancer Research, United States (2015).
Fong, J.T., et al., "Alternative signaling pathways as potential therapeutic targets for overcoming EGFR and c-Met inhibitor resistance in non-small cell lung cancer," PLoS One 4;8(11):e78398, Public Library of Science, United States(Nov. 2013).
Freeman D., et al., "Panitumumab and Cetuximab Epitope Mapping and in Vitro Activity," Journal of Clinical Oncology 26(15):14536-14536, American Society of Clinical Oncology (May 20, 2008).
Fu et al. (MAbs. 2014; 6 (4): 978-90).
Gaborit, N., et al., "Emerging anti-cancer antibodies and combination therapies targeting HER3/ERBB3," Human Vaccines and Immunotherapies, 12(3): 576-592, Taylor & Frances (2015).
Gale, N.W et al. "Grb2 Mediates the Egf-Dependent Activation of GuanineNucleotide Exchange on Ras," Nature 363:88-92, Springer Nature Limited (May 1993).
Garrett, T.P., et al., "Crystal Structure of a Truncated Epidermal Growth Factor Receptor Extracellular Domain Bound to Transforming Growth Factor alpha," Cell 110(6):763-773, Cell Press, United States (Sep. 2002).
Geginat, J., et al., "Proliferation and Differentiation Potential of Human CD8+ Memory T-cell Subsets in Response to Antigen or Homeostatic Cytokines," Blood 101(11):4260-4266, American Society of Hematology, United States (Jun. 2003).
George et al. (Circulation. 1998; 97: 900-906).

Geuijen, C., et al., "Abstract LB-261: Mechanism of action of MCLA-128, a humanized bispecific IgG1 antibody targeting the HER2: HER3 heterodimer," Cancer Research; 1 061h Annual Meeting of The American Association for Cancer Research (AAACR), 75, Suppl. 15, pp. LB-261, Philadelphia (2015).
Giard D.J., et al., "In Vitro Cultivation of Human Tumors: Establishment of Cell Lines Derived From a Series of Solid tumors," Journal of National Cancer Institution 51:1417-1423 (Nov. 1973).
Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).
Giusti, A.M., et al., "Somatic diversification of S107 from an antiphosphocholine to an anti-DNA autoantibody is due to a single base change in its heavy chain variable region," Proceedings of the National Academy of Sciences 84(9):2926-2930, National Academy of Sciences, United States, (1987).
Greco, W.R., et al., "The Search for Synergy: a Critical Review From a Response Surface Perspective," Pharmacological Reviews 47(2):331-385, American Society for Pharmacology and Experimental Therapeutics, United States (Jun. 1995).
Greenspan, N.S. and Di Cera, E., "Defining Epitopes: It's not as Easy as it Seems," Nature Biotechnology 17(10):936-937, Nature Publishing Group, United States (1999).
Griffiths, A.D., et al., "Human Anti-Self Antibodies with High Specificity from Phage Display Libraries," The EMBO Journal 12(2):725-734, Wiley Blackwell, England (Feb. 1993).
Gulli, L.F., et al., "Epidermal Growth Factor-induced Apoptosis in A431 Cells Can Be Reversed by Reducing the Tyrosine Kinase Activity," Cell Growth & Differentiation 7(2):173-178, The Association, United States (Feb. 1996).
Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).
Gussow, D. and Seemann, G., "Humanization of Monoclonal Antibodies," Methods in Enzymology 203:99-121, Elsevier Science, United States (1991).
Haagen, I.A., et al., "The Efficacy of CD3 X CD19 Bispecific Monoclonal Antibody (BsAB) in a Clonogenic Assay: The Effect of Repeated Addition of Bsab and Interleukin-2," Blood 85(11):3208-3212, American Society of Hematology, United States (Jun. 1995).
Han, Y., et al., "KLRL1, a Novel Killer Cell Lectinlike Receptor, Inhibits Natural Killer Cell Cytotoxicity," Blood 104(9):2858-2866, American Society of Hematology, United States (Nov. 2004).
Hao, H.X., et al., "ZNRF3 Promotes Wnt Receptor Turnover in an R-Spondin-Sensitive Manner," Nature 485(7397):195-200, Nature Publishing Group, England (2012).
Hao, H.X., et al., "ZNRF3 Promotes Wnt Receptor Turnover in an R-Spondin-Sensitive Manner," Nature 485(7397):195-200, Nature Publishing Group, England (2012), with Supplemental Information.
Harms B., et al., "Understanding the Role of Cross-arm Binding Efficiency in the Activity of Monoclonal and Multispecific Therapeutic Antibodies", Methods 65(1):95-104, Duluth, MN (Jan. 2014).
Hathaway et al. (Breast Cancer Res. Nov. 3, 2011; 13 (5): R 1 08; pp. 1-14).
Hayes, N.V.L., and Gullick, W.J., "The Neuregulin Family of Genes and their Multiple Splice Variants in Breast Cancer," J. Mammary Gland Bioi Neoplasia, 13(205): 214, Springer, New York (2008).
Hendsch, Z.S., et al., "Preferential Heterodimer Formation via Undercompensated Electrostatic Interactions," Journal of the American Chemical Society 123(6):1264-1265, American Chemical Society, United States (Feb. 2001).
Holm, P., et al., "Functional Mapping and Single Chain Construction of the Anti-cytokeratin 8 Monoclonal Antibody TS1," Molecular Immunology 44(6):1075-1084, Pergamon Press, England (Feb. 2007).
Hommel, U., et al., "Human Epidermal Growth Factor. High ResolutionSolution Structure And Comparison With Human Transforming Growth Factor Alpha,"Journal of Molecular Biology 227(1):271-282, Elsevier, England (Sep. 1992).

(56) References Cited

OTHER PUBLICATIONS

Horsten, H., et al., "Production of Non-Fucosylated Antibodies by Co-expression of Heterologous GDP-6-Deoxy-D-Lyxo-4-Hexulose Reductase," Glycobiology, 20(12):1607-1618, IRL Press at Oxford University Press, England, (Dec. 2010).

Hu, T., and Li, C., "Convergence between Wnt —catenin and EGFR signaling in cancer," Cancer 2010; 9(236):2-7.

HUGO Gene Nomenclature Committee (HGNC), "Epidermal growth factor receptor," HGNC ID:3236, accessed at https://www.genenames.org/, accessed on Sep. 29, 2020, 4 pages.

HUGO Gene Nomenclature Committee (HGNC), "Immunoglobulin kappa variable 1-39," HGNC ID: 5740, accessed at https://www.genenames.org/, accessed on Sep. 29, 2020, 4 pages.

HUGO Gene Nomenclature Committee (HGNC), "MET protooncogene, receptor tyrosine kinase," HGNC ID: 7029, accessed at https://www.genenames.org/, accessed on Sep. 29, 2020, 5 pages.

Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).

Ionescu, R.M., et al., "Contribution of Variable Domains to the Stability of Humanized IgG1 Monoclonal Antibodies," Journal of Pharmaceutical Sciences 97(4):1414-1426, Elsevier, United States (Apr. 2008 ).

Jackson et al. (Int. J. Cell Bioi. 2013; 2013: 973584; pp. 1-9).

Jain K.K., et al., "A Prospective Randomized Comparison of Epirubicin and Doxorubicin in Patients With Advanced Breast Cancer," Journal of Clinical Oncology 3(6):818-820, American Society of Clinical Oncology, United States (Jun. 1985).

Jelovac, D., et al., "HER2-Directed Therapy for Metastatic Breast Cancer," Oncology (Williston Park) 27(3):166-175, CMP Healthcare Media, United States (Mar. 2013).

Ji H. et al. Epidermal growth factor receptor variant III mutations in lung tumorigenesis and sensitivity to tyrosine kinase inhibitors. PNAS 2006 103(20):7817-7822.

Jiang, B., et al., "A Novel Peptide Isolated from a Phage Display Peptide Library with Trastuzumab Can Mimic Antigen Epitope of HER-2," The Journal of Biological Chemistry 280(6):4656-4662, The American Society for Biochemistry and Molecular Biology (2005).

Jin, H., et al., "Metmab, the One-Armed 5d5 Anti-C-Met Antibody, InhibitsOrthotopic Pancreatic Tumor Growth and Improves Survival," Cancer Research 68(11):4360-4368, American Association for Cancer Research, United States(Jun. 2008).

Jorissen, R.N., et al., "Epidermal GrowthFactor Receptor: Mechanisms of Activation and Signalling," Experimental Cell Research 284(1):31-53, Academic Press, United States (Mar. 2003).

Jung, Y., et al., "VAMP2-NRG1 Fusion Gene is a Novel Oncogenic Driver of Non-Small-Cell Lung Adenocarcinoma," J Thor Oncol1 0(7): 1107-1111, International Association for the Study of Lung Cancer, Colorado (2015).

Junttila, T.T., et al., "Ligand-Independent HER2/HER3/PI3K Complex Is Disrupted by Trastuzumab and Is Effectively Inhibited by the PI3K Inhibitor GDC-0941," Cancer Cell 15(5):429-440, Cell Press, United States (May 2009).

Kabat, E.A., et al., "Identical V Region Amino Acid Sequences and Segments of Sequences in Antibodies of Different Specificities. Relative Contributions of Vh and Vl Genes, Minigenes, and Complementarity-determining Regions to Binding of Antibody-combining Sites," Journal of Immunology 147(5):1709-1719, American Association of Immunologists, United States (Sep. 1991).

Kang J.C., et al., "Engineering Multivalent Antibodies to Target Heregulin-Induced HER3 Signaling in Breast Cancer Cells," Comparative Study 6(2):340-353, Landes Bioscience, United states (Apr. 2014).

Kim, G.P., et al. "Targeting Colorectal Cancer with Human Anti-Egfr MonoclonocalAntibodies: Focus on Panitumumab," Biologics 2(2):223-228, Dove Medical Press, New Zealand (Jun. 2008).

Kim, K.A., et al., "Mitogenic Influence of Human R-Spondin1 on the Intestinal Epithelium," Science 309(5738):1256-1259, American Association for the Advancement of Science, United States (2005).

Kim, K.H., et al., "Progress of Antibody-BasedInhibitors of the Hgf-Cmet Axis in Cancer Therapy," Experimental & Molecular medicine 49(3):e307, Nature Publishing Group, United States (Mar. 2017).

Kipriyanov, S.M., et al., "Bispecific CD3×CD19 Diabody for T Cell-Mediated Lysis of Malignant Human B Cells," International Journal of Cancer 77(5):763-772, Wiley-Liss, United States (1998).

Klein, C., et al., "Progress in Overcoming the Chain Association Issue in Bispecific Heterodimeric IgG Antibodies," MAbs 4(6):653-663, Taylor & Francis, United States (Nov.-Dec. 2012).

Klimka, A., et al., "Human Anti-CD30 Recombinant Antibodies by Guided Phage Antibody Selection Using Cell Panning," British Journal of Cancer 83(2):252-260, Nature Publishing Group, England (Jul. 2000).

Kodack D.P., et al., "Combined Targeting of HER2 and VEGFR2 for Effective Treatment of HER2-amplified Breast Cancer Brain Metastases," Proceedings of the National Academy of Sciences 109(45):E3119-E3127 (Nov. 2012).

Koide, A., et al., "The Fibronectin Type III Domain as a Scaffold for Novel Binding Proteins," Journal of Molecular Biology 284(4):1141-1151, Academic Press, United States (Dec. 1998).

Kol, A., et al., "HER3, Serious Partner in Crime: Therapeutic Approaches and Potential Biomarkers for Effect of HER3-targeting," Pharmacology & Therapeutics 143(1):1-11, Pergamon Press, England (Jul. 2014).

Kontermann, R.E., "Dual Targeting Strategies with Bispecific Antibodies," mAbs 4(2):182-197, Taylor and Francis, United States (2012).

Krausova,M and Korinek, V.,"Wnt Signaling In Adult Intestinal Stem Cells and Cancer," Cell signalling 26(3):570-579, Elsevier Science Ltd, England (Mar. 2014).

Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).

Kubota T, et al., "Engineerde therapeutic antibodies with improved effector functions," Cancer Sci. Sep. 2009;100{9):1566-72.

Kubota, T., et al., "Engineered therapeutic antibodies with improved effector functions," Cancer Science 100(9):1566-1572, Wiley Publishing on behalf of the Japanese Cancer Association, England(Sep. 2009).

Kulkarni-Kale, U., et al., "CEP: a Conformational Epitope Prediction Server," Nucleic Acids Research 33:W168-W171, Oxford University Press, England (Jul. 2005).

Kumar, R., et al., "The Second Pdz Domain of Inad Is a Type I Domain Involved in Binding to Eye Protein Kinase C. Mutational Analysis and Naturally Occurring Variants," Journal of Biological Chemistry 276(27):24971-24977, American Society for Biochemistry and Molecular Biology, United States (Jul. 2001).

Labrijn, A.F., et al., "Efficient Generation of Stable Bispecific IgG1 by Controlled Fab-arm Exchange," Proceedings of the National Academy of Sciences of the United States of America, 110(13):5145-5150, United States (Mar. 26, 2013).

Lakowicz, J.R., "Principles of Fluorescence Spectroscopy," 3rd Edition, Kluwer Academic/Plenum Publisher, 469 pages (2006).

Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).

Le Clorennec, C., et al., "Neuregulin 1 Allosterically Enhances the Antitumor Effects of the Noncompeting Anti-HER3 Antibody 9 F7-F11 by Increasing Its Binding to HER3," Molecular Cancer Therapeutics, 16(7): 1312-1323, American Association for Cancer Research, United States (2017).

Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, England (Apr. 2004).

(56) References Cited

OTHER PUBLICATIONS

Ledon N., et al., "Comparative Analysis of Binding Affinities to Epidermal Growth Factor Receptor of Monoclonal Antibodies Nimotuzumab and Cetuximab Using Different Experimental Animal Models," Placenta 32: 531-534 (2011).

Lee, B., et al., "The Interpretation of Protein Structures: Estimation of Static Accessibility," Journal of Molecular Biology 55(3):379-400, Elsevier, England (Feb. 1971).

Lee, D., et al., "Development of antibody-based c-Met inhibitors for targeted cancer therapy," Immuntargets and Therapy 9(4):34-44, Dove Medical Press, New Zealand (2015).

Lee H.J., et al., "Gemini Vitamin D Analog Suppresses Erbb2-positive mammary tumor growth via inhibition of ErbB2/AKT/ERK Signaling", Journal of Steroid Biochemistry and Molecular Biology, Elsevier Science LTD., Oxford, DB, 121(1-2):408-412, England (Jul. 2010).

Lee-Hoeflich, S.T., et al., "A Central Role for HER3 in HER2-Amplified Breast Cancer: Implications for Targeted Therapy," Cancer Research, 68(14): 5878-5887, American Association for Cancer Research, United States (2008).

Li et al., "Structural basis for inhibition of the epidermal growth factor receptor by cetuximab.," Cancer Cell. Apr. 2005;7(4):301-11. pdb reference 1 YY9.

Lichtenberger, B.M., et aL., "Epidermal Egfr Controls Cutaneous Host Defense and Prevents Inflammation," Science Translational Medicine 5(199):14, (2013).

Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).

Lindmo et al., Determination of the immunoreactive fraction of radiolabeled monoclonal antibodies by linear extrapolation to binding at infinite antigen excess. J Immunol Methods. Aug. 3, 1984;72(1):77-89.

Liu, C and Lee, A., "ADCC Enhancement Technologies for Next Generation Therapeutic Antibody," Trends in Bio/Pharmaceutical Industry, 9 pages, 2009.

Liu, H., et al., "Heterogeneity of Monoclonal Antibodies," Journal of Pharmaceutical Sciences 97(7):2426-2447, Wiley-Liss, United States (Jul. 2008).

Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).

Loffler, A., et al., "A Recombinant Bispecific Single-chain Antibody, CD19×CD3, Induces Rapid and High Lymphoma-directed Cytotoxicity by Unstimulated T Lymphocytes," Blood 95(6):2098-2103, American Society of Hematology, United States (Mar. 2000).

Logtenberg, T., "Hub for Organoids", Poster Presentation, www.innovationforhealth.nl/index.php/page/getFileUID/id/82364b177dfed9754d785aafffb21363/cr_usedb/25, 29 pages, Mar. 22, 2016.

Lotenberg, T., "Hub for organoids can we take it beyond the buzz" https://www.innovatiforhea lt h.nl/ind ex.php/page/getFile UI Dluid/82364b17 7 dfed 97 54d 785a afffb21363/cr usedb/25.

Luo, H., et al., "Noninvasive Brain Cancer Imaging With a Bispecific Antibody Fragment, Generated via Click Chemistry," Proceedings of the National Academy of Sciences of the United States of America 112(41):12806-12811, National Academy of Sciences, United States (Oct. 2015).

Ma, P.C., et al., "C-Met: Structure, Functions and Potential for TherapeuticInhibition," Cancer and Metastasis Reviews 22:309-325, Kluwer Academic, Netherlands (Dec. 2003).

MacCallum, R.M., et al., "Antibody-antigen Interactions: Contact Analysis and Binding Site Topography," Journal of Molecular Biology 262(5):732-745, Academic Press, England (Oct. 1996).

Malm, M., et al.,"Engineering of a Bispecific Affibody Molecule Towards HER2 and HER3 by Addition of an Albumin-Binding Domain Allows for Affinity Purification and in Vivo Half-Life Extension," Biotechnology Journal 9(9):1215-1222, Wiley-VCH Verlag, Germany (Sep. 2014).

Malm, M., et al., "Targeting HER3 Using Mono-and Bispecific Antibodies or Alternative Scaffolds," MABS 8(7):1195-1209, Taylor & Francis, United States (Oct. 2016).

Mariuzza, R.A., et al., "The Structural Basis of Antigen-antibody Recognition," Annual Review of Biophysics and Biomolecular Structure 16:139-159, Annual Reviews, United States (1987).

Marks, J.D., et al., "By-Passing Immunization: Building High Affinity Human Antibodies by Chain Shuffling," Biotechnology 10(7):779-783, Nature Publishing Company, United States (Jul. 1992).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).

Marvin, U.S., et al., "Redesigning an Antibody Fragment for Faster Association With Its Antigen," Biochemistry 42(23):7077-7083, American Chemical Society, United States (Jun. 2003).

Maulik, G., et al., Role of the hepatocyte growth factor receptor, c-Met, in oncogenesis and potential for therapeutic inhibition, Cytokine & Growth Factor Reviews13(1):41-59, Elsevier Science, England (Feb. 2002).

Maussang ., et al., The Binding Mode of the Bispecific Anti-Her2xHer3 antibody MCLA-128 is Responsible for its Potent Inhibition of HRG-Driven Tumorigenesis, Research Poster Presentation Design, 2001, Apr. 1, 2017, Retrieved from the Internet: (URL: http://www.merus.nl/wordpress/wp-content/uploads/2017/04/MCLA-128-poster-AACR2017- final-.pdf).

May C., et al., "Advances in Bispecific Biotherapeutics for the Treatment of Cancer," Biochemical Pharmacology 84:1105-1112 (2012).

McDonagh, C.F., et al., "Antitumor Activity of a Novel Bispecific Antibody that Targets the ErbB2/ErbB3 Oncogenic Unit And Inhibits Heregulin-Induced Activation of ErbB3," Molecular Cancer Therapeutics 11(3):582-593, American Association for Cancer Research, United States (Mar. 2012).

McPhee, F., et al., "Engineering Human Immunodeficiency Virus 1 Protease Heterodimers as Macromolecular Inhibitors of Viral Maturation," Proceedings of the National Academy of Sciences of the United States of America 93(21):11477-11481, National Academy of Sciences, United States (Oct. 1996).

Merlino, GT et al, "Amplification and Enhanced Expression of the Epidermal Growth Factor Receptor Gene in A431Human Carcinoma Cells," Science, vol. 224{4647}: 417-419 {1984}.

Merten, H., et al., "Antibody-drug Conjugates for Tumor Targeting-novel Conjugation Chemistries and the Promise of Non-IgG Binding Proteins," Bioconjugate Chemistry 26(11):2176-2185, American Chemical Society, United States (Nov. 2015).

Merus, www.merus.nl, press release, 2 pages, dated Jan. 7, 2013.

Merus, www.merus.nl, press release, 3 pages, dated Jun. 17, 2013.

Meulemans, E.V., et al., "Selection of Phage-displayed Antibodies Specific for a Cytoskeletal Antigen by Competitive Elution With a Monoclonal Antibody," Journal of Molecular Biological 244(4):353-360 (1994).

Miller, S, "Protein-protein Recognition and the Association of Immunoglobulin Constant Domains," Journal of Molecular Biology 216(4):965-973, Elsevier Ltd (Dec. 1990).

Momeny M., et al., "Heregulin-HER3-HER2 signaling promotes matrix metalloproteinase-dependent blood-brain-barrier transendothelial migration of human breast cancer cell lines," Oncotarget 6(6):3932-3946 (Feb. 2015).

Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).

(56) References Cited

OTHER PUBLICATIONS

Moores, S.L., et al., "A Novel Bispecific Antibody Targeting EGFR and cMet Is Effective against EGFR Inhibitor-Resistant Lung Tumors," Cancer Research, 76(13):3942-3953, United States (May 23, 2016).
Morgillo, F et al. Mechanisms of resistance to EGFRtargeted drugs: lung cancer. ESMO Open 2016 1:e000060. doi:10.1136/esmoopen-2016-000060.
Morita, H., et al., "Neonatal Lethality of LGR5 Null Mice Is Associated with Ankyloglossia and Gastrointestinal Distension," Molecular Cell Biology 24(22):9736-9743, American Society for Microbiology, United States (2004).
Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).
Mosmi, S., et al., "Role of MetMAb (OA-5D5) in c-MET Active Lung Malignancies," Expert Opinion on Biological Therapy, 11(12):1655-1662, Taylor & Francis, England (Dec. 1, 2011).
Mullard, A., et al., "Maturing Antibody-drug Conjugate Pipeline Hits 30," Nature Reviews Drug Discovery 12(5):329-332, Nature Publishing Group, England (May 2013).
Musolino, A., et al., "Immunoglobulin G Fragment C Receptor Polymorphisms and Clinical Efficacy of Trastuzumab-based Therapy in Patients With Her-2/neu-positive Metastatic Breast Cancer," Journal of Clinical Oncology 26(11):1789-1796, American Society of Clinical Oncology, United States (2008).
Nakade, J. et al. "Triple Inhibition of Egfr, Met, and Vegf Suppresses Regrowth ofHgf-Triggered, Erlotinib-Resistant Lung Cancer Harboring an EGFR Mutation," Journal of Thoracic Oncology 9(6):775-783, Elsevier, United States(Jun. 2014).
Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, England (Apr. 1997).
Noh Jin Park., et al., "Measurement of Cetuximab and Panitumumab-Unbound Serum EGFR Extracellular Domain Using an Assay Based on Slow Off-Rate Modified Aptamer (SOMAmer) Reagents," PloS One, 8(8):e71703, Public Library of Science, United States (Aug. 21, 2013).
Nohaile, M.J., et al., "Altering dimerization specificity by changes in surface electrostatics," Proceedings of the National Academy of Sciences 98(6):3109-3114, National Academy of Sciences, United States (2001).
Norde, W.J., et al., "Myeloid Leukemic Progenitor Cells Can Be Specifically Targeted by Minor Histocompatibility Antigen LRH-1-reactive Cytotoxic T Cells," Blood 113(10):2312-2323, American Society of Hematology, United States (Mar. 2009 ).
Ocana, A., et al., "HER3 Overexpression and Survival In Solid Tumors: A Meta-Analysis," Journal of the National Cancer Institute 105(4):266-273, Oxford University Press, United States (Feb. 2013).
Offner, S., et al., "Induction of Regular Cytolytic T Cell Synapses by Bispecific Single-chain Antibody Constructs on MHC Class I-negative Tumor Cells," Molecular Immunology 43(6):763-771, Pergamon Press, England (Feb. 2006).
Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).
Ogiso, H., et al., "Crystal Structure of the Complex of Human Epidermal Growth Factor and Receptor Extracellular Domains," Cell 110(6):775-787, Cell Press, United States (Sep. 2002).
Olayioye, M.A., et al., "TheErbb Signaling Network: Receptor Heterodimerization In Development and Cancer," EMBO Journal, Jul. 2000, vol. 19(13), pp. 3159-3167.
Omenn et al. (J. Proteomics. 2014; 107: 1 03-112; pp. 1-22).
Online Mendelian Inheritance in Man (OMIM), "Epidermal growth factor receptor; EGFR," Omim Entry: 131550, accessed at https://omim.org/, accessed on Sep. 29, 2020, 19 pages.
Online Mendelian Inheritance in Man (OMIM), "Oncogene MET hepatocyte growth factor receptor; HGFR," OMIM Entry: 164860, accessed at https://omim.org/, accessed on Sep. 29, 2020, 9 pages.
Organ S.L., et al., "An Overview of the C-Met Signaling Pathway," Therapeutic Advances in Medical Oncology3(1 Suppl):S7-S19, Sage, England(2011).
Padlan, E.A, "X-Ray Crystallography of Antibodies," Advances in Protein Chemistry 49:57-133, Academic Press, United States (1996).
Pan, D.S., et al., "Binding Characteristic of Fully Human Anti-EGFR Monoclonal Antibody to EGFR in Skin Tissues of Different Species of Animals," Chinese Journal of New Drugs Co. Ltd, 21(1):26-30, China (Jan. 2012).
Panke C., et al., "Quantification of Cell Surface Proteins with Bispecific Antibodies", Protein Engineering Design and Selection, Oxford University Press 26(10):645-654, England (Aug. 2013).
Papadea, C., et al., "Human Immunoglobulin G and Immunoglobulin G Subclasses: Biochemical, Genetic, and Clinical Aspects," Critical Reviews in Clinical Laboratory Sciences 27(1):27-58, Informa Healthcare, England (1989).
Pastore, S et al., "Erk1/2 Regulates Epidermal Chemokine Expression and Skin Inflammation," Journal of Immunology 174:5047-5056 (2005).
Patel, D.K., "Clinical Use of Anti-epidermal Growth Factor Receptor Monoclonal Antibodies in Metastatic Colorectal Cancer," Pharmacotherapy 28(11):31S-41S (2008).
Paul, I., et al., "Current Understanding on EGFR and Wnt/Beta-Catenin Signaling inGlioma and Their Possible Crosstalk," Genes & Cancer 2013; 4(11-12):427-446.
Peng et al., "Structures of Wnt-Antagonist ZNRF3 and Its Complex with R-Spondin 1 and Implications for Signaling," PLoS One. Dec. 12, 2013;8(12):e83110.
Peng, R., et al., "Bleomycin Induces Molecular Changes Directly Relevant to Idiopathic Pulmonary Fibrosis: A Modelor "Active'," Disease,"Pios One, 8{4): e59348, 15 pages {2013).
Peng, W., et al., "Blockade of the PD-1 Pathway Enhances the Efficacy of Adoptive Cell Therapy against Cancer," Oncoimmunology 2(2):e22691, Taylor & Francis, United States (Feb. 2013).
Peng, W.C., et al., "Structure of Stem Cell Growth Factor R-spondin 1 in Complex with the Ectodomain of its Receptor LGR5," Cell Reports 3(6):1885-1892, Cell Press, United States (2013) (D16 as cited in Opposition of EP 2173379).
Petterson, R.D., et al., "CD47 Signals T Cell Death," Journal of Immunolgy 15; 162 (12): 7031-7040, American Association of Immunologists, United States (Jun. 1999).
Pole, J.C.M., et al., High-resolution analysis of chromosome rearrangements on 8p in breast, colon and pancreatic cancer reveals a complex pattern of loss, gain and translocation, Oncogene, 25: 5693-5706, Nature Publishing Group, United Kingdom (2006).
Press et al. (J. Immunol. Dec. 15, 1988; 141 (12): 4410-4417).
Prigent SA et al. Identification of cErbB-3 binding sites for phosphatidylinositol 30-kinase and SHC using an EGF receptor/c-ErbB-3 chimera. EMBO J 1994;13:2831-41.
Prigent, S., et al., "Identification of C-erbb-3 Binding Sites for Phosphatidylinositol 3'-kinase and Shc Using an Egf Receptor/c-erbb-3 Chimera," The EMBO Journal 13(12):2831-2841, National Center for Biotechnology Information (Jun. 1994).
Raffen, R., et al., "Reengineering Immunoglobulin Domain Interactions by Introduction of Charged Residues," Protein Engineering 11(4):303-309, Oxford University Press, England (Apr. 1998 ).
Regina, A., et al., "ANG4043, a Novel Brain-Penetrant peptide-mAb Conjugate, Is Efficacious Against HER2-positive Intracranial Tumors in Mice," Molecular Cancer Therapeutics 14(1):129-140, American Association for Cancer Research, Inc, United States (Jan. 2015).
Reusch, U., et al., "Beyond mAbs with TandAbs," Innovations in Pharmaceutical Technology, 4 pages, (2011).
Richards, D.A., et al., "A Phase 1 Study of Mm-111, a Bispecific HER2/HER3 Antibody Fusion Protein, Combined with Multiple Treatment Regimens in Patients with Advanced HER2-Positive Solid Tumors," Journal of Clinical Oncology 32(15):651 (2014).
Ridgway, J.B., et al., "Knobs-Into-Holes' Engineering of Antibody CH3 Domains for Heavy Chain Heterodimerization," Protein Engineering 9(7):617-621, Oxford University Press, England (1996).

(56) References Cited

OTHER PUBLICATIONS

Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, England (2005).

Robertson, S.C., et al., "Rtk Mutations and Human Syndromes when Good Receptors Turn Bad," Trends in genetics 16(6):265-271 (Jun. 2000).

Robertson, S.C et al., "RTK mutations and human syndromes: when good receptors turn bad," Trends in Genetics;16(6):368, Elsevier Science Publishers B.V, England (Jun. 2000).

Robinson M.K., et al., "Targeting ErbB2 and ErbB3 with a bispecific single-chain FV Enhances targeting selectivity and induces a therapeutic effect in Vitro", British Journal of CA, Nature Publishing Group, GB 99(9):1415-1425, England, London (Oct. 2008).

Rohrer, T., et al. Consideration for the Safe and Effective Manufacturing of Antibody-drug conjugates ADC, Journal of Antibody-drug Conjugates, 30(5):4, Published online 2012, doi:10.14229/jadc.2013.6.1.003.

Rohrer, T., et al. Consideration for the Safe and Effective Manufacturing of Antibody-drug conjugates ADC, Jun. 2013, Biotechnology+ Chemistry = Antibody drug Conjugates, Retrieved from the Internet https://www.adcreview.com/articles/consideration-safe-effective-manufacturing-antibody-drug-conjugates/, 2020, 10 pages.

Roskoski, R., "The ErbB/HER Family of Protein-Tyrosine Kinases and Cancer," Pharmacological Research 79:34-74, Elsevier, Netherlands (Jan. 2014).

Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).

Sali, A., et al., "Comparative Protein Modelling By Satisfaction of Spatial Restraints," Journal of Molecular Biology 234(3):779-815, Elsevier, England (Dec. 1993).

Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).

Sanchez-Valdivieso, E.A., et al., "y-Heregulin has no biological significance in primary breast cancer," British Journal of Cancer, 86(8): 1362-1366, Cancer Research UK, United Kingdom (2002).

Sandercock et al., "Identification of anti-tumour biologics using primary tumour models, 3-D phenotypic screening and image-based multi-parametric profiling." Mol Cancer. Jul. 31, 2015;14:147. PMID 26227951.

Sato et al., "Long-term expansion of epithelial organoids from human colon, adenoma, adenocarcinoma, and Barrett's epithelium," Gastroenterology. Nov. 2011; 141 ( 5): 1762- 72.

Sato, T., et al., "Long-term Expansion of Epithelial Organoids From Human Colon, Adenoma, Adenocarcinoma, and Barrett's Epithelium," Gastroenterology 141:1762-1772, W.B. Saunders, United states (Nov. 2011).

Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).

Schiffer, M., et al., "Analysis of Immunoglobulin Domain Interactions. Evidence for a Dominant Role of Salt Bridges," Journal of Molecular Biology 203(3):799-802, Elsevier, England (Oct. 1988).

Schlom, J., et al., "Therapeutic Advantage of High-affinity Anticarcinoma Radioimmunoconjugates," Cancer Research 52(5):1067-1072, American Association for Cancer Research, United States (Mar. 1992).

Schmidt M et al. "High-resolution insertion-site analysis by linear amplification-mediated PCR (LAM-PCR)," Nature Methods 4, 1051-1057(2007).

Schmitz, K., and Ferguson K.M., "Interaction of Antibodies With Erbb Receptor Extracellular Regions," Experimental Cell Research 315(4):659-670, Academic Press, United states (Feb. 2009).

Schoeberl, B., et al., "An ErbB3 Antibody, MM-121, is Active in Cancers with Ligand-Dependent Activation," Cancer Research 70(6):2485-2494, American Association for Cancer Research, United States (Mar. 2010).

Seidel, C. et al., "Role of hepatocyte growth factor and its receptorc-met in multiple myeloma," Medical Oncology 15:145-153, Springer Nature Switzerland AG(Sep. 1998).

Selzer, T., et al., "Rational Design of Faster Associating and Tighter Binding Protein Complexes," Nature Structural & Molecular Biology 7(7):537-541, Nature Publishing Group, United States (Jul. 2000).

Sergina, N.V., et al., "Escape from HER-Family Tyrosine Kinase Inhibitor Therapy By The Kinase-Inactive HER3," Nature 445(7126):437-441, Nature Publishing Group, England (Jan. 2007).

Seshagiri, S., et al., "Recurrent R-spondin Fusions in Colon Cancer," Nature 488(7413):660-664, Nature Publishing Group, England (2012).

Shames, D.S., et al., "High Heregulin Expression Is Associated with Activated HER3 and May Define an Actionable Biomarker in Patients with Squamous Cell Carcinomas of the Head and Neck," PLoS One 8(2):e56765, Public Library of Science, United States (2013).

Sheinerman, F.B., et al., "Electrostatic Aspects of Protein-protein Interactions," Current Opinion in Structural Biology 10(2):153-159, Elsevier Science, England (Apr. 2000).

Sheridan, C., "Amgen Swallows Micromet to BiTE Into All Market," Nature Biotechnology 30(4):300-301, Nature America Publishing, United States (Apr. 2012).

Shields, R.L., et al., "High resolution mapping of the binding site on human IgG 1 for Fc gamma Ri, F c gamma RII, Fe gamma RII, and FeRn and design of IgG 1 variants with improved binding to the Fe gamma R," J Bioi Chem., 276(9): 6591-6604, The American Society for Biochemistry and Molecular Biology, Inc., United States (2001).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

Shiraiwa H., et al., "Engineering a Bispecific Antibody With a Common Light Chain: Identification and Optimization of an Anti-cd3 Epsilon and Anti-gpc3 Bispecific Antibody, Ery974," Methods 154:10-20, Academic Press (Feb. 2019).

Siegfried, J.M et al., "The clinical significance of hepatocyte growth factor for non-small cell lung cancer," The Annals of Thoracic Surgery 66(6):1915-1918, Elsevier, Netherlands (Dec. 1998).

Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).

Sinha, N., et al., "Electrostatics in Protein Binding and Function," Current Protein and Peptide Science 3(6):601-614, Bentham Science Publishers, Netherlands (Dec. 2002).

Sluijter, B.J., et al., "4-1BB-mediated Expansion Affords Superior Detection of in Vivo Primed Effector Memory CD8+ T Cells from Melanoma Sentinel Lymph Nodes," Clinical Immunology 137(2):221-233, Academic Press, United States (Nov. 2010).

Soltoff, S.P., et al., "ErbB3 is involved in activation of phosphatidylinositol 3-kinase by epidermal growth factor," Molecular and Cellular Biology 14(6):3550-3558, American Society for Microbiology, United States(Jun. 1994).

Sorkin, A., "Internalization of the Epidermal Growth Factor Receptor: Role InSignalling," Biochemical Society Transactions 29(Pt 4):480-484, Portland PressOn The Behalf Of The Biochemical Society, England (Aug. 2001).

Spiess, C., et al., "Alternative Molecular Formats and Therapeutic Applications for Bispecific Antibodies," Molecular Immunology 67(2 Pt A):95-106, Pergamon Press, England (Oct. 2015).

Staerz, U.D., and Bevan, M.J., "Hybrid Hybridoma Producing a Bispecific Monoclonal Antibody that can Focus Effector T-cell

(56) References Cited

OTHER PUBLICATIONS

Activity," Proceedings of the National Academy of Sciences USA 83(5):1453-1457, National Academy of Sciences, United States (1986).

Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).

Strelkauskas, A., et al., "Human Monoclonal Antibody: 2. Simultaneous Expression of IgG and IgM with Similar Binding Specificities by a Human Hybrid Clone," Hybridoma 6(5):479-488, Mary Ann Liebert, United states (Oct. 1987).

Strelkauskas et al., Human Monoclonal Antibody: 2. Simultaneous Expression of IgG and IgM with Similar Binding Specificities by a Human Hybrid Clone, Hybridoma, 1987, pp. 479-487, vol. 6, No. 5, Mary Ann Liebert Inc., Publishers.

Suntharalingam, G., et al., "Cytokine Storm in a Phase 1 Trial of the Anti-CD28 Monoclonal Antibody TGN1412," The New England Journal of Medicine 355(10):1018-1028, Massachusetts Medical Society, United States (Sep. 2006).

Surati, M., et al., "Role of MetMab (OA-5D5) in c-MET active lung malignancies," Expert Opinion on Biological Therapy 11(12):1655-1662, Taylor & Francis, England (Dec. 2011).

Tahallah, N., et al., "The Effect of the Source Pressure on the Abundance of Ions of Noncovalent Protein Assemblies in an Electrospray Ionization Orthogonal Time-of-flight Instrument," Rapid Communications in Mass Spectrometry 15(8):596-601, John Wiley And Sons Ltd, England (2001).

Tanner, M., et al., "Characterization of a Novel Cell Line Established From a Patient With Herceptin-resistant Breast Cancer," Molecular Cancer Therapeutics 3(12):1585-1592, American Association for Cancer Research, United States (Dec. 2004).

Thery, J.C., et al., "Resistance to Human Epidermal Growth Factor Receptor Type 2-targeted Therapies," European Journal of Cancer 50(5):892-901, (Mar. 2014).

Troise, F., et al., "A novel ErbB2 epitope targeted by human antitumor immunoagents," FEBS Journal, 278: 1156-1166, John Wiley & Sons, United States (2011).

Uberall, I. et ai., "The status and role of ErbB receptors in human cancer," Exp Mol Pathol., vol. 84:79-89 (2008).

U.S. Appl. No. 61/635,935, inventor Kruif; C.A.D, filed Apr. 20, 2012.

Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, England (Jul. 2002).

Van de Wetering, "Prospective derivation of a living organoid biobank of colo rectal cancer patients." Cell. May 7, 2015;161(4):933-45.

Van De Wetering, M., et al., "Prospective Derivation of a Living Organoid Biobank of Colorectal Cancer Patients," Cell, vol. 161:933-945, Science direct (Jun. 2015).

Van Rhenen, A., et al., "The Novel AML Stem Cell Associated Antigen CII-1 Aids in Discrimination Between Normal and Leukemic Stem Cells," Blood 110(7):2659-2666, American Society of Hematology, United States (Oct. 2007).

Van Uhm et al., "The ultimate radiochemical nightmare: upon radio-iodination of Botulinum neurotoxin A, the introduced iodine atom itself seems to be fatal for the bioactivity of this macromolecule." EJNMMI Res. Feb. 19, 2015;5:5.
Vecchione, L. et al., "EGFR-targeted therapy," Experimental cell research 317(19): 2765-2771, Academic Press, United States(Nov. 2011).
Volpi,CC., et al., The Landscape of D16her2 Splice Variant Expression Across Her2-positive Cancers Sci. Rep. Mar. 5, 2019; 9 (1): 3545; pp. 1-12.
Wadhwa, D., et al., "Trastuzumab Mediated Cardiotoxicity in the Setting of Adjuvant Chemotherapy for Breast Cancer: a Retrospective Study," Breast Cancer Research and Treatment 117(2):357-364, Kluwer Academic, Netherlands (Sep. 2009).
Ward, E.S., et al., "Binding Activities of a Repertoire of Single Immunoglobulin Variable Domains Secreted from *Escherichia Coli*," Nature 341(6242):544-546, Nature Publishing Group, England (Oct. 1989).
Wehrman, T.S., et al., "A System for Quantifying Dynamic Protein Interactions Defines a Role for Herceptin in Modulating ErbB2 Interactions," Proceedings of the National Academy of Sciences of the United States of America 103(50):19063-19068, National Academy of Sciences, United States (Dec. 2006).
Weidle, UH. et al., "The Intriguing Options of Multispecific Antibody Formats for Treatment of Cancer," Cancer3enomics & Proteomics, vol. 10: 1-18 {2013).
Weinert,B.T., "Acetylation dynamics and stoichiometry in *Saccharomyces cerevisiae*," Molecular Systems Biology , 10(716), 12 pages (2017).
Weinstein, E.J., et al., The oncogene heregulin induces apoptosos in breast wpithelial cells and tumors, Oncogene, 17: 2107-2113, Stockton Press, United Kingdom (1998).
Wick, M.J ., et al., Establishment and Characterization of a HER2-positive, TDM1-Resistant PDX Breast Model. Abstract C74 at AACR-NCI-EORTC International Conference: Molecular Targets and Cancer Therapeutics, Nov. 5-9, 2015, Boston and Drug Resistance and Modifiers, vol. 14, No. 12, Supplement 2, 4 pages.
Wilson, T.R., et al., "Neuregulin-1-Mediated Autocrine Signaling Underlies Sensitivity to HER2 Kinase Inhibitors in a Subset of Human Cancer," Cancer Cells, 20(2): 158-172, Elsevier, Inc., Netherlands (2011).
Wilson, T.R., et al., "Widespread Potential for Growth-factor-driven Resistance to Anticancer Kinase Inhibitors," Nature 487(7408):505-509, Nature Publishing Group, England (Jul. 2012).
Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (2000).
Woning, S.V.D., et al., "Quantification of ErbB3 Receptor Density on Human Breast Cancer Cells, Using a Stable Radio-Labeled Mutant of Nrg1beta," Biochemical and Biophysical Research Communications, 378(2):285-289, Elsevier, United States (Jan. 2009).
Wu, H., et al., "Humanization of a Murine Monoclonal Antibody by Simultaneous Optimization of Framework and CDR Residues," Journal of Molecular Biology 294(1):151-162, Elsevier, England (Nov. 1999).
Xu, F., et al., "Antibody-Induced Growth Inhibition is Mediated Through Immunochemically and Functionally Distinct Epitopes on the Extracellular Domain of the c-erb-2 (HER-2/neu) Gene Product p185," International Journal of Cancer 53(3):401-408, Wiley-Liss, United States (1993).
Xu, J.L. and Davis, M.M., "Diversity in the CDR3 Region of V(H) is Sufficient for Most Antibody Specificities," Immunity 13(1):37-45, Cell Press, United States (Jul. 2000).
Yano, S. et al. "Hepatocyte Growth Factor Induces Gefitinib Resistance of Lung Adenocarcinoma With Epidermal Growth Factor Receptor-activating Mutations," Cancer Research 68(22):9479-9487, American Association for Cancer Research , United States (Nov. 2008).
Yano, S.,"Molecular Mechanism of EGFR-TK1 Resistance," Japanese Journal of Lung Cancer 49(6):939-943, The Japan Lung Cancer Society (Oct. 2009).
Yarden, Y. et al., "The EGFR family and its ligands in human cancer: signalling mechanisms and therapeutic opportunities," European Journal of Cancer 37(Supp4): S3-S8, ResearchGate GmbH(Sep. 2001).
Yarden, Y. et al., "The ERBB network: at last, cancer therapy meets systems biology," Nat Rev Cancer, 12: 553-563, Macmillan Publishers, Limited, United Kingdom (2012).
Yarden, Y., et al., "The ERBB Network: At Last, Cancer Therapy Meets Systems Biology," Nature Reviews Cancer 12(8):553-563, Nature Publishing Group, England (Jul. 2012).
Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).

(56) References Cited

OTHER PUBLICATIONS

Yu, H., et al., "Plasma Levels of Insulin-like Growth Factor-I and Lung Cancer Risk: A Case-control Analysis," Journal of the National Cancer Institute 91(2):151-156, Oxford University Press, United States (Jan. 1999).

Zebisch M and Jones EY, "Crystal structure of R-spondin 2 in complex with the ectodomains of its receptors LGR5 and ZNRF3." J Struct Biol. Aug. 2015;191(2):149-55.

Zebisch M and Jones EY, "ZNRF3/RNF43—A direct linkage of extracellular recognition and E3 ligase activity to modulate cell surface signalling." Prog Biophys Mol Biol. Sep. 2015; 118(3):112-8.

Zeidler, R., et al., "Simultaneous Activation of T Cells and Accessory Cells by a New Class of Intact Bispecific Antibody Results in Efficient Tumor Cell Killing," Journal of Immunology 163(3):1246-1252, American Association of Immunologists, United States (1999).

Zhang, H., et al., "ErbB Receptors: From Oncogenes to Targeted Cancer Therapies," Journal of Clinical Investigation 117(8):2051-2058, American Society for Clinical Investigation, United States (Aug. 2007).

Zhang, Y.W et al., "MET kinase inhibitor SGX523 synergizes with epidermal growth factor receptor inhibitor erlotinib in a hepatocyte growth factor-dependent fashion to suppress carcinoma growth," Cancer Research, 70(17):6880-6890, American Association for Cancer Research, United States(Sep. 2010).

Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).

Zhu, Z., et al., "Remodeling Domain Interfaces to Enhance Heterodimer Formation," Protein science 6(4):781-788, Cold Spring Harbor Laboratory Press, United States (Apr. 1997).

Zolot, R.S., et al., "Antibody-Drug Conjugates," Nature Reviews Drug Discovery 12(4):259-260, Nature Publishing Group, England (Apr. 2013).

\* cited by examiner

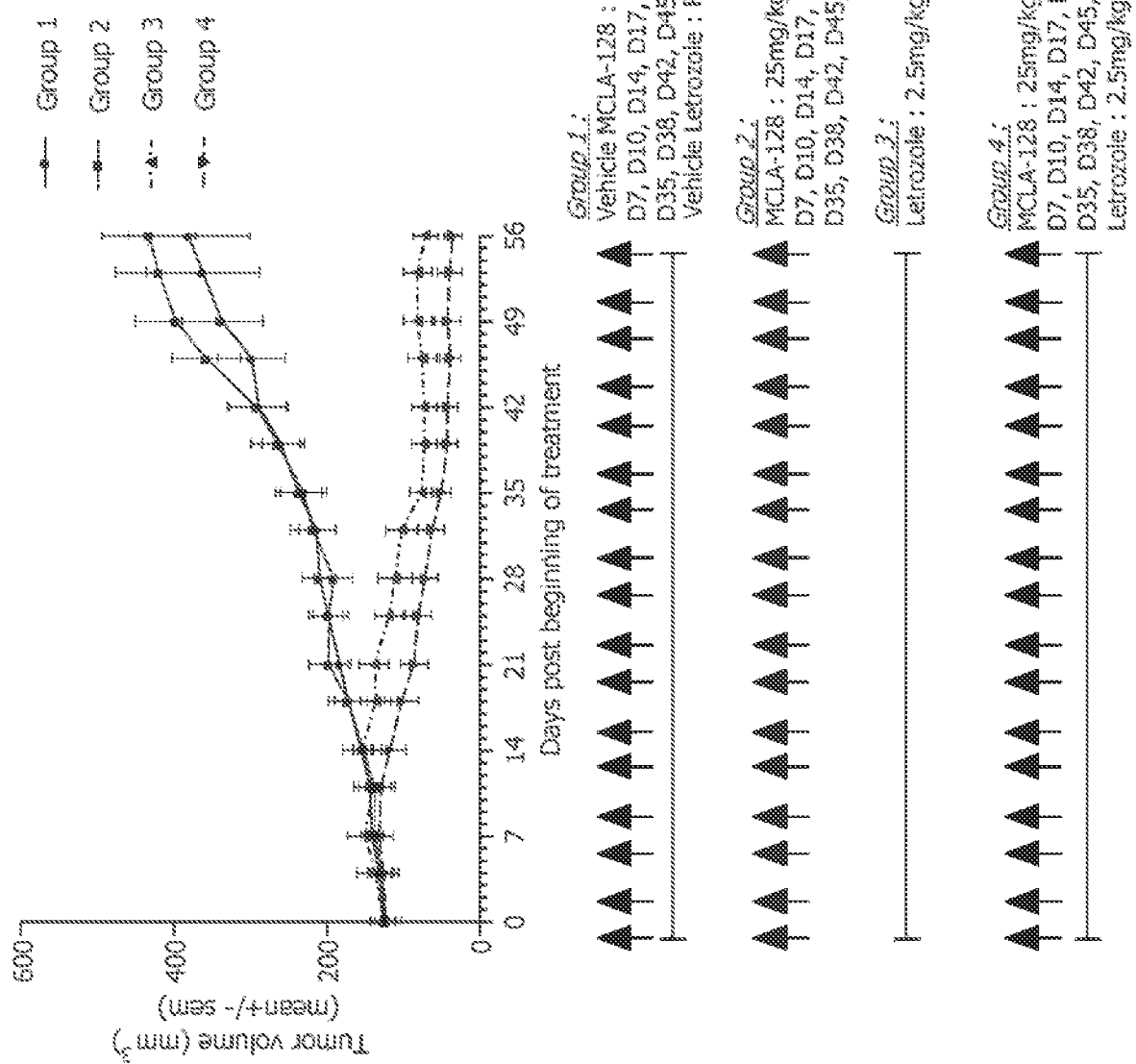

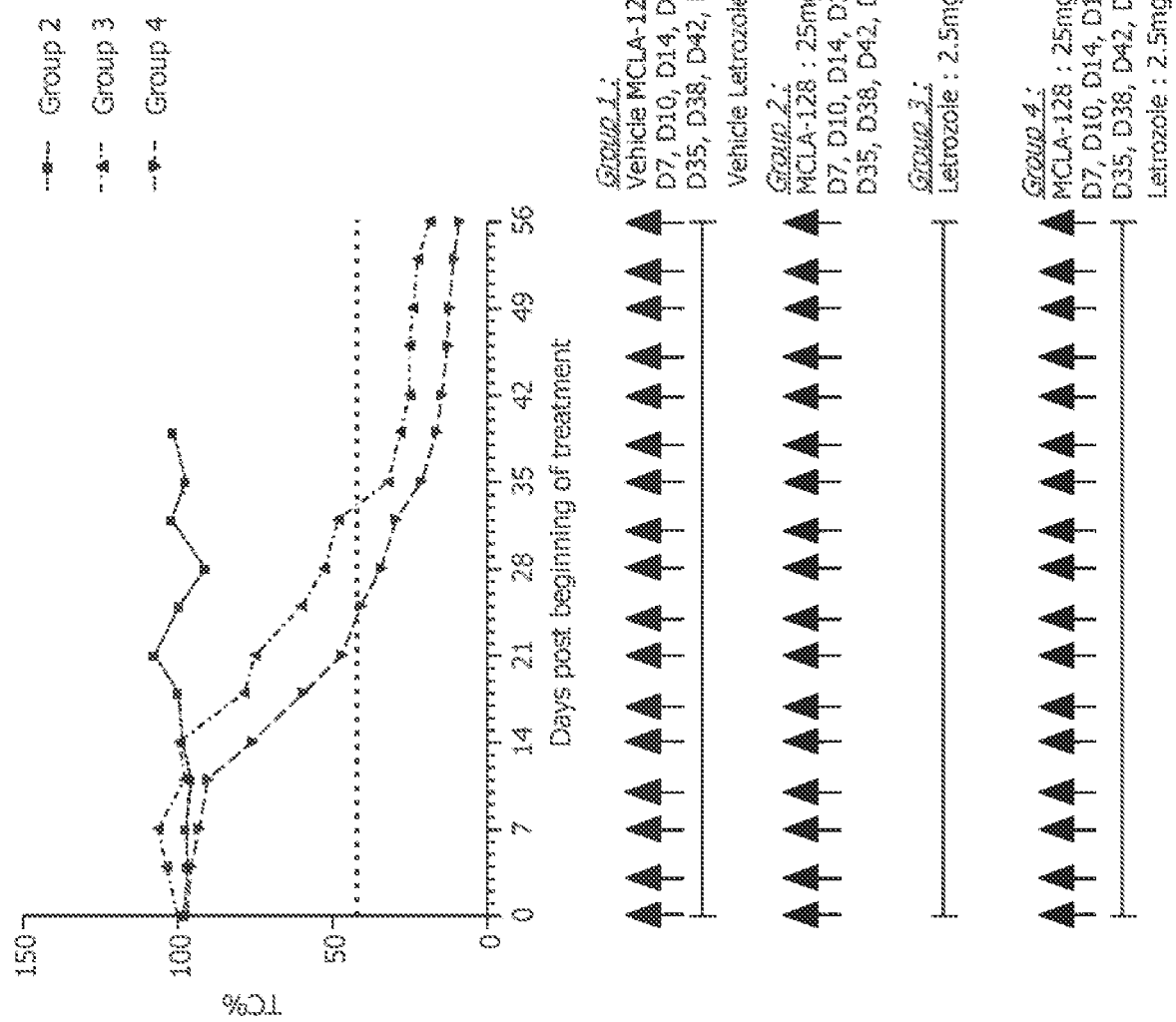

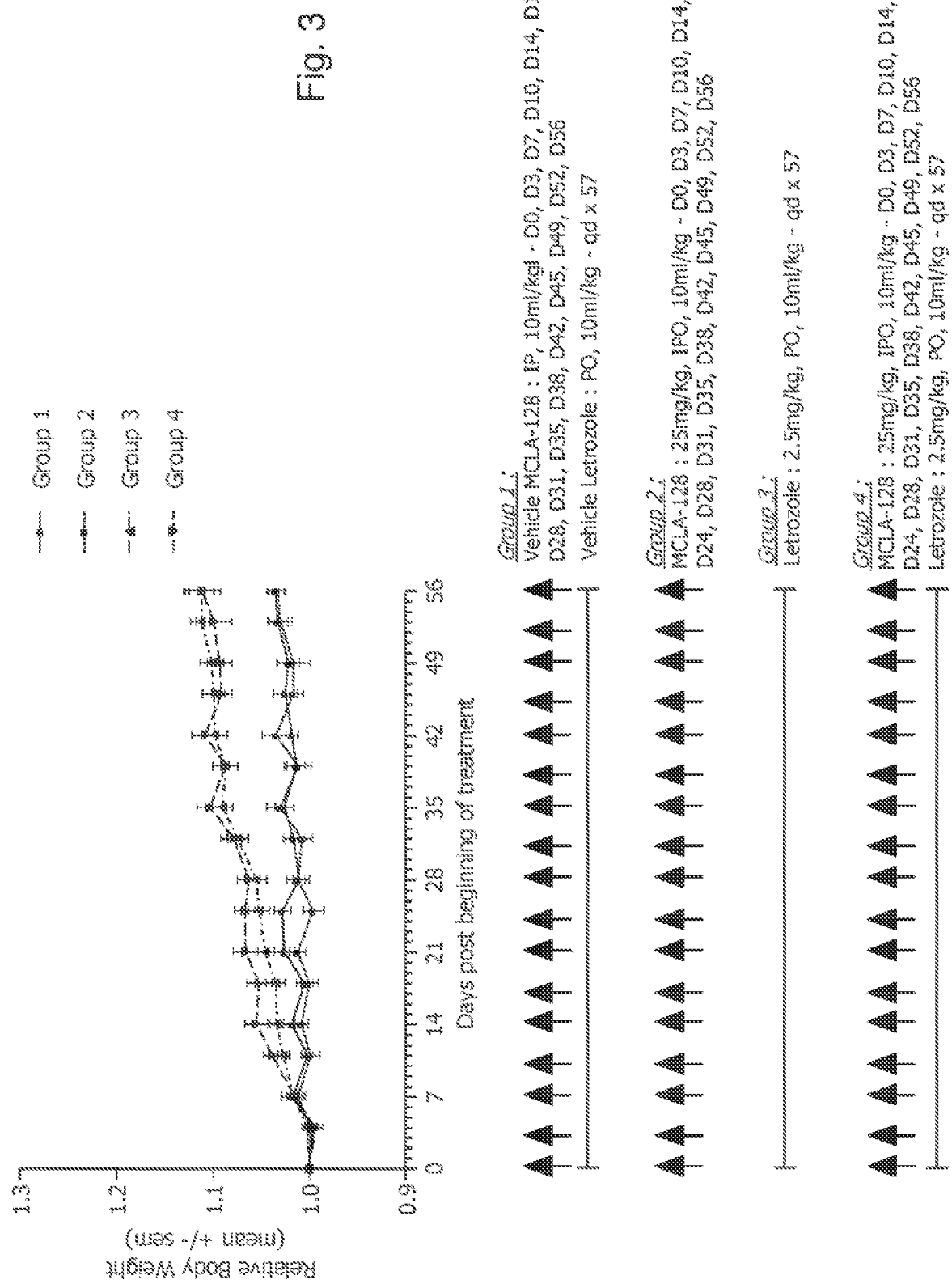

| Tumor code | IHC protein expression | | | |
| --- | --- | --- | --- | --- |
| | Ki67 (Human) | ER (Human) | PR (Human) | Her2 (Human) |
| HBCx-34 | 46% ± 3 | + (80% ± 24) | + (47% ± 39) | 2+ |

Fig. 4A

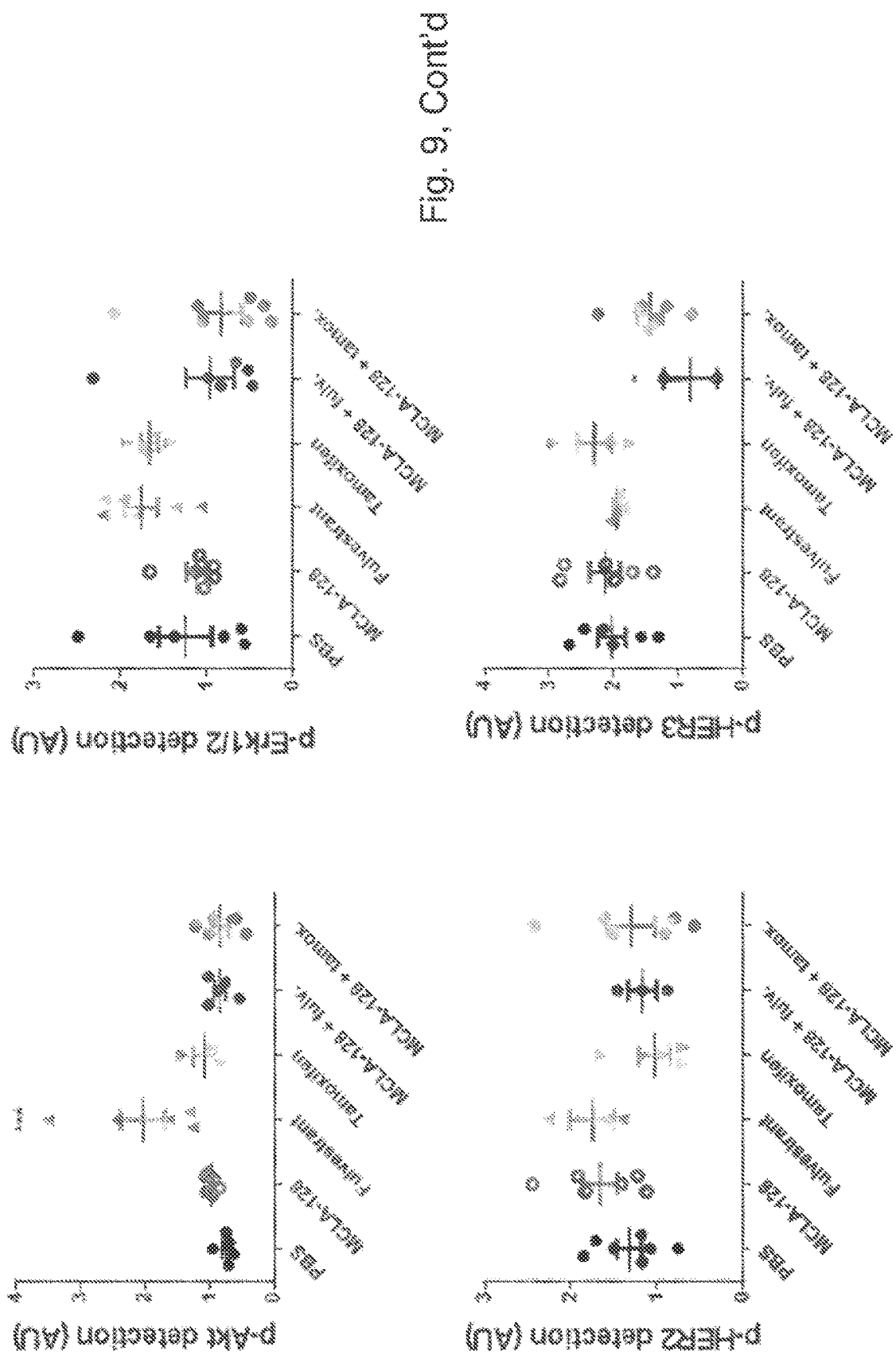
Fig. 9, Cont'd

Fig. 10A

MF2926: heavy chain variable region sequence of an erbB-2 binding antibody
Nucleic acid sequence (underlined sequence encodes end of leader peptide):

SEQ ID NO: 1
```
  1  GGCCCAGCCG GCCATGGCCC AGGTCCAGCT GCAGCAGTCT GGACCTGAGC TGGTGAAACC
 61  TGGGGCTTCA GTGATGATTT CCTGCAAGGC TTCTGGTTAC TCATTCACTG GCTACCACAT
121  GAACTGGGTG AAGCAAAGTC CTGAAAAGAG CCTTGAGTGG ATTGGAGACA TAAATCCTAG
181  CATTGGTACG ACTGCCACA ACCAGATTTT CAGGGCCAAG GCCACAATGA CTGTTGACAA
241  ATCCTCCAAC ACAGCCTACA TGCAGCTCAA GAGCCTGACA TCTGAAGACT CTGGAGTCT
301  TTACTGTGTT AGAAGAGGGG ACTGGTCCTT CGATGTCTGG GGCACAGGGA CCACGGTCAC
361  CGTCTCCAGT
```

Amino acid sequence:
SEQ ID NO: 2 QVQLQQSGPELVKPGASVMISCKASGYSFTGYHMNWVKQSPEKSLEWIGDINPSIGTTA
HNQIFRAKATMTVDKSSNTAYMQLKSLTSEDSGVFYCVRRGDWSFDVWGTGTTVTVSS CDR1:     GYHMNWVKQSPEKSLE SEQ ID NO: 3
CDR2:     NQIFRA SEQ ID NO: 4
CDR3:     RGDWSFDV SEQ ID NO: 5

MF2930: heavy chain variable region sequence of an erbB-2 binding antibody
Nucleic acid sequence (underlined sequence encodes end of leader peptide):

SEQ ID NO: 6
```
  1  GGCCCAGCCG GCCATGGCCG AGGTCCAGCT GCAGCAGTCT GGGGCTGAAC TGGTGAAGCC
 61  TGGAGCTTCA GTGATGATGT CCTGTAAGGT TTCTGGCTAC ACCTTCACTT CCTATCCTAT
121  AGCCTGGATG AAGCAGGTC ATGGAAAGAG CCTAGAGTGG ATTGGAAATT TTCATCCTTA
181  CAGTGATGAT ACTAAGTACA ATGAAAACTT CAAGGGCAAG GCCACATTGA CTGTAGAAAA
241  ATCCTCTAGC ACAGTCTACT TGGAGCTCAG CCGATTAACA TCTGATGACT CTGCTGTTTA
301  TTACTGTGCA AGAAGTAACC CATTATATTA CTTTGCTATG GACTACTGGG GTCAAGGAAC
361  CTCGGTCACC GTCTCCAGT
```

Amino acid sequence:
SEQ ID NO: 7 EVQLQQSGAELVKPGASVMMSCKVSGYTFTSYPIAWMKQVHGKSLEWIGNFHPYSDDT
KYNENFKGKATLTVEKSSSTVYLELSRLTSDDSAVYYCARSNPLYYFAMDYWGQGTSVT
VSS CDR1:     SYPIAWMKQVHGKSLE SEQ ID NO: 8
CDR2:     NENFKG SEQ ID NO: 9
CDR3:     SNPLYYFAMDY SEQ ID NO: 10

MF1849: heavy chain variable region sequence of an erbB-2 binding antibody
Nucleic acid sequence (underlined sequence encodes end of leader peptide):

SEQ ID NO: 11
```
  1  GGCCCAGCCG GCCATGGCCC AGGTGCAGCT GGTGGAGTCT GCGGGAGGCG TGGTCCAGCC
 61  TGGGAGGTCC CTGAGACTCT CCTGTGCAGC GTCTGGATTC ACCTTCAGTA GCTATGGCAT
121  GCACTGGGTC CGCCAGGCTC CAGGCAAGGG GCTGGAGTGG GTGGCAGTTA TATCATATGA
181  TGGAAGTAAT AAATACTATG CAGACTCTGT GAAGGGCCGA TTCACCATCT CCAGAGACAA
241  TTCCAAGAAC ACGCTGTATC TGCAAATGAA CAGCCTGAGA GCTGAGGACA CGGCCGTGTA
301  TTACTGTGCA AAAGGTCACT ACGGTTCTTA CTTCTGTTAC GGTTTGATT ATTGGGGCCA
361  AGGTACCCTG GTCACCGTCT CCAGT
```

Fig. 10A, Cont'd

Amino acid sequence:
SEQ ID NO: 12    QVQLVESGGGVVQPGRSLRLSCAASGFTFSSYGMHWVRQAPGKGLEWVAVISYDGSNK
YYADSVKGRFTISRDNSKNTLYLQMNSLRAEDTAVYYCAKGDYGSYSSYAFDYWGQGTL
VTVSS
CDR1:    SYGMH SEQ ID NO: 13
CDR2:    VISYDGSNKYYADSVKG SEQ ID NO: 14
CDR3:    GDYGSYSSYAFDY SEQ ID NO: 15

MF2973: heavy chain variable region sequence of an erbB-2 binding antibody
Nucleic acid sequence (underlined sequence encodes end of leader peptide):
SEQ ID NO: 16    [nucleic acid sequence, illegible]

Amino acid sequence:
SEQ ID NO: 17    QVQLKQSGAELVRPGASVKLSCKASGYIFTGYYINWLRQRPGQGLEWIAKIYPGSGNTYY
NEKFRGKATLTAEESSSTAYMQLSSLTSEDSAVYFCARGPHYDYDGPWFVYWGQGTLVT
VSS
CDR1:    GYYINWLRQRPGQGLE SEQ ID NO: 18
CDR2:    NEKFRG SEQ ID NO: 19
CDR3:    GPHYDYDGPWFVY SEQ ID NO: 20

MF3004: heavy chain variable region sequence of an erbB-2 binding antibody
Nucleic acid sequence (underlined sequence encodes end of leader peptide):
SEQ ID NO: 21    [nucleic acid sequence, illegible]

Amino acid sequence:
SEQ ID NO: 22    QVQLKQSGAELVRPGASVKLSCKASGYTFTGYYINWVKQRPGQGLEWIARIYPGSGYTY
YNEKFKGKATLTAEESSSTAYMHLSSLTSEDSAVYFCARPHYGYDDWYFGVWGTGTTV
TVSS
CDR1:    GYYINWVKQRPGQGLE SEQ ID NO: 23
CDR2:    NEKFKG SEQ ID NO: 24
CDR3:    PHYGYDDWYFGV SEQ ID NO: 25

Fig. 10A, Cont'd

MF2971: heavy chain variable region sequence of an erbB-2 binding antibody
Nucleic acid sequence (underlined sequence encodes end of leader peptide):

SEQ ID NO: 26
```
  1 GCCCCAGCCG GCCATGGCCC AGGTGCAGCT GAAGCAGTCT GGGGCTGAGC TGGTGAGGCC
 61 TGGGGCTTCA GTGAAGCTGT CCTGCAAGGC TTCTGGCTAC ACTTTCACTG CCTACTATAT
121 AAACTGGGTG AAGCAGAGGC CTGGACAGGG ACTTGAGTGG ATTGCAAGGA TTTATCCTGG
181 AAGTGGCTAT ACTTACTACA ATGAGATTTT CAAGGGCAGG GCCACACTGA CTGCAGACGA
241 ATCCTCCAGC ACTGCCTACA TGCAACTCAG CAGCCTGACA TCTGAGGACT CTGCTGTCTA
301 TTTCTGTGCA AGACCTCCGG TCTACTATGA CTCGGCCTGG TTTGCTTACT GGGGCCAAGG
361 GACTCTGGTC ACCGTCTCCA GT
```

Amino acid sequence:
SEQ ID NO: 27 QVQLKQSGAELVRPGASVKLSCKASGYTFTAYYINWVKQRPGQGLEWIARIYPGSGYT
YYNEIFKGRATLTADESSSTAYMQLSSLTSEDSAVYFCARPPVYYDSAWFAYWGQGTLVT
VSS CDR1: AYYINWVKQRPGQGLE SEQ ID NO: 28
CDR2: NEIFKG SEQ ID NO: 29
CDR3: PPVYYDSAWFAY SEQ ID NO: 30

MF3025: heavy chain variable region sequence of an erbB-2 binding antibody
Nucleic acid sequence (underlined sequence encodes end of leader peptide):

SEQ ID NO: 31
```
  1 GCCCCAGCCG GCCATGGCCC AGGTGCAGCT GAAGCAGTCT GGGGCTGAGC TGGTGAGGCC
 61 TGGGACTTCA GTGAAGTTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 AAGTGGCTAT ACTTACTACA ATGAGAAGTT CAAGGGCAAG GCCACACTGA CTGCAGAAGA
241 ATCCTCCAAC ACTGCCTATA TGCACCTCAG CAGCCTGACA TCTGAGGACT CTGCTGTCTA
301 TTTCTGTGCA AGGCCCCACT ATGGTTACGA CGACTGGTAC TTCGCTGTCT GGGGCACAGG
361 GACCACGGTC ACCGTTTCCA GT
```

Amino acid sequence:
SEQ ID NO: 32 QVQLKQSGAELVRPGTSVKLSCKASGYTFTGYYINWVKQRPGQGLEWIARIYPGSGYT
YYNEKFKGKATLTAEESSNTAYMHLSSLTSEDSAVYFCARPHYGYDDWYFAVWGTGTTV
TVSS CDR1: GYYINWVKQRPGQGLE SEQ ID NO: 33
CDR2: NEKFKG SEQ ID NO: 34
CDR3: PHYGYDDWYFAV SEQ ID NO: 35

MF2916: heavy chain variable region sequence of an erbB-2 binding antibody
Nucleic acid sequence (underlined sequence encodes end of leader peptide):

SEQ ID NO: 36
```
  1 GCCCCAGCCG GCCATGGCCC AGGTCCAGCT GCAGCAGTCT GGGGCTGAGC TGGTGAGGCC
 61 TGGGGTTTCA GTGAAGCTGT CCTGCAAGGC TTCTGGCTAC ACTTTCACTG CTACTATAT
121 AAACTGGGTG AAGCAGAGGC CTGCACAGGG ACTTGAGTGG ATTGCAAGGA TTTATCCTGG
181 CAGTGGTCAT ACTTCCTACA ATGAGAAGTT CAAGGGCAAG GCCACACTGA CTACAGAAAA
241 ATCCTCCAGC ACTGCCTACA TGCAGCTCAG CAGCCTGACA TCTGAGGACT CTGCTGTCTA
301 TTTCTGTGCA ACAGCTATCT ACTTCATTA CGCAGGGGG TACTTCGATG TCTGGGGCAC
361 AGGGACCTCG GTCACCGTCT CCACT
```

Fig. 10A, Cont'd

Amino acid sequence:
SEQ ID NO: 37 QVQLQQSGAELVRPGASVKLSCKASGYTFTGYYINWVKQRPGQGLEWIARIYPGSGITS
YNEKFKGKATLTTEKSSSTAYMQLSSLTSEDSAVYFCARPIYFDYAGGYFDVWGTRTSVT
VSS CDR1:    GYYINWVKQRPGQGLE SEQ ID NO: 38
CDR2:    NEKFKG SEQ ID NO: 39
CDR3:    PIYFDYAGGYFDV SEQ ID NO: 40

MF3958: heavy chain variable region sequence of an erbB-2 binding antibody
Nucleic acid sequence (underlined sequence encodes end of leader peptide):
SEQ ID NO: 41    [nucleic acid sequence, illegible]

Amino acid sequence:
SEQ ID NO: 42 QVQLVQSGAEVKKPGASVKLSCKASGYTFTAYYINWVRQAPGQGLEWIGRIYPGSGYTS
AQKFQGRATLTADESTSTAYMELSSLRSEDTAVYFCARPPVYYDSAWFAYWGQGTLVT
VSS CDR1:    AYYIN SEQ ID NO: 43
CDR2:    RIYPGSGYTSYAQKFQG SEQ ID NO: 44
CDR3:    PPVYYDSAWFAY SEQ ID NO: 45

MF3031: heavy chain variable region sequence of an erbB-2 binding antibody
Nucleic acid sequence (underlined sequence encodes end of leader peptide):
SEQ ID NO: 46    [nucleic acid sequence, illegible]

Amino acid sequence:
SEQ ID NO: 47 QVQLQQSGAELVRPGASVKLSCKASGYTFTAYYINWVKQRPGQGLEWIAKIYPGSGYTY
YNENFRGKATLTAEESSSTAYIQLSSLTSEDSAVYFCARGVYDYDGAWFAYWGQGTLVT
VSS CDR1:    AYYINWVKQRPGQGLE SEQ ID NO: 48
CDR2:    NENFRG SEQ ID NO: 49
CDR3:    GVYDYDGAWFAY SEQ ID NO: 50

Fig. 10A, Cont'd

MF3991: heavy chain variable region sequence of an erbB-2 binding antibody
Nucleic acid sequence (underlined sequence encodes end of leader peptide):
SEQ ID NO: 51

Amino acid sequence:
SEQ ID NO: 52 QVQLVQSGAEVKKPGASVKLSCKASGYTFTAYYINWVRQAPGQGLEWIGRIYPGSGYTS
YAQKFQGRATLTADESTSTAYMELSSLRSEDTAVYFCARPHYGYDDWYFGVWGQGTLV
TVSS
CDR1: AYYIN SEQ ID NO: 53
CDR2: RIYPGSGYTSYAQKFQG SEQ ID NO: 54
CDR3: PHYGYDDWYFGV SEQ ID NO: 55

Fig. 10B

MF3178: heavy chain variable region sequence of an erbB-3 binding antibody
Nucleic acid sequence (underlined sequence encodes end of leader peptide):
SEQ ID NO: 56 [nucleic acid sequence illegible]

Amino acid sequence:
SEQ ID NO: 57 QVQLVQSGAEVKKPGASVKVSCKASGYTFTGYYMHWVRQAPGQGLEWMGWINPNSGG
TNYAQKFQGRVTMTRDTSISTAYMELSRLRSDDTAVYYCARDHGSRHFWSYWGFDYWG
QGTLVTVSS

| CDR1: | GYYMH | SEQ ID NO: 58 |
| CDR2: | WINPNSGGTNYAQKFQG | SEQ ID NO: 59 |
| CDR3: | DHGSRHFWSYWGFDY | SEQ ID NO: 60 |

MF3176: heavy chain variable region sequence of an erbB-3 binding antibody
Nucleic acid sequence (underlined sequence encodes end of leader peptide):
SEQ ID NO: 61 [nucleic acid sequence illegible]

Amino acid sequence:
SEQ ID NO: 62 EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARDWWYPPYYWGFDYWGQGTL
VTVSS

| CDR1: | SYAMS | SEQ ID NO: 63 |
| CDR2: | AISGSGGSTYYADSVKG | SEQ ID NO: 64 |
| CDR3: | DWWYPPYYWGFDY | SEQ ID NO: 65 |

MF3163: heavy chain variable region sequence of an erbB-3 binding antibody
Nucleic acid sequence (underlined sequence encodes end of leader peptide):
SEQ ID NO: 66 [nucleic acid sequence illegible]

Fig. 10B, Cont'd

Amino acid sequence:
SEQ ID NO: 67 QVQLVQSGAEVKKPGASVKVSCKASGYTFTGYYMHWVRQAPGQGLEWMGWINPNSGG
TNYAQKFQGRVTMTRDTSISTAYMELSRLRSDDTAVYYCAKDSYSRHFYSWWAFDYWG
QGTLVTVSS

| | | |
|---|---|---|
| CDR1: | GYYMH | SEQ ID NO: 68 |
| CDR2: | WINPNSGGTNYAQKFQG | SEQ ID NO: 69 |
| CDR3: | DSYSRHFYSWWAFDY | SEQ ID NO: 70 |

MF3099: heavy chain variable region sequence of an erbB-3 binding antibody

Nucleic acid sequence (underlined sequence encodes end of leader peptide):
SEQ ID NO: 71
```
  1 GCCCCAGCCG GCCATGGCCG AGGTCCAGCT GCAGCAGCCT GGGGCTGAGC TGGTGAAGCC
 61 TGGGACTTCA GTGAAGTTGT CCTGCAAGGC TTCTGGCTAC ACCTTCACCA GTACTGGGAT
121 GCATTGGGTA AAGCAGAGGC CTGGACAAGG CCTTGAGTGG ATCGGAATTC TTGATCCTTC
181 TGATAGTTAT ACTACCTACA ATCAAAAGTT CAAGGGCAAG GCCACATTAA CAGTAGACAC
241 ATCCTCCAGC ATAGCCTACA TGCAGCTCAG CAGCCTGACA TCTGAGGACT CTGCGGTCTA
301 TTACTGTGCA AGAGGGGGAG ATTACGACGA GGGAGGTGCT ATGGACTACT GGGGTCAAGG
361 AACCTCGGTC ACCGTCTCCA GT
```

Amino acid sequence:
SEQ ID NO: 72 EVQLQQPGAELVRPGTSVKLSCKASGYTFTSYWMHWVKQRPGQGLEWIGILDPSDSYTT
YNQKFKGKATLTVDTSSSIAYMQLSSLTSEDSALYYCARGGDYDEGGAMDYWGQGTSVT
VSS

| | | |
|---|---|---|
| CDR1: | SYWMH | SEQ ID NO: 73 |
| CDR2: | ILDPSDSYTTYNQKFKG | SEQ ID NO: 74 |
| CDR3: | GGDYDEGGAMDY | SEQ ID NO: 75 |

MF3307: heavy chain variable region sequence of an erbB-3 binding antibody
Nucleic acid sequence (underlined sequence encodes end of leader peptide):
SEQ ID NO: 76
```
  1 GCCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GTTACTATAT
121 GCATTGGGTG CGACAGGCCC CTGGACAAGG CCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AGAGGTTCGC GTAAGCGTCT GTTAACTCC TTCAACGCTT TTGATTATTG
361 GGGCCAAGGT ACCCTGGTCA CCGTCTCCAG T
```

Amino acid sequence:
SEQ ID NO: 77 QVQLVQSGAEVKKPGASVKVSCKASGYTFTGYYMHWVRQAPGQGLEWMGWINPNSGG
TNYAQKFQGRVTMTRDTSISTAYMELSRLRSDDTAVYYCARGSRKRLSNYFNAFDYWGQ
GTLVTVSS

| | | |
|---|---|---|
| CDR1: | GYYMH | SEQ ID NO: 78 |
| CDR2: | WINPNSGGTNYAQKFQG | SEQ ID NO: 79 |
| CDR3: | GSRKRLSNYFNAFDY | SEQ ID NO: 80 |

Fig. 10C a) Common Light Chain
SEQ ID NO: 81 DIQMTQSPSSLSASVGDRVTITCRASQSISSYLNWYQQKPGKAPKLLIYAASSLQSGVPSR
FSGSGSGTDFTLTISSLQPEDFATYYCQQSYSTPPTFGQGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC

Fig. 10D heavy chain for erbB-2 binding
SEQ ID NO: 82 QVQLVQSGAEVKKPGASVKLSCKASGYTFTAYYINWVRQAPGQGLEWIGRIYPGSGYTS
YAQKFQGRATLTADESTSTAYMELSSLRSEDTAVYFCARPPVYYDSAWFAYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTDP
PSREEMTKNQVSLTCEVKGFYPSDIAVEWESNGQPENNYKTTPPVLDSDGSFFLYSKLT
VDKSRWQQGNVFSCSVMHEALHNHYTQKSLSLSPG heavy chain for erbB-3 binding
SEQ ID NO: 83 QVQLVQSGAEVKKPGASVKVSCKASGYTFTGYYMHWVRQAPGQGLEWMGWINPNSGG
TNYAQKFQGRVTMTRDTSISTAYMELSRLRSDDTAVYYCARDHGSRHFWSYWGFDYWG
QGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTCPP
CPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTKPPSREEMTKNQVSLKCLVKGFYPSDIAVEWESNGQPENNYKTTPPVLDSDGSFF
LYSKLTVDKSRWQQGNVFSCSVMHEALHNHYTQKSLSLSPG

Fig. 10E

HER2-specific Ab sequences

MF2889: heavy chain variable region sequence of an erbB-2 binding antibody
Nucleic acid sequence (underlined sequence encodes end of leader peptide):

SEQ ID NO: 84

Amino acid sequence:
SEQ ID NO: 85 EVQLQQSGAELVRPGTSVKVSCKASGYAFTNYLIEWVKQRPGQGLEWIGVIYPEGGGTIY
NEKFKGKATLTADKSSSTAYMQLSGLTSEDSAVYFCARGDYDYKYAMDYWGQGTSVTV
SS CDR1: NYLIE SEQ ID NO: 86
CDR2: VIYPEGGGTIYNEKFKG SEQ ID NO: 87
CDR3: GDYDYKYAMDY SEQ ID NO: 88

MF2913: heavy chain variable region sequence of an erbB-2 binding antibody
Nucleic acid sequence (underlined sequence encodes end of leader peptide):

SEQ ID NO: 89

Amino acid sequence:
SEQ ID NO: 90 EVKLQQSGPELVKPGASVKISCKASGYSFTDYKMDWVKQSHGKSLEWIGNINPNSGGVI
YNQKFRGKVTLTVDRSSSAAYMELRSLTSEDTAVYYCSRGLWDAMDSWGQGTSVTVSS CDR1: DYKMDWVKQSHGKSLE SEQ ID NO: 91
CDR2: NQKFRG SEQ ID NO: 92
CDR3: GLWDAMDS SEQ ID NO: 93

Fig. 10E, Cont'd

MF1847: heavy chain variable region sequence of an erbB-2 binding antibody
Nucleic acid sequence (underlined sequence encodes end of leader peptide):

SEQ ID NO: 94   [nucleic acid sequence illegible]

Amino acid sequence:

SEQ ID NO: 95   QVQLVESGGGVVQPGRSLRLSCAASGFTFSSYGMHWVRQAPGKGLEWVAVISYDGSNK
YYADSVKGRFTISRDNSKNTLYLQMNSLRAEDTAVYYCAKGWWHPLLSGFDYWGQGTL
VTVSS

CDR1:    SYGMH SEQ ID NO: 96
    CDR2:    VISYDGSNKYYADSVKG SEQ ID NO: 97
    CDR3:    GWWHPLLSGFDY SEQ ID NO: 98

MF3001: heavy chain variable region sequence of an erbB-2 binding antibody
Nucleic acid sequence (underlined sequence encodes end of leader peptide):

SEQ ID NO: 99   [nucleic acid sequence illegible]

Amino acid sequence:

SEQ ID NO: 100  EVQLQQSGAELAKPGASVKLSCKTSGYNFPIYWMHWVKQRPGRGLEWIGYINPSTGYIK
NNQKFKDKATLTADKSSNTAYMQLNSLTYEDSAVYYCTREGTGFTYWGQGTLVTVSS

CDR1:    IYWMHWVKQRPGRGLE SEQ ID NO: 101
    CDR2:    NQKFKD SEQ ID NO: 102
    CDR3:    EGTGFTY SEQ ID NO: 103

Fig. 10E, Cont'd

MF1898: heavy chain variable region sequence of an erbB-2 binding antibody
Nucleic acid sequence (underlined sequence encodes end of leader peptide):

SEQ ID NO: 104 [nucleic acid sequence illegible]

Amino acid sequence:
SEQ ID NO: 105 QVQLVESGGGVVQPGRSLRLSCAASGFTFSSYGMHWVRQAPGKGLEWVAVISYDGSNK
YYADSVKGRFTISRDNSKNTLYLQMNSLRAEDTAVYYCAKDGFRRTTLSGFDYWGQGTL
VTVSS CDR1: SYGMH SEQ ID NO: 106
CDR2: VISYDGSNKYYADSVKG SEQ ID NO: 107
CDR3: DGFRRTTLSGFDY SEQ ID NO: 108

MF3003 heavy chain variable region sequence of an erbB-2 binding antibody
Nucleic acid sequence (underlined sequence encodes end of leader peptide):

SEQ ID NO: 109 [nucleic acid sequence illegible]

Amino acid sequence:
SEQ ID NO: 110 QVQLKQSGPELVKPGASVKISCKASGDAFSYSWMNWVKQRPGKGLEWIGRIYPGDGDI
NYNGKFKGKATLTADKSSSTAHLQLNSLTSEDSAVYFCARGQLGLEAWFAYWGQGTLV
TVSS CDR1: YSWMNWVKQRPGKGLE SEQ ID NO: 111
CDR2: NGKFKG SEQ ID NO: 112
CDR3: GQLGLEAWFAY SEQ ID NO: 113

Fig. 10E, Cont'd

HER3-specific Ab sequences

MF6058: heavy chain variable region sequence of an erbB-3 binding antibody
Nucleic acid sequence (underlined sequence encodes end of leader peptide):

SEQ ID NO: 114
```
  1 GGCCCAGCCG GCCATGGCC AGGTGCAGCT GGTGCAGTCT GGGGCTGACG TGAAGAAGCC
 61 TGGGGCCTCA GTGAAGGTCA CCTGCAAGGC TTCTGGATAC ACCTTCACC GCTACTATAT
121 GCACTGGGTG CGACAGGCCC CTGGACAAGC TCTTGAGTGG ATGGGATGGA TCAACCCTCA
181 AAGTGGTGGC ACAAACTATG CAAAGAAGTT TCAGGGCAGG GTCTCTATGA CCAGGGACAC
241 GTCCACAAGC ACAGCCTACA TGCAGCTGAG CAGGCTGAGA TCTGACGACA CGGCTACGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:
SEQ ID NO: 115 QVQLVQSGADVKKPGASVKVTCKASGYTFTGYYMHWVRQAPGQALEWMGWINPQSGG
TNYAKKFQGRVSMTRETSTSTAYMQLSRLRSDDTATYYCARDHGSRHFWSYWGFDYW
GQGTLVTVSS
CDR1: GYYMH SEQ ID NO: 116
CDR2: WINPQSGGTNYAKKFQG SEQ ID NO: 117
CDR3: DHGSRHFWSYWGFDY SEQ ID NO: 118

MF6061: heavy chain variable region sequence of an erbB-3 binding antibody
Nucleic acid sequence (underlined sequence encodes end of leader peptide):

SEQ ID NO: 119
```
  1 GGCCAGCCG GCCATGGCC AGGTGCAGCT GGTGCAGTCT GGGGCTGAGG TGAAGAAGCC
 61 TGGGGCCTCA GTGAAGGTCT CCTGCAAGGC TTTTGGATAC ACCTTCACC GCTACTATAT
121 GCACTGGGTG CGACAGGCCC CTGGACAAGG GCTTGAGTGG ATGGGATGGA TCAACCCTCA
181 GAGTGGTGGC ACAAACTATG CACAGAAGTT TAAGGGCAGG GTCACCATGA CCAGGGACAC
241 GTCCACCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:
SEQ ID NO: 120 QVQLVQSGAEVKKPGASVKVSCKASGYTFTGYYMHWVRQAPGQGLEWMGWINPQSGG
TNYAQKFKGRVTMTRDTSTSTAYMELSRLRSDDTAVYYCARDHGSRHFWSYWGFDYW
GQGTLVTVSS
CDR1: GYYMH SEQ ID NO: 121
CDR2: WINPQSGGTNYAQKFKG SEQ ID NO: 122
CDR3: DHGSRHFWSYWGFDY SEQ ID NO: 123

Fig. 10E, Cont'd

MF6065: heavy chain variable region sequence of an erbB-3 binding antibody
Nucleic acid sequence (underlined sequence encodes end of leader peptide):

SEQ ID NO: 124   [nucleic acid sequence illegible]

Amino acid sequence:
SEQ ID NO: 125 QVQLVQSGAEVKKPGASVKVSCKASGYTFTSYYMHWVRQAPGQGLEWMGWINPQGGS
TNYAQKFQGRVTMTRDTSTSTVYMELSRLRSEDTAVYYCARDHGSRHFWSYWGFDYW
GQGTLVTVSS CDR1:   SYYMH SEQ ID NO: 126
CDR2:   WINPQGGSTNYAQKFQG SEQ ID NO: 127
CDR3:   DHGSRHFWSYWGFDY SEQ ID NO: 128

Fig. 11

Amino acid alignment of MF3178 variants
The CDR1, CDR2 and CDR3 sequences of MF3178 are in bold and underlined

```
                                    CDR1                           CDR2
                 1        10        20        30        40        50        60
SEQ ID NO: 57   MF3178  XVQLVQSGAEVKKPGASVKVSCKASGYTFX GYYMH WVRQAPGQGLEWMG WINPNSGGTNYAQKFQG
SEQ ID NO: 130  MF6055  .........D...................  .....  ........A.....  ....S.......K....
SEQ ID NO: 132  MF6056  .........D...........T.......  .....  ........A.....  ....S.......K....
SEQ ID NO: 134  MF6057  .........D...........T.......  .....  ..............  ....Q............
SEQ ID NO: 115  MF6058  .........D...........T.......  .....  ........A.....  ....Q.......K....
SEQ ID NO: 138  MF6059  .............................  .....  ..............  ....G..S.........
SEQ ID NO: 140  MF6060  .........D...................  .....  ........A.....  ....Q.......K....
SEQ ID NO: 120  MF6061  .............................  .....  ..............  ....Q..........K.
SEQ ID NO: 144  MF6062  .............................  .....  ..............  ....G..S.........
SEQ ID NO: 146  MF6063  .............................  .....  ..............  ....Q.......K....
SEQ ID NO: 148  MF6064  .............................  .....  .......K......  ....Q............
SEQ ID NO: 125  MF6065  .............................  S....  ..............  ....QG.S.........
SEQ ID NO: 152  MF6066  .............................  .....  ..............  ....Q..S.........
SEQ ID NO: 154  MF6067  .............................  .....  ..............  ....Q............
SEQ ID NO: 156  MF6068  .............................  .....  ..............  ....Q............
SEQ ID NO: 158  MF6069  .............................  .....  ..............  ....Q............
SEQ ID NO: 160  MF6070  .............................  S....  ..............  ....SG.S.........
SEQ ID NO: 162  MF6071  .............................  .....  ..............  ....S..S.........
SEQ ID NO: 164  MF6072  .............................  .....  ..............  ....S............
SEQ ID NO: 166  MF6073  .............................  .....  ..............  ....S............
SEQ ID NO: 168  MF6074  .............................  .....  ..............  ....S............

CDR3
                 70        80        90        100       110       120
        MF3178  RVTXTPDTSISTAXMELSRLRSDXTAVYYCAK DHGSRHFWSYWGFDY WGQGTLVTVSS
        MF6055  ......E..T.....................T ............... ...........
        MF6056  ..S..E..T......Q...............T ............... ...........
        MF6057  ...............Q................ ............... ...........
        MF6058  ..S..E..T......Q...............T ............... ...........
        MF6059  ................................ ............... ...........
        MF6060  ......E..T.....................T ............... ...........
        MF6061  .........T...................... ............... ...........
        MF6062  .........T...................... ............... ...........
        MF6063  .........T...................... ............... ...........
        MF6064  .........T...................... ............... ...........
        MF6065  .........T..V........E.......... ............... ...........
        MF6066  .........T.........S...E........ ............... ...........
        MF6067  .........T..V........S.......... ............... ...........
        MF6068  .........T...................... ............... ...........
        MF6069  .........T...................... ............... ...........
        MF6070  .........T..V........E.......... ............... ...........
        MF6071  .........T.........S...E........ ............... ...........
        MF6072  .........T..V......S............ ............... ...........
        MF6073  .........T...................... ............... ...........
        MF6074  ................................ ............... ...........
```

Fig. 11, Cont'd

**Nucleic acid alignment of MF3178 variants (*without* end of leader sequence)**

```
SEQ ID NO: 56   MF3178  CAGGTGCAGCTGGTGCAGTCTGGGGCTGAGGTGAAGAAGCCTGGGGCCTCAGTGAAGGTTTCCTGCAAG
SEQ ID NO: 114  MF6059  ..........................C...........................A.G......
SEQ ID NO: 119  MF6061  ..................................................................
SEQ ID NO: 124  MF6065  ..................................................................

CDR1
                MF3178  GGTTCTGGATACACCTTCACC  GGCTACTATATGCAC  TGGGTGCGACAGGCCCCTGGACAAGGGCTTG
                MF6059  .....................  ...............  ..........................CT...
                MF6061  .....................  ...............  ................................
                MF6065  .....................  TCT............  ................................

CDR2
                MF3178  AGTGGATGGGA  TGGATCAACCCTAACAGTGGTGGCACAAACTATGCACAGAAGTTTCAGGGC  AGGGT
                MF6059  ...........  ......C.A..........................A..............  .....
                MF6061  ...........  ......C.G..........................A..............  .....
                MF6065  ...........  ......C.GG.G...TCT...................................  .....

MF3178  CACCATGACCAGGGACACGTCCATCAGCACAGCCTACATGGAGCTGAGCAGGCTGAGATCTGACGACAC
                MF6059  .T.T........G.........CA..............C...........................
                MF6061  ........................C...........................................
                MF6065  ........................C...........TG...........................G....

CDR3
                MF3178  GGCTGTGTATTACTGTGCAAGA  GATCATGGTTCTGTCATTTCTGGTCTTACTGGGCTTGATTAT
                MF6059  ....AC................  ..........................................
                MF6061  ......................  ..........................................
                MF6065  ......................  ..........................................

MF3178  TGGGGCCAAGGTACCCTGGTCACCGTTTCCAGT
                MF6059  .................................
                MF6061  .................................
                MF6065  .................................
```

DNA sequences of MF3178 variants

MF6055

>MF6055_VH

SEQ ID NO: 129  caggtgcagctggtgcagtctggggctgaggtgaagaagcctggggcctcagtgaaggtctcctgcaag
gcttctggatacaccttcaccggctactatatgcactgggtgcgacaggcccctggacaaggcttgagtg
gatgggatggatcaaccctctagtggtggcacaaactatgcaaagaagtttcagggcagggtcaccatg
accaggagagacgtctcaacaagcacagcctacatggagctgagcaggctgagatctgacgacacggctgt
attactgtgcaagagatcatggttctgtcatttctggtcttactgggcttgattattggggccaagg
tacctggtcacc

SEQ ID NO: 131　caggtgcagctgttgcagtctggggctgacgtgaagaagcctggggcctcagtgaaggtcacgtgcaagg
cttctggatacaccttcactggctactatatgcactgggtgcgacaggcccctggacaagctcttgagtg
gatgggatggatcaaccctctagtggtggcacaaactatgcaaagaagtttcagggcagggtctctatg
accagggagacgtccacaagcacagcctacatggagctgagcaggctgagatctgacgacacggctgtgt
attactgtgcaagagatcatggttctcgtcatttctggtcttactggggctttgattatggggccaagg
taccctggtcacc

MF6057

>MF6057_VH

SEQ ID NO: 133　caggtgcagctggtgcagtctggggctgatgtgaagaagcctggggcctcagtgaaggtcacgtgcaagg
cttctggatacaccttcactggctactatatgcactgggtgcgacaggcccctggacaagggctgagtg
gatggatggatcaaccctcagtggtggcacaaactatgcacagaagtttcagggcagggtcacgatg
accagggacacgtccatcagcacagcctacatgcagctgagcaggctgagatctgacgacacggctgtgt
attactgtgcaagagatcatggttctcgtcatttctggtcttactggggctttgattattggggccaagg
taccctggtcacc

MF6058

>MF6058_VH

SEQ ID NO: 135　caggtgcagctggtgcagtctggggctgacgtgaagaagcctggggcctcagtgaaggtcacgtgcaagg
cttctggatacaccttcacgggctactatatgcactgggtgcgacaggcccctggacaagctcttgagtg
gatggatggatcaaccctcagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactggggctttgattatggggccaagg
taccctggtcacc

MF6059

>MF6059_VH

SEQ ID NO: 137　caggtgcagctggtgcagtctggggctgaggtgaagaagcctggggcctcagtgaaggtctcctgcaagg
cttctggatacaccttcaccggctactatatgcactgggtgcgacaggcccctggacaagggctgagtg
gatgggatggatcaaccctggcagtggttctacaaactatgcacagaagtttcagggcaggtcacgatg
accagggacacgtccatcagcacagcctacatggagctgagcaggctgagatctgacgacacggctgtgt
attactgtgcaagagatcatggttctcgtcatttctggtcttactggggctttgattatggggccaagg
taccctggtcacc

MF6060

>MF6060_VH

SEQ ID NO: 139　caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatggatggatcaaccctcaagtggtggcacaaactatgcaaagaagtttcagggcaggtcacgatg
accagggagacgtccacaagcacagcctacatggagctgagcaggctgagatctgacgacacggctacgt
attactgtgcaagagatcatggttctcgtcatttctggtcttactggggctttgattatggggccaagg
taccctggtcacc

MF6061

>MF6061_VH

SEQ ID NO: 141　caggtgcagctggtgcagtctggggctgaggtgaagaagcctggggcctcagtgaaggtctcctgcaagg
cttctggatacaccttcaccggctactatatgcactgggtgcgacaggcccctggacaagggctgagtg
gatgggatggatcaaccctcagagtggtggcacaaactatgcaaagaagtttcagggcaggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcacc

SEQ ID NO: 143   caggtgcagctggtgcagtctgggctgaggtgaagaagcctggggcctcagtgaaggtctcctgcaagg
cttctggatacaccttcacggctactatatgcactgggtgcgacagcccctggacagggtgagtg
gatggatggatcaaccctggcagtggttctacaaactatgcacagaagtttcagggcaggtcacgatg
accagggacacgtccacaagcacagtctacatggagctgagcaggctgagatctgacgacacggctgtgt
attactgtgcaagagatcatggttctgtcatttctggtcttactggggcttgattattggggccaagg
taccctggtcacc

MF6063
>MF6063_VH

SEQ ID NO: 145   caggtgcagctggtgcagtctggggctgaggtgaagaagcctggggcctcagtgaaggtctcctgcaagg
cttctggatacaccttcacggctactatatgcactgggtgcgacaggcccctggacagggcttgagtg
gatggatggatcaaccctagagtggtggcacaaactatgcagaagtttcagggcagggtcacgatg
accgggacacgtccaccagcacagcctacatggagctgagcaggctgagatctgacgacacggctgtgt
attactgtgcaagagatcatggttctgtcatttctggtcttactgggctttgattattggggccaagg
taccctggtcacc

MF6064
>MF6064_VH

SEQ ID NO: 147   caggtgcagctggtgcagtctggggctgaggtgaagaagcctggggcctcagtgaaggtctcctgcaagg
cttctggatacaccttcacggctactatatgcactgggtgcgacaggcccctggacagggcttgagtg
gatggatggatcaaccctcagtgtggcacaaactatgcagaagtttcagggcagggtcacgatg
accgggacacgtccacgagcacagcctacatggagctgagcaggctgagatctgacgacacggctgtgt
attactgtgcaagagatcatggttctgtcatttctggtcttactgggctttgattattggggccaagg
taccctggtcacc

MF6065
>MF6065_VH

SEQ ID NO: 149   caggtgcagctggtgcagtctggggctgaggtgaagaagcctggggcctcagtgaaggtctcctgcaagg
cttctggatacaccttcacctctactatatgcactgggtgcgacaggcccctggacaagggcttgagtg
gatggatggatcaaccctaggggtggttctacaaactatgcagaagtttcagggcagggtcacgatg
accagggacacgtccaccagcacagtgtacatggagctgagcaggctgagatctgacgacacggctgtgt
attactgtgcaagagatcatggttctgtcatttctggtcttactggggcttgattattggggccaagg
taccctggtcacc

MF6066
>MF6066_VH

SEQ ID NO: 151   caggtgcagctggtgcagtctggggctgaggtgaagaagcctggggcctcagtgaaggtctcctgcaagg
cttctggatacaccttcacggctactatatgcactgggtgcgacagcccctggacagggcttgagtg
gatggatggatcaaccctagagtggtggcacaaactatgcagaagtttcagggcagggtcacgatg
accgggacacgtccaccagcacagcctacatggagctgagcaggctgagatctgacgacacggctgtgt
attactgtgcaagagatcatggttctgtcatttctggtcttactgggctttgattattggggccaagg
taccctggtcacc

Fig. 11, Cont'd

MF6067
>MF6067_VH
SEQ ID NO: 153  caggtgcagctggtgcagtctgggctgaggtgaagaagcctggggcctcagtgaaggtctcctgcaagg
cttctggatacaccttcaccggctactatatgcactgggtgcgacaggcccctggacagggcttgagtg
gatgggatggatcaaccctcagagtggtggcacaaactatgcacagaagtttcagggcagggtcacgatg
accagggacacgtccaccagcacagtctacatggagctgagtctctgagatctgacgacacggctgtgt
attactgtgcaagagatcatggttctgtcatttctggtcttactggggcttgattattggggccaagg
taccctggtcacc MF6068
>MF6068_VH
SEQ ID NO: 155  caggtgcagctggtgcagtctggggctgaggtgaagaagcctggggcctcagtgaaggtctcctgcaagg
cttctggatacaccttcaccggctactatatgcactgggtgcgacaggcccctggacagggcttgagtg
gatgggatggatcaaccctcagagtggtggcacaaactatgcacagaagtttcagggcagggtcacgatg
accagggacacgtccaccagcacagtctacatggagctgagcaggctgagatctgacgacacggctgtgt
attactgtgcaagagatcatggttctgtcatttctggtcttactggggcttgattattggggccaagg
taccctggtcacc MF6069
>MF6069_VH
SEQ ID NO: 157  caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccatcagcacagctacatggagctgagcaggctgagatctgagcacggctgtgt
attactgtgcaagagatcatggttctgtcatttctggtcttactggggcttgattattggggccaagg
taccctggtcacc MF6070
>MF6070_VH
SEQ ID NO: 159  caggtgcagctggtgcagtctgggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctctgagtggttctacaaactatgcacagaagtttcagggcagggtcacgatg
accagggacacgtccaccagcacagtctacatggagctgagtactctgagatctgaggacacggctgtgt
attactgtgcaagagatcatggttctgtcatttctggtcttactggggcttgattattggggccaagg
taccctggtcacc MF6071
>MF6071_VH
SEQ ID NO: 161  caggtgcagctggtgcagtctggggctgaggtgaagaagcctgggctcagtgaaggtctcctgcaagg
cttctggatacaccttcaccggctactatatgcactgggtgcgacaggcccctggacaagggcttgagtg
gatgggatggatcaaccctctagtgttctacaaactatgcacagaagtttcagggcagggtcacgatg
accagggacacgtccaccagcacagctacatggagctgagtctctgagatctgaggacacggctgtgt
attactgtgcaagagatcatggttctgtcatttctggtcttactggggcttgattattggggccaagg
taccctggtcacc

SEQ ID NO: 163  caggtgcagctggtgcagtctggggctgaggtgaagaagcctggggcctcagtgaaggtctcctgcaagg
cttctggatacaccttcaccggctactatatgcactgggtgcgacaggcccctggacaaggggctgagtg
gatggatggatcaaccctctcagtggtggcacaaactatgcacagaagtttcagggcagggtcacgatg
accagggacacgtccaccagcacagtctacatggagctgagtctctgagatctgacgacacggctgtgt
attactgtgcaagagatcatggttctcgtcatttctggtcttactgggcttgattattgggccaagg
tacctggtcacc

MF6073
>MF6073_VH

SEQ ID NO: 165  caggtgcagctggtgcagtctgggggctgaggtgaagaagcctgggcctcagtgaaggtctcctgcaagg
cttctggatacaccttcaccggctactatatgcactgggtgcgacaggcccctggacaggggctgagtg
gatggatggatcaaccctctcagtggtggcacaaactatgcacagaagtttcagggcagggtcacgatg
accagggacacgtccaccagcacagctacatggagctgagcaggctgagatctgacgacacggctgtgt
attactgtgcaagagatcatggttctcgtcatttctggtcttactgggcttgattattgggccaagg
tacctggtcacc

MF6074
>MF6074_VH

SEQ ID NO: 167  caggtgcagctggtgcagtctggggctgaggtgaagaagcctggggcctcagtgaaggtctcctgcaagg
cttctggatacaccttcaccggctactatatgcactgggtgcgacaggcccctggacaaggggctgagtg
gatggatggatcaaccctctcagtggtggcacaaactatgcacagaagtttcagggcagggtcacgatg
accagggacacgtccatcagcacagctacatggagctgagcaggctgagatctgacgacacggctgtgt
attactgtgcaagagatcatggttctcgtcatttctggtcttactgggcttgattattgggccaagg
tacctggtcacc

SEQUENCE LISTING

<160> NUMBER OF SEQ ID NOS: 171

<210> SEQ ID NO 1
<211> LENGTH: 370
<212> TYPE: DNA

-continued

```
<213> ORGANISM: Artificial Sequence
<220> FEATURE:
<223> OTHER INFORMATION: heavy chain variable region MF2926
<220> FEATURE:
<221> NAME/KEY: CDS
<222> LOCATION: (20)..(370)

<400> SEQUENCE: 1
ggcccagccg gccatggcc cag gtc cag ctg cag cag tct gga cct gag ctg        52
                      Gln Val Gln Leu Gln Gln Ser Gly Pro Glu Leu
                       1               5                      10 gtg aaa cct ggg gct tca gtg atg att tcc tgc aag gct tct ggt tac        100
Val Lys Pro Gly Ala Ser Val Met Ile Ser Cys Lys Ala Ser Gly Tyr
         15                  20                  25 tca ttc act ggc tac cac atg aac tgg gtg aag caa agt cct gaa aag        148
Ser Phe Thr Gly Tyr His Met Asn Trp Val Lys Gln Ser Pro Glu Lys
     30                  35                  40 agc ctt gag tgg att gga gac ata aat cct agc att ggt acg act gcc        196
Ser Leu Glu Trp Ile Gly Asp Ile Asn Pro Ser Ile Gly Thr Thr Ala
 45                  50                  55 cac aac cag att ttc agg gcc aag gcc aca atg act gtt gac aaa tcc        244
His Asn Gln Ile Phe Arg Ala Lys Ala Thr Met Thr Val Asp Lys Ser
60                  65                  70                  75 tcc aac aca gcc tac atg cag ctc aag agc ctg aca tct gaa gac tct        292
Ser Asn Thr Ala Tyr Met Gln Leu Lys Ser Leu Thr Ser Glu Asp Ser
                 80                  85                  90 gga gtc ttt tac tgt gtt aga aga ggg gac tgg tcc ttc gat gtc tgg        340
Gly Val Phe Tyr Cys Val Arg Arg Gly Asp Trp Ser Phe Asp Val Trp
             95                 100                 105 ggc aca ggg acc acg gtc acc gtc tcc agt                                370
Gly Thr Gly Thr Thr Val Thr Val Ser Ser
        110                 115

<210> SEQ ID NO 2
<211> LENGTH: 117
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Gln Gln Ser Gly Pro Glu Leu Val Lys Pro Gly Ala
 1               5                  10                  15

Ser Val Met Ile Ser Cys Lys Ala Ser Gly Tyr Ser Phe Thr Gly Tyr
             20                  25                  30

His Met Asn Trp Val Lys Gln Ser Pro Glu Lys Ser Leu Glu Trp Ile
         35                  40                  45

Gly Asp Ile Asn Pro Ser Ile Gly Thr Thr Ala His Asn Gln Ile Phe
     50                  55                  60

Arg Ala Lys Ala Thr Met Thr Val Asp Lys Ser Ser Asn Thr Ala Tyr
65                  70                  75                  80

Met Gln Leu Lys Ser Leu Thr Ser Glu Asp Ser Gly Val Phe Tyr Cys
                 85                  90                  95

Val Arg Arg Gly Asp Trp Ser Phe Asp Val Trp Gly Thr Gly Thr Thr
            100                 105                 110

Val Thr Val Ser Ser
        115

<210> SEQ ID NO 3
<211> LENGTH: 16
<212> TYPE: PRT
```

-continued

```
<213> ORGANISM: Artificial Sequence
<220> FEATURE:
<223> OTHER INFORMATION: CDR1

<400> SEQUENCE: 3

Gly Tyr His Met Asn Trp Val Lys Gln Ser Pro Glu Lys Ser Leu Glu
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: CDR2

<400> SEQUENCE: 4

Asn Gln Ile Phe Arg Ala
1               5

<210> SEQ ID NO 5
<211> LENGTH: 8
<212> TYPE: PRT
<213> ORGANISM: Artificial Sequence
<220> FEATURE:
<223> OTHER INFORMATION: CDR3

<400> SEQUENCE: 5

Arg Gly Asp Trp Ser Phe Asp Val
1               5

<210> SEQ ID NO 6
<211> LENGTH: 379
<212> TYPE: DNA
<213> ORGANISM: Artificial Sequence
<220> FEATURE:
<223> OTHER INFORMATION: heavy chain variable region MF2930
<220> FEATURE:
<221> NAME/KEY: CDS
<222> LOCATION: (20)..(379)

<400> SEQUENCE: 6
ggcccagccg gccatggcc gag gtc cag ctg cag cag tct ggg gct gaa ctg      52
                     Glu Val Gln Leu Gln Gln Ser Gly Ala Glu Leu
                      1               5                  10 gtg aag cct gga gcc tca gtg atg atg tcc tgt aag gtt tct ggc tac       100
Val Lys Pro Gly Ala Ser Val Met Met Ser Cys Lys Val Ser Gly Tyr
            15                  20                  25 acc ttc act tcc tat cct ata gcg tgg atg aag cag gtt cat gga aag       148
Thr Phe Thr Ser Tyr Pro Ile Ala Trp Met Lys Gln Val His Gly Lys
        30                  35                  40 agc cta gag tgg att gga aat ttt cat cct tac agt gat gat act aag       196
Ser Leu Glu Trp Ile Gly Asn Phe His Pro Tyr Ser Asp Asp Thr Lys
    45                  50                  55 tac aat gaa aac ttc aag ggc aag gcc aca ttg act gta gaa aaa tcc       244
Tyr Asn Glu Asn Phe Lys Gly Lys Ala Thr Leu Thr Val Glu Lys Ser
60                  65                  70                  75 tct agc aca gtc tac ttg gag ctc agc cga tta aca tct gat gac tct       292
Ser Ser Thr Val Tyr Leu Glu Leu Ser Arg Leu Thr Ser Asp Asp Ser
                80                  85                  90 gct gtt tat tac tgt gca aga agt aac cca tta tat tac ttt gct atg       340
Ala Val Tyr Tyr Cys Ala Arg Ser Asn Pro Leu Tyr Tyr Phe Ala Met
            95                  100                 105 gac tac tgg ggt caa gga acc tcg gtc acc gtc tcc agt                   379
Asp Tyr Trp Gly Gln Gly Thr Ser Val Thr Val Ser Ser
        110                 115                 120
```

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

```
Glu Val Gln Leu Gln Gln Ser Gly Ala Glu Leu Val Lys Pro Gly Ala
1               5                   10                  15

Ser Val Met Met Ser Cys Lys Val Ser Gly Tyr Thr Phe Thr Ser Tyr
            20                  25                  30

Pro Ile Ala Trp Met Lys Gln Val His Gly Lys Ser Leu Glu Trp Ile
        35                  40                  45

Gly Asn Phe His Pro Tyr Ser Asp Asp Thr Lys Tyr Asn Glu Asn Phe
    50                  55                  60

Lys Gly Lys Ala Thr Leu Thr Val Glu Lys Ser Ser Thr Val Tyr
65                  70                  75                  80

Leu Glu Leu Ser Arg Leu Thr Ser Asp Asp Ser Ala Val Tyr Tyr Cys
                85                  90                  95

Ala Arg Ser Asn Pro Leu Tyr Tyr Phe Ala Met Asp Tyr Trp Gly Gln
            100                 105                 110

Gly Thr Ser Val Thr Val Ser Ser
        115                 120
```

<210> SEQ ID NO 8
<211> LENGTH: 16
<212> TYPE: PRT
<213> ORGANISM: Artificial Sequence
<220> FEATURE:
<223> OTHER INFORMATION: CDR1

<400> SEQUENCE: 8

```
Ser Tyr Pro Ile Ala Trp Met Lys Gln Val His Gly Lys Ser Leu Glu
1               5                   10                  15
```

<210> SEQ ID NO 9
<211> LENGTH: 6
<212> TYPE: PRT
<213> ORGANISM: Artificial Sequence
<220> FEATURE:
<223> OTHER INFORMATION: CDR2

<400> SEQUENCE: 9

```
Asn Glu Asn Phe Lys Gly
1               5
```

<210> SEQ ID NO 10
<211> LENGTH: 11
<212> TYPE: PRT
<213> ORGANISM: Artificial Sequence
<220> FEATURE:
<223> OTHER INFORMATION: CDR3

<400> SEQUENCE: 10

```
Ser Asn Pro Leu Tyr Tyr Phe Ala Met Asp Tyr
1               5                   10
```

<210> SEQ ID NO 11
<211> LENGTH: 385
<212> TYPE: DNA
<213> ORGANISM: Artificial Sequence

```
<220> FEATURE:
<223> OTHER INFORMATION: heavy chain variable region MF1849
<220> FEATURE:
<221> NAME/KEY: CDS
<222> LOCATION: (20)..(385)

<400> SEQUENCE: 11
ggcccagccg gccatggcc cag gtg cag ctg gtg gag tct ggg gga ggc gtg        52
                     Gln Val Gln Leu Val Glu Ser Gly Gly Gly Val
                      1               5                  10 gtc cag cct ggg agg tcc ctg aga ctc tcc tgt gca gcc tct gga ttc         100
Val Gln Pro Gly Arg Ser Leu Arg Leu Ser Cys Ala Ala Ser Gly Phe
             15                  20                  25 acc ttc agt agc tat ggc atg cac tgg gtc cgc cag gct cca ggc aag         148
Thr Phe Ser Ser Tyr Gly Met His Trp Val Arg Gln Ala Pro Gly Lys
         30                  35                  40 ggg ctg gag tgg gtg gca gtt ata tca tat gat gga agt aat aaa tac         196
Gly Leu Glu Trp Val Ala Val Ile Ser Tyr Asp Gly Ser Asn Lys Tyr
     45                  50                  55 tat gca gac tcc gtg aag ggc cga ttc acc atc tcc aga gac aat tcc         244
Tyr Ala Asp Ser Val Lys Gly Arg Phe Thr Ile Ser Arg Asp Asn Ser
 60                  65                  70                  75 aag aac acg ctg tat ctg caa atg aac agc ctg aga gct gag gac acg         292
Lys Asn Thr Leu Tyr Leu Gln Met Asn Ser Leu Arg Ala Glu Asp Thr
                 80                  85                  90 gcc gtg tat tac tgt gca aaa ggt gac tac ggt tct tac tct tct tac         340
Ala Val Tyr Tyr Cys Ala Lys Gly Asp Tyr Gly Ser Tyr Ser Ser Tyr
             95                 100                 105 gcc ttt gat tat tgg ggc caa ggt acc ctg gtc acc gtc tcc agt             385
Ala Phe Asp Tyr Trp Gly Gln Gly Thr Leu Val Thr Val Ser Ser
         110                 115                 120

<210> SEQ ID NO 12
<211> LENGTH: 122
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asp Tyr Gly Ser Tyr Ser Ser Tyr Ala Phe Asp Tyr Trp
            100                 105                 110

Gly Gln Gly Thr Leu Val Thr Val Ser Ser
        115                 120

<210> SEQ ID NO 13
<211> LENGTH: 5
<212> TYPE: PRT
<213> ORGANISM: Artificial Sequence
```

```
<220> FEATURE:
<223> OTHER INFORMATION: CDR1

<400> SEQUENCE: 13

Ser Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: CDR2

<400> SEQUENCE: 14

Val Ile Ser Tyr Asp Gly Ser Asn Lys Tyr Tyr Ala Asp Ser Val Lys
1               5                   10                  15

Gly

<210> SEQ ID NO 15
<211> LENGTH: 13
<212> TYPE: PRT
<213> ORGANISM: Artificial Sequence
<220> FEATURE:
<223> OTHER INFORMATION: CDR3

<400> SEQUENCE: 15

Gly Asp Tyr Gly Ser Tyr Ser Ser Tyr Ala Phe Asp Tyr
1               5                   10

<210> SEQ ID NO 16
<211> LENGTH: 385
<212> TYPE: DNA
<213> ORGANISM: Artificial Sequence
<220> FEATURE:
<223> OTHER INFORMATION: heavy chain variable region MF2973
<220> FEATURE:
<221> NAME/KEY: CDS
<222> LOCATION: (20)..(385)

<400> SEQUENCE: 16
ggcccagccg gccatggcc cag gtg cag ctg aag cag tct ggg gct gag ctg       52
                     Gln Val Gln Leu Lys Gln Ser Gly Ala Glu Leu
                      1               5                   10 gtg agg cct ggg gct tca gtg aag ttg tcc tgc aag gct tct ggc tac       100
Val Arg Pro Gly Ala Ser Val Lys Leu Ser Cys Lys Ala Ser Gly Tyr
            15                  20                  25 att ttc act ggc tac tat ata aac tgg ttg agg cag agg cct gga cag       148
Ile Phe Thr Gly Tyr Tyr Ile Asn Trp Leu Arg Gln Arg Pro Gly Gln
        30                  35                  40 gga ctt gaa tgg att gca aaa att tat cct gga agt ggt aat act tac       196
Gly Leu Glu Trp Ile Ala Lys Ile Tyr Pro Gly Ser Gly Asn Thr Tyr
    45                  50                  55 tac aat gag aag ttc agg ggc aag gcc aca ctg act gca gaa gaa tcc       244
Tyr Asn Glu Lys Phe Arg Gly Lys Ala Thr Leu Thr Ala Glu Glu Ser
60                  65                  70                  75 tcc agc act gcc tac atg cag ctc agc agc ctg aca tct gag gac tct       292
Ser Ser Thr Ala Tyr Met Gln Leu Ser Ser Leu Thr Ser Glu Asp Ser
                80                  85                  90 gct gtc tat ttc tgt gca aga ggg ccc cac tat gat tac gac ggc ccc       340
Ala Val Tyr Phe Cys Ala Arg Gly Pro His Tyr Asp Tyr Asp Gly Pro
            95                  100                 105 tgg ttt gtt tac tgg ggc caa ggg act ctg gtc acc gtc tcc agt           385
Trp Phe Val Tyr Trp Gly Gln Gly Thr Leu Val Thr Val Ser Ser
```

<210> SEQ ID NO 17
<211> LENGTH: 122
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Lys Gln Ser Gly Ala Glu Leu Val Arg Pro Gly Ala
1               5                   10                  15
Ser Val Lys Leu Ser Cys Lys Ala Ser Gly Tyr Ile Phe Thr Gly Tyr
            20                  25                  30
Tyr Ile Asn Trp Leu Arg Gln Arg Pro Gly Gln Gly Leu Glu Trp Ile
        35                  40                  45
Ala Lys Ile Tyr Pro Gly Ser Gly Asn Thr Tyr Tyr Asn Glu Lys Phe
    50                  55                  60
Arg Gly Lys Ala Thr Leu Thr Ala Glu Glu Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Gly Pro His Tyr Asp Tyr Asp Gly Pro Trp Phe Val Tyr Trp
            100                 105                 110
Gly Gln Gly Thr Leu Val Thr Val Ser Ser
        115                 120

<210> SEQ ID NO 18
<211> LENGTH: 16
<212> TYPE: PRT
<213> ORGANISM: Artificial Sequence
<220> FEATURE:
<223> OTHER INFORMATION: CDR1

<400> SEQUENCE: 18

Gly Tyr Tyr Ile Asn Trp Leu Arg Gln Arg Pro Gly Gln Gly Leu Glu
1               5                   10                  15

<210> SEQ ID NO 19
<211> LENGTH: 6
<212> TYPE: PRT
<213> ORGANISM: Artificial Sequence
<220> FEATURE:
<223> OTHER INFORMATION: CDR2

<400> SEQUENCE: 19

Asn Glu Lys Phe Arg Gly
1               5

<210> SEQ ID NO 20
<211> LENGTH: 13
<212> TYPE: PRT
<213> ORGANISM: Artificial Sequence
<220> FEATURE:
<223> OTHER INFORMATION: CDR3

<400> SEQUENCE: 20

Gly Pro His Tyr Asp Tyr Asp Gly Pro Trp Phe Val Tyr
1               5                   10

<210> SEQ ID NO 21
<211> LENGTH: 382
<212> TYPE: DNA

```
<213> ORGANISM: Artificial Sequence
<220> FEATURE:
<223> OTHER INFORMATION: heavy chain variable region MF3004
<220> FEATURE:
<221> NAME/KEY: CDS
<222> LOCATION: (20)..(382)

<400> SEQUENCE: 21
ggcccagccg gccatggcc cag gtg cag ctg aag cag tct ggg gct gag ctg         52
                      Gln Val Gln Leu Lys Gln Ser Gly Ala Glu Leu
                        1               5                  10 gtg agg cct ggg gct tca gtg aag ctg tcc tgc aag gct tct ggc tac         100
Val Arg Pro Gly Ala Ser Val Lys Leu Ser Cys Lys Ala Ser Gly Tyr
             15                  20                  25 act ttc act ggc tac tat ata aac tgg gtg aag cag agg cct gga cag         148
Thr Phe Thr Gly Tyr Tyr Ile Asn Trp Val Lys Gln Arg Pro Gly Gln
         30                  35                  40 gga ctt gag tgg att gca agg att tat cct gga agt ggt tat act tac         196
Gly Leu Glu Trp Ile Ala Arg Ile Tyr Pro Gly Ser Gly Tyr Thr Tyr
     45                  50                  55 tac aat gag aag ttc aag ggc aag gcc aca ctg act gca gaa gaa tcc         244
Tyr Asn Glu Lys Phe Lys Gly Lys Ala Thr Leu Thr Ala Glu Glu Ser
 60                  65                  70                  75 tcc agc act gcc tac atg cac ctc agc agc ctg aca tct gag gac tct         292
Ser Ser Thr Ala Tyr Met His Leu Ser Ser Leu Thr Ser Glu Asp Ser
                 80                  85                  90 gct gtc tat ttc tgt gca aga ccc cac tat ggt tac gac gac tgg tac         340
Ala Val Tyr Phe Cys Ala Arg Pro His Tyr Gly Tyr Asp Asp Trp Tyr
             95                 100                 105 ttc ggt gtc tgg ggc aca ggc acc acg gtc acc gtc tcc agt                 382
Phe Gly Val Trp Gly Thr Gly Thr Thr Val Thr Val Ser Ser
         110                 115                 120

<210> SEQ ID NO 22
<211> LENGTH: 121
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Lys Gln Ser Gly Ala Glu Leu Val Arg Pro Gly Ala
  1               5                  10                  15

Ser Val Lys Leu Ser Cys Lys Ala Ser Gly Tyr Thr Phe Thr Gly Tyr
             20                  25                  30

Tyr Ile Asn Trp Val Lys Gln Arg Pro Gly Gln Gly Leu Glu Trp Ile
         35                  40                  45

Ala Arg Ile Tyr Pro Gly Ser Gly Tyr Thr Tyr Tyr Asn Glu Lys Phe
     50                  55                  60

Lys Gly Lys Ala Thr Leu Thr Ala Glu Glu Ser Ser Ser Thr Ala Tyr
 65                  70                  75                  80

Met His Leu Ser Ser Leu Thr Ser Glu Asp Ser Ala Val Tyr Phe Cys
                 85                  90                  95

Ala Arg Pro His Tyr Gly Tyr Asp Asp Trp Tyr Phe Gly Val Trp Gly
            100                 105                 110

Thr Gly Thr Thr Val Thr Val Ser Ser
        115                 120

<210> SEQ ID NO 23
<211> LENGTH: 16
<212> TYPE: PRT
```

```
<213> ORGANISM: Artificial Sequence
<220> FEATURE:
<223> OTHER INFORMATION: CDR1

<400> SEQUENCE: 23

Gly Tyr Tyr Ile Asn Trp Val Lys Gln Arg Pro Gly Gln Gly Leu Glu
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: CDR2

<400> SEQUENCE: 24

Asn Glu Lys Phe Lys Gly
1               5

<210> SEQ ID NO 25
<211> LENGTH: 12
<212> TYPE: PRT
<213> ORGANISM: Artificial Sequence
<220> FEATURE:
<223> OTHER INFORMATION: CDR3

<400> SEQUENCE: 25

Pro His Tyr Gly Tyr Asp Asp Trp Tyr Phe Gly Val
1               5                   10

<210> SEQ ID NO 26
<211> LENGTH: 382
<212> TYPE: DNA
<213> ORGANISM: Artificial Sequence
<220> FEATURE:
<223> OTHER INFORMATION: heavy chain variable region MF2971
<220> FEATURE:
<221> NAME/KEY: CDS
<222> LOCATION: (20)..(382)

<400> SEQUENCE: 26
ggcccagccg ccatggcc cag gtg cag ctg aag cag tct ggg gct gag ctg      52
                    Gln Val Gln Leu Lys Gln Ser Gly Ala Glu Leu
                    1               5                   10 gtg agg cct ggg gct tca gtg aaa ctg tcc tgc aag gct tct ggc tac     100
Val Arg Pro Gly Ala Ser Val Lys Leu Ser Cys Lys Ala Ser Gly Tyr
            15                  20                  25 act ttc act gcc tac tat ata aac tgg gtg aag cag agg cct gga cag     148
Thr Phe Thr Ala Tyr Tyr Ile Asn Trp Val Lys Gln Arg Pro Gly Gln
        30                  35                  40 gga ctt gag tgg att gca agg att tat cct gga agt ggc tat act tac     196
Gly Leu Glu Trp Ile Ala Arg Ile Tyr Pro Gly Ser Gly Tyr Thr Tyr
    45                  50                  55 tac aat gag att ttc aag ggc agg gcc aca ctg act gca gac gaa tcc     244
Tyr Asn Glu Ile Phe Lys Gly Arg Ala Thr Leu Thr Ala Asp Glu Ser
60                  65                  70                  75 tcc agc act gcc tac atg caa ctc agc agc ctg aca tct gag gac tct     292
Ser Ser Thr Ala Tyr Met Gln Leu Ser Ser Leu Thr Ser Glu Asp Ser
                80                  85                  90 gct gtc tat ttc tgt gca aga cct ccg gtc tac tat gac tcg gcc tgg     340
Ala Val Tyr Phe Cys Ala Arg Pro Pro Val Tyr Tyr Asp Ser Ala Trp
            95                  100                 105 ttt gct tac tgg ggc caa ggg act ctg gtc acc gtc tcc agt             382
Phe Ala Tyr Trp Gly Gln Gly Thr Leu Val Thr Val Ser Ser
        110                 115                 120
```

```
<210> SEQ ID NO 27
<211> LENGTH: 121
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Tyr Thr Tyr Tyr Asn Glu Ile Phe
    50                  55                  60

Lys Gly Arg Ala Thr Leu Thr Ala Asp Glu Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Pro Pro Val Tyr Tyr Asp Ser Ala Trp Phe Ala Tyr Trp Gly
            100                 105                 110

Gln Gly Thr Leu Val Thr Val Ser Ser
        115                 120

<210> SEQ ID NO 28
<211> LENGTH: 16
<212> TYPE: PRT
<213> ORGANISM: Artificial Sequence
<220> FEATURE:
<223> OTHER INFORMATION: CDR1

<400> SEQUENCE: 28

Ala Tyr Tyr Ile Asn Trp Val Lys Gln Arg Pro Gly Gln Gly Leu Glu
1               5                   10                  15

<210> SEQ ID NO 29
<211> LENGTH: 6
<212> TYPE: PRT
<213> ORGANISM: Artificial Sequence
<220> FEATURE:
<223> OTHER INFORMATION: CDR2

<400> SEQUENCE: 29

Asn Glu Ile Phe Lys Gly
1               5

<210> SEQ ID NO 30
<211> LENGTH: 12
<212> TYPE: PRT
<213> ORGANISM: Artificial Sequence
<220> FEATURE:
<223> OTHER INFORMATION: CDR3

<400> SEQUENCE: 30

Pro Pro Val Tyr Tyr Asp Ser Ala Trp Phe Ala Tyr
1               5                   10

<210> SEQ ID NO 31
<211> LENGTH: 382
<212> TYPE: DNA
<213> ORGANISM: Artificial Sequence
```

```
<220> FEATURE:
<223> OTHER INFORMATION: heavy chain variable region MF3025
<220> FEATURE:
<221> NAME/KEY: CDS
<222> LOCATION: (20)..(382)

<400> SEQUENCE: 31
ggcccagccg gccatggcc cag gtg cag ctg aag cag tct ggg gct gag ctg      52
                     Gln Val Gln Leu Lys Gln Ser Gly Ala Glu Leu
                      1               5                  10 gtg agg cct ggg act tca gtg aag ctg tcc tgc aag gct tct ggc tac      100
Val Arg Pro Gly Thr Ser Val Lys Leu Ser Cys Lys Ala Ser Gly Tyr
             15                  20                  25 act ttc act ggc tac tat ata aac tgg gtg aag cag agg cct gga cag      148
Thr Phe Thr Gly Tyr Tyr Ile Asn Trp Val Lys Gln Arg Pro Gly Gln
             30                  35                  40 gga ctt gag tgg att gca agg att tat cct gga agt ggt tat act tac      196
Gly Leu Glu Trp Ile Ala Arg Ile Tyr Pro Gly Ser Gly Tyr Thr Tyr
 45                  50                  55 tac aat gag aag ttc aag ggc aag gcc aca ctg act gca gaa gaa tcc      244
Tyr Asn Glu Lys Phe Lys Gly Lys Ala Thr Leu Thr Ala Glu Glu Ser
 60                  65                  70                  75 tcc aac act gcc tat atg cac ctc agc agc ctg aca tct gag gac tct      292
Ser Asn Thr Ala Tyr Met His Leu Ser Ser Leu Thr Ser Glu Asp Ser
             80                  85                  90 gct gtc tat ttc tgt gca agg ccc cac tat ggt tac gac gac tgg tac      340
Ala Val Tyr Phe Cys Ala Arg Pro His Tyr Gly Tyr Asp Asp Trp Tyr
             95                  100                 105 ttc gct gtc tgg ggc aca ggg acc acg gtc acc gtc tcc agt               382
Phe Ala Val Trp Gly Thr Gly Thr Thr Val Thr Val Ser Ser
             110                 115                 120

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Lys Gln Ser Gly Ala Glu Leu Val Arg Pro Gly Thr
 1               5                  10                  15

Ser Val Lys Leu Ser Cys Lys Ala Ser Gly Tyr Thr Phe Thr Gly Tyr
             20                  25                  30

Tyr Ile Asn Trp Val Lys Gln Arg Pro Gly Gln Gly Leu Glu Trp Ile
         35                  40                  45

Ala Arg Ile Tyr Pro Gly Ser Gly Tyr Thr Tyr Tyr Asn Glu Lys Phe
     50                  55                  60

Lys Gly Lys Ala Thr Leu Thr Ala Glu Glu Ser Ser Asn Thr Ala Tyr
 65                  70                  75                  80

Met His Leu Ser Ser Leu Thr Ser Glu Asp Ser Ala Val Tyr Phe Cys
                 85                  90                  95

Ala Arg Pro His Tyr Gly Tyr Asp Asp Trp Tyr Phe Ala Val Trp Gly
             100                 105                 110

Thr Gly Thr Thr Val Thr Val Ser Ser
         115                 120

<210> SEQ ID NO 33
<211> LENGTH: 16
<212> TYPE: PRT
<213> ORGANISM: Artificial Sequence
```

```
<220> FEATURE:
<223> OTHER INFORMATION: CDR1

<400> SEQUENCE: 33

Gly Tyr Tyr Ile Asn Trp Val Lys Gln Arg Pro Gly Gln Gly Leu Glu
1               5                   10                  15

<210> SEQ ID NO 34
<211> LENGTH: 6
<212> TYPE: PRT
<213> ORGANISM: Artificial Sequence
<220> FEATURE:
<223> OTHER INFORMATION: CDR2

<400> SEQUENCE: 34

Asn Glu Lys Phe Lys Gly
1               5

<210> SEQ ID NO 35
<211> LENGTH: 12
<212> TYPE: PRT
<213> ORGANISM: Artificial Sequence
<220> FEATURE:
<223> OTHER INFORMATION: CDR3

<400> SEQUENCE: 35

Pro His Tyr Gly Tyr Asp Asp Trp Tyr Phe Ala Val
1               5                   10

<210> SEQ ID NO 36
<211> LENGTH: 385
<212> TYPE: DNA
<213> ORGANISM: Artificial Sequence
<220> FEATURE:
<223> OTHER INFORMATION: heavy chain variable region MF2916
<220> FEATURE:
<221> NAME/KEY: CDS
<222> LOCATION: (20)..(385)

<400> SEQUENCE: 36
ggcccagccg gccatggcc cag gtc cag ctg cag cag tct ggg gct gag ctg        52
                     Gln Val Gln Leu Gln Gln Ser Gly Ala Glu Leu
                       1               5                  10 gtg agg cct ggg gct tca gtg aag ctg tcc tgc aag gct tct ggc tac        100
Val Arg Pro Gly Ala Ser Val Lys Leu Ser Cys Lys Ala Ser Gly Tyr
                15                  20                  25 act ttc act ggc tac tat ata aac tgg gtg aag cag agg cct gga cag        148
Thr Phe Thr Gly Tyr Tyr Ile Asn Trp Val Lys Gln Arg Pro Gly Gln
            30                  35                  40 gga ctt gag tgg att gca agg att tat cct ggc agt ggt cat act tcc        196
Gly Leu Glu Trp Ile Ala Arg Ile Tyr Pro Gly Ser Gly His Thr Ser
        45                  50                  55 tac aat gag aag ttc aag ggc aag gcc aca ctg act aca gaa aaa tcc        244
Tyr Asn Glu Lys Phe Lys Gly Lys Ala Thr Leu Thr Thr Glu Lys Ser
60                  65                  70                  75 tcc agc act gcc tac atg cag ctc agc agc ctg aca tct gag gac tct        292
Ser Ser Thr Ala Tyr Met Gln Leu Ser Ser Leu Thr Ser Glu Asp Ser
                80                  85                  90 gct gtc tat ttc tgt gca aga cct atc tac ttt gat tac gca ggg ggg        340
Ala Val Tyr Phe Cys Ala Arg Pro Ile Tyr Phe Asp Tyr Ala Gly Gly
            95                  100                 105 tac ttc gat gtc tgg ggc aca aga acc tcg gtc acc gtc tcc agt            385
Tyr Phe Asp Val Trp Gly Thr Arg Thr Ser Val Thr Val Ser Ser
        110                 115                 120
```

```
<210> SEQ ID NO 37
<211> LENGTH: 122
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Gly Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly His Thr Ser Tyr Asn Glu Lys Phe
    50                  55                  60

Lys Gly Lys Ala Thr Leu Thr Thr Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Pro Ile Tyr Phe Asp Tyr Ala Gly Gly Tyr Phe Asp Val Trp
            100                 105                 110

Gly Thr Arg Thr Ser Val Thr Val Ser Ser
        115                 120

<210> SEQ ID NO 38
<211> LENGTH: 16
<212> TYPE: PRT
<213> ORGANISM: Artificial Sequence
<220> FEATURE:
<223> OTHER INFORMATION: CDR1

<400> SEQUENCE: 38

Gly Tyr Tyr Ile Asn Trp Val Lys Gln Arg Pro Gly Gln Gly Leu Glu
1               5                   10                  15

<210> SEQ ID NO 39
<211> LENGTH: 6
<212> TYPE: PRT
<213> ORGANISM: Artificial Sequence
<220> FEATURE:
<223> OTHER INFORMATION: CDR2

<400> SEQUENCE: 39

Asn Glu Lys Phe Lys Gly
1               5

<210> SEQ ID NO 40
<211> LENGTH: 13
<212> TYPE: PRT
<213> ORGANISM: Artificial Sequence
<220> FEATURE:
<223> OTHER INFORMATION: CDR3

<400> SEQUENCE: 40

Pro Ile Tyr Phe Asp Tyr Ala Gly Gly Tyr Phe Asp Val
1               5                   10

<210> SEQ ID NO 41
<211> LENGTH: 382
<212> TYPE: DNA
<213> ORGANISM: Artificial Sequence
<220> FEATURE:
```

<223> OTHER INFORMATION: heavy chain variable region MF3958
<220> FEATURE:
<221> NAME/KEY: CDS
<222> LOCATION: (20)..(382)

<400> SEQUENCE: 41

```
ggcccagccg ccatggcc cag gtg cag ctg gtg cag tct ggc gcc gaa gtg        52
                    Gln Val Gln Leu Val Gln Ser Gly Ala Glu Val
                     1               5                  10 aag aaa cct ggc gcc agc gtg aag ctg agc tgc aag gcc agc ggc tac       100
Lys Lys Pro Gly Ala Ser Val Lys Leu Ser Cys Lys Ala Ser Gly Tyr
             15                  20                  25 acc ttc acc gcc tac tac atc aac tgg gtc cga cag gcc cca ggc cag       148
Thr Phe Thr Ala Tyr Tyr Ile Asn Trp Val Arg Gln Ala Pro Gly Gln
         30                  35                  40 ggc ctg gaa tgg atc ggc aga atc tac ccc ggc tcc ggc tac acc agc       196
Gly Leu Glu Trp Ile Gly Arg Ile Tyr Pro Gly Ser Gly Tyr Thr Ser
     45                  50                  55 tac gcc cag aag ttc cag ggc aga gcc acc ctg acc gcc gac gag agc       244
Tyr Ala Gln Lys Phe Gln Gly Arg Ala Thr Leu Thr Ala Asp Glu Ser
 60                  65                  70                  75 acc agc acc gcc tac atg gaa ctg agc agc ctg cgg agc gag gat acc       292
Thr Ser Thr Ala Tyr Met Glu Leu Ser Ser Leu Arg Ser Glu Asp Thr
                 80                  85                  90 gcc gtg tac ttc tgc gcc aga ccc ccc gtg tac tac gac agc gct tgg       340
Ala Val Tyr Phe Cys Ala Arg Pro Pro Val Tyr Tyr Asp Ser Ala Trp
             95                 100                 105 ttt gcc tac tgg ggc cag ggc acc ctg gtc acc gtc tcc agt              382
Phe Ala Tyr Trp Gly Gln Gly Thr Leu Val Thr Val Ser Ser
        110                 115                 120
```

<210> SEQ ID NO 42
<211> LENGTH: 121
<212> TYPE: PRT
<213> ORGANISM: Artificial Sequence
<220> FEATURE:
<223> OTHER INFORMATION: Synthetic Construct

<400> SEQUENCE: 42

```
Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ala Tyr
             20                  25                  30

Tyr Ile Asn Trp Val Arg Gln Ala Pro Gly Gln Gly Leu Glu Trp Ile
         35                  40                  45

Gly Arg Ile Tyr Pro Gly Ser Gly Tyr Thr Ser Tyr Ala Gln Lys Phe
     50                  55                  60

Gln Gly Arg Ala Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Pro Pro Val Tyr Tyr Asp Ser Ala Trp Phe Ala Tyr Trp Gly
            100                 105                 110

Gln Gly Thr Leu Val Thr Val Ser Ser
        115                 120
```

<210> SEQ ID NO 43
<211> LENGTH: 5
<212> TYPE: PRT
<213> ORGANISM: Artificial Sequence
<220> FEATURE:

```
<223> OTHER INFORMATION: CDR1

<400> SEQUENCE: 43

Ala Tyr Tyr Ile Asn
1               5

<210> SEQ ID NO 44
<211> LENGTH: 17
<212> TYPE: PRT
<213> ORGANISM: Artificial Sequence
<220> FEATURE:
<223> OTHER INFORMATION: CDR2

<400> SEQUENCE: 44

Arg Ile Tyr Pro Gly Ser Gly Tyr Thr Ser Tyr Ala Gln Lys Phe Gln
1               5                   10                  15

Gly

<210> SEQ ID NO 45
<211> LENGTH: 12
<212> TYPE: PRT
<213> ORGANISM: Artificial Sequence
<220> FEATURE:
<223> OTHER INFORMATION: CDR3

<400> SEQUENCE: 45

Pro Pro Val Tyr Tyr Asp Ser Ala Trp Phe Ala Tyr
1               5                   10

<210> SEQ ID NO 46
<211> LENGTH: 382
<212> TYPE: DNA
<213> ORGANISM: Artificial Sequence
<220> FEATURE:
<223> OTHER INFORMATION: heavy chain variable region MF3031
<220> FEATURE:
<221> NAME/KEY: CDS
<222> LOCATION: (20)..(382)

<400> SEQUENCE: 46
ggcccagccg ccatggcc cag gtc cag ctg cag cag tct ggg gct gag ctg        52
                    Gln Val Gln Leu Gln Gln Ser Gly Ala Glu Leu
                     1               5                  10 gtg agg cct ggg gct tca gtg aag ctg tcc tgc aag gct tct ggc tac       100
Val Arg Pro Gly Ala Ser Val Lys Leu Ser Cys Lys Ala Ser Gly Tyr
             15                  20                  25 act ttc act gcc tac tat ata aac tgg gtg aag cag agg cct gga cag       148
Thr Phe Thr Ala Tyr Tyr Ile Asn Trp Val Lys Gln Arg Pro Gly Gln
         30                  35                  40 gga ctt gag tgg att gca aag att tat cct gga agt ggt tat act tac       196
Gly Leu Glu Trp Ile Ala Lys Ile Tyr Pro Gly Ser Gly Tyr Thr Tyr
     45                  50                  55 tac aat gag aat ttc agg ggc aag gcc aca ctg act gca gaa gaa tcc       244
Tyr Asn Glu Asn Phe Arg Gly Lys Ala Thr Leu Thr Ala Glu Glu Ser
 60                  65                  70                  75 tcc agt act gcc tac ata caa ctc agc agc ctg aca tct gag gac tct       292
Ser Ser Thr Ala Tyr Ile Gln Leu Ser Ser Leu Thr Ser Glu Asp Ser
                 80                  85                  90 gct gtc tat ttc tgt gca aga ggc gtc tat gat tac gac ggg gcc tgg       340
Ala Val Tyr Phe Cys Ala Arg Gly Val Tyr Asp Tyr Asp Gly Ala Trp
             95                  100                 105 ttt gct tac tgg ggc caa ggg act ctg gtc acc gtc tcc agt               382
Phe Ala Tyr Trp Gly Gln Gly Thr Leu Val Thr Val Ser Ser
         110                 115                 120
```

```
<210> SEQ ID NO 47
<211> LENGTH: 121
<212> TYPE: PRT
<213> ORGANISM: Artificial Sequence
<220> FEATURE:
<223> OTHER INFORMATION: Synthetic Construct

<400> SEQUENCE: 47
```

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Lys Gln Arg Pro Gly Gln Gly Leu Glu Trp Ile
        35                  40                  45

Ala Lys Ile Tyr Pro Gly Ser Gly Tyr Thr Tyr Tyr Asn Glu Asn Phe
    50                  55                  60

Arg Gly Lys Ala Thr Leu Thr Ala Glu Glu Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Gly Val Tyr Asp Tyr Asp Gly Ala Trp Phe Ala Tyr Trp Gly
            100                 105                 110

Gln Gly Thr Leu Val Thr Val Ser Ser
        115                 120

```
<210> SEQ ID NO 48
<211> LENGTH: 16
<212> TYPE: PRT
<213> ORGANISM: Artificial Sequence
<220> FEATURE:
<223> OTHER INFORMATION: CDR1

<400> SEQUENCE: 48
```

Ala Tyr Tyr Ile Asn Trp Val Lys Gln Arg Pro Gly Gln Gly Leu Glu
1               5                   10                  15

```
<210> SEQ ID NO 49
<211> LENGTH: 6
<212> TYPE: PRT
<213> ORGANISM: Artificial Sequence
<220> FEATURE:
<223> OTHER INFORMATION: CDR2

<400> SEQUENCE: 49
```

Asn Glu Asn Phe Arg Gly
1               5

```
<210> SEQ ID NO 50
<211> LENGTH: 12
<212> TYPE: PRT
<213> ORGANISM: Artificial Sequence
<220> FEATURE:
<223> OTHER INFORMATION: CDR3

<400> SEQUENCE: 50
```

Gly Val Tyr Asp Tyr Asp Gly Ala Trp Phe Ala Tyr
1               5                   10

```
<210> SEQ ID NO 51
<211> LENGTH: 382
<212> TYPE: DNA
<213> ORGANISM: Artificial Sequence
```

```
<220> FEATURE:
<223> OTHER INFORMATION: heavy chain variable region MF3991
<220> FEATURE:
<221> NAME/KEY: CDS
<222> LOCATION: (20)..(382)

<400> SEQUENCE: 51
ggcccagccg gccatggcc cag gtg cag ctg gtg cag tct ggc gcc gaa gtg           52
                     Gln Val Gln Leu Val Gln Ser Gly Ala Glu Val
                      1               5                  10 aag aaa cct ggc gcc agc gtg aag ctg agc tgc aag gcc agc ggc tac          100
Lys Lys Pro Gly Ala Ser Val Lys Leu Ser Cys Lys Ala Ser Gly Tyr
             15                  20                  25 acc ttc acc gcc tac tac atc aac tgg gtc cga cag gcc cca ggc cag          148
Thr Phe Thr Ala Tyr Tyr Ile Asn Trp Val Arg Gln Ala Pro Gly Gln
             30                  35                  40 ggc ctg gaa tgg atc ggc aga atc tac ccc ggc tcc ggc tac acc agc          196
Gly Leu Glu Trp Ile Gly Arg Ile Tyr Pro Gly Ser Gly Tyr Thr Ser
     45                  50                  55 tac gcc cag aag ttc cag ggc aga gcc acc ctg acc gcc gac gag agc          244
Tyr Ala Gln Lys Phe Gln Gly Arg Ala Thr Leu Thr Ala Asp Glu Ser
 60                  65                  70                  75 acc agc acc gcc tac atg gaa ctg agc agc ctg cgg agc gag gat acc          292
Thr Ser Thr Ala Tyr Met Glu Leu Ser Ser Leu Arg Ser Glu Asp Thr
                 80                  85                  90 gcc gtg tac ttc tgc gcc aga ccc cac tac ggc tac gac gac tgg tac          340
Ala Val Tyr Phe Cys Ala Arg Pro His Tyr Gly Tyr Asp Asp Trp Tyr
                 95                 100                 105 ttc ggc gtg tgg ggc cag ggc acc ctg gtc acc gtc tcc agt                  382
Phe Gly Val Trp Gly Gln Gly Thr Leu Val Thr Val Ser Ser
        110                 115                 120

<210> SEQ ID NO 52
<211> LENGTH: 121
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ala Tyr
             20                  25                  30

Tyr Ile Asn Trp Val Arg Gln Ala Pro Gly Gln Gly Leu Glu Trp Ile
         35                  40                  45

Gly Arg Ile Tyr Pro Gly Ser Gly Tyr Thr Ser Tyr Ala Gln Lys Phe
     50                  55                  60

Gln Gly Arg Ala Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Pro His Tyr Gly Tyr Asp Asp Trp Tyr Phe Gly Val Trp Gly
            100                 105                 110

Gln Gly Thr Leu Val Thr Val Ser Ser
        115                 120

<210> SEQ ID NO 53
<211> LENGTH: 5
<212> TYPE: PRT
<213> ORGANISM: Artificial Sequence
```

<220> FEATURE:
<223> OTHER INFORMATION: CDR1

<400> SEQUENCE: 53

Ala Tyr Tyr Ile Asn
1               5

<210> SEQ ID NO 54
<211> LENGTH: 17
<212> TYPE: PRT
<213> ORGANISM: Artificial Sequence
<220> FEATURE:
<223> OTHER INFORMATION: CDR2

<400> SEQUENCE: 54

Arg Ile Tyr Pro Gly Ser Gly Tyr Thr Ser Tyr Ala Gln Lys Phe Gln
1               5                   10                  15

Gly

<210> SEQ ID NO 55
<211> LENGTH: 12
<212> TYPE: PRT
<213> ORGANISM: Artificial Sequence
<220> FEATURE:
<223> OTHER INFORMATION: CDR3

<400> SEQUENCE: 55

Pro His Tyr Gly Tyr Asp Asp Trp Tyr Phe Gly Val
1               5                   10

<210> SEQ ID NO 56
<211> LENGTH: 391
<212> TYPE: DNA
<213> ORGANISM: Artificial Sequence
<220> FEATURE:
<223> OTHER INFORMATION: heavy chain variable region MF3178
<220> FEATURE:
<221> NAME/KEY: CDS
<222> LOCATION: (20)..(391)

<400> SEQUENCE: 56

```
ggcccagccg gccatggcc cag gtg cag ctg gtg cag tct ggg gct gag gtg        52
                     Gln Val Gln Leu Val Gln Ser Gly Ala Glu Val
                      1               5                   10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa        148
Thr Phe Thr Gly Tyr Tyr Met His Trp Val Arg Gln Ala Pro Gly Gln
             30                  35                  40 ggg ctt gag tgg atg gga tgg atc aac cct aac agt ggt ggc aca aac        196
Gly Leu Glu Trp Met Gly Trp Ile Asn Pro Asn Ser Gly Gly Thr Asn
         45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg        292
Ile Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct        340
Ala Val Tyr Tyr Cys Ala Arg Asp His Gly Ser Arg His Phe Trp Ser
                 95                 100                 105 tac tgg ggc ttt gat tat tgg ggc caa ggt acc ctg gtc acc gtc tcc        388
Tyr Trp Gly Phe Asp Tyr Trp Gly Gln Gly Thr Leu Val Thr Val Ser
```

```
                      110             115              120
agt                                                                       391
Ser
```

<210> SEQ ID NO 57
<211> LENGTH: 124
<212> TYPE: PRT
<213> ORGANISM: Artificial Sequence
<220> FEATURE:
<223> OTHER INFORMATION: Synthetic Construct

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 58
<211> LENGTH: 5
<212> TYPE: PRT
<213> ORGANISM: Artificial Sequence
<220> FEATURE:
<223> OTHER INFORMATION: CDR1

<400> SEQUENCE: 58

```
Gly Tyr Tyr Met His
1               5
```

<210> SEQ ID NO 59
<211> LENGTH: 17
<212> TYPE: PRT
<213> ORGANISM: Artificial Sequence
<220> FEATURE:
<223> OTHER INFORMATION: CDR2

<400> SEQUENCE: 59

```
Trp Ile Asn Pro Asn Ser Gly Gly Thr Asn Tyr Ala Gln Lys Phe Gln
1               5                   10                  15

Gly
```

<210> SEQ ID NO 60
<211> LENGTH: 15
<212> TYPE: PRT
<213> ORGANISM: Artificial Sequence
<220> FEATURE:
<223> OTHER INFORMATION: CDR3

<400> SEQUENCE: 60

```
Asp His Gly Ser Arg His Phe Trp Ser Tyr Trp Gly Phe Asp Tyr
1               5                   10                  15
```

<210> SEQ ID NO 61
<211> LENGTH: 385
<212> TYPE: DNA
<213> ORGANISM: Artificial Sequence
<220> FEATURE:
<223> OTHER INFORMATION: heavy chain variable region MF3176
<220> FEATURE:
<221> NAME/KEY: CDS
<222> LOCATION: (20)..(385)

<400> SEQUENCE: 61

```
ggcccagccg gccatggcc gag gtg cag ctg ttg gag tct ggg gga ggc ttg         52
                     Glu Val Gln Leu Leu Glu Ser Gly Gly Gly Leu
                      1               5                  10 gta cag cct ggg ggg tcc ctg aga ctc tcc tgt gca gcc tct gga ttc          100
Val Gln Pro Gly Gly Ser Leu Arg Leu Ser Cys Ala Ala Ser Gly Phe
             15                  20                  25 acc ttt agc agc tat gcc atg agc tgg gtc cgc cag gct cca ggg aag         148
Thr Phe Ser Ser Tyr Ala Met Ser Trp Val Arg Gln Ala Pro Gly Lys
         30                  35                  40 ggg ctg gag tgg gtc tca gct att agt ggt agt ggt ggt agc aca tac         196
Gly Leu Glu Trp Val Ser Ala Ile Ser Gly Ser Gly Gly Ser Thr Tyr
 45                  50                  55 tac gca gac tcc gtg aag ggc cgg ttc acc atc tcc aga gac aat tcc         244
Tyr Ala Asp Ser Val Lys Gly Arg Phe Thr Ile Ser Arg Asp Asn Ser
 60                  65                  70                  75 aag aac acg ctg tat ctg caa atg aac agc ctg aga gcc gag gac acg         292
Lys Asn Thr Leu Tyr Leu Gln Met Asn Ser Leu Arg Ala Glu Asp Thr
                 80                  85                  90 gct gtg tat tac tgt gca aga gat tgg tgg tac ccg ccg tac tac tgg         340
Ala Val Tyr Tyr Cys Ala Arg Asp Trp Trp Tyr Pro Pro Tyr Tyr Trp
             95                 100                 105 ggc ttt gat tat tgg ggc caa ggt acc ctg gtc acc gtc tcc agt             385
Gly Phe Asp Tyr Trp Gly Gln Gly Thr Leu Val Thr Val Ser Ser
        110                 115                 120
```

<210> SEQ ID NO 62
<211> LENGTH: 122
<212> TYPE: PRT
<213> ORGANISM: Artificial Sequence
<220> FEATURE:
<223> OTHER INFORMATION: Synthetic Construct

<400> SEQUENCE: 62

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Trp Tyr Pro Pro Tyr Tyr Trp Gly Phe Asp Tyr Trp
            100                 105                 110

Gly Gln Gly Thr Leu Val Thr Val Ser Ser
        115                 120
```

<210> SEQ ID NO 63
<211> LENGTH: 5
<212> TYPE: PRT
<213> ORGANISM: Artificial Sequence
<220> FEATURE:
<223> OTHER INFORMATION: CDR1

<400> SEQUENCE: 63

Ser Tyr Ala Met Ser
1               5

<210> SEQ ID NO 64
<211> LENGTH: 17
<212> TYPE: PRT
<213> ORGANISM: Artificial Sequence
<220> FEATURE:
<223> OTHER INFORMATION: CDR2

<400> SEQUENCE: 64

Ala Ile Ser Gly Ser Gly Gly Ser Thr Tyr Tyr Ala Asp Ser Val Lys
1               5                   10                  15

Gly

<210> SEQ ID NO 65
<211> LENGTH: 13
<212> TYPE: PRT
<213> ORGANISM: Artificial Sequence
<220> FEATURE:
<223> OTHER INFORMATION: CDR3

<400> SEQUENCE: 65

Asp Trp Trp Tyr Pro Tyr Tyr Trp Gly Phe Asp Tyr
1               5                   10

<210> SEQ ID NO 66
<211> LENGTH: 391
<212> TYPE: DNA
<213> ORGANISM: Artificial Sequence
<220> FEATURE:
<223> OTHER INFORMATION: heavy chain variable region MF3163
<220> FEATURE:
<221> NAME/KEY: CDS
<222> LOCATION: (20)..(391)

<400> SEQUENCE: 66

```
ggcccagccg gccatggcc cag gtg cag ctg gtg cag tct ggg gct gag gtg      52
                     Gln Val Gln Leu Val Gln Ser Gly Ala Glu Val
                      1               5                  10 aag aag cct ggg gcc tca gtg aag gtc tcc tgc aag gct tct gga tac     100
Lys Lys Pro Gly Ala Ser Val Lys Val Ser Cys Lys Ala Ser Gly Tyr
         15                  20                  25 acc ttc acc ggc tac tat atg cac tgg gtg cga cag gcc cct gga caa     148
Thr Phe Thr Gly Tyr Tyr Met His Trp Val Arg Gln Ala Pro Gly Gln
     30                  35                  40 ggg ctt gag tgg atg gga tgg atc aac cct aac agt ggt ggc aca aac     196
Gly Leu Glu Trp Met Gly Trp Ile Asn Pro Asn Ser Gly Gly Thr Asn
 45                  50                  55 tat gca cag aag ttt cag ggc agg gtc acg atg acc agg gac acg tcc     244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg     292
Ile Ser Thr Ala Tyr Met Glu Leu Ser Arg Leu Arg Ser Asp Asp Thr
             80                  85                  90
```

```
gcc gtg tat tac tgt gca aaa gat tct tac tct cgt cat ttc tac tct    340
Ala Val Tyr Tyr Cys Ala Lys Asp Ser Tyr Ser Arg His Phe Tyr Ser
         95                 100                 105 tgg tgg gcc ttt gat tat tgg ggc caa ggt acc ctg gtc acc gtc tcc    388
Trp Trp Ala Phe Asp Tyr Trp Gly Gln Gly Thr Leu Val Thr Val Ser
        110                 115                 120 agt                                                                391
Ser

<210> SEQ ID NO 67
<211> LENGTH: 124
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Asp Ser Tyr Ser Arg His Phe Tyr Ser Trp Trp Ala Phe Asp
            100                 105                 110

Tyr Trp Gly Gln Gly Thr Leu Val Thr Val Ser Ser
        115                 120

<210> SEQ ID NO 68
<211> LENGTH: 5
<212> TYPE: PRT
<213> ORGANISM: Artificial Sequence
<220> FEATURE:
<223> OTHER INFORMATION: CDR1

<400> SEQUENCE: 68

Gly Tyr Tyr Met His
1               5

<210> SEQ ID NO 69
<211> LENGTH: 17
<212> TYPE: PRT
<213> ORGANISM: Artificial Sequence
<220> FEATURE:
<223> OTHER INFORMATION: CDR2

<400> SEQUENCE: 69

Trp Ile Asn Pro Asn Ser Gly Gly Thr Asn Tyr Ala Gln Lys Phe Gln
1               5                   10                  15

Gly

<210> SEQ ID NO 70
<211> LENGTH: 15
<212> TYPE: PRT
<213> ORGANISM: Artificial Sequence
<220> FEATURE:
```

```
<223> OTHER INFORMATION: CDR3

<400> SEQUENCE: 70

Asp Ser Tyr Ser Arg His Phe Tyr Ser Trp Trp Ala Phe Asp Tyr
1               5                   10                  15

<210> SEQ ID NO 71
<211> LENGTH: 382
<212> TYPE: DNA
<213> ORGANISM: Artificial Sequence
<220> FEATURE:
<223> OTHER INFORMATION: heavy chain variable region MF3099
<220> FEATURE:
<221> NAME/KEY: CDS
<222> LOCATION: (20)..(382)

<400> SEQUENCE: 71
ggcccagccg gccatggcc gag gtc cag ctg cag cag cct ggg gct gag ctg        52
                     Glu Val Gln Leu Gln Gln Pro Gly Ala Glu Leu
                     1               5                   10 gtg agg cct ggg act tca gtg aag ttg tcc tgc aag gct tct ggc tac        100
Val Arg Pro Gly Thr Ser Val Lys Leu Ser Cys Lys Ala Ser Gly Tyr
            15                  20                  25 acc ttc acc agc tac tgg atg cac tgg gta aag cag agg cct gga caa        148
Thr Phe Thr Ser Tyr Trp Met His Trp Val Lys Gln Arg Pro Gly Gln
        30                  35                  40 ggc ctt gag tgg atc gga att ctt gat cct tct gat agt tat act acc        196
Gly Leu Glu Trp Ile Gly Ile Leu Asp Pro Ser Asp Ser Tyr Thr Thr
    45                  50                  55 tac aat caa aag ttc aag ggc aag gcc aca tta aca gta gac aca tcc        244
Tyr Asn Gln Lys Phe Lys Gly Lys Ala Thr Leu Thr Val Asp Thr Ser
60                  65                  70                  75 tcc agc ata gcc tac atg cag ctc agc agc ctg aca tct gag gac tct        292
Ser Ser Ile Ala Tyr Met Gln Leu Ser Ser Leu Thr Ser Glu Asp Ser
                80                  85                  90 gcg ctc tat tac tgt gca aga ggg gga gat tac gac gag gga ggt gct        340
Ala Leu Tyr Tyr Cys Ala Arg Gly Gly Asp Tyr Asp Glu Gly Gly Ala
            95                  100                 105 atg gac tac tgg ggt caa gga acc tcg gtc acc gtc tcc agt              382
Met Asp Tyr Trp Gly Gln Gly Thr Ser Val Thr Val Ser Ser
        110                 115                 120

<210> SEQ ID NO 72
<211> LENGTH: 121
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ile Leu Asp Pro Ser Asp Ser Tyr Thr Thr Tyr Asn Gln Lys Phe
    50                  55                  60

Lys Gly Lys Ala Thr Leu Thr Val Asp Thr Ser Ser Ser Ile Ala Tyr
65                  70                  75                  80

Met Gln Leu Ser Ser Leu Thr Ser Glu Asp Ser Ala Leu Tyr Tyr Cys
                85                  90                  95
```

```
Ala Arg Gly Gly Asp Tyr Asp Glu Gly Gly Ala Met Asp Tyr Trp Gly
            100                 105                 110

Gln Gly Thr Ser Val Thr Val Ser Ser
        115                 120

<210> SEQ ID NO 73
<211> LENGTH: 5
<212> TYPE: PRT
<213> ORGANISM: Artificial Sequence
<220> FEATURE:
<223> OTHER INFORMATION: CDR1

<400> SEQUENCE: 73

Ser Tyr Trp Met His
1               5

<210> SEQ ID NO 74
<211> LENGTH: 17
<212> TYPE: PRT
<213> ORGANISM: Artificial Sequence
<220> FEATURE:
<223> OTHER INFORMATION: CDR2

<400> SEQUENCE: 74

Ile Leu Asp Pro Ser Asp Ser Tyr Thr Thr Tyr Asn Gln Lys Phe Lys
1               5                   10                  15

Gly

<210> SEQ ID NO 75
<211> LENGTH: 12
<212> TYPE: PRT
<213> ORGANISM: Artificial Sequence
<220> FEATURE:
<223> OTHER INFORMATION: CDR3

<400> SEQUENCE: 75

Gly Gly Asp Tyr Asp Glu Gly Gly Ala Met Asp Tyr
1               5                   10

<210> SEQ ID NO 76
<211> LENGTH: 391
<212> TYPE: DNA
<213> ORGANISM: Artificial Sequence
<220> FEATURE:
<223> OTHER INFORMATION: heavy chain variable region MF3307
<220> FEATURE:
<221> NAME/KEY: CDS
<222> LOCATION: (20)..(391)

<400> SEQUENCE: 76
ggcccagccg gccatggcc cag gtg cag ctg gtg cag tct ggg gct gag gtg        52
                     Gln Val Gln Leu Val Gln Ser Gly Ala Glu Val
                       1               5                  10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
            15                  20                  25 acc ttc acc ggc tac tat atg cac tgg gtg cga cag gcc cct gga caa       148
Thr Phe Thr Gly Tyr Tyr Met His Trp Val Arg Gln Ala Pro Gly Gln
        30                  35                  40 ggg ctt gag tgg atg gga tgg atc aac cct aac agt ggt ggc aca aac       196
Gly Leu Glu Trp Met Gly Trp Ile Asn Pro Asn Ser Gly Gly Thr Asn
    45                  50                  55 tat gca cag aag ttt cag ggc agg gtc acg atg acc agg gac acg tcc       244
Tyr Ala Gln Lys Phe Gln Gly Arg Val Thr Met Thr Arg Asp Thr Ser
```

```
                60                  65                  70                  75
atc agc aca gcc tac atg gag ctg agc agg ctg aga tct gac gac acg      292
Ile Ser Thr Ala Tyr Met Glu Leu Ser Arg Leu Arg Ser Asp Asp Thr
                    80                  85                  90 gcc gtg tat tac tgt gca aga ggt tct cgt aaa cgt ctg tct aac tac      340
Ala Val Tyr Tyr Cys Ala Arg Gly Ser Arg Lys Arg Leu Ser Asn Tyr
        95                  100                 105 ttc aac gcc ttt gat tat tgg ggc caa ggt acc ctg gtc acc gtc tcc      388
Phe Asn Ala Phe Asp Tyr Trp Gly Gln Gly Thr Leu Val Thr Val Ser
            110                 115                 120 agt                                                                   391
Ser

<210> SEQ ID NO 77
<211> LENGTH: 124
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Arg Lys Arg Leu Ser Asn Tyr Phe Asn Ala Phe Asp
            100                 105                 110

Tyr Trp Gly Gln Gly Thr Leu Val Thr Val Ser Ser
        115                 120

<210> SEQ ID NO 78
<211> LENGTH: 5
<212> TYPE: PRT
<213> ORGANISM: Artificial Sequence
<220> FEATURE:
<223> OTHER INFORMATION: CDR1

<400> SEQUENCE: 78

Gly Tyr Tyr Met His
1               5

<210> SEQ ID NO 79
<211> LENGTH: 17
<212> TYPE: PRT
<213> ORGANISM: Artificial Sequence
<220> FEATURE:
<223> OTHER INFORMATION: CDR2

<400> SEQUENCE: 79

Trp Ile Asn Pro Asn Ser Gly Gly Thr Asn Tyr Ala Gln Lys Phe Gln
1               5                   10                  15

Gly
```

<210> SEQ ID NO 80
<211> LENGTH: 15
<212> TYPE: PRT
<213> ORGANISM: Artificial Sequence
<220> FEATURE:
<223> OTHER INFORMATION: CDR3

<400> SEQUENCE: 80

Gly Ser Arg Lys Arg Leu Ser Asn Tyr Phe Asn Ala Phe Asp Tyr
1               5                   10                  15

<210> SEQ ID NO 81
<211> LENGTH: 214
<212> TYPE: PRT
<213> ORGANISM: Artificial Sequence
<220> FEATURE:
<223> OTHER INFORMATION: common light chain

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 450
<212> TYPE: PRT
<213> ORGANISM: Artificial Sequence
<220> FEATURE:
<223> OTHER INFORMATION: heavy chain for erbB-2 binding

<400> SEQUENCE: 82

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ala Tyr

-continued

```
                20                  25                  30
Tyr Ile Asn Trp Val Arg Gln Ala Pro Gly Gln Gly Leu Glu Trp Ile
                35                  40                  45
Gly Arg Ile Tyr Pro Gly Ser Gly Tyr Thr Ser Tyr Ala Gln Lys Phe
         50                  55                  60
Gln Gly Arg Ala Thr Leu Thr Ala Asp Glu Ser Thr Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Pro Pro Val Tyr Tyr Asp Ser Ala Trp Phe Ala Tyr Trp Gly
            100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Asp Pro Pro Ser Arg Glu Glu Met Thr Lys Asn Gln Val Ser
            355                 360                 365
Leu Thr Cys Glu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
```

```
Pro Gly
    450

<210> SEQ ID NO 83
<211> LENGTH: 453
<212> TYPE: PRT
<213> ORGANISM: Artificial Sequence
<220> FEATURE:
<223> OTHER INFORMATION: heavy chain for erbB-3 binding

<400> SEQUENCE: 83

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

```
Pro Gln Val Tyr Thr Lys Pro Pro Ser Arg Glu Glu Met Thr Lys Asn
            355                 360                 365

Gln Val Ser Leu Lys Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 84
<211> LENGTH: 379
<212> TYPE: DNA
<213> ORGANISM: Artificial Sequence
<220> FEATURE:
<223> OTHER INFORMATION: heavy chain variable region MF2889
<220> FEATURE:
<221> NAME/KEY: CDS
<222> LOCATION: (20)..(379)

<400> SEQUENCE: 84
ggcccagccg gccatggcc gag gtc cag ctg cag cag tct gga gct gag ctg        52
                     Glu Val Gln Leu Gln Gln Ser Gly Ala Glu Leu
                       1               5                  10 gta agg cct ggg act tca gtg aag gtg tcc tgc aag gct tct gga tac       100
Val Arg Pro Gly Thr Ser Val Lys Val Ser Cys Lys Ala Ser Gly Tyr
         15                  20                  25 gcc ttc act aat tat ttg ata gag tgg gta aag cag agg cct ggc cag       148
Ala Phe Thr Asn Tyr Leu Ile Glu Trp Val Lys Gln Arg Pro Gly Gln
     30                  35                  40 ggc ctt gag tgg att gga gtg att tat cct gaa ggt ggt ggt act atc       196
Gly Leu Glu Trp Ile Gly Val Ile Tyr Pro Glu Gly Gly Gly Thr Ile
 45                  50                  55 tac aat gag aag ttc aag ggc aag gca aca ctg act gca gac aaa tcc       244
Tyr Asn Glu Lys Phe Lys Gly Lys Ala Thr Leu Thr Ala Asp Lys Ser
 60                  65                  70                  75 tcc agc act gcc tac atg cag ctc agc ggc ctg aca tct gag gac tct       292
Ser Ser Thr Ala Tyr Met Gln Leu Ser Gly Leu Thr Ser Glu Asp Ser
             80                  85                  90 gcg gtc tat ttc tgt gca aga gga gac tat gat tac aaa tat gct atg       340
Ala Val Tyr Phe Cys Ala Arg Gly Asp Tyr Asp Tyr Lys Tyr Ala Met
         95                 100                 105 gac tac tgg ggt caa gga acc tcg gtc acc gtc tcc agt                   379
Asp Tyr Trp Gly Gln Gly Thr Ser Val Thr Val Ser Ser
    110                 115                 120

<210> SEQ ID NO 85
<211> LENGTH: 120
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Gln Gln Ser Gly Ala Glu Leu Val Arg Pro Gly Thr
 1               5                  10                  15
```

```
Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Tyr Pro Glu Gly Gly Thr Ile Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Gly Asp Tyr Asp Tyr Lys Tyr Ala Met Asp Tyr Trp Gly Gln
            100                 105                 110

Gly Thr Ser Val Thr Val Ser Ser
        115                 120
```

<210> SEQ ID NO 86
<211> LENGTH: 5
<212> TYPE: PRT
<213> ORGANISM: Artificial Sequence
<220> FEATURE:
<223> OTHER INFORMATION: CDR1

<400> SEQUENCE: 86

```
Asn Tyr Leu Ile Glu
1               5
```

<210> SEQ ID NO 87
<211> LENGTH: 17
<212> TYPE: PRT
<213> ORGANISM: Artificial Sequence
<220> FEATURE:
<223> OTHER INFORMATION: CDR2

<400> SEQUENCE: 87

```
Val Ile Tyr Pro Glu Gly Gly Gly Thr Ile Tyr Asn Glu Lys Phe Lys
1               5                   10                  15

Gly
```

<210> SEQ ID NO 88
<211> LENGTH: 11
<212> TYPE: PRT
<213> ORGANISM: Artificial Sequence
<220> FEATURE:
<223> OTHER INFORMATION: CDR3

<400> SEQUENCE: 88

```
Gly Asp Tyr Asp Tyr Lys Tyr Ala Met Asp Tyr
1               5                   10
```

<210> SEQ ID NO 89
<211> LENGTH: 370
<212> TYPE: DNA
<213> ORGANISM: Artificial Sequence
<220> FEATURE:
<223> OTHER INFORMATION: heavy chain variable region MF2913
<220> FEATURE:
<221> NAME/KEY: CDS
<222> LOCATION: (20)..(370)

<400> SEQUENCE: 89

```
ggcccagccg gccatggcc gag gtc aag ctg cag cag tct gga cct gag ctg      52
                     Glu Val Lys Leu Gln Gln Ser Gly Pro Glu Leu
                      1               5                   10
```

```
gtg aag cct ggc gct tca gtg aag ata tcc tgc aag gct tct ggt tac      100
Val Lys Pro Gly Ala Ser Val Lys Ile Ser Cys Lys Ala Ser Gly Tyr
            15                  20                  25 tca ttc act gac tac aaa atg gac tgg gtg aag cag agc cat gga aag      148
Ser Phe Thr Asp Tyr Lys Met Asp Trp Val Lys Gln Ser His Gly Lys
        30                  35                  40 agc ctc gaa tgg att gga aat att aat cct aac agt ggt ggt gtt atc      196
Ser Leu Glu Trp Ile Gly Asn Ile Asn Pro Asn Ser Gly Gly Val Ile
45                  50                  55 tac aac cag aag ttc agg ggc aag gtc aca ttg act gtt gac agg tcc      244
Tyr Asn Gln Lys Phe Arg Gly Lys Val Thr Leu Thr Val Asp Arg Ser
60                  65                  70                  75 tcc agc gca gcc tac atg gag ctc cgc agc ctg aca tct gag gac act      292
Ser Ser Ala Ala Tyr Met Glu Leu Arg Ser Leu Thr Ser Glu Asp Thr
                80                  85                  90 gca gtc tat tat tgt tca aga gga ctg tgg gat gct atg gac tcc tgg      340
Ala Val Tyr Tyr Cys Ser Arg Gly Leu Trp Asp Ala Met Asp Ser Trp
            95                  100                 105 ggt caa gga acc tcg gtc acc gtc tcc agt                              370
Gly Gln Gly Thr Ser Val Thr Val Ser Ser
        110                 115

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90

Glu Val Lys Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Lys Met Asp Trp Val Lys Gln Ser His Gly Lys Ser Leu Glu Trp Ile
        35                  40                  45

Gly Asn Ile Asn Pro Asn Ser Gly Gly Val Ile Tyr Asn Gln Lys Phe
    50                  55                  60

Arg Gly Lys Val Thr Leu Thr Val Asp Arg Ser Ser Ser Ala Ala Tyr
65                  70                  75                  80

Met Glu Leu Arg Ser Leu Thr Ser Glu Asp Thr Ala Val Tyr Tyr Cys
                85                  90                  95

Ser Arg Gly Leu Trp Asp Ala Met Asp Ser Trp Gly Gln Gly Thr Ser
            100                 105                 110

Val Thr Val Ser Ser
        115

<210> SEQ ID NO 91
<211> LENGTH: 16
<212> TYPE: PRT
<213> ORGANISM: Artificial Sequence
<220> FEATURE:
<223> OTHER INFORMATION: CDR1

<400> SEQUENCE: 91

Asp Tyr Lys Met Asp Trp Val Lys Gln Ser His Gly Lys Ser Leu Glu
1               5                   10                  15

<210> SEQ ID NO 92
<211> LENGTH: 6
```

<210> SEQ ID NO 92
<211> LENGTH: 5
<212> TYPE: PRT
<213> ORGANISM: Artificial Sequence
<220> FEATURE:
<223> OTHER INFORMATION: CDR2

<400> SEQUENCE: 92

Asn Gln Lys Phe Arg Gly
1               5

<210> SEQ ID NO 93
<211> LENGTH: 8
<212> TYPE: PRT
<213> ORGANISM: Artificial Sequence
<220> FEATURE:
<223> OTHER INFORMATION: CDR3

<400> SEQUENCE: 93

Gly Leu Trp Asp Ala Met Asp Ser
1               5

<210> SEQ ID NO 94
<211> LENGTH: 382
<212> TYPE: DNA
<213> ORGANISM: Artificial Sequence
<220> FEATURE:
<223> OTHER INFORMATION: heavy chain variable region MF1847
<220> FEATURE:
<221> NAME/KEY: CDS
<222> LOCATION: (20)..(382)

<400> SEQUENCE: 94

```
ggcccagccg gccatggcc cag gtg cag ctg gtg gag tct ggg gga ggc gtg      52
                     Gln Val Gln Leu Val Glu Ser Gly Gly Gly Val
                      1               5                  10 gtc cag cct ggg agg tcc ctg aga ctc tcc tgt gca gcc tct gga ttc      100
Val Gln Pro Gly Arg Ser Leu Arg Leu Ser Cys Ala Ala Ser Gly Phe
         15                  20                  25 acc ttc agt agc tat ggc atg cac tgg gtc cgc cag gct cca ggc aag      148
Thr Phe Ser Ser Tyr Gly Met His Trp Val Arg Gln Ala Pro Gly Lys
     30                  35                  40 ggg ctg gag tgg gtg gca gtt ata tca tat gat gga agt aat aaa tac      196
Gly Leu Glu Trp Val Ala Val Ile Ser Tyr Asp Gly Ser Asn Lys Tyr
 45                  50                  55 tat gca gac tcc gtg aag ggc cga ttc acc atc tcc aga gac aat tcc      244
Tyr Ala Asp Ser Val Lys Gly Arg Phe Thr Ile Ser Arg Asp Asn Ser
 60                  65                  70                  75 aag aac acg ctg tat ctg caa atg aac agc ctg aga gct gag gac acg      292
Lys Asn Thr Leu Tyr Leu Gln Met Asn Ser Leu Arg Ala Glu Asp Thr
                 80                  85                  90 gcc gtg tat tac tgt gca aaa ggt tgg tgg cat ccg ctg ctg tct ggc      340
Ala Val Tyr Tyr Cys Ala Lys Gly Trp Trp His Pro Leu Leu Ser Gly
             95                 100                 105 ttt gat tat tgg ggc caa ggt acc ctg gtc acc gtc tcc agt              382
Phe Asp Tyr Trp Gly Gln Gly Thr Leu Val Thr Val Ser Ser
        110                 115                 120
```

<210> SEQ ID NO 95
<211> LENGTH: 121
<212> TYPE: PRT
<213> ORGANISM: Artificial Sequence
<220> FEATURE:
<223> OTHER INFORMATION: Synthetic Construct

<400> SEQUENCE: 95

Gln Val Gln Leu Val Glu Ser Gly Gly Gly Val Val Gln Pro Gly Arg

```
              1               5                  10                 15
            Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Gly Trp Trp His Pro Leu Leu Ser Gly Phe Asp Tyr Trp Gly
                       100                 105                 110

Gln Gly Thr Leu Val Thr Val Ser Ser
                       115                 120
```

<210> SEQ ID NO 96
<211> LENGTH: 5
<212> TYPE: PRT
<213> ORGANISM: Artificial Sequence
<220> FEATURE:
<223> OTHER INFORMATION: CDR1

<400> SEQUENCE: 96

```
Ser Tyr Gly Met His
1               5
```

<210> SEQ ID NO 97
<211> LENGTH: 17
<212> TYPE: PRT
<213> ORGANISM: Artificial Sequence
<220> FEATURE:
<223> OTHER INFORMATION: CDR2

<400> SEQUENCE: 97

```
Val Ile Ser Tyr Asp Gly Ser Asn Lys Tyr Tyr Ala Asp Ser Val Lys
1               5                   10                  15

Gly
```

<210> SEQ ID NO 98
<211> LENGTH: 12
<212> TYPE: PRT
<213> ORGANISM: Artificial Sequence
<220> FEATURE:
<223> OTHER INFORMATION: CDR3

<400> SEQUENCE: 98

```
Gly Trp Trp His Pro Leu Leu Ser Gly Phe Asp Tyr
1               5                   10
```

<210> SEQ ID NO 99
<211> LENGTH: 370
<212> TYPE: DNA
<213> ORGANISM: Artificial Sequence
<220> FEATURE:
<223> OTHER INFORMATION: heavy chain variable region MF3001
<220> FEATURE:
<221> NAME/KEY: CDS
<222> LOCATION: (20)..(370)

<400> SEQUENCE: 99

```
ggcccagccg gccatggcc gag gtc cag ctg cag cag tct ggg gct gaa ctg      52
                     Glu Val Gln Leu Gln Gln Ser Gly Ala Glu Leu
```

```
                   1               5                   10
gca aaa cct ggg gcc tca gtg aag ctg tcc tgc aag act tct ggc tac    100
Ala Lys Pro Gly Ala Ser Val Lys Leu Ser Cys Lys Thr Ser Gly Tyr
        15                  20                  25 aac ttt cct atc tac tgg atg cac tgg gta aaa cag agg cct gga cgg    148
Asn Phe Pro Ile Tyr Trp Met His Trp Val Lys Gln Arg Pro Gly Arg
            30                  35                  40 ggt ctg gaa tgg att gga tac att aat cct agt act ggt tat att aag    196
Gly Leu Glu Trp Ile Gly Tyr Ile Asn Pro Ser Thr Gly Tyr Ile Lys
    45                  50                  55 aac aat cag aag ttc aag gac aag gcc acc ttg act gca gac aaa tcc    244
Asn Asn Gln Lys Phe Lys Asp Lys Ala Thr Leu Thr Ala Asp Lys Ser
60                  65                  70                  75 tcc aac aca gcc tac atg cag ctg aac agc ctg aca tat gag gac tct    292
Ser Asn Thr Ala Tyr Met Gln Leu Asn Ser Leu Thr Tyr Glu Asp Ser
                80                  85                  90 gca gtc tat tac tgt aca aga gaa ggg ata act ggg ttt act tac tgg    340
Ala Val Tyr Tyr Cys Thr Arg Glu Gly Ile Thr Gly Phe Thr Tyr Trp
            95                  100                 105 ggc caa ggg act ctg gtc acc gtc tcc agt                            370
Gly Gln Gly Thr Leu Val Thr Val Ser Ser
        110                 115

<210> SEQ ID NO 100
<211> LENGTH: 117
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Gln Gln Ser Gly Ala Glu Leu Ala Lys Pro Gly Ala
1               5                   10                  15

Ser Val Lys Leu Ser Cys Lys Thr Ser Gly Tyr Asn Phe Pro Ile Tyr
            20                  25                  30

Trp Met His Trp Val Lys Gln Arg Pro Gly Arg Gly Leu Glu Trp Ile
        35                  40                  45

Gly Tyr Ile Asn Pro Ser Thr Gly Tyr Ile Lys Asn Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Asn Ser Leu Thr Tyr Glu Asp Ser Ala Val Tyr Tyr Cys
                85                  90                  95

Thr Arg Glu Gly Ile Thr Gly Phe Thr Tyr Trp Gly Gln Gly Thr Leu
            100                 105                 110

Val Thr Val Ser Ser
        115

<210> SEQ ID NO 101
<211> LENGTH: 16
<212> TYPE: PRT
<213> ORGANISM: Artificial Sequence
<220> FEATURE:
<223> OTHER INFORMATION: CDR1

<400> SEQUENCE: 101

Ile Tyr Trp Met His Trp Val Lys Gln Arg Pro Gly Arg Gly Leu Glu
1               5                   10                  15

<210> SEQ ID NO 102
```

```
<211> LENGTH: 6
<212> TYPE: PRT
<213> ORGANISM: Artificial Sequence
<220> FEATURE:
<223> OTHER INFORMATION: CDR2

<400> SEQUENCE: 102

Asn Gln Lys Phe Lys Asp
1               5

<210> SEQ ID NO 103
<211> LENGTH: 8
<212> TYPE: PRT
<213> ORGANISM: Artificial Sequence
<220> FEATURE:
<223> OTHER INFORMATION: CDR3

<400> SEQUENCE: 103

Glu Gly Ile Thr Gly Phe Thr Tyr
1               5

<210> SEQ ID NO 104
<211> LENGTH: 385
<212> TYPE: DNA
<213> ORGANISM: Artificial Sequence
<220> FEATURE:
<223> OTHER INFORMATION: heavy chain variable region MF1898
<220> FEATURE:
<221> NAME/KEY: CDS
<222> LOCATION: (20)..(385)

<400> SEQUENCE: 104
ggcccagccg gccatggcc cag gtg cag ctg gtg gag tct ggg gga ggc gtg    52
                     Gln Val Gln Leu Val Glu Ser Gly Gly Gly Val
                      1               5                  10 gtc cag cct ggg agg tcc ctg aga ctc tcc tgt gca gcc tct gga ttc    100
Val Gln Pro Gly Arg Ser Leu Arg Leu Ser Cys Ala Ala Ser Gly Phe
             15                  20                  25 acc ttc agt agc tat ggc atg cac tgg gtc cgc cag gct cca ggc aag    148
Thr Phe Ser Ser Tyr Gly Met His Trp Val Arg Gln Ala Pro Gly Lys
         30                  35                  40 ggg ctg gag tgg gtg gca gtt ata tca tat gat gga agt aat aaa tac    196
Gly Leu Glu Trp Val Ala Val Ile Ser Tyr Asp Gly Ser Asn Lys Tyr
     45                  50                  55 tat gca gac tcc gtg aag ggc cga ttc acc atc tcc aga gac aat tcc    244
Tyr Ala Asp Ser Val Lys Gly Arg Phe Thr Ile Ser Arg Asp Asn Ser
 60                  65                  70                  75 aag aac acg ctg tat ctg caa atg aac agc ctg aga gct gag gac acg    292
Lys Asn Thr Leu Tyr Leu Gln Met Asn Ser Leu Arg Ala Glu Asp Thr
                 80                  85                  90 gcc gtg tat tac tgt gca aaa gat ggt ttc cgt cgt act act ctg tct    340
Ala Val Tyr Tyr Cys Ala Lys Asp Gly Phe Arg Arg Thr Thr Leu Ser
             95                 100                 105 ggc ttt gat tat tgg ggc caa ggt acc ctg gtc acc gtc tcc agt        385
Gly Phe Asp Tyr Trp Gly Gln Gly Thr Leu Val Thr Val Ser Ser
        110                 115                 120

<210> SEQ ID NO 105
<211> LENGTH: 122
<212> TYPE: PRT
<213> ORGANISM: Artificial Sequence
<220> FEATURE:
<223> OTHER INFORMATION: Synthetic Construct

<400> SEQUENCE: 105
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Phe Arg Arg Thr Thr Leu Ser Gly Phe Asp Tyr Trp
            100                 105                 110

Gly Gln Gly Thr Leu Val Thr Val Ser Ser
        115                 120
```

<210> SEQ ID NO 106
<211> LENGTH: 5
<212> TYPE: PRT
<213> ORGANISM: Artificial Sequence
<220> FEATURE:
<223> OTHER INFORMATION: CDR1

<400> SEQUENCE: 106

```
Ser Tyr Gly Met His
1               5
```

<210> SEQ ID NO 107
<211> LENGTH: 17
<212> TYPE: PRT
<213> ORGANISM: Artificial Sequence
<220> FEATURE:
<223> OTHER INFORMATION: CDR2

<400> SEQUENCE: 107

```
Val Ile Ser Tyr Asp Gly Ser Asn Lys Tyr Tyr Ala Asp Ser Val Lys
1               5                   10                  15

Gly
```

<210> SEQ ID NO 108
<211> LENGTH: 13
<212> TYPE: PRT
<213> ORGANISM: Artificial Sequence
<220> FEATURE:
<223> OTHER INFORMATION: CDR3

<400> SEQUENCE: 108

```
Asp Gly Phe Arg Arg Thr Thr Leu Ser Gly Phe Asp Tyr
1               5                   10
```

<210> SEQ ID NO 109
<211> LENGTH: 379
<212> TYPE: DNA
<213> ORGANISM: Artificial Sequence
<220> FEATURE:
<223> OTHER INFORMATION: heavy chain variable region MF3003
<220> FEATURE:
<221> NAME/KEY: CDS
<222> LOCATION: (20)..(379)

<400> SEQUENCE: 109

```
ggcccagccg gccatggcc cag gtg cag ctg aag cag tct gga cct gag ctg      52
```

```
                Gln Val Gln Leu Lys Gln Ser Gly Pro Glu Leu
                 1               5                  10 gtg aag cct ggg gcc tca gtg aag att tcc tgc aag gct tct ggc gac        100
Val Lys Pro Gly Ala Ser Val Lys Ile Ser Cys Lys Ala Ser Gly Asp
         15                  20                  25 gca ttc agt tac tcc tgg atg aac tgg gtg aag cag agg cct gga aag        148
Ala Phe Ser Tyr Ser Trp Met Asn Trp Val Lys Gln Arg Pro Gly Lys
             30                  35                  40 ggt ctt gag tgg att gga cgg att tat cct gga gat gga gat att aac        196
Gly Leu Glu Trp Ile Gly Arg Ile Tyr Pro Gly Asp Gly Asp Ile Asn
     45                  50                  55 tac aat ggg aag ttc aag ggc aag gcc aca ctg act gca gac aaa tcc        244
Tyr Asn Gly Lys Phe Lys Gly Lys Ala Thr Leu Thr Ala Asp Lys Ser
 60                  65                  70                  75 tcc agc aca gcc cac ctg caa ctc aac agc ctg aca tct gag gac tct        292
Ser Ser Thr Ala His Leu Gln Leu Asn Ser Leu Thr Ser Glu Asp Ser
                 80                  85                  90 gcg gtc tac ttc tgt gca aga gga cag ctc gga cta gag gcc tgg ttt        340
Ala Val Tyr Phe Cys Ala Arg Gly Gln Leu Gly Leu Glu Ala Trp Phe
             95                 100                 105 gct tat tgg ggc cag ggg act ctg gtc acc gtc tcc agt                    379
Ala Tyr Trp Gly Gln Gly Thr Leu Val Thr Val Ser Ser
        110                 115                 120

<210> SEQ ID NO 110
<211> LENGTH: 120
<212> TYPE: PRT
<213> ORGANISM: Artificial Sequence
<220> FEATURE:
<223> OTHER INFORMATION: Synthetic Construct

<400> SEQUENCE: 110

Gln Val Gln Leu Lys Gln Ser Gly Pro Glu Leu Val Lys Pro Gly Ala
 1               5                  10                  15

Ser Val Lys Ile Ser Cys Lys Ala Ser Gly Asp Ala Phe Ser Tyr Ser
             20                  25                  30

Trp Met Asn Trp Val Lys Gln Arg Pro Gly Lys Gly Leu Glu Trp Ile
         35                  40                  45

Gly Arg Ile Tyr Pro Gly Asp Gly Asp Ile Asn Tyr Asn Gly Lys Phe
     50                  55                  60

Lys Gly Lys Ala Thr Leu Thr Ala Asp Lys Ser Ser Ser Thr Ala His
 65                  70                  75                  80

Leu Gln Leu Asn Ser Leu Thr Ser Glu Asp Ser Ala Val Tyr Phe Cys
                 85                  90                  95

Ala Arg Gly Gln Leu Gly Leu Glu Ala Trp Phe Ala Tyr Trp Gly Gln
            100                 105                 110

Gly Thr Leu Val Thr Val Ser Ser
        115                 120

<210> SEQ ID NO 111
<211> LENGTH: 16
<212> TYPE: PRT
<213> ORGANISM: Artificial Sequence
<220> FEATURE:
<223> OTHER INFORMATION: CDR1

<400> SEQUENCE: 111

Tyr Ser Trp Met Asn Trp Val Lys Gln Arg Pro Gly Lys Gly Leu Glu
 1               5                  10                  15
```

```
<210> SEQ ID NO 112
<211> LENGTH: 6
<212> TYPE: PRT
<213> ORGANISM: Artificial Sequence
<220> FEATURE:
<223> OTHER INFORMATION: CDR2

<400> SEQUENCE: 112

Asn Gly Lys Phe Lys Gly
1               5

<210> SEQ ID NO 113
<211> LENGTH: 11
<212> TYPE: PRT
<213> ORGANISM: Artificial Sequence
<220> FEATURE:
<223> OTHER INFORMATION: CDR3

<400> SEQUENCE: 113

Gly Gln Leu Gly Leu Glu Ala Trp Phe Ala Tyr
1               5                   10

<210> SEQ ID NO 114
<211> LENGTH: 391
<212> TYPE: DNA
<213> ORGANISM: Artificial Sequence
<220> FEATURE:
<223> OTHER INFORMATION: heavy chain variable region MF6058
<220> FEATURE:
<221> NAME/KEY: CDS
<222> LOCATION: (20)..(391)

<400> SEQUENCE: 114
ggcccagccg gccatggcc cag gtg cag ctg gtg cag tct ggg gct gac gtg      52
                     Gln Val Gln Leu Val Gln Ser Gly Ala Asp Val
                      1               5                  10 aag aag cct ggg gcc tca gtg aag gtc acg tgc aag gct tct gga tac      100
Lys Lys Pro Gly Ala Ser Val Lys Val Thr Cys Lys Ala Ser Gly Tyr
            15                  20                  25 acc ttc acc ggc tac tat atg cac tgg gtg cga cag gcc cct gga caa      148
Thr Phe Thr Gly Tyr Tyr Met His Trp Val Arg Gln Ala Pro Gly Gln
        30                  35                  40 gct ctt gag tgg atg gga tgg atc aac cct caa agt ggt ggc aca aac      196
Ala Leu Glu Trp Met Gly Trp Ile Asn Pro Gln Ser Gly Gly Thr Asn
    45                  50                  55 tat gca aag aag ttt cag ggc agg gtc tct atg acc agg gag acg tcc      244
Tyr Ala Lys Lys Phe Gln Gly Arg Val Ser Met Thr Arg Glu Thr Ser
60                  65                  70                  75 aca agc aca gcc tac atg cag ctg agc agg ctg aga tct gac gac acg      292
Thr Ser Thr Ala Tyr Met Gln Leu Ser Arg Leu Arg Ser Asp Asp Thr
                80                  85                  90 gct acg tat tac tgt gca aga gat cat ggt tct cgt cat ttc tgg tct      340
Ala Thr Tyr Tyr Cys Ala Arg Asp His Gly Ser Arg His Phe Trp Ser
            95                  100                 105 tac tgg ggc ttt gat tat tgg ggc caa ggt acc ctg gtc acc gtc tcc      388
Tyr Trp Gly Phe Asp Tyr Trp Gly Gln Gly Thr Leu Val Thr Val Ser
        110                 115                 120 agt                                                                  391
Ser

<210> SEQ ID NO 115
<211> LENGTH: 124
<212> TYPE: PRT
<213> ORGANISM: Artificial Sequence
<220> FEATURE:
```

<223> OTHER INFORMATION: Synthetic Construct

<400> SEQUENCE: 115

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 116
<211> LENGTH: 5
<212> TYPE: PRT
<213> ORGANISM: Artificial Sequence
<220> FEATURE:
<223> OTHER INFORMATION: CDR1

<400> SEQUENCE: 116

Gly Tyr Tyr Met His
1               5

<210> SEQ ID NO 117
<211> LENGTH: 17
<212> TYPE: PRT
<213> ORGANISM: Artificial Sequence
<220> FEATURE:
<223> OTHER INFORMATION: CDR2

<400> SEQUENCE: 117

Trp Ile Asn Pro Gln Ser Gly Gly Thr Asn Tyr Ala Lys Lys Phe Gln
1               5                   10                  15

Gly

<210> SEQ ID NO 118
<211> LENGTH: 15
<212> TYPE: PRT
<213> ORGANISM: Artificial Sequence
<220> FEATURE:
<223> OTHER INFORMATION: CDR3

<400> SEQUENCE: 118

Asp His Gly Ser Arg His Phe Trp Ser Tyr Trp Gly Phe Asp Tyr
1               5                   10                  15

<210> SEQ ID NO 119
<211> LENGTH: 391
<212> TYPE: DNA
<213> ORGANISM: Artificial Sequence
<220> FEATURE:
<223> OTHER INFORMATION: heavy chain variable region MF6061
<220> FEATURE:
<221> NAME/KEY: CDS
<222> LOCATION: (20)..(391)

<400> SEQUENCE: 119

```
ggcccagccg gccatggcc cag gtg cag ctg gtg cag tct ggg gct gag gtg        52
                     Gln Val Gln Leu Val Gln Ser Gly Ala Glu Val
                       1               5                  10 aag aag cct ggg gcc tca gtg aag gtc tcc tgc aag gct tct gga tac         100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa         148
Thr Phe Thr Gly Tyr Tyr Met His Trp Val Arg Gln Ala Pro Gly Gln
         30                  35                  40 ggg ctt gag tgg atg gga tgg atc aac cct cag agt ggt ggc aca aac         196
Gly Leu Glu Trp Met Gly Trp Ile Asn Pro Gln Ser Gly Gly Thr Asn
     45                  50                  55 tat gca cag aag ttt aag ggc agg gtc acg atg acc agg gac acg tcc         244
Tyr Ala Gln Lys Phe Lys Gly Arg Val Thr Met Thr Arg Asp Thr Ser
 60                  65                  70                  75 acc agc aca gcc tac atg gag ctg agc agg ctg aga tct gac gac acg         292
Thr Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct         340
Ala Val Tyr Tyr Cys Ala Arg Asp His Gly Ser Arg His Phe Trp Ser
                     95                 100                 105 tac tgg ggc ttt gat tat tgg ggc caa ggt acc ctg gtc acc gtc tcc         388
Tyr Trp Gly Phe Asp Tyr Trp Gly Gln Gly Thr Leu Val Thr Val Ser
             110                 115                 120 agt                                                                     391
Ser
```

<210> SEQ ID NO 120
<211> LENGTH: 124
<212> TYPE: PRT
<213> ORGANISM: Artificial Sequence
<220> FEATURE:
<223> OTHER INFORMATION: Synthetic Construct

<400> SEQUENCE: 120

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Gln Ser Gly Gly Thr Asn Tyr Ala Gln Lys Phe
     50                  55                  60

Lys Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120
```

<210> SEQ ID NO 121
<211> LENGTH: 5
<212> TYPE: PRT
<213> ORGANISM: Artificial Sequence
<220> FEATURE:
<223> OTHER INFORMATION: CDR1

<400> SEQUENCE: 121

Gly Tyr Tyr Met His
1               5

<210> SEQ ID NO 122
<211> LENGTH: 17
<212> TYPE: PRT
<213> ORGANISM: Artificial Sequence
<220> FEATURE:
<223> OTHER INFORMATION: CDR2

<400> SEQUENCE: 122

Trp Ile Asn Pro Gln Ser Gly Gly Thr Asn Tyr Ala Gln Lys Phe Lys
1               5                   10                  15
Gly

<210> SEQ ID NO 123
<211> LENGTH: 15
<212> TYPE: PRT
<213> ORGANISM: Artificial Sequence
<220> FEATURE:
<223> OTHER INFORMATION: CDR3

<400> SEQUENCE: 123

Asp His Gly Ser Arg His Phe Trp Ser Tyr Trp Gly Phe Asp Tyr
1               5                   10                  15

<210> SEQ ID NO 124
<211> LENGTH: 391
<212> TYPE: DNA
<213> ORGANISM: Artificial Sequence
<220> FEATURE:
<223> OTHER INFORMATION: heavy chain variable region MF6065
<220> FEATURE:
<221> NAME/KEY: CDS
<222> LOCATION: (20)..(391)

<400> SEQUENCE: 124

```
ggcccagccg gccatggcc cag gtg cag ctg gtg cag tct ggg gct gag gtg        52
                     Gln Val Gln Leu Val Gln Ser Gly Ala Glu Val
                      1               5                   10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
                 15                  20                  25 acc ttc acc tct tac tat atg cac tgg gtg cga cag gcc cct gga caa        148
Thr Phe Thr Ser Tyr Tyr Met His Trp Val Arg Gln Ala Pro Gly Gln
             30                  35                  40 ggg ctt gag tgg atg gga tgg atc aac cct cag ggg ggt tct aca aac        196
Gly Leu Glu Trp Met Gly Trp Ile Asn Pro Gln Gly Gly Ser Thr Asn
         45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
 60                  65                  70                  75 acc agc aca gtg tac atg gag ctg agc agg ctg aga tct gag gac acg        292
Thr Ser Thr Val Tyr Met Glu Leu Ser Arg Leu Arg Ser Glu Asp Thr
                 80                  85                  90 gct gtg tat tac tgt gca aga gat cat ggt tct cgt cat ttc tgg tct        340
Ala Val Tyr Tyr Cys Ala Arg Asp His Gly Ser Arg His Phe Trp Ser
             95                  100                 105 tac tgg ggc ttt gat tat tgg ggc caa ggt acc ctg gtc acc gtc tcc        388
Tyr Trp Gly Phe Asp Tyr Trp Gly Gln Gly Thr Leu Val Thr Val Ser
        110                 115                 120
```

```
agt                                                         391
Ser
```

<210> SEQ ID NO 125
<211> LENGTH: 124
<212> TYPE: PRT
<213> ORGANISM: Artificial Sequence
<220> FEATURE:
<223> OTHER INFORMATION: Synthetic Construct

<400> SEQUENCE: 125

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
50                  55                  60

Gln Gly Arg Val Thr Met Thr Arg Asp Thr Ser Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 126
<211> LENGTH: 5
<212> TYPE: PRT
<213> ORGANISM: Artificial Sequence
<220> FEATURE:
<223> OTHER INFORMATION: CDR1

<400> SEQUENCE: 126

```
Ser Tyr Tyr Met His
1               5
```

<210> SEQ ID NO 127
<211> LENGTH: 17
<212> TYPE: PRT
<213> ORGANISM: Artificial Sequence
<220> FEATURE:
<223> OTHER INFORMATION: CDR2

<400> SEQUENCE: 127

```
Trp Ile Asn Pro Gln Gly Gly Ser Thr Asn Tyr Ala Gln Lys Phe Gln
1               5                   10                  15

Gly
```

<210> SEQ ID NO 128
<211> LENGTH: 15
<212> TYPE: PRT
<213> ORGANISM: Artificial Sequence
<220> FEATURE:
<223> OTHER INFORMATION: CDR3

<400> SEQUENCE: 128

```
Asp His Gly Ser Arg His Phe Trp Ser Tyr Trp Gly Phe Asp Tyr
1               5                   10                  15
```

-continued

```
<210> SEQ ID NO 129
<211> LENGTH: 363
<212> TYPE: DNA
<213> ORGANISM: Artificial Sequence
<220> FEATURE:
<223> OTHER INFORMATION: heavy chain variable region MF6055
<220> FEATURE:
<221> NAME/KEY: CDS
<222> LOCATION: (1)..(363)

<400> SEQUENCE: 129 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct tct agt ggt ggc aca aac tat gca aag aag ttt     192
Gly Trp Ile Asn Pro Ser Ser Gly Gly Thr Asn Tyr Ala Lys Lys Phe
    50                  55                  60 cag ggc agg gtc acg atg acc agg gag acg tcc aca agc aca gcc tac     240
Gln Gly Arg Val Thr Met Thr Arg Glu Thr Ser Thr Ser Thr Ala Tyr
65                  70                  75                  80 atg gag ctg agc agg ctg aga tct gac gac acg gct acg tat tac tgt     288
Met Glu Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 130
<211> LENGTH: 121
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Ser Ser Gly Gly Thr Asn Tyr Ala Lys Lys Phe
    50                  55                  60

Gln Gly Arg Val Thr Met Thr Arg Glu Thr Ser Thr Ser Thr Ala Tyr
65                  70                  75                  80

Met Glu Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 131
<211> LENGTH: 363
<212> TYPE: DNA
<213> ORGANISM: Artificial Sequence
<220> FEATURE:
<223> OTHER INFORMATION: heavy chain variable region MF6056
<220> FEATURE:
<221> NAME/KEY: CDS
<222> LOCATION: (1)..(363)

<400> SEQUENCE: 131

```
cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct tct agt ggt gga aca aac tat gca aag aag ttt     192
Gly Trp Ile Asn Pro Ser Ser Gly Gly Thr Asn Tyr Ala Lys Lys Phe
    50                  55                  60 cag ggc agg gtc tct atg acc agg gag acg tcc aca agc aca gcc tac     240
Gln Gly Arg Val Ser Met Thr Arg Glu Thr Ser Thr Ser Thr Ala Tyr
65                  70                  75                  80 atg cag ctg agc agg ctg aga tct gac gac acg gct acg tat tac tgt     288
Met Gln Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120
```

<210> SEQ ID NO 132
<211> LENGTH: 121
<212> TYPE: PRT
<213> ORGANISM: Artificial Sequence
<220> FEATURE:
<223> OTHER INFORMATION: Synthetic Construct

<400> SEQUENCE: 132

```
Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Ser Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 133
<211> LENGTH: 363
<212> TYPE: DNA
<213> ORGANISM: Artificial Sequence
<220> FEATURE:
<223> OTHER INFORMATION: heavy chain variable region MF6057
<220> FEATURE:
<221> NAME/KEY: CDS
<222> LOCATION: (1)..(363)

<400> SEQUENCE: 133 cag gtg cag ctg gtg cag tct ggg gct gat gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg cag ctg agc agg ctg aga tct gac gac acg gct gtg tat tac tgt     288
Met Gln Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 134
<211> LENGTH: 121
<212> TYPE: PRT
<213> ORGANISM: Artificial Sequence
<220> FEATURE:
<223> OTHER INFORMATION: Synthetic Construct

<400> SEQUENCE: 134

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 135
<211> LENGTH: 363
<212> TYPE: DNA
<213> ORGANISM: Artificial Sequence
<220> FEATURE:
<223> OTHER INFORMATION: heavy chain variable region MF6058
<220> FEATURE:
<221> NAME/KEY: CDS
<222> LOCATION: (1)..(363)

<400> SEQUENCE: 135 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt     192
Gly Trp Ile Asn Pro Gln Ser Gly Gly Thr Asn Tyr Ala Lys Lys Phe
    50                  55                  60 cag ggc agg gtc tct atg acc agg gag acg tcc aca agc aca gcc tac     240
Gln Gly Arg Val Ser Met Thr Arg Glu Thr Ser Thr Ser Thr Ala Tyr
65                  70                  75                  80 atg cag ctg agc agg ctg aga tct gac gac acg gct acg tat tac tgt     288
Met Gln Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 136
<211> LENGTH: 121
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 137
<211> LENGTH: 363
<212> TYPE: DNA
<213> ORGANISM: Artificial Sequence
<220> FEATURE:
<223> OTHER INFORMATION: heavy chain variable region MF6059
<220> FEATURE:
<221> NAME/KEY: CDS
<222> LOCATION: (1)..(363)

<400> SEQUENCE: 137
```

| | | | | | | | | | | | | | | | | |
|---|---|---|---|---|---|---|---|---|---|---|---|---|---|---|---|---|
| cag | gtg | cag | ctg | gtg | cag | tct | ggg | gct | gag | gtg | aag | aag | cct | ggg | gcc | 48 |
| Gln | Val | Gln | Leu | Val | Gln | Ser | Gly | Ala | Glu | Val | Lys | Lys | Pro | Gly | Ala | |
| 1 | | | | 5 | | | | | 10 | | | | | 15 | | |
| tca | gtg | aag | gtc | tcc | tgc | aag | gct | tct | gga | tac | acc | ttc | acc | ggc | tac | 96 |
| Ser | Val | Lys | Val | Ser | Cys | Lys | Ala | Ser | Gly | Tyr | Thr | Phe | Thr | Gly | Tyr | |
| | | | 20 | | | | | 25 | | | | | 30 | | | |
| tat | atg | cac | tgg | gtg | cga | cag | gcc | cct | gga | caa | ggg | ctt | gag | tgg | atg | 144 |
| Tyr | Met | His | Trp | Val | Arg | Gln | Ala | Pro | Gly | Gln | Gly | Leu | Glu | Trp | Met | |
| | | 35 | | | | | 40 | | | | | 45 | | | | |
| gga | tgg | atc | aac | cct | ggc | agt | ggt | tct | aca | aac | tat | gca | cag | aag | ttt | 192 |
| Gly | Trp | Ile | Asn | Pro | Gly | Ser | Gly | Ser | Thr | Asn | Tyr | Ala | Gln | Lys | Phe | |
| 50 | | | | | 55 | | | | | 60 | | | | | | |
| cag | ggc | agg | gtc | acg | atg | acc | agg | gac | acg | tcc | atc | agc | aca | gcc | tac | 240 |
| Gln | Gly | Arg | Val | Thr | Met | Thr | Arg | Asp | Thr | Ser | Ile | Ser | Thr | Ala | Tyr | |
| 65 | | | | 70 | | | | | 75 | | | | | 80 | | |
| atg | gag | ctg | agc | agg | ctg | aga | tct | gac | gac | acg | gct | gtg | tat | tac | tgt | 288 |
| Met | Glu | Leu | Ser | Arg | Leu | Arg | Ser | Asp | Asp | Thr | Ala | Val | Tyr | Tyr | Cys | |
| | | | | 85 | | | | | 90 | | | | | 95 | | |
| gca | aga | gat | cat | ggt | tct | cgt | cat | ttc | tgg | tct | tac | tgg | ggc | ttt | gat | 336 |
| Ala | Arg | Asp | His | Gly | Ser | Arg | His | Phe | Trp | Ser | Tyr | Trp | Gly | Phe | Asp | |
| | | | 100 | | | | | 105 | | | | | 110 | | | |
| tat | tgg | ggc | caa | ggt | acc | ctg | gtc | acc | | | | | | | | 363 |
| Tyr | Trp | Gly | Gln | Gly | Thr | Leu | Val | Thr | | | | | | | | |
| | 115 | | | | | 120 | | | | | | | | | | |

```
<210> SEQ ID NO 138
<211> LENGTH: 121
<212> TYPE: PRT
<213> ORGANISM: Artificial Sequence
<220> FEATURE:
<223> OTHER INFORMATION: Synthetic Construct

<400> SEQUENCE: 138
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120

-continued

```
<210> SEQ ID NO 139
<211> LENGTH: 363
<212> TYPE: DNA
<213> ORGANISM: Artificial Sequence
<220> FEATURE:
<223> OTHER INFORMATION: heavy chain variable region MF6060
<220> FEATURE:
<221> NAME/KEY: CDS
<222> LOCATION: (1)..(363)

<400> SEQUENCE: 139 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt     192
Gly Trp Ile Asn Pro Gln Ser Gly Gly Thr Asn Tyr Ala Lys Lys Phe
    50                  55                  60 cag ggc agg gtc acg atg acc agg gag acg tcc aca agc aca gcc tac     240
Gln Gly Arg Val Thr Met Thr Arg Glu Thr Ser Thr Ser Thr Ala Tyr
65                  70                  75                  80 atg gag ctg agc agg ctg aga tct gac gac acg gct acg tat tac tgt     288
Met Glu Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 140
<211> LENGTH: 121
<212> TYPE: PRT
<213> ORGANISM: Artificial Sequence
<220> FEATURE:
<223> OTHER INFORMATION: Synthetic Construct

<400> SEQUENCE: 140

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Thr Met Thr Arg Glu Thr Ser Thr Ser Thr Ala Tyr
65                  70                  75                  80

Met Glu Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 141
<211> LENGTH: 363
<212> TYPE: DNA
<213> ORGANISM: Artificial Sequence
<220> FEATURE:
<223> OTHER INFORMATION: heavy chain variable region MF6061
<220> FEATURE:
<221> NAME/KEY: CDS
<222> LOCATION: (1)..(363)

<400> SEQUENCE: 141 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 aag ggc agg gtc acg atg acc agg gac acg tcc acg agc aca gcc tac     240
Lys Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 142
<211> LENGTH: 121
<212> TYPE: PRT
<213> ORGANISM: Artificial Sequence
<220> FEATURE:
<223> OTHER INFORMATION: Synthetic Construct

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Lys Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

-continued

```
<210> SEQ ID NO 143
<211> LENGTH: 363
<212> TYPE: DNA
<213> ORGANISM: Artificial Sequence
<220> FEATURE:
<223> OTHER INFORMATION: heavy chain variable region MF6062
<220> FEATURE:
<221> NAME/KEY: CDS
<222> LOCATION: (1)..(363)

<400> SEQUENCE: 143 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct ggc agt ggt tct aca aac tat gca cag aag ttt       192
Gly Trp Ile Asn Pro Gly Ser Gly Ser Thr Asn Tyr Ala Gln Lys Phe
    50                  55                  60 cag ggc agg gtc acg atg acc agg gac acg tcc aca agc aca gcc tac       240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt       288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                   363
Tyr Trp Gly Gln Gly Thr Leu Val Thr
        115                 120

<210> SEQ ID NO 144
<211> LENGTH: 121
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

-continued

```
<210> SEQ ID NO 145
<211> LENGTH: 363
<212> TYPE: DNA
<213> ORGANISM: Artificial Sequence
<220> FEATURE:
<223> OTHER INFORMATION: heavy chain variable region MF6063
<220> FEATURE:
<221> NAME/KEY: CDS
<222> LOCATION: (1)..(363)

<400> SEQUENCE: 145 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt ggc aca aac tat gca aag aag ttt       192
Gly Trp Ile Asn Pro Gln Ser Gly Gly Thr Asn Tyr Ala Lys Lys Phe
    50                  55                  60 cag ggc agg gtc acg atg acc agg gac acg tcc acc agc aca gcc tac       240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt       288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                   363
Tyr Trp Gly Gln Gly Thr Leu Val Thr
        115                 120

<210> SEQ ID NO 146
<211> LENGTH: 121
<212> TYPE: PRT
<213> ORGANISM: Artificial Sequence
<220> FEATURE:
<223> OTHER INFORMATION: Synthetic Construct

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 147
<211> LENGTH: 363
<212> TYPE: DNA
<213> ORGANISM: Artificial Sequence
<220> FEATURE:
<223> OTHER INFORMATION: heavy chain variable region MF6064
<220> FEATURE:
<221> NAME/KEY: CDS
<222> LOCATION: (1)..(363)

<400> SEQUENCE: 147 cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30 tat atg cac tgg gtg cga cag gcc cct gga aag ggg ctt gag tgg atg      144
Tyr Met His Trp Val Arg Gln Ala Pro Gly Lys Gly Leu Glu Trp Met
        35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
    50                  55                  60 cag ggc agg gtc acg atg acc agg gac acg tcc acg agc aca gcc tac      240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120

<210> SEQ ID NO 148
<211> LENGTH: 121
<212> TYPE: PRT
<213> ORGANISM: Artificial Sequence
<220> FEATURE:
<223> OTHER INFORMATION: Synthetic Construct

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Lys Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 149
<211> LENGTH: 363
<212> TYPE: DNA
<213> ORGANISM: Artificial Sequence
<220> FEATURE:
<223> OTHER INFORMATION: heavy chain variable region MF6065
<220> FEATURE:
<221> NAME/KEY: CDS
<222> LOCATION: (1)..(363)

<400> SEQUENCE: 149
```

| cag gtg cag ctg gtg cag tct ggg gct gag gtg aag aag cct ggg gcc | 48 |
|---|---|
| Gln Val Gln Leu Val Gln Ser Gly Ala Glu Val Lys Lys Pro Gly Ala | |
| 1               5                  10                  15 | |

| tca gtg aag gtc tcc tgc aag gct tct gga tac acc ttc acc tct tac | 96 |
|---|---|
| Ser Val Lys Val Ser Cys Lys Ala Ser Gly Tyr Thr Phe Thr Ser Tyr | |
|           20                  25                  30 | |

| tat atg cac tgg gtg cga cag gcc cct gga caa ggg ctt gag tgg atg | 144 |
|---|---|
| Tyr Met His Trp Val Arg Gln Ala Pro Gly Gln Gly Leu Glu Trp Met | |
|       35                  40                  45 | |

| gga tgg atc aac cct cag ggg ggt tct aca aac tat gca cag aag ttt | 192 |
|---|---|
| Gly Trp Ile Asn Pro Gln Gly Gly Ser Thr Asn Tyr Ala Gln Lys Phe | |
|   50                  55                  60 | |

| cag ggc agg gtc acg atg acc agg gac acg tcc acc agc aca gtg tac | 240 |
|---|---|
| Gln Gly Arg Val Thr Met Thr Arg Asp Thr Ser Thr Ser Thr Val Tyr | |
| 65                  70                  75                  80 | |

| atg gag ctg agc agg ctg aga tct gag gac acg gct gtg tat tac tgt | 288 |
|---|---|
| Met Glu Leu Ser Arg Leu Arg Ser Glu Asp Thr Ala Val Tyr Tyr Cys | |
|               85                  90                  95 | |

| gca aga gat cat ggt tct cgt cat ttc tgg tct tac tgg ggc ttt gat | 336 |
|---|---|
| Ala Arg Asp His Gly Ser Arg His Phe Trp Ser Tyr Trp Gly Phe Asp | |
|           100                 105                 110 | |

| tat tgg ggc caa ggt acc ctg gtc acc | 363 |
|---|---|
| Tyr Trp Gly Gln Gly Thr Leu Val Thr | |
|       115                 120 | |

```
<210> SEQ ID NO 150
<211> LENGTH: 121
<212> TYPE: PRT
<213> ORGANISM: Artificial Sequence
<220> FEATURE:
<223> OTHER INFORMATION: Synthetic Construct

<400> SEQUENCE: 150
```

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120

```
<210> SEQ ID NO 151
<211> LENGTH: 363
<212> TYPE: DNA
<213> ORGANISM: Artificial Sequence
<220> FEATURE:
<223> OTHER INFORMATION: heavy chain variable region MF6066
<220> FEATURE:
<221> NAME/KEY: CDS
<222> LOCATION: (1)..(363)

<400> SEQUENCE: 151 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt tct aca aac tat gca cag aag ttt       192
Gly Trp Ile Asn Pro Gln Ser Gly Ser Thr Asn Tyr Ala Gln Lys Phe
    50                  55                  60 cag ggc agg gtc acg atg acc agg gac acg tcc acg agc aca gcc tac       240
Gln Gly Arg Val Thr Met Thr Arg Asp Thr Ser Thr Ser Thr Ala Tyr
65                  70                  75                  80 atg gag ctg agc tct ctg aga tct gag gac acg gct gtg tat tac tgt       288
Met Glu Leu Ser Ser Leu Arg Ser Glu Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                    363
Tyr Trp Gly Gln Gly Thr Leu Val Thr
        115                 120

<210> SEQ ID NO 152
<211> LENGTH: 121
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 153
<211> LENGTH: 363
<212> TYPE: DNA
<213> ORGANISM: Artificial Sequence
<220> FEATURE:
<223> OTHER INFORMATION: heavy chain variable region MF6067
<220> FEATURE:
<221> NAME/KEY: CDS
<222> LOCATION: (1)..(363)

<400> SEQUENCE: 153

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt       192
Gly Trp Ile Asn Pro Gln Ser Gly Gly Thr Asn Tyr Ala Gln Lys Phe
    50                  55                  60 cag ggc agg gtc acg atg acc agg gac acg tcc acg agc aca gtc tac       240
Gln Gly Arg Val Thr Met Thr Arg Asp Thr Ser Thr Ser Thr Val Tyr
65                  70                  75                  80 atg gag ctg agc tct ctg aga tct gac gac acg gct gtg tat tac tgt       288
Met Glu Leu Ser Ser Leu Arg Ser Asp Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                   363
Tyr Trp Gly Gln Gly Thr Leu Val Thr
        115                 120
```

<210> SEQ ID NO 154
<211> LENGTH: 121
<212> TYPE: PRT
<213> ORGANISM: Artificial Sequence
<220> FEATURE:
<223> OTHER INFORMATION: Synthetic Construct

<400> SEQUENCE: 154

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 155
<211> LENGTH: 363
<212> TYPE: DNA
<213> ORGANISM: Artificial Sequence
<220> FEATURE:
<223> OTHER INFORMATION: heavy chain variable region MF6068
<220> FEATURE:
<221> NAME/KEY: CDS
<222> LOCATION: (1)..(363)

<400> SEQUENCE: 155 cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt    192
Gly Trp Ile Asn Pro Gln Ser Gly Gly Thr Asn Tyr Ala Gln Lys Phe
    50                  55                  60 cag ggc agg gtc acg atg acc agg gac acg tcc acg agc aca gcc tac    240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt    288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc                                363
Tyr Trp Gly Gln Gly Thr Leu Val Thr
        115                 120

<210> SEQ ID NO 156
<211> LENGTH: 121
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 157
<211> LENGTH: 363
<212> TYPE: DNA
<213> ORGANISM: Artificial Sequence
<220> FEATURE:
<223> OTHER INFORMATION: heavy chain variable region MF6069
<220> FEATURE:
<221> NAME/KEY: CDS
<222> LOCATION: (1)..(363)

<400> SEQUENCE: 157

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120
```

<210> SEQ ID NO 158
<211> LENGTH: 121
<212> TYPE: PRT
<213> ORGANISM: Artificial Sequence
<220> FEATURE:
<223> OTHER INFORMATION: Synthetic Construct

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 159
<211> LENGTH: 363
<212> TYPE: DNA
<213> ORGANISM: Artificial Sequence
<220> FEATURE:
<223> OTHER INFORMATION: heavy chain variable region MF6070
<220> FEATURE:
<221> NAME/KEY: CDS
<222> LOCATION: (1)..(363)

<400> SEQUENCE: 159 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac      96
Ser Val Lys Val Ser Cys Lys Ala Ser Gly Tyr Thr Phe Thr Ser Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct ggg ggt tct aca aac tat gca cag aag ttt     192
Gly Trp Ile Asn Pro Ser Gly Gly Ser Thr Asn Tyr Ala Gln Lys Phe
    50                  55                  60 cag ggc agg gtc acg atg acc agg gac acg tcc acc agc aca gtg tac     240
Gln Gly Arg Val Thr Met Thr Arg Asp Thr Ser Thr Ser Thr Val Tyr
65                  70                  75                  80 atg gag ctg agc agg ctg aga tct gag gac acg gct gtg tat tac tgt     288
Met Glu Leu Ser Arg Leu Arg Ser Glu Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 160
<211> LENGTH: 121
<212> TYPE: PRT
<213> ORGANISM: Artificial Sequence
<220> FEATURE:
<223> OTHER INFORMATION: Synthetic Construct

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

-continued

```
<210> SEQ ID NO 161
<211> LENGTH: 363
<212> TYPE: DNA
<213> ORGANISM: Artificial Sequence
<220> FEATURE:
<223> OTHER INFORMATION: heavy chain variable region MF6071
<220> FEATURE:
<221> NAME/KEY: CDS
<222> LOCATION: (1)..(363)

<400> SEQUENCE: 161 cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg   144
Tyr Met His Trp Val Arg Gln Ala Pro Gly Gln Gly Leu Glu Trp Met
        35                  40                  45 gga tgg atc aac cct tct agt ggt tct aca aac tat gca cag aag ttt   192
Gly Trp Ile Asn Pro Ser Ser Gly Ser Thr Asn Tyr Ala Gln Lys Phe
    50                  55                  60 cag ggc agg gtc acg atg acc agg gac acg tcc acg agc aca gcc tac   240
Gln Gly Arg Val Thr Met Thr Arg Asp Thr Ser Thr Ser Thr Ala Tyr
65                  70                  75                  80 atg gag ctg agc tct ctg aga tct gag gac acg gct gtg tat tac tgt   288
Met Glu Leu Ser Ser Leu Arg Ser Glu Asp Thr Ala Val Tyr Tyr Cys
                85                  90                  95 gca aga gat cat ggt tct cgt cat ttc tgg tct tac tgg ggc ttt gat   336
Ala Arg Asp His Gly Ser Arg His Phe Trp Ser Tyr Trp Gly Phe Asp
            100                 105                 110 tat tgg ggc caa ggt acc ctg gtc acc                                363
Tyr Trp Gly Gln Gly Thr Leu Val Thr
        115                 120

<210> SEQ ID NO 162
<211> LENGTH: 121
<212> TYPE: PRT
<213> ORGANISM: Artificial Sequence
<220> FEATURE:
<223> OTHER INFORMATION: Synthetic Construct

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 163
<211> LENGTH: 363
<212> TYPE: DNA
<213> ORGANISM: Artificial Sequence
<220> FEATURE:
<223> OTHER INFORMATION: heavy chain variable region MF6072
<220> FEATURE:
<221> NAME/KEY: CDS
<222> LOCATION: (1)..(363)

<400> SEQUENCE: 163 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt     192
Gly Trp Ile Asn Pro Ser Ser Gly Gly Thr Asn Tyr Ala Gln Lys Phe
    50                  55                  60 cag ggc agg gtc acg atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc tct ctg aga tct gac gac acg gct gtg tat tac tgt     288
Met Glu Leu Ser Ser Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 164
<211> LENGTH: 121
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

-continued

```
<210> SEQ ID NO 165
<211> LENGTH: 363
<212> TYPE: DNA
<213> ORGANISM: Artificial Sequence
<220> FEATURE:
<223> OTHER INFORMATION: heavy chain variable region MF6073
<220> FEATURE:
<221> NAME/KEY: CDS
<222> LOCATION: (1)..(363)

<400> SEQUENCE: 165 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt     192
Gly Trp Ile Asn Pro Ser Ser Gly Gly Thr Asn Tyr Ala Gln Lys Phe
    50                  55                  60 cag ggc agg gtc acg atg acc agg gac acg tcc acg agc aca gcc tac     240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 166
<211> LENGTH: 121
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
<210> SEQ ID NO 167
<211> LENGTH: 363
<212> TYPE: DNA
<213> ORGANISM: Artificial Sequence
<220> FEATURE:
<223> OTHER INFORMATION: heavy chain variable region MF6074
<220> FEATURE:
<221> NAME/KEY: CDS
<222> LOCATION: (1)..(363)

<400> SEQUENCE: 167 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt     192
Gly Trp Ile Asn Pro Ser Ser Gly Gly Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 168
<211> LENGTH: 121
<212> TYPE: PRT
<213> ORGANISM: Artificial Sequence
<220> FEATURE:
<223> OTHER INFORMATION: Synthetic Construct

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

```
-continued

<210> SEQ ID NO 169
<211> LENGTH: 6
<212> TYPE: PRT
<213> ORGANISM: Artificial Sequence
<220> FEATURE:
<223> OTHER INFORMATION: Common Light Chain CDR1

<400> SEQUENCE: 169

Gln Ser Ile Ser Ser Tyr
1               5

<210> SEQ ID NO 170
<211> LENGTH: 3
<212> TYPE: PRT
<213> ORGANISM: Artificial Sequence
<220> FEATURE:
<223> OTHER INFORMATION: Common Light Chain CDR2

<400> SEQUENCE: 170

Ala Ala Ser
1

<210> SEQ ID NO 171
<211> LENGTH: 9
<212> TYPE: PRT
<213> ORGANISM: Artificial Sequence
<220> FEATURE:
<223> OTHER INFORMATION: Common Light Chain CDR3

<400> SEQUENCE: 171

Gln Gln Ser Tyr Ser Thr Pro Pro Thr
1               5
```

COMBINATION OF AN ErbB-2/ErbB-3 BISPECIFIC ANTIBODY WITH ENDOCRINE THERAPY FOR BREAST CANCER

CROSS-REFERENCE TO RELATED APPLICATIONS

This application is a 35 U.S.C. § 371 filing of PCT/NL2018/050329, filed May 17, 2018; which claims priority to U.S. Provisional Patent Application No. 62/507,675, filed May 17, 2017. The entire contents of these patent applications are hereby incorporated by reference.

REFERENCE TO SEQUENCE LISTING SUBMITTED ELECTRONICALLY VIA EFS-WEB

The content of the electronically submitted sequence listing (Name: "4096_0120001_Seqlisting_ST25.txt"; Size: 169,393 bytes; Date of Creation: Jul. 5, 2023) submitted in this application is incorporated herein by reference in its entirety.

The invention relates to the field of antibodies. In particular it relates to the field of therapeutic (human) antibodies for the treatment of diseases involving aberrant cells. More in particular it relates to antibodies that can bind ErbB-2 and ErbB-3 and the treatment of subjects with breast cancer with these antibodies in combination with an endocrine therapy drug.

Some types of breast cancer are affected by hormones in the blood. Estrogen receptor (ER) positive and progesterone receptor (PR) positive breast cancer cells have receptors that attach to hormones, which help them grow. About 2 out of 3 breast cancers are hormone receptor-positive. Their cells have receptors that attach to the hormones estrogen (ER-positive cancers) and/or progesterone (PR-positive cancers). For these cancers, high estrogen levels help the cancer cells grow and spread.

There are various drugs that interfere with this mechanism.

Drugs that Block Estrogen Receptors

These drugs work by stopping estrogen from affecting breast cancer cells. An example of such a drug is Tamoxifen. This drug blocks estrogen receptors in breast cancer cells. This stops estrogen from binding to the cancer cells and telling them to grow and divide. While Tamoxifen acts like an anti-estrogen in breast cells, it acts like estrogen in other tissues, like the uterus and the bones. Because of this, it is called a selective estrogen receptor modulator (SERM). Tamoxifen is among the most well-known SERMs. Other SERMs that have been approved for medical use include, bazedoxifene (Duavee), broparestrol (Acnestrol), clomifene (Clomid), cyclofenil (Sexovid), lasofoxifene (Fablyn), ormeloxifene (Centron, Novex, Novex-DS, Sevista), ospemifene (Osphena), raloxifene (Evista), Tamoxifen (Nolvadex), and toremifene (Fareston), some of which have been approved for treatment of hormone receptor positive breast cancer. Many more SERMS have not (yet) been approved but are also functional.

Tamoxifen can be started either after surgery (adjuvant therapy) or before surgery (neoadjuvant therapy) and is usually taken for 5 to 10 years. After menopause, aromatase inhibitors may be used.

In women at high risk of breast cancer, Tamoxifen can be used to help lower the risk of developing breast cancer.

Toremifene (Fareston) is another SERM presently approved to treat metastatic breast cancer. These drugs mostly are taken orally, most often as a pill.

Fulvestrant (Faslodex)

Fulvestrant is a drug that blocks estrogen receptors and also eliminates them temporarily. Fulvestrant is a selective estrogen receptor degrader (SERD). Other SERDs include Brilanestrant and Elacestrant. Fulvestrant is used to treat metastatic breast cancer, including after other hormone drugs (like Tamoxifen and often an aromatase inhibitor) have stopped working.

It can be administered by intramuscular injection. Fulvestrant is currently approved for use in post-menopausal women.

Aromatase Inhibitors (AIs)

Aromatase inhibitors (AIs) are drugs that stop estrogen production. Before menopause, most estrogen is made by the ovaries. But for women whose ovaries are no longer working, either due to menopause or medical treatments, a small amount of estrogen is still made by an enzyme (called aromatase) in the adipose tissue, breast or skin. It is understood that AIs work by blocking aromatase from making estrogen.

These drugs are used in post-menopausal women, although they can also be used in premenopausal women if combined with ovarian ablation.

There are various AIs. The exemplary AIs include: Letrozole (Femara); Anastrozole (Arimidex) and Exemestane (Aromasin)

These drugs are pills that may be taken daily.

For post-menopausal women whose cancers are hormone receptor-positive, doctors may recommend taking an AI during adjuvant therapy.

Luteinizing hormone-releasing hormone (LHRH) analogs: These drugs are used more often than oophorectomy. It is understood that they stop the signal that the body sends to ovaries to make estrogen, which causes temporary menopause. Common LHRH drugs include Goserelin (Zoladex) and Leuprolide (Lupron). They can be used alone or with other hormone drugs (Tamoxifen, aromatase inhibitors, Fulvestrant) as hormone therapy in pre-menopausal women.

Chemotherapy drugs: Some chemotherapeutic drugs can damage the ovaries of pre-menopausal women so they no longer make estrogen. For some women, ovarian function returns months or years later, but in others, the damage to the ovaries is permanent and leads to menopause.

The drugs mentioned above are collectively referred to as endocrine therapy drugs of breast cancer. Endocrine therapy and the accompanying drugs have recently been reviewed by Lumachi et al (Lumachi, F., et al. "Endocrine therapy of breast cancer." Current medicinal chemistry 18.4 (2011): 513-522). In the context of the present invention endocrine therapy drugs refers to drugs that are used for endocrine therapy of breast cancer.

In the context of an invention described herein, the term endocrine therapy includes therapy drugs that interfere with the action of a hormone, typically the hormone estrogen or progesterone in the cancer cell. This can be directly by the action of the drug in the cancer cell, or indirectly by for instance lowering the amount of estrogen that can reach the cancer cell, including by interfering directly or indirectly with the action of estrogen on the tumor.

SUMMARY OF THE INVENTION

The invention provides a method of treating of a subject that has breast cancer or is at risk of having said cancer, comprising administering to the subject in need thereof a combination of a therapeutically effective amount of an ErbB-2/ErbB-3 bispecific antibody and a therapeutically effective amount of an endocrine therapy drug, wherein the bispecific antibody has an antigen binding site that can bind an extra-cellular part of ErbB-2 and an antigen binding site that can bind an extra-cellular part of ErbB-3.

The invention provides a combination of an ErbB-2/ErbB-3 bispecific antibody and an endocrine therapy drug for use in the treatment of a subject that has breast cancer or is at risk of having said cancer, wherein the bispecific antibody has an antigen binding site that can bind an extra-cellular part of ErbB-2 and an antigen binding site that can bind an extra-cellular part of ErbB-3.

The invention also provides use of an ErbB-2/ErbB-3 bispecific antibody and an endocrine therapy drug in the manufacture of a medicament for use in the treatment of a subject that has breast cancer or is at risk of having said cancer, wherein the bispecific antibody has an antigen binding site that can bind an extra cellular part of ErbB-2 and an antigen binding site that can bind an extra-cellular part of ErbB-3.

Also provided is a product comprising an ErbB-2/ErbB-3 bispecific antibody and an endocrine therapy drug for simultaneous, separate or sequential use in the treatment of a subject that has breast cancer or is at risk of having said cancer, wherein the bispecific antibody has an antigen binding site that can bind an extra-cellular part of ErbB-2 and an antigen binding site that can bind an extra-cellular part of ErbB-3.

The invention also provides a method of treating of a subject that has breast cancer or is at risk of having said cancer, comprising administering to the subject in need thereof a therapeutically effective amount of an antibody that can bind an extra cellular part of ErbB-2 and that inhibits ErbB-2/ErbB-3 dimerization on the cancer cell, wherein the cancer is a hormone receptor positive cancer.

Also provided is an antibody that can bind an extra-cellular part of ErbB-2 and that inhibits ErbB-2/ErbB-3 dimerization on a cancer cell for use in the treatment of a subject that has breast cancer or is at risk of having said cancer, wherein the cancer is a hormone receptor positive cancer.

Also provided is a combination of an ErbB-2 and/or ErbB-3 antibody and an endocrine therapy drug for use in the treatment of a subject that has breast cancer or is at risk of having said cancer, wherein the breast cancer is a hormone receptor positive breast cancer and wherein the antibody inhibits ErbB-2, ErbB-3 dimerization.

The invention also provides use of an ErbB-2 and/or ErbB-3 antibody and an endocrine therapy drug in the manufacture of a medicament for use in the treatment of a subject that has breast cancer or is at risk of having said cancer, wherein the breast cancer is a hormone receptor positive breast cancer and wherein the antibody inhibits ErbB-2, ErbB-3 dimerization.

Also provided is a product comprising an ErbB-2 and/or ErbB-3 antibody and an endocrine therapy drug for simultaneous, separate or sequential use in the treatment of a subject that has breast cancer or is at risk of having said cancer, wherein the cancer is a hormone receptor positive cancer and wherein the antibody inhibits ErbB-2, ErbB-3 dimerization The antibody is preferably a bispecific antibody that has an antigen binding site that can bind an extra-cellular part of ErbB-2 and an antigen binding site that can bind an extra-cellular part of ErbB-3. In one embodiment the method further comprises administering a therapeutically effective amount of an endocrine therapy drug to the subject in need thereof.

The antibody may be MCLA-128.

The endocrine therapy drug is preferably a drug that interferes with the action of the hormone estrogen or progesterone in the cancer cell. The endocrine therapy drug preferably comprises an aromatase inhibitor; a selective estrogen receptor modulator (SERM); or a selective estrogen receptor downregulator (SERD). The endocrine therapy drug may comprise a selective estrogen receptor modulator (SERM) selected from the group consisting of Tamoxifen (Nolvadex), broparestrol (Acnestrol), cyclofenil (Sexovid), raloxifene (Evista) and toremifene (Fareston). The endocrine therapy drug preferably comprises Tamoxifen, Fulvestrant or an equivalent thereof. In one embodiment the endocrine therapy drug comprises Letrozole or an equivalent thereof.

In one embodiment the cancer is an immunohistochemistry ErbB-2+ cancer or an immunohistochemistry ErbB-2++ without ErbB-2 gene amplification cancer.

In one embodiment the breast cancer is ER-positive with low HER2 expression metastatic breast cancer MBC IHC 1+, or IHC 2+ combined with negative FISH.

In one embodiment, the method further comprises administering to the patient a cyclin dependent kinase 4/6 inhibitor. The cyclin dependent kinase 4/6 inhibitor may be, for example, Palbociclib, Ribociclib or Abemaciclib.

In one embodiment the subject that has breast cancer or is at risk of having said cancer which includes subjects at risk of relapse is a subject that had received 1 and preferably 2 endocrine therapy treatments prior to initiation of a treatment with an ErbB-2/ErbB-3 bispecific antibody as described herein. The subject preferably received these prior treatments for treatment of a metastasis. The subject in addition preferably had received a cyclin-dependent kinase inhibitor prior to initiation of a treatment with an ErbB-2/ErbB-3 bispecific antibody as described herein.

DETAILED DESCRIPTION OF THE INVENTION

ErbB-2/ErbB-3 bispecific antibodies are described in PCT/NL2015/050125 published as WO2015/130173. This application is incorporated by reference herein. It is particularly referred for the nucleic acid molecules, the amino acid molecules and sequences encoding such a bispecific antibody or constant or variable parts thereof. It is also specifically referred to (and the references therein) for the production such a bispecific antibody.

EP17164292; EP17164382 and U.S. Ser. No. 15/476,260 also describe ErbB-2/ErbB-3 bispecific antibodies and uses thereof. EP17164292; EP17164382 and U.S. Ser. No. 15/476,260 are incorporated by reference herein.

In one embodiment the breast cancer is a hormone receptor positive breast cancer. In one embodiment the hormone positive breast cancer is an estrogen receptor positive breast cancer. In one embodiment the hormone positive breast cancer is a progesterone receptor positive breast cancer. Breast cancers are routinely tested for the presence of the mentioned hormone receptors and generally accepted classifications and tests are 25 available to the skilled person. Reference is made to Hammond et al (2010: J. of Clinical Oncology Vol 28: pp 2784-2794) which describe suitable tests and provides guidelines therefore. For example, a patient suitable for treatment according to the invention is one in which at least 1% of tumor nuclei, for example in a tumor biopsy, are immunoreactive; positive to estrogen receptor and/or progesterone receptor as determined by immunohistochemistry.

Further, another example of a suitable patient for treatment according to the invention is one with a cancer with documented hormone receptor positive status, estrogen receptor positive [ER+] and/or progesterone receptor positive [PR+]), including ≥1% positive stained cells by local standards, based on local analysis on the most recent tumor biopsy.

Further, another example of a suitable patient for treatment according to the invention is one with a cancer with documented hormone receptor positive status (estrogen receptor positive [ER+] and/or progesterone receptor positive [PR+]), for ≥1% positive cells as determined by immunohistochemistry on a tumor biopsy.

The breast cancer can be ErbB-2 negative or ErbB-2 positive. Wolff et al (2013: J. of Clinical Oncology Vol 31: pp 3997-4013) describe such tests and provide recommendations. A generally accepted stratification of breast cancers on the basis of ErbB-2 expression is ErbB-2−; ErbB-2+; ErbB-2++ without ErbB-2 gene amplification; ErbB-2++ with ErbB-2 gene amplification and ErbB-2+++. In one embodiment the breast cancer is an ErbB-2+ or an ErbB-2++ without ErbB-2 gene amplification breast cancer, which includes the absence of gene amplification at the level of detection. Fluorescence in situ hybridization (FISH) may be used to determine the presence or absence of gene amplification. Accordingly, a patient suitable for treatment according to the invention may be one with a cancer which shows no ErbB-2 gene amplification according to FISH analysis, understood by the person of ordinary skill in the art to be FISH negative.

A suitable patient for treatment according to the invention may be one which is ER-positive with low HER2 expression metastatic breast cancer (MBC) (immunohistochemistry (IHC) 1+, or IHC 2+ combined with negative fluorescence in situ hybridization (FISH).

In one embodiment the breast cancer is an ErbB-3 positive breast cancer.

In one embodiment bispecific antibody can reduce a ligand-induced receptor function of ErbB-3 on a ErbB-2 and ErbB-3 positive cell.

As used herein, the term "antigen-binding site" refers to a site derived from and preferably as present on an antibody which is capable of binding to antigen. An unmodified antigen binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain of the invention comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

As used herein, antigen binding refers to the typical binding capacity of an antibody to its antigen. An antibody comprising an antigen-binding site that binds to ErbB-3, binds to ErbB-3 and, under otherwise identical conditions, not to the homologous receptors ErbB-1 and ErbB-4 of the same species. Considering that the ErbB-family is a family of cell surface receptors, the binding is typically assessed on cells that express the receptor(s). An antibody of the invention preferably binds human ErbB-2, human ErbB-3 or a combination thereof.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other compounds as well, antibodies according to the present invention that bind ErbB-2 and/or ErbB-3 may recognize other proteins as well, if such other compounds contain the same epitope. Hence, the term "binding" does not exclude binding of the antibodies to another protein or protein(s) that contain the same epitope. Such other protein(s) is preferably not a human protein. An ErbB-2 antigen-binding site and an ErbB-3 antigen-binding site as defined in the present invention typically do not bind to other proteins on the membrane of cells in a post-natal, preferably adult human. A bispecific antibody according to the present invention is typically capable of binding ErbB-2 or ErbB-3 with a binding affinity of at least 1×10e-6 M, as outlined in more detail below.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand from binding to ErbB-3.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least 1×10e-6 M, more preferably 1×10e-7 M, more preferably higher than 1×10e-9 M. Typically, antibodies for therapeutic applications have affinities of up to 1×10e-10 M or higher. Antibodies such as the bispecific antibodies of the present invention may comprise the constant domains (Fc part) of a natural antibody. An antibody of the invention is typically a bispecific full length antibody, preferably of the human IgG subclass. Preferably, an antibody of the present invention is of the human IgG1 subclass. Such antibodies of the invention have good ADCC properties, have favorable half life upon in vivo administration to humans and CH3 engineering technology exists that can provide for modified heavy chains that preferentially form heterodimers over homodimers upon co-expression in clonal cells.

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fc portion. The terms 'variable domain', 'VH/VL pair', 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region. For instance, ADCC activity of an antibody can be improved when the antibody itself has a low ADCC activity, by slightly modifying the constant region of the antibody (Junttila, T. T., K. Parsons, et al. (2010). "Superior In vivo Efficacy of Afucosylated Trastuzumab in the Treatment of HER2-Amplified Breast Cancer." Cancer Research 70 (11): 4481-4489)

Full length IgG antibodies are preferred because of their favourable half life and the need to stay as close to fully autologous (human) molecules for reasons of immunogenicity. An antibody of the invention is preferably a bispecific IgG antibody, preferably a bispecific full length IgG1 antibody. IgG1 is favoured based on its long circulatory half life in man. In order to prevent any immunogenicity in humans it is preferred that the bispecific IgG antibody according to the invention is a human IgG1.

The term 'bispecific' (bs) means that one part of the antibody (as defined above) binds to one epitope on an antigen whereas a second part binds to a different epitope. The different epitope is typically present on a different antigen. According to the present invention, said first and second antigens are in fact two different proteins. A preferred bispecific antibody is an antibody that comprises parts of two different monoclonal antibodies and consequently binds to two different types of antigen. One arm of the bispecific antibody typically contains the variable domain of one antibody and the other arm contains the variable domain of another antibody. The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same, or a common, light chain is also referred to as a bispecific antibody with a common light chain. Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible heterodimerization domains, as defined hereunder.

The term 'compatible heterodimerization domains' as used herein refers to protein domains that are engineered such that engineered domain A' will preferentially form heterodimers with engineered domain B' and vice versa, whereas homodimerization between A'-A' and B'-B' is diminished.

The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998 and Nissim et al. 1994). Preferably, the common light chain has a germline sequence. A preferred germline sequence is a light chain variable region that is frequently used in the human repertoire and has good thermodynamic stability, yield and solubility. A preferred germline light chain is O12, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org). Further provided is therefore a bispecific antibody according to the invention, wherein said common light chain is a germline light chain, preferably a rearranged germline human kappa light chain comprising the IgVK1-39 gene segment, most preferably the rearranged germline human kappa light chain IgVK1-39*01/IGJK1*01. The terms rearranged germline human kappa light chain IgVκ1-39*01/IGJκ1*01, IGKV1-39/IGKJ1, huVκ1-39 light chain or in short huVκ1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-5 amino acid insertions, deletions, substitutions or a combination thereof.

Also contemplated are antibodies wherein a VH is capable of specifically recognizing a first antigen and the VL, paired with the VH in an immunoglobulin variable domain, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011), are different from bispecific antibodies of the invention and are further referred to as "two-in-one" antibodies.

The term ErbB-2' as used herein refers to the protein that in humans is encoded by the ERBB-2 gene. Alternative names for the gene or protein include CD340; HER-2; HER-2/neu; MLN 19; NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive tumor cells.

The term 'ErbB-3' as used herein refers to the protein that in humans is encoded by the ERBB-3 gene. Alternative names for the gene or protein are HER3; LCCS2; MDA-BF-1; c-ErbB-3; c-erbb-3; erbb-3-8; p180-Erbb-3; p45-sErbb-3; and p85-sErbb-3. Where reference is made herein to ErbB-3, the reference refers to human ErbB-3. An antibody comprising an antigen-binding site that binds ErbB-3, binds human ErbB-3. The ErbB-3 antigen-binding site, may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11 NC_018923.2 NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells.

A bispecific antibody of the invention that comprises a first antigen-binding site that binds ErbB-2 and a second antigen-binding site that binds ErbB-3, can reduce or reduces a ligand-induced receptor function of ErbB-3 on an ErbB-2 and ErbB-3 positive cell. In the presence of excess ErbB-2, ErbB-2/ErbB-3 heterodimers may provide a growth signal to the expressing cell in the absence of detectable ligand for the ErbB-8 chain in the heterodimer. This ErbB-3 receptor function is herein referred as a ligand-independent receptor function of ErbB-3. The ErbB-2/ErbB-3 heterodimer also provide a growth signal to the expressing cell in the presence of an ErbB-3 ligand. This ErbB-3 receptor function is herein referred to as a ligand-induced receptor function of ErbB-3.

The term "ErbB-3 ligand" as used herein refers to polypeptides which bind and activate ErbB-3. Examples of ErbB-3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

In a preferred embodiment of the invention the ligand-induced receptor function of ErbB-3 is ErbB-3 ligand-induced growth of an ErbB-2 and ErbB-3 positive cell. In a preferred embodiment said cell is an MCF-7 cell (ATCC® HTB-22™); an SKBR3 (ATCC® HTB-30™) cell; an NCI-87 (ATCC® CRL-5822™) cell; a BxPC-3-luc2 cell (Perkin Elmer 125058), a BT-474 cell (ATCC® HTB-20™) or a JIMT 1 cell (DSMZ no.: ACC 589).

In a preferred embodiment the ErbB-2 and ErbB-3 positive cell comprises at least 50.000 ErbB-2 receptors on the cell surface. In a preferred embodiment at least 100.000 ErbB-2 receptors. In one preferred embodiment, the ErbB-2 and ErbB-3 positive cell comprises at least 1.000.000 ErbB-2 receptors on the cell surface. In another preferred embodiment the ErbB-2 and ErbB-3 positive cell comprises no more than 1.000.000 ErbB-2 receptors on the cell surface. Currently used therapies such as trastuzumab (Herceptin) and pertuzumab are only prescribed for patients with malignant ErbB-2 positive cells that have more than 1.000.000 ErbB-2 receptors on their cell surface, in order to obtain a clinical response. Patients with ErbB-2 positive tumor cells with more than 1.000.000 ErbB-2 receptors on their cell surface are typically classified as ErbB-2 [+++]. Patients are for instance classified using the HercepTest™ and/or HER2 FISH (pharm Dx™), marketed both by Dako Denmark A/S, and/or using a HERmark® assay, marketed by Monogram Biosciences. Trastuzumab and pertuzumab are only prescribed to ErbB-2 [+++] patients because patients with lower ErbB-2 concentrations typically do not exhibit a sufficient clinical response when treated with trastuzumab and pertuzumab. The invention, however, provides bispecific antibodies that also have an improved binding affinity for cells with a lower ErbB-2 receptor concentration, as compared to trastuzumab. As shown in the Examples, proliferation of such cells with lower ErbB2 expression is effectively counteracted with an antibody according to the invention. Such lower ErbB-2 receptor concentration is present on malignant cells of patients that are classified as ErbB-2 [++] or ErbB-2 [+]. Also, relapsed ErbB-2 positive tumors often have an ErbB-2 receptor concentration of lower than 1.000.000 receptors per cell. Such ErbB-2 [++] or ErbB-2 [+] patients, as well as patients with a relapsed ErbB-2 positive tumor, are therefore preferably 20 treated with a bispecific antibody according to the present invention. Further provided is therefore a bispecific antibody comprising a first antigen-binding site that binds ErbB-2 and a second antigen-binding site that binds ErbB-3, wherein the antibody can reduce ligand-induced growth of an ErbB-2 and ErbB-3 positive cell that has less than 1.000.000 ErbB-2 cell-surface receptors. Also provided is a method for the treatment of a subject having a ErbB-2, ErbB-3 or ErbB-2/ErbB-3 positive tumor or at risk of having said tumor, wherein said tumor has less than 1.000.000 ErbB-2 cell-surface receptors per cell, the method comprising administering to the subject a bispecific antibody or pharmaceutical composition according to the invention. A bispecific antibody according to the invention for use in the treatment of a subject having or at risk of having an ErbB-2, ErbB-3 or ErbB-2/ErbB-3 positive tumor, wherein said tumor has less than 1.000.000 ErbB-2 cell-surface receptors per cell, is also herewith provided. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity of said second antigen-binding site for an ErbB-3 positive cell is equal to, or higher than, the affinity of said first antigen-binding site for an ErbB-2 positive cell, as explained herein below in more detail. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody according to the invention preferably comprises an antigen-binding site that binds at least one amino acid of domain III of ErbB-3 selected from the group consisting of R426 and surface exposed amino acid residues that are located within 11.2 Å from R426 in the native ErbB-3 protein.

To establish whether a tumor is positive for ErbB-3 the skilled person can for instance determine the ErbB-3 gene amplification and/or staining in immunohistochemistry. At least 10% tumor cells in a biopsy should be positive. The biopsy can also contain 20%, 30% 40% 50% 60% 70% or more positive cells.

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody of the invention, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the MCF-7 cell line (ATCC® HTB-22™), the SKBR3 cell line (ATCC® HTB-30™) cells, the JIMT 1 cell line (DSMZ ACC 589) or the NCI-87 cell line (ATCC® CRL-5822™). The test and/or the ligand for determining ErbB-3 ligand-induced receptor function is preferably a test for ErbB-3 ligand induced growth reduction as specified in the examples.

The ErbB-2 protein contains several domains (see for reference FIG. 1 of Landgraf, R. Breast Cancer Res. 2007; 9 (1); 202-). The extracellular domains are referred to as domains I-IV. The place of binding to the respective domains of antigen-binding sites of antibodies described herein has been mapped (see examples). A bispecific antibody of the invention with an antigen-binding site (first antigen-binding site) that binds domain I or domain IV of ErbB-2 (first antigen-binding site) comprises a heavy chain variable region that maintains significant binding specificity and affinity for ErbB-2 when combined with various light chains. Bispecific antibodies with an antigen-binding site (first antigen-binding site) that binds domain I or domain IV of ErbB-2 (first antigen-binding site) and an antigen-binding site for ErbB-3 (second antigen-binding site) were found to be more effective in reducing a ligand-induced receptor function of ErbB-3 when compared to a bispecific antibody comprising an antigen-binding site (first antigen-binding site) that binds to another extra-cellular domain of ErbB-2. A bispecific 20 antibody comprising an antigen-binding site (first antigen-binding site) that binds ErbB-2, wherein said antigen-binding site binds to domain I or domain IV of ErbB-2 is preferred. Preferably said antigen-binding site binds to domain IV of ErbB-2. A bispecific antibody with an antigen-binding site (first antigen-binding site) that binds ErbB-2, and that further comprises ADCC was found to be more effective than other ErbB-2 binding antibodies that did not have significant ADCC activity, particularly in vivo. A bispecific antibody according to the invention which exhibits ADCC is therefore preferred. It was found that antibodies wherein said first antigen-binding site binds to domain IV of ErbB-2 had intrinsic ADCC activity. A domain I binding ErbB-2 binding antibody that has low intrinsic ADCC activity can be engineered to enhance the ADCC activity Fc regions mediate antibody function by binding to different receptors on immune effector cells such as macrophages, natural killer cells, B-cells and neutrophils. Some of these receptors, such as CD16A (FcγRIIIA) and CD32A (FcγRIIA), activate the cells to build a response against antigens. Other receptors, such as CD32B, inhibit the activation of immune cells. By engineering Fc regions (through introducing amino acid substitutions) that bind to activating receptors with greater selectivity, antibodies can be created that have greater capability to mediate cytotoxic activities desired by an anti-cancer Mab.

One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb.

Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are typically co-incubated with the antibody-labeled target cells. Target cell lysis is subsequently typically measured by release of intracellular label, for instance by a scintillation counter or spectrophotometry. A preferred test is detailed in the Examples.

One advantage of the present invention is the fact that binding of antibodies according to the invention such as for instance PB4188 to ErbB-2 and ErbB-3 positive cells results in internalization that is to the same extent as compared to trastuzumab. If a combination of trastuzumab and pertuzumab is used, internalization of these antibodies is enhanced. This enhanced internalization, however, results in reduced ADCC. An antibody according to the present invention resulting in internalization that is essentially to the same extent as compared to trastuzumab is, therefore, preferred over a combination of trastuzumab and pertuzumab because with such antibody the ADCC activity is better maintained.

An antibody of the invention comprising an antigen-binding site that binds ErbB-3, interferes with binding of an ErbB-3 ligand to ErbB-3. Such antibodies are more effective in reducing a ligand-induced receptor function of ErbB-3 on an ErbB-2 and ErbB-3 positive cell line, particularly in the context of a bispecific antibody that also comprises an antigen-binding site that binds ErbB-2.

Preferred embodiments of the current invention provide a bispecific antibody comprising a first antigen-binding site that binds ErbB-2 and a second antigen-binding site that binds ErbB-3, wherein said first antigen-binding site binds domain I of ErbB-2. As shown in the Examples, bispecific antibodies having these characteristics are well capable of binding ErbB-2 and ErbB-3 positive cells and counteracting their activity (such as the ligand-induced receptor function of ErbB-3 and the ligand-induced growth of an ErbB-2 and ErbB-3 positive cell). Moreover, bispecific antibodies according to the invention comprising a first antigen-binding site that binds domain I of ErbB-2 are particularly suitable for use in combination with existing anti-ErbB-2 therapies like trastuzumab and pertuzumab, because trastuzumab and pertuzumab bind different domains of ErbB-2. Trastuzumab binds domain IV of ErbB-2 and pertuzumab binds domain II of ErbB-2. Hence, bispecific antibodies according to the invention that bind domain I of ErbB-2 are preferred because they do not compete with trastuzumab and pertuzumab for the same epitope.

Another preferred embodiment provides a bispecific antibody comprising a first antigen-binding site that binds ErbB-2 and a second antigen-binding site that binds ErbB-3, wherein said second antigen-binding site binds domain III of ErbB-3. Such antibody according to the invention is particularly suitable for combination therapy with currently used anti-ErbB-3 binding molecules that do not bind domain III of ErbB-3, such as MM-121 (Merrimack Pharmaceuticals; also referred to as #Ab6) and RG7116 (Roche) that bind domain I of ErbB-3, because then the different binding molecules do not compete with each other for the same epitope.

Preferably, a bispecific antibody is provided that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3. Such antibody is particularly suitable for combination therapy with anti-ErbB-2 binding molecules that do not bind domain I of ErbB-2, such as trastuzumab and pertuzumab, and with anti-ErbB-3 binding molecules 35 that do not bind domain III of ErbB-8, such as MM-121 (#Ab6) and RG7116.

One preferred embodiment provides a bispecific antibody that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3 and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

Further embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Contrary to bispecific compounds such as for instance MM 111 from Merrimack Pharmaceuticals, which have a higher affinity for ErbB-2 than for ErbB-3, the present invention provides bispecific antibodies which have an ErbB-3-specific arm with an affinity for ErbB-3 on cells that is higher than the affinity of the ErbB-2-specific arm for ErbB-2 on cells. Such bispecific antibodies are better capable of binding ErbB-3, despite the low cell surface concentration of ErbB-3. This provides the advantage that the functional activity against ErbB-3 is enhanced as compared to prior art 20 compounds, meaning that these bispecific antibodies according to the invention are better capable of counteracting ErbB-3 activity (such as ligand-induced growth).

As used herein, the term "affinity" refers to the KD value.

The affinity (KD) of said second antigen-binding site for an ErbB-3 positive cell is preferably lower than or equal to 2.0 nM, more preferably lower than or equal to 1.5 nM, more preferably lower than or equal to 1.39 nM, more preferably lower than or equal to 0.99 nM. In one preferred embodiment, the affinity of said second antigen-binding site for ErbB-3 on SK BR 3 cells is lower than or equal to 2.0 nM, more preferably lower than or equal to 1.5 nM, more preferably lower than or equal to 1.39 nM, preferably lower than or equal to 0.99 nM. In one embodiment, said affinity is within the range of 1.39-0.59 nM. In one preferred embodiment, the affinity of said second antigen-binding site for ErbB-3 on BT 474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples.

The affinity (KD) of said first antigen-binding site for an ErbB-2 positive cell is preferably lower than or equal to 5.0 nM, more preferably lower than or equal to 4.5 nM, more preferably lower than or equal to 3.9 nM. In one preferred embodiment, the affinity of said first antigen-binding site for ErbB-2 on SK BR 3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said first antigen-binding site for ErbB-2 on BT 474 cells is lower than or equal to 5.0 nM, preferably lower than or equal to 4.5 nM, more preferably lower than or equal to 3.9 nM. In one embodiment, said affinity is within the range of 4.5-3.3 nM. The above-mentioned affinities are preferably as measured using steady state cell affinity measurements, wherein cells are incubated at 4° C. using radioactively labeled antibody, where after cell-bound radioactivity is measured, as described in the Examples.

In one preferred embodiment, a bispecific antibody according to the invention is provided, wherein the affinity (KD) of said bispecific antibody for BT 474 cells is lower than or equal to 5.0 nM, preferably lower than or equal to 4.5 nM, more preferably lower than or equal to 4.0 nM, more preferably lower than or equal to 3.5 nM, more preferably lower than or equal to 3.7 nM, preferably lower than or equal to 3.2 nM. In one embodiment, said affinity is within the range of 3.7-2.7 nM. In one preferred embodiment, a bispecific antibody according to the invention is provided, wherein the affinity of said bispecific antibody for SK BR 3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, preferably lower than or equal to 2.5 nM, more preferably lower than or equal to 2.0 nM. In one embodiment, said affinity is within the range of 2.4-1.6 nM. Again, the above-mentioned affinities are preferably as measured using steady state cell affinity measurements, wherein cells are incubated at 4° C. using radioactively labeled antibody, where after cell-bound radioactivity is measured, as described in the Examples.

Further preferred embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell, and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

The above-mentioned antibodies according to the invention with a high affinity for ErbB-3 preferably bind domain I of ErbB2 and/or domain III of ErbB-3. Further provided is, therefore, a bispecific antibody according to the invention that comprises a first antigen-binding site that binds domain I of ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Also provided is a bispecific antibody according to the invention that comprises a first antigen-binding site that binds ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell. In a particularly preferred embodiment a bispecific antibody according to the invention is provided that comprises a first antigen-binding site that binds domain I of ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell.

Said second antigen-binding site preferably binds domain III of ErbB-3 and has an affinity (KD) for an ErbB-S positive cell that is lower than or equal to 2.0 nM, more preferably lower than or equal to 1.5 nM, preferably lower than or equal to 1.39 nM, more preferably lower than or equal to 0.99 nM. In one preferred embodiment, said second antigen-binding site binds domain III of ErbB-3 and has an affinity for ErbB-3 on SK BR 3 cells that is lower than or equal to 2.0 nM, more preferably lower than or equal to 1.5 nM, preferably lower than or equal to 1.39 nM, more preferably lower than or equal to 0.99 nM. In one embodiment, said affinity is within the range of 1.39-0.59 nM. In one preferred embodiment, said second antigen-binding site binds domain III of ErbB-3 and has an affinity for ErbB-3 on BT 474 cells that is lower than or equal to 2.0 nM, more preferably lower than or equal to 1.5 nM, more preferably lower than or equal to 1.0 nM, more preferably lower than or equal to 0.5 M, more preferably lower than or equal to 0.31 nM, more preferably lower than or equal to 0.23 nM. In one embodiment, said affinity is within the range of 0.31-0.15 nM.

Said first antigen-binding site preferably binds domain I of ErbB-2 and has an affinity (KD) for an ErbB-2 positive cell that is lower than or equal to 5.0 nM, more preferably lower than or equal to 4.5 nM, more preferably lower than or equal to 3.9 nM. In one preferred embodiment, said first antigen-binding site binds domain I of ErbB-2 and has an affinity for ErbB-2 on SK BR 3 cells that is lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.3 nM. In one embodiment, said affinity is within the range of 3.0-1.6 nM. The affinity of said bispecific antibody for SK BR 3 cells is preferably lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.4 nM, more preferably lower than or equal to 2.0 nM. In one embodiment, said affinity is within the range of 2.4-1.6 nM.

In one preferred embodiment, said first antigen-binding site binds domain I of ErbB-2 and has an affinity (KD) for ErbB-2 on BT 474 cells that is lower than or equal to 5.0 nM, more preferably lower than or equal to 4.5 nM, preferably lower than or equal to 3.9 nM. In one embodiment, said affinity is within the range of 4.5-3.3 nM. The affinity of said bispecific antibody for BT 474 cells is preferably lower than or equal to 5.0 nM, more preferably lower than or equal to 4.5 nM, more preferably lower than or equal to 4.0 nM, more preferably lower than or equal to 3.7 nM, more preferably lower than or equal to 3.2 nM. In one embodiment, said affinity is within the range of 3.7-2.7 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

Another preferred embodiment provides a bispecific antibody according to the invention comprising a first antigen-binding site that binds ErbB-2 and a second antigen-binding site that binds ErbB-3, wherein the antibody can reduce a ligand-induced receptor function of ErbB-3 on a ErbB-2 and ErbB-3 positive cell, wherein said bispecific antibody does not significantly affect the survival of cardiomyocytes. Cardiotoxicity is a known risk factor in ErbB-2 targeting therapies and the frequency of complications is increased when trastuzumab is used in conjunction with anthracyclines thereby inducing cardiac stress. For instance, the combination of doxycycline (DOX) with trastuzumab induces severe cardiac side effects. Clinical studies have estimated that 5% to 10% of patients who receive trastuzumab in the adjuvant setting of breast cancer develop cardiac dysfunction (Guarneri et al., J Clin Oncol., 1986, 3:818-26; Ewer M S et al., Nat Rev Cardiol 2010; 7:564-75). However, in a retrospective study, it was demonstrated that the risk for developing asymptomatic cardiac dysfunction is actually as high as about 25% when trastuzumab is used in the adjuvant setting with DOX (Wadhwa et al., Breast Cancer Res Treat 2009; 117:357-64). As shown in the Examples, the present invention provides antibodies that target ErbB-2 and that do not, or to a significantly lesser extent as compared to trastuzumab and pertuzumab, affect the survival of cardiomyocytes. This provides an important advantage since cardiotoxicity is reduced. This is already advantageous for people who do not suffer from an impaired cardiac function, and even more so for people who do suffer from an impaired cardiac function, or who are at risk thereof, such as for instance subjects suffering from congestive heart failure (CHF), loft ventricular dysfunction (LVD) and/or a ≥10% decreased Left Ventricular Ejection Fraction (LVEF), and/or subjects who have had a myocardial infarction. Antibodies according to the invention that do not significantly affect the survival of cardiomyocytes are, therefore, preferred. In vitro, the function of cardiomyocytes is for instance measured by determining the viability of cardiomyocytes, by determining BNP (B-type natriuretic peptide, which is a cardiac biomarker), by determining QT prolongation, and/or by determining mitochondrial membrane potential.

Said antibody according to the invention preferably comprises a first antigen-binding site that binds domain I of ErbB-2 and a second antigen-binding site that binds domain III of ErbB-3. One embodiment provides an antibody according to the invention that does not significantly affect the survival of cardiomyocytes, comprising a first antigen-binding site that binds ErbB-2 and a second antigen-binding site that binds ErbB-3, wherein the affinity of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment said antibody that does not significantly affect the survival of cardiomyocytes comprises:
at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2016, MF3991, MF3031, MF2889, MF2913, MF1847. MF3001, MF3003 and MF1898 as depicted in FIG. 10A or FIG. 10E, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or
at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6056; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or a heavy chain variable region sequence that differs in at most amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences. In one preferred embodiment, said antibody is PB4188.

Another aspect of the present invention provides an antibody according to the invention, comprising a first antigen-binding site that binds ErbB-2 and a second antigen-binding site that binds ErbB-3, wherein said antibody comprises an antigen-binding site that binds at least one amino acid residue of domain 1 of ErbB-2 selected from the group consisting of T144, T164, R166, P172. G179, S180 and R181, and surface-exposed amino acid residues that are located within about 5 amino acid positions from T144, T164, R166, P172, S179, S180 or R181. The amino acid residue numbering is that of Protein Data Bank (PDB) ID #1878. As shown in the Examples, antibodies binding this region of domain 1 of ErbB-2 exhibit, particularly good binding characteristics and they are capable of counteracting the activity of ErbB-2 positive cells (such as ligand-induced receptor function of ErbB-3 on a ErbB-2 and ErbB-3 positive cell, and/or ligand-induced growth of such cell). Moreover, such antibodies are particularly suitable for combination therapy with currently known anti-ErbB-2 monoclonal antibodies like trastuzumab (that binds domain IV of ErbB-2) and pertuzumab (that binds domain II of ErbB-2) because they bind different domains of ErbB-2. Hence, these antibodies can be used, simultaneously without competition for the same epitope. The term "surface-exposed amino acid residues that are located within about 6 amino acid positions from T144, T164, R166, P172, G179, 8180 or R181" refers to amino acid residues that are in the primary amino acid sequence located within about the first five amino acid residues adjacent to the recited residues and that are at least in part exposed to the outside of the protein, so that they can be bound by antibodies (see for instance FIG. 21B of WO2015/130173). Preferably, said amino acid residue located within about 5 amino acid positions from T144, T164, R166, P172, G179, S180 or R181 is selected from the group consisting of L139, C140, Y141, Q142, D143, I145, L146, W147, K148, D149, L159, T160, L161, 1162, D163, N165, S167, R168, A169, C170, H171, C173, S174, P175, M176, C177, K178, C182, W183, G184, E185 and 8186. Preferably, said antibody comprises an antigen-binding site that binds at least 2 or at least 3 amino acid residues of domain I of ErbB-2 selected from the group consisting of T144, T164, R166, P172, G179, S180 and R181, and surface-exposed amino acid residues that are located within 6 amino acid positions from T144, T164, R166, P172, G179, S180 or R181.

In one preferred embodiment, a bispecific antibody according to the invention is provided, wherein said antibody comprises an antigen-binding site that binds at least T144, R166 and R181 of domain I of ErbB-2. Another embodiment provides a bispecific antibody according to the invention, wherein said antibody comprises an antigen-binding site that binds at least T144, R166, P172, G179 and R181 of domain I of ErbB-2. Another embodiment provides a bispecific antibody according to the invention, wherein said antibody comprises an antigen-binding site that binds at least T144, T164, R166, P172. G179, S180 and R181 of domain I of ErbB-2.

Another aspect of the present invention provides an antibody comprising a first antigen-binding site that binds ErbB-2 and a second antigen-binding site that binds ErbB-3, wherein said antibody comprises an antigen-binding site that binds at least one amino acid of domain III of ErbB-3 selected from the group consisting R426 and surface-exposed amino acid residues that are located within 11.2 Å from R426 in the native ErbB-3 protein. The amino acid residue numbering is that of Protein Data Bank (PDB) ID #4P59. As shown in the Examples, antibodies binding this region of domain III of ErbB-3 exhibit particularly good binding characteristics and they are capable of counteracting the activity of ErbB-3 positive cells (such as ligand-induced receptor function of ErbB-3 on a ErbB-2 and ErbB-3 positive cell, and/or ligand-induced growth of such cell). The term "surface-exposed amino acid residues that are located within 11.2 Å from R426 in the native ErbB-3 protein" refers to amino acid residues that are in the tertiary structure of the ErbB-3 protein spatially positioned within 11.2 Å from R426 and that are at least in part exposed to the outside of the protein, so that they can be bound by antibodies. Preferably, said amino acid residues that are located within 11.2 Å from R426 in the native ErbB-3 protein are selected from the group consisting of L423, Y424, N425, G427, G452, R453, Y455, E480, R481, L482, D483 and K485 (see for instance FIG. 21C and Table 15 of WO2015/130173). In one preferred embodiment, a bispecific antibody according to the invention is provided, wherein said antibody comprises an antigen-binding site that binds at least R426 of domain III of ErbB-3. Preferably, said antibody comprises an antigen-binding site that binds at least R426 of domain III of ErbB-3.

A bispecific antibody of the invention is preferably afucosylated in order to enhance ADCC activity. A bispecific antibody of the invention preferably comprises a reduced amount of fucosylation of the N-linked carbohydrate structure in the Fc region, when compared to the same antibody produced in a normal CHO cell.

A bispecific antibody of the present invention is preferably used in humans. To this end a bispecific antibody of the invention is preferably a human or humanized antibody.

Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region. The constant region may contain one or more, preferably not more than 10, preferably not more than amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR region. The variable region of an ErbB-2 binding VH, an ErbB-3 binding VH, or a light chain in an antibody of the invention may contain one or more, preferably not more than 10, preferably not more than 5 amino acid differences with the variable region of a naturally occurring human antibody, not counting possible differences in the amino acid sequence of the CDR regions. Such mutations occur also in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

Such deimmunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an IgG1 constant region, preferably a mutated IgG1 constant region. Some variation in the constant region of IgG1 occurs in nature, such as for instance the allotypes G1m1, 17 and G1m3, and/or is allowed without changing the immunological properties of the resulting antibody. Typically between about 1-10 amino acid insertions, deletions, substitutions or a combination thereof are allowed in the constant region.

The invention in one embodiment provides an antibody comprising a variable domain that binds ErbB-2, wherein said antibody comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 10A or FIG. 10E, or wherein said antibody comprises a heavy chain CDR3 sequence that differs in at most three, preferably in at most two, preferably in no more than one amino acid from a CDR3 sequence of a VH selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 10A or FIG. 10E. Said antibody preferably comprises at least the CDR3 sequence of MF1849, MF2971, MF3958, MF3004 or MF3991, most preferably at least the CDR3 sequence of MF3958.

Said antibody preferably comprises at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 10A or FIG. 10E, or heavy chain CDR1, CDR2 and CDR3 sequences that differ in at most three, preferably in at most two, preferably in at most one amino acid from the CDR1, CDR2 and CDR3 sequences of MF2920, MF2930. MF1849; MF2973, MF3004, MF3958, MF2971, MF3025, MF2916, MF3991, MF3031, MF2889, MF2913, MF1847, MF3001, MF3003 or MF1898. Said antibody preferably comprises at least the CDR1, CDR2 and CDR3 sequences of MF1849, MF2971, MF3968, MF3004 or MF3991, most preferably at least the CDR1, CDR2 and CDR3 sequences of MF3958.

The invention also provides an antibody comprising a variable domain that binds ErbB-3, wherein said antibody comprises at least the CDR3 sequence of an ErbB-8 specific heavy chain variable region selected from the group consisting of MF3178; MF3176; MF3163; MF3099; MF3307;

MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or wherein said antibody comprises a heavy chain CDR3 sequence that differs in at most three, preferably in at most two, preferably in no more than one amino acid from a CDR3 sequence of a VH selected from the group consisting of MF3178; MF3176; MF3163; MF3099; MF3307; MF6055; MF6056; MF6057; MF6058; MF6069; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11. Said antibody preferably comprises at least the CDR3 sequence of MF3178, MF3176, MF3163, MF6058, MF6061 or MF6065, most preferably at least the CDR3 sequence of MF3178.

Said antibody preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074. Said antibody preferably comprises at least the CDR1, CDR2 and CDR3 sequences of MF3178, MF3176, MF3163, MF6068, MF6001 or MF6065, most preferably at least the CDR1, CDR2 and CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 10A or FIG. 10E, or a heavy chain CDR3 sequence that differs in at most three, preferably in at most two, preferably in no more than one amino acid from a CDRS sequence of a VH selected from the group consisting of MF2926, MF2930, MF1849; MF2973, MF3004, MF3958, MF2971, MF3025, MF2016, MF3991, MF3031, MF2889, MF2913, MF1847. MF3001, MF3003 and MF1898 as depicted in FIG. 10A or FIG. 10E, and wherein said second antigen-binding site comprises at least the CDR3 sequence of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or a heavy chain CDR3 sequence that differs in at most three, preferably in at most two, preferably in no more than one amino acid from a CDR3 sequence of a VH selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11. Said first antigen-binding site preferably comprises at least the CDR3 sequence of MF1849, MF2971, MF3958, MF3004 or MF3991, most preferably at least the CDR3 sequence of MF3958 and said second antigen-binding site preferably comprises at least the CDR3 sequence of MF3178, MF3176, MF3163, MF6058, MF6061 or MF6065, most preferably at least the CDR3 sequence of MF3178.

Said first antigen-binding site preferably comprises at least the CDR1, CDR2 and CDRS sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 10A or FIG. 10E, or heavy chain CDR1, CDR2 and CDR3 sequences that differ in at most three, preferably in at most two, preferably in at most one amino acid from the CDR1, CDR2 and CDR3 sequences of MF2926, MF2930, MF1849; MF2973, MF3004, MF3958, MF2971, MF3026, MF2916, MF3991, MF3031, MF2889, MF2913, MF1847. MF3001, MF3003 or MF1898, and said second antigen-binding site preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6056; MF6056; MF6057; MF6058; MF6059; MF6060; MF6001; MF6062; MF6063; MF6064; MF6065; MF6066; MF6067; MF6068; MF6069; MF6070; MF6071; MF6072; MF6073 or MF6074 as depicted in FIG. 10B or FIG. 10E or FIG. 11. Said first antigen-binding site preferably comprises at least the CDR1, CDR2 and CDR3 sequences of MF1849, MF2971, MF3958, MF3004 or MF3991, most preferably at least the CDR1, CDR2 and CDR3 sequences of MF3958, and said second antigen-binding site preferably comprises at least the CDR1, CDR2 and CDR3 sequences of MF3178, MF3176, MF3163, MF6058, MF6061 or MF6065, most preferably at least the CDR1, CDR2 and CDR3 sequence of MF3178.

One preferred embodiment provides a bispecific antibody comprising a first antigen-binding site that binds ErbB-2 and a second antigen-binding site that binds ErbB-3, wherein said first antigen-binding site comprises at least the CDR3 sequence of MF3958, or a CDR3 sequence that differs in at most three, preferably in at most two, preferably in no more than one amino acid from the CDR3 sequence of MF3958, and wherein said second antigen-binding site comprises at least the CDR3 sequence of MF3178, or a CDR3 sequence that differs in at most three, preferably in at most two, preferably in no more than one amino acid from the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3958, or CDR1. CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of MF3958 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-8, wherein said first antigen-binding site comprises at least the CDR1, CDR2 and CDR3 sequences of MF3958 80 and wherein said second antigen-binding site comprises at least the CDR1, CDR2 and CDR3 sequence of MF3178.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved ErbB-2 or ErbB-3-specific CDR sequence is preferably selected. A skilled person is well capable of generating antibody variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The invention in one embodiment provides an antibody comprising a variable domain that binds ErbB-2, wherein the VII chain of said variable domain comprises the amino acid sequence of VH chain MF2926; MF2930; MF1849; MF2973; MF3004; MF3958 (is humanized MF2971); MF2971; MF3026; MF2916; MF3991 (is humanized MF3004); MF3031; MF2889; MF2913; MF1847; MF3001, MF3003 or MF1898 as depicted in FIG. 10A or FIG. 10E; or comprises the amino acid sequence of VH chain MF2926; MF2930; MF1849; MF2978; MF8004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 10A or FIG. 10E having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the above mentioned VH chain sequence of FIG. 10A or FIG. 10E. The VH chain of the variable domain that binds ErbB-2 preferably comprises the amino acid sequence of:
  MF1849; or
  MF2071 or a humanized version thereof, wherein said humanized version preferably comprises the amino acid sequence of MF3958; or
  MF3004 or a humanized version thereof, wherein said humanized version preferably comprises the amino acid sequence of MF3991;
  as depicted in FIG. 10A. In one embodiment, the VH chain of the variable domain that binds ErbB-2 comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991, wherein the recited VH sequences have at most 15, preferably 1, 2, 3, 4, 6, 6, 7, 8, 9 or 10, more preferably at most 1, 2, 3, 4 or 5, amino acid insertions, deletions, substitutions or a combination thereof with respect to the respective sequence depicted in FIG. 10A. In a preferred embodiment the VH chain of the variable domain that binds ErbB-2 comprises the amino acid sequence of MF3958; or comprises the amino acid sequence of MF3958 depicted in FIG. 10A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-2 is preferably a bispecific antibody that preferably further comprises a variable domain that binds ErbB-3. The VH chain of the variable domain that binds Erb-B3 preferably comprises the amino acid sequence of VH chain MF3178; MF3176; MF3103; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 10B or FIG. 10E or FIG. 11; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 10B or FIG. 10E or FIG. 11 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VE chain sequence of FIG. 10B or FIG. 10E or FIG. 11. The VH chain of the variable domain that binds Erb-B3 preferably comprises the amino acid sequence of MF3178, MF3176, MF3163, MF6058, MF6061 or MF6065; or comprises the amino acid sequence of MF3178, MF3176, MF3163, MF6058, MF6061 or MF6065 having at most 15, preferably 1, 2, 3, 4, 5, 6, 7, 8, 9 or 10, more preferably in at most 1, 2, 3, 4 or 5, amino acid insertions, deletions, substitutions or a combination thereof with respect to the respective VH chain sequence of FIG. 10B or FIG. 11. In a preferred embodiment the VH chain of the variable domain that binds ErbB-3 comprises the amino acid sequence of MF3178; or comprises the amino acid sequence of MF3178 depicted in FIG. 10B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

The invention further provides an antibody comprising a variable domain that binds ErbB-3, wherein the VH chain of said variable region comprises the amino acid sequence of VH chain MF3178; MF3176; MF3163; MF3099; MF3307; MF6056; MF6056; MF6057; MF6058; MF6069; MF6060; MF6061; MF6062; MF6063; MF6064; MF0065; MF6066; MF6067; MF6068; MF6069; MF6070; MF6071; MF6072; MF6073 or MF6074 as depicted in FIG. 10B or FIG. 10E or FIG. 11, or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 10B or FIG. 10E or FIG. 11 having at most 15, preferably 1, 2, 3, 4, 5, 6, 7, 8, 9 or 10, more preferably at most 1, 2, 3, 4 or 6, amino acid insertions, deletions, substitutions or a combination thereof with respect to said VH chain sequence. The VH chain of the variable domain that binds ErbB3 preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH chain sequence. In a preferred embodiment the VH chain of the variable domain that binds ErbB-3 comprises the amino acid sequence of VH chain MF3178 depicted in FIG. 10B; or comprises the amino acid sequence of VH chain MF3178 depicted in FIG. 10B having at 25 most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-3, is preferably a bispecific antibody that preferably further comprises a variable domain that binds ErbB-2. The VH chain of the variable domain that binds ErbB-2 preferably comprises the amino acid sequence of a VH chain of FIG. 10A or FIG. 10E. The VH chain of the variable domain that binds ErbB-2 preferably comprises the amino acid sequence of MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 10A. In one embodiment, the recited Erb-B2 binding VII sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 10A. In one preferred embodiment, said ErbB-2 binding VH chain of FIG. 10A comprises the amino acid sequence of MF3958; or comprises the amino acid sequence of MF3958 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

Further provided is an antibody according to the invention, wherein said antibody comprises an ErbB-2 specific heavy chain variable region sequence selected from the group consisting of the heavy chain variable region sequences of MF2926, MF2930, MF1849; MF2978, MF3004, MF3958, MF2971, MF3025, MF2916, MF3991, MF3031, MF2889, MF2913, MF1847, MF3001, MF3003 and MF1898 as depicted in FIG. 10A or FIG. 10E, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 or MF1898.

Further provided is an antibody according to the invention, wherein said antibody comprises an ErbB-3 specific heavy chain variable region sequence selected from the group consisting of the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 10B or FIG. 10E or FIG. 11, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074.

The invention in one embodiment provides an antibody comprising two antigen-binding sites that bind ErbB-2, wherein at least one of said antigen-binding sites binds domain I of ErbB-2. Preferably, both antigen-binding sites bind domain I of ErbB-2. Such antibody according to the invention is particularly suitable for combination therapy with currently used anti-ErbB-2 binding molecules that do not bind domain I of ErbB-2, such as trastuzumab that binds domain IV of ErbB-2 and pertuzumab that binds domain II of ErbB-2, because then the different binding molecules do not compete with each other for the same epitope.

Farther provided is an antibody comprising two antigen-binding sites that bind ErbB-2, wherein at least one of said antigen-binding sites binds domain I of ErbB-2 and wherein the affinity (KD) of said at least one antigen-binding site for an ErbB-2 positive cell is lower than or equal to 5.0 nM, preferably lower than or equal to 4.5 nM, more preferably lower than or equal to 3.9 nM. Preferably, both antigen-binding sites bind domain I of ErbB-2. In one preferred embodiment, the affinity of said at least one antigen-binding site for ErbB-2 on SK BR 3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said at least one antigen-binding site for ErbB-2 on BT 474 cells is lower than or equal to 5.0 nM, preferably lower than or equal to 4.5 nM, more preferably lower than or equal to 3.9 nM. In one embodiment, said affinity is within the range of 4.5-3.3 nM.

The above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that bind ErbB-2, wherein a VH chain of said variable domains comprises the amino acid sequence of the VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 10A or FIG. 10E; or the amino acid sequence of the VH chain MF2926; MF2930; MF1849; MF2973; MF3004; MF3968 (is humanized MF2971); MF2971; MF3025; MF2916; MF3991 (is humanized MF3004); MF3031; MF2889; MF2913; MF1847; MF3001, MF3003 or MF1898 VH-chains as depicted in FIG. 10A or FIG. 10E, having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 10A or FIG. 10E. Said VH preferably comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 10A; or comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 10A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 10A. The variable domains of the antibody preferably comprise identical VH chains, preferably having a sequence as depicted in FIG. 10A or FIG. 10E. An antibody with variable domains with identical VH chains is not a bispecific antibody. VH chains are identical for the present invention if they comprise the same VH chain sequence as depicted in FIG. 10A or FIG. 10E or FIG. 11, or the same VH chain sequence but for 1, 2, 3, 4 or 5 amino acid insertions, deletions, substitutions or a combination thereof with respect to the respective sequence depicted in FIG. 10A or FIG. 10E or FIG. 11.

The invention in one embodiment provides an antibody comprising two antigen-binding sites that bind ErbB-3, wherein at least one of said antigen-binding sites binds domain III of ErbB-3. Preferably, both antigen-binding sites bind domain III of ErbB-3. Such antibody according to the invention is particularly suitable for combination therapy with currently used anti-ErbB-3 binding molecules that do not bind domain III of ErbB-3, such as MM-121 (#Ab6) and RG7116 that bind domain I of ErbB-3, because then the different binding molecules do not compete with each other for the same epitope.

Further provided is an antibody comprising two antigen-binding sites that bind ErbB-3, wherein at least one of said antigen-binding sites binds domain III of ErbB-3 and wherein the affinity (KD) of said at least one antigen-binding site for an ErbB-3 positive cell is lower than or equal to 2.0 nM, preferably lower than or equal to 1.5 nM, more preferably lower than or equal to 1.39 nM, more preferably lower than or equal to 0.99 nM. Preferably, both antigen-binding sites bind domain III of ErbB-3. In one preferred embodiment, the affinity of said at least one antigen-binding site for ErbB-3 on SK BR 3 cells is lower than or equal to 2.0 nM, preferably lower than or equal to 1.5 nM, more preferably lower than or equal to 1.39 nM, more preferably lower than or equal to 0.99 nM. In one embodiment, said affinity is within the range of 1.39-0.59 nM. In one preferred embodiment, the affinity of said at least one antigen-binding site for ErbB-3 on BT 474 cells is lower than or equal to 2.0 nM, more preferably lower than or equal to 1.5 nM, more preferably lower than or equal to 1.0 nM, more preferably lower than or equal to 0.5 nM, more preferably lower than or equal to 0.31 nM, more preferably lower than or equal to 0.23 nM. In one embodiment, said affinity is within the range of 0.31-0.15 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that each bind ErbB3 wherein a VH of the variable domains comprises the amino acid sequence of VH chain MF3178; MF3176; MF3163; MF3099; MF3307; MF6055; MF6056; MF6057; MF6058; MF6050; MF6060; MF6061; MF6062; MF6063; MF6064; MF6065; MF6066; MF6067; MF6068; MF6069; MF6070; MF6071; MF6072; MF6073 or MF6074 as depicted in FIG. 10B or FIG. 10E or FIG. 11; or comprises the amino acid, sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178; or comprises the amino acid sequence of VH chain MF3178 depicted in FIG. 10B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the MF3178 VH chain sequence. The variable domains of the antibody preferably comprise identical VH chains, preferably having a sequence as depicted in FIG. 10B or FIG. 10E or FIG. 11. An antibody with variable domains with identical VH chains is not a bispecific antibody. The VH chains are identical if they comprise the same VH chain sequence as depicted in FIG. 10B or FIG. 10E or FIG. 11, or the same VH chain sequence but for 1, 2, 3, 4 or 5 amino acid insertions, deletions, substitutions or a combination thereof with respect to the VH chain sequence of FIG. 10B or FIG. 10E or FIG. 11.

The ErbB-2/ErbB-3 specific antibody as disclosed herein is preferably a bispecific antibody. The antibody preferably comprises a variable domain with a heavy chain variable region comprising at least the CDR1, CDR2 and CDR3 sequence of an ErbB-2 specific heavy chain variable region of MF3958 as depicted in FIG. 10 or CDR sequences that differ in at most 3 amino acids, preferably in at most 2 amino acids, preferably in at most 1 amino acid from the CDR1, CDR2 and CDR3 sequence of MF3958 and a variable domain with a heavy chain variable region comprising at least the CDR1, CDR2 and CDR3 sequence of an ErbB-3 specific heavy chain variable region of MF3178 as depicted in FIG. 10 or CDR sequences that differ in at most 3 amino acids, preferably in at most 2 amino acids, preferably in at most 1 amino acid from the CDR1, CDR2 and CDR3 sequences of MF3178.

The ErbB-2/ErbB-3 specific antibody preferably comprises an ErbB-2 specific variable domain with a heavy chain variable region comprising the amino acid sequence of the heavy chain variable region of MF3958 as depicted in FIG. 10 with 0-10, preferably 0-6, preferably 0, 1 or 2 amino acid substitutions and an ErbB-3 specific variable domain with a heavy chain variable region comprising the amino acid sequence of the heavy chain variable region of MF3178 as depicted in FIG. 10 with 0-10, preferably 0-5, preferably 0, 1 or 2 amino acid substitutions. The light chain in these antibodies is preferably a light chain of FIG. 10C.

The method of treatment of a subject that has breast cancer or is at risk of having breast cancer preferably further comprises determining the expression level of the estrogen receptor, ErbB-2, ErbB-3, or a combination thereof on cells of said cancer.

The subject that has breast cancer or is at risk of having breast cancer is preferably a human. A person is said to be at risk of having breast cancer if that person has had breast cancer in the past but it is in remission thereof such that the cancer cannot be detected with routine check-ups. Such a person can be considered cured but this person has a higher risk of having breast cancer when compared to a normal healthy individual of the same age. The breast cancer can be a recurrent cancer at the position of the primary cancer which was in remission or a metastasis of the breast cancer typically at a position different from the position of the primary cancer site.

The invention also provides a method of treating of a subject that has breast cancer or is at risk of having said cancer, comprising administering to the subject in need thereof a therapeutically effective amount of an antibody that can bind an extra-cellular part of ErbB-2 and that inhibits ErbB-2/ErbB-3 dimerization on the cancer cell, wherein the cancer is a hormone receptor positive cancer. The antibody is preferably a bispecific antibody that has an antigen binding site that can bind an extra-cellular part of ErbB-2 and an antigen binding site that can bind an extra-cellular part of ErbB-3. The antibody is preferably a bispecific ErbB-2/ErbB-3 specific antibody as disclosed herein. The method preferably further comprises administering a therapeutically effective amount of an endocrine therapy drug to the subject in need thereof. The cancer is preferably an immunohistochemistry ErbB-2+ cancer or an immunohistochemistry ErbB-2++ without ErbB-2 gene amplification cancer Typically, the bispecific antibody and endocrine therapy will be administered repeatedly, over a course of treatment. For example, in certain embodiments, multiple (e.g., 2, 3, 4, 5, 6, 7, 8, 9, 10 or more) doses of an endocrine therapy and multiple (e.g., 2, 3, 4, 5, 6, 7, 8, 9, 10 or more) doses of a bispecific antibody are administered to a subject in need of treatment.

In some embodiments, administrations of an endocrine therapy may be given daily, on several days of the week, weekly, biweekly, every 3 or 4 weeks, or with longer intervals) and a bispecific antibody may be given weekly, biweekly, every 3 or 4 weeks, or with longer intervals. The bispecific antibody and endocrine therapy may be, but are not necessarily administered according to the same regimen of administration. Thus, endocrine therapy and the bispecific antibody may be given the same day or in different days, in different sequences (first endocrine, second bispecific, or vice versa). The endocrine therapy may be administered 1 or more days before or after the bispecific antibody or vice versa.

In some embodiments, the dose of the bispecific antibody and/or endocrine therapy is varied over time. The dose of the endocrine therapy and or the bispecific can be the same along the whole treatment. Alternatively, the dose of the endocrine therapy and/or the bispecific can be higher at the beginning, for example a load higher dose (which could be a unique or several doses) followed by a maintenance dose. Alternatively, the dose of the endocrine therapy and/or the bispecific can be lower at the beginning (which could be a unique or several doses) followed by a maintenance dose. In addition, or alternatively, the initial regimen of administration of the endocrine therapy of the agents or both, that started as a weekly regimen can change to biweekly regimen or other. A clinician may utilize preferred dosages and/or dosage regimes as warranted by the condition of the patient being treated Treatment with the endocrine therapy may be initiated with smaller dosages which are less than the optimum dose of the compound. Thereafter, the dosage may be increased by small amounts until the optimum effect under the circumstances is reached. For convenience, the total daily dosage may be divided and administered in portions during the day if desired. Intermittent therapy (e.g., one week out of three weeks or three out of four weeks) may also be used.

In certain embodiments, the bispecific antibody is administered at a flat dose of about 750 mg every 3 weeks, but alternatively may be given in a range of dose of from 300 mg to 900 mg flat dose in a regimen of administration of weekly, biweekly, every 3 weeks, every 4 weeks or with longer intervals.

Where herein ranges are given as between number 1 and number 2, the range includes the number 1 and number 2. For instance a range of between 2-5 includes the numbers 2 and 5.

When herein reference is made to an affinity that is higher than another, the Kd=lower than the other Kd. For the avoidance of doubt a Kd of 10e-9 M is lower than a Kd of 10e-8 M. The affinity of an antibody with a Kd of 10e-9 M for a target is higher than when the Kd is 10e-8 M.

For the purpose of clarity and a concise description, features are described herein as part of the same or separate embodiments, however, it will be appreciated that the scope of the invention may include embodiments having combinations of all or some of the features described.

BRIEF DESCRIPTION OF THE DRAWINGS

FIG. 1. Mean and Individual tumor growth changes in human HBCx-34 breast tumor xenograft. Treatments started 36 days post HBCx-34 implantation. Vehicle MCLA-128 and MCLA-128 25 mg/kg were administered on D0, D3, D7, D10, D14, D17, D21, D24, D28, D31, D35, D38, D42, D45, D49, D52, D56 and vehicle Letrozole and Letrozole 2.5 mg/kg were administered daily for 57 days. Initial group size: 9-10 animals.

FIG. 2. T/C % in human HBCx-34 breast tumor xenograft. Treatments started 36 days post HBCx-34 implantation. Vehicle MCLA-128 and MCLA-128 25 mg/kg were administered D0, D3, D7, D10, D14, D17, D21, D24, D28.

D31, D35, D38, D42, D45, D49, D52, D56 and vehicle Letrozole and Letrozole 2.5 mg/kg were administered daily for 57 days. Initial group size: 9-10 animals.

FIG. 3. Mean and Individual relative body weight changes in human HBCx-34 breast tumor xenograft. Treatments started 36 days post HBCx-34 implantation. Vehicle MCLA-128, MCLA-128 25 mg/kg were administered on DO, D3, D7, D10, D14, D17, D21, D24, D28, D31, D35, D38, D42, D45, D49, D52, D56 and vehicle Letrozole and Letrozole 2.5 mg/kg were administered daily for 57 days. Initial group size: 9-10 animals.

Figure 4B:
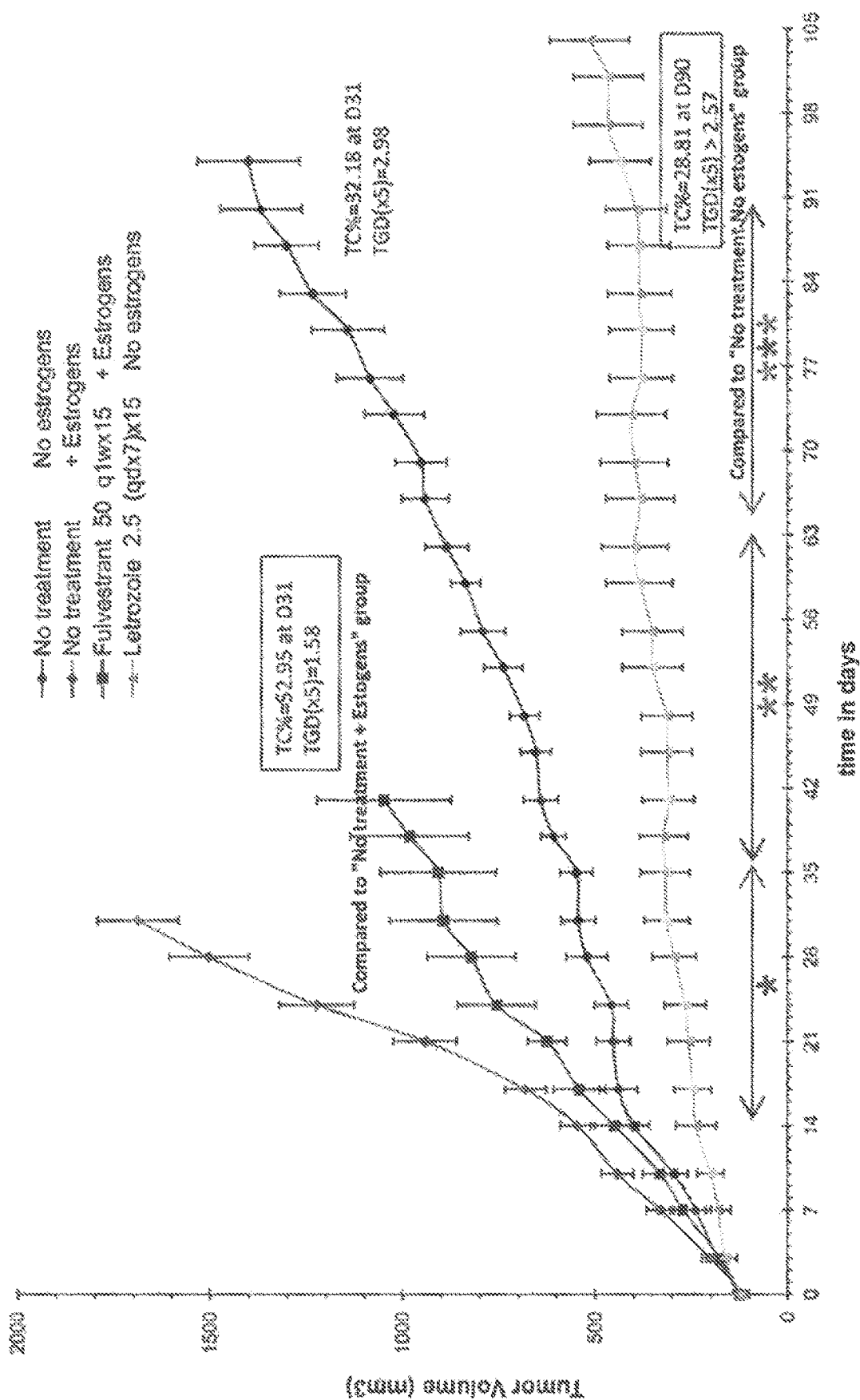

FIG. 4. In vivo growth characteristics of the HBCx-34 PDX model. A, IHC characteristics of HBCx-34 PDX tumors. B, Athymic nude mice were engrafted s.c. with HBCx-34 tumors. Animals supplemented with estrogens were treated with either vehicle of Fulvestrant and animals that did not receive estrogens were treated with vehicle or Letrozole. The supplementation of estrogen induced a faster tumor growth and Letrozole significantly reduced the formation of estrogen-independent tumors. T-tests were performed to compare tumor volumes from estrogen-independent tumors treated with vehicle or Letrozole (*, $p<0.05$, , $p<0.01$, *, $p<0.001$).

Figure 5:
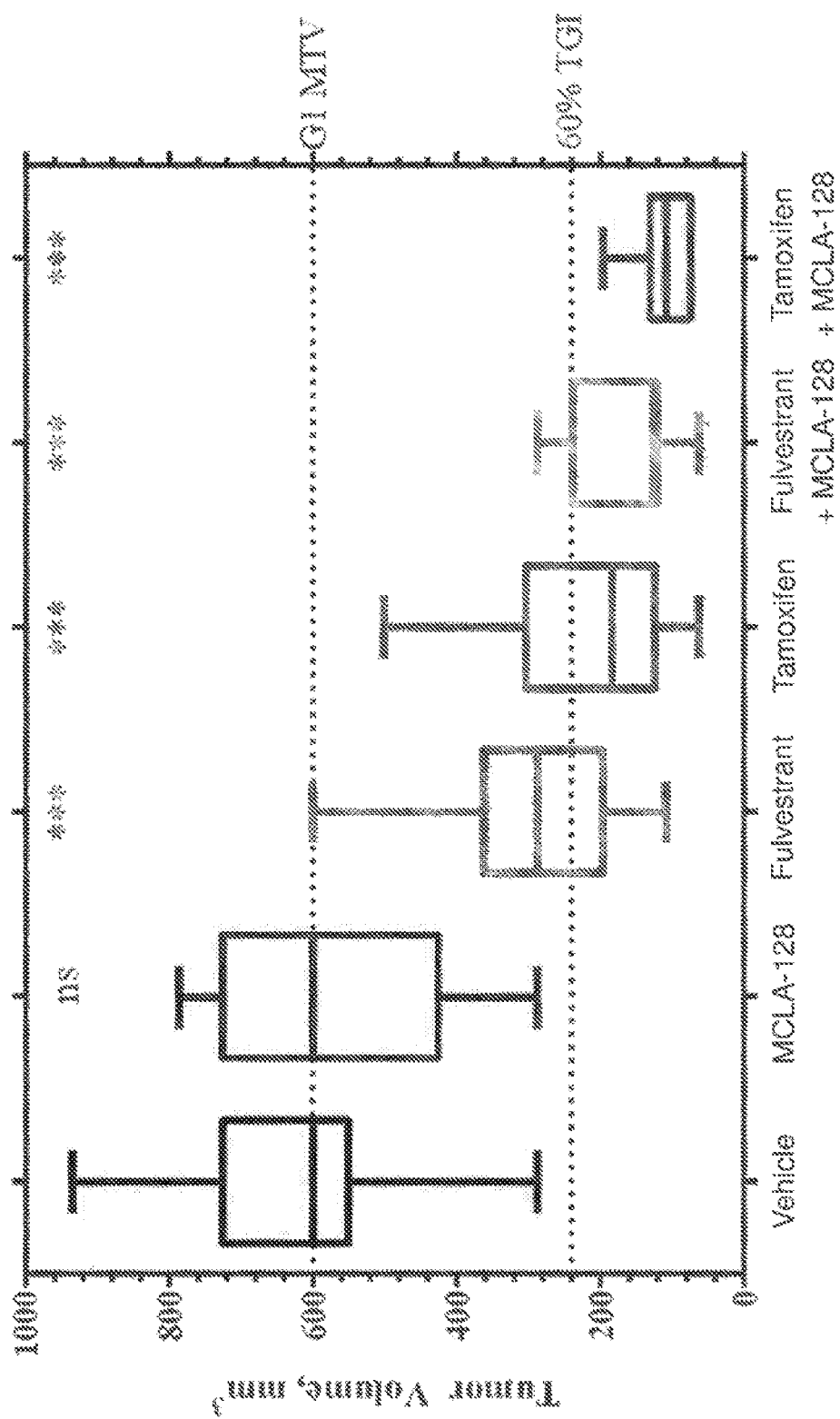

FIG. 5. Tumor volumes of MCF-7 xenograft mice at day 25. Treatments started

MCLA-128 vehicle, MCLA-128 25 mg/kg were administered on DO, D1, D4, D8, D11, D15 D22 and D25 and hormone therapy vehicle and Tamoxifen were administered every other day (D1, D3, D5, etc.). Fulvestrant was administered once weekly. Statistical significance for Kruskal Wallis Dunn's or Mann-Whitney U test for comparison with vehicle group: ns indicates non-significant, * indicates $0.01<P<0.05$,  indicates $0.001<P<0.01$, * indicates $P<0.001$. TGI>60% indicates potential therapeutic activity. MTV: mean tumor volume, G1 MTV: Group 1 (vehicle) MTV, TGI: tumor growth inhibition.

Figure 6:
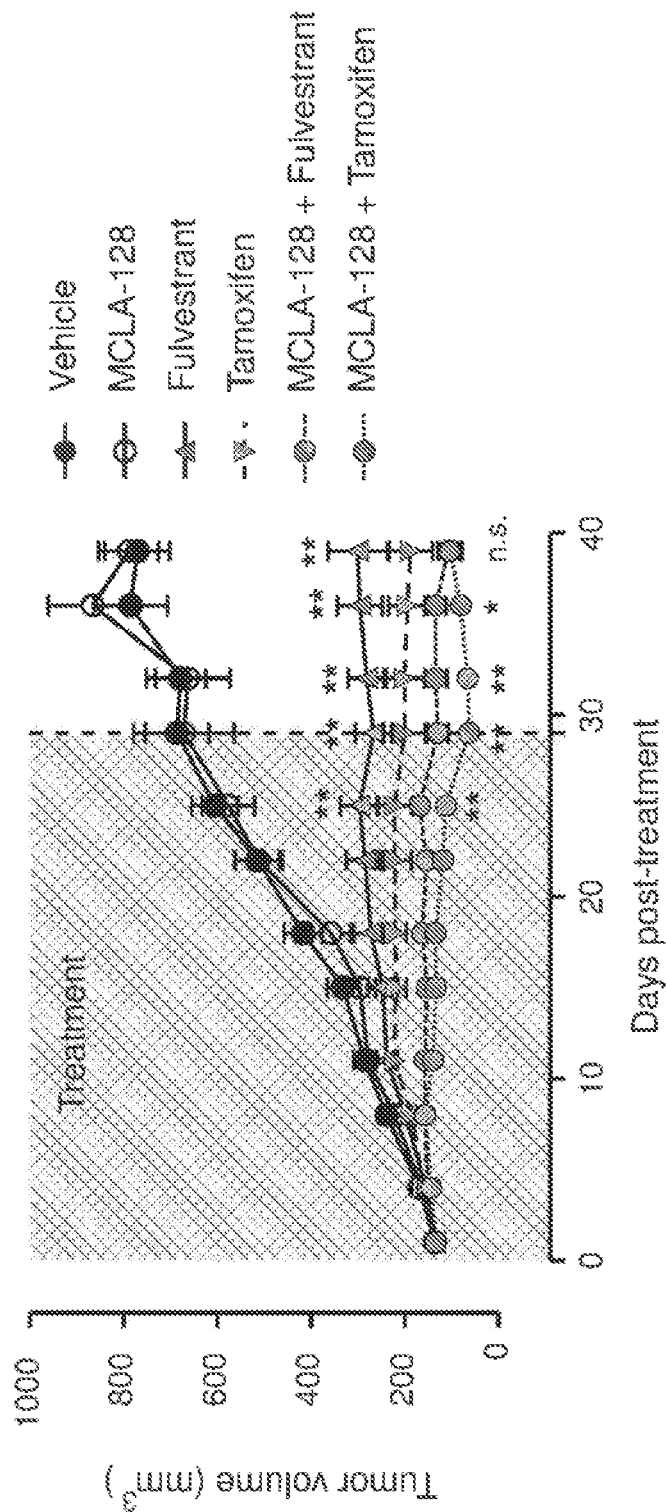

FIG. 6. Tumor volumes of MCF-7 xenograft mice treated with MCLA-128, Fulvestrant or Tamoxifen as single agent or combination therapies. For each timepoint, a statistical t-test compared Fulvestrant vs Fulvestrant+MCLA-128 and Tamoxifen vs Tamoxifen+MCLA-128. N.s. indicates non-significant, * indicates $P<0.05$; ** indicates $P<0.01$.

Figure 7:
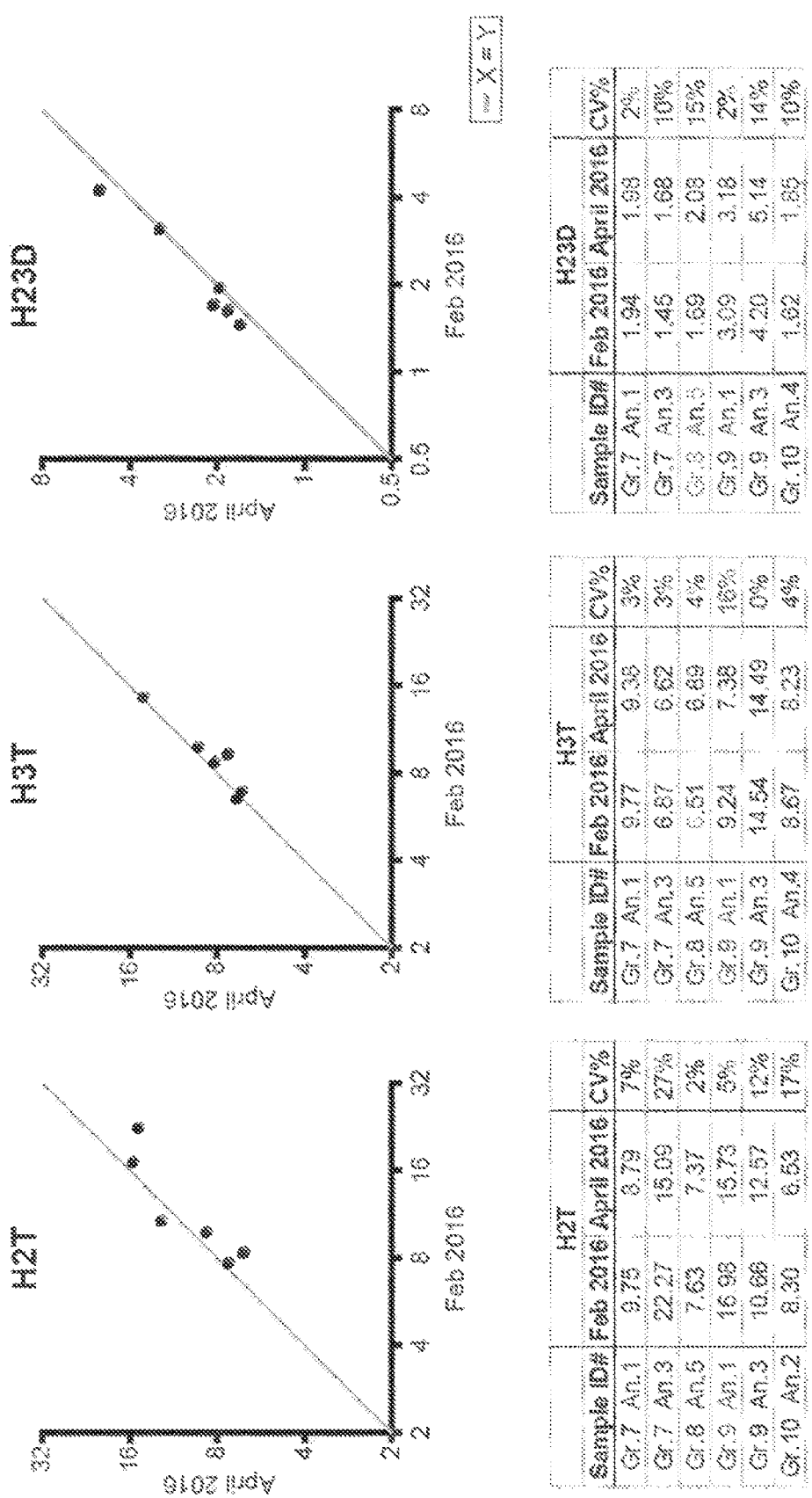

FIG. 7. Inter assay correlation between two independent VeraTag assays. Assay scores obtained in assays Round 1 and Round 2 were plotted in an XY graph and compared using x=y linear regression. All assays showed good correlation between the results of the two time points with only the "Gr.7 An.3" sample showing more than 20% coefficient variation (CV %).

Figure 8:
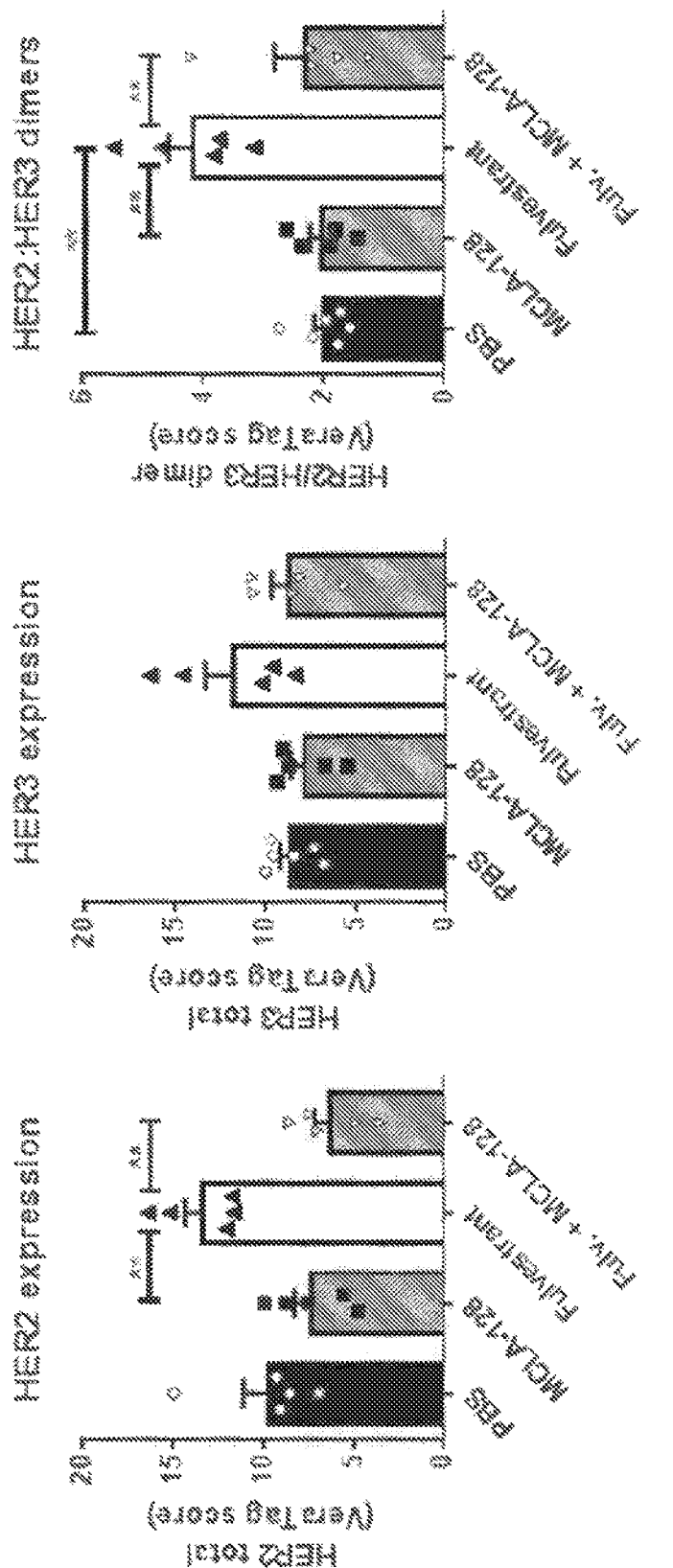

FIG. 8. Modulation of levels of total HER2, total HER3 and HER2:HER3 dimers in MCF-7 tumors after 8 day treatment period. Xenograft mice were treated for 8 days with a total of 3 doses of MCLA-128 or 2 doses of Fulvestrant or the combination thereof. 24 hours after the last dose, tumors were harvested, processed to FFPE and subjected to VeraTag analysis for the indicated assays. Five independent tumors per treatment group were used for the final analysis. A statistical t-test compared all groups independently. * indicates $P<0.01$.

Figure 9:
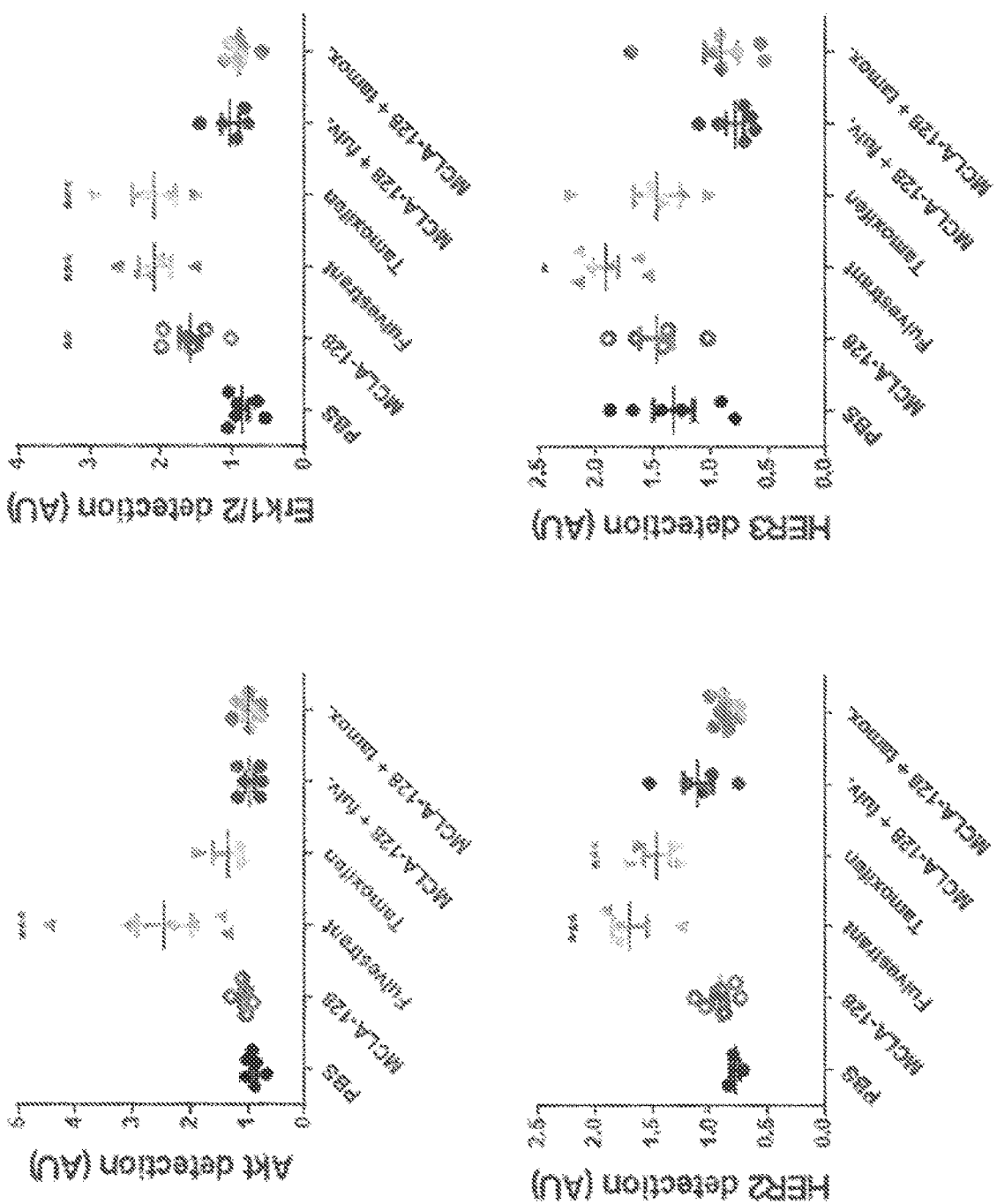

FIG. 9. Reverse phase protein array (RPPA) in MCF-7 tumor xenografts treated with vehicle, MCLA-128, Fulvestrant, Tamoxifen, MCLA-128+ Fulvestrant or MCLA-128+ Tamoxifen. Proteins detected in this assay included (phospho)-Akt and (phospho)-HER3 (full data provided in Appendix 4). One-way ANOVA compared levels in all tumors derived from treatment groups with those derived from the PBS group. ** indicates $P<0.01$.

FIG. 10. Nucleic acid and amino acid sequences of VH-chains (10A, SEQ ID NOs: 1-55; 10B, SEQ ID NOs: 56-80; 10E, SEQ ID NOs: 84-128), common light chain (10C, SEQ ID NO:81) and heavy chains (10D, SEQ ID NOs: 82-83) of antibodies of the invention. Where in this figure a leader sequence is indicated this is not part of 20 the VH chain or antibody, but is typically cleaved of during processing of the protein in the cell that produces the protein.

FIG. 11. Amino acid and nucleotide alignments of the MF3178 variants. The amino acid sequence of MF3178 (SEQ ID NO:57) is compared to the amino acid sequences of MF3178 variants (SEQ ID NOs: 130, 132, 134, 115, 138, 140, 120, 144, 146, 148, 125, 152, 154, 156, 158, 160, 162, 164, 166, and 168). CDR regions are indicated. A alignment for the variant nucleic acid sequences (SEQ ID NOs: 114, 119, and 124) is presented, showing the sequences aligned to nucleotides 20-391 of the nucleic acid sequence of MF3178 (SEQ ID NO: 56). MF3178 variant DNA sequences are presented (SEQ ID NOs: 129, 131, 135, 137, 139, 141, 143, 145, 147, 149, 151, 153, 155, 157, 159, 161, 163, 165, and 167).

Figure 12:
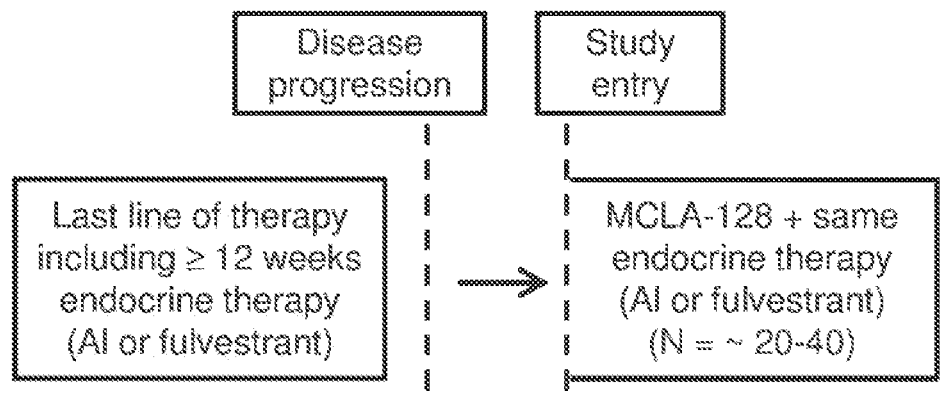

FIG. 12. Study design for combination therapy: MCLA-128+ endocrine treatment.

Figure 13:
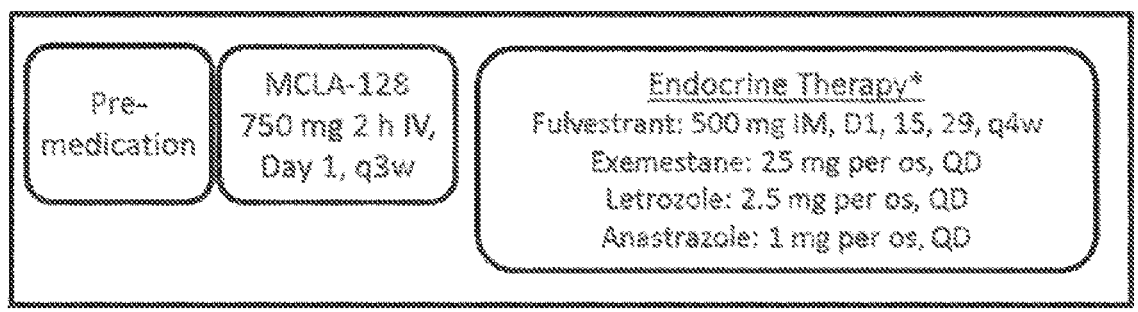

FIG. 13. Treatment administration for combination therapy study: MCLA-128+ endocrine treatment-all cycles.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of the variable region of the light chain of FIG. 10C. The light chain is typically the light chain as indicated in FIG. 10C. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The VH variable regions of the heavy chains differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example 1

Antitumor efficacy of an HER2/HER3 targeting antibody was determined in the context of a combination treatment together with an aromatase inhibitor. MCLA-128 was used as a preferred example of a bispecific Her2/Her3 targeting antibody. It was used as single agent and in combination with the aromatase inhibitor Letrozole. The hormone-dependent HBCx-34 patient-derived breast cancer xenograft model established in immunodeficient mice was used as an example of a breast cancer.

The Human Tumor Xenograft Models

Human tumor samples of various histological origins were obtained with informed consent from patients treated at cancer centers and established as transplantable xenografts in immunodeficient mice. The grafted samples are residual material from primary tumors or metastases obtained before or after treatment. These patient-derived xenograft (PDX)

models have been established without prior in vitro culture and have been studied for histology, cytogenetics, genetic and other biological markers, and for their response to standard-of-care (SOC) therapies.

The HBCx-34 PDX model was derived from a treatment-naïve primary breast infiltrating ductal carcinoma. The HBCx-34 PDX model has a mutated ATM (gene coding for a protein implicated in double strand DNA repair) and wt p53, is ER+/PR+, and is responder to Docetaxel, Capecitabine, Tamoxifen and the combination Adriamycin/Cyclophosphamide and low responder to Letrozole.

The HBCx-34 tumor model takes about 35 days to obtain the maximum of tumors in the range 60 to 200 mm$^3$ and about 80 days to reach 2000 mm$^3$ from implantation day (with estrogen supplementation). HBCx-34 has got no overt cachectic properties, but not body weight gain is observed in HBCx-34-bearing mice MCLA-128 is as an ADCC-enhanced IgG1 bispecific antibody that targets the HER2:HER3 dimer. MCLA-128 demonstrates an in vitro potency superior to other anti-HER2 and anti-HER3 antibodies in cells stimulated with high concentrations of heregulin (HRG) thereby overcoming one of the resistance mechanisms of current HER2 therapies.

Tumor-bearing mice received estrogen diluted in drinking water (β-oestradiol, 8.5 mg/l), from the date of tumor implant to the date of inclusion. During the treatment period, mice were not supplemented with estrogen.

Animals and Maintenance Conditions

Outbred athymic (nu/nu) female mice (<<HSD: Athymic Nude-Fox$^{nu}$>>) weighing 18-25 grams (Harlan Laboratories, Gannat, France) were allocated to acclimate in the animal facility with access to food and water ad libitum for at least 6 days prior to manipulation (Scheme 4-1).

Scheme 4-1 Animal Characteristics

| Species | Strain | Supplier | Gender | Weight | Age at reception |
|---|---|---|---|---|---|
| Mouse (Mus musculus) | Athymic Nude - Foxn1$^{nu}$ | Harlan, France | Female | 18-25 | 5 weeks |

Test Compound and Formulations

The MCLA-128 vehicle was ready-to-use and used for dosing from day 0 to day 38 and stored at +4° C. Then, from day 42 to day 56 (end of the study), 0.9% NaCl (CDM Lavoisier batch 6F134) was used as vehicle for dosing and MCLA-128 preparation. The 0.9% NaCl aliquots (CDM Lavoisier batch 6F134) were weekly prepared from day 42 to day 56 and stored at +4° C. The Letrozole vehicle (CDM Lavoisier batch 6F134): 0.9% NaCl was ready-to-use. The 0.9% NaCl aliquots (CDM Lavoisier batch 6F134) were weekly prepared and stored at +4° C.

MCLA-128 was ready-to-use and used for injections from day 0 to day 42. After that, MCLA-128 aliquots were diluted in 0.9% NaCl to obtain the working solutions at 2.5 mg/ml which were prepared before each injection. They were used for dosing from day 42 to day 56 (end of the study). Letrozole tablets (Letrozole Actavis) were dissolved in 0.9% NaCl under magnetic agitation to form the final solution at 0.25 mg/ml. The dosing solution was stable for 7 days and stored at +4° C. light protected.

Tumor Graft Models Induction

Tumors of the same passage were transplanted subcutaneously onto 6-24 mice (donor mice, passage (n−1)). When these tumors reached 1000 to 2000 mm$^3$, donor mice were sacrificed by cervical dislocation, tumors were aseptically excised and dissected. After removing necrotic areas, tumors were cut into fragments measuring approximately 20 mm$^3$ and transferred in culture medium before grafting.

95 mice were anaesthetized with 100 mg/kg ketamine hydrochloride (batch 5D92, Exp: 2017/03, Virbac) and 10 mg/kg xylazine (batch KP0AX9X, Exp: 2017/08, Bayer), and then skin was aseptized with a chlorhexidine solution, incised at the level of the interscapular region, and a 20 mm$^3$ tumor fragment was placed in the subcutaneous tissue. Skin was closed with clips. All mice from the same experiment were implanted on the same day.

Treatment Phase mice with a subcutaneously growing HBCx-34 tumor between 62.5 and 256 mm$^3$ were allocated, according to their tumor volume to give homogenous mean and median tumor volume in each treatment arm. Treatments were randomly attributed to boxes housing up to 5 mice and were initiated 36 days post implantation of the tumor (42% inclusion rate). The study was terminated following 57 days after the start of treatment.

Tumor Measurement and Animal Observations

Tumor volume was evaluated by measuring tumor diameters, with a calliper, biweekly during the experimental period.

The formula TV (mm3)=[length (mm)×width (mm)2]/2 was used, where the length and the width are the longest and the shortest diameters of the tumor, respectively.

All animals were weighed biweekly during the experimental period.

Toxicity of the different treatments was determined as: body weight loss percent (% BWL)=100−(mean BWx/mean BW0×100), where BWx is the mean BW at any day during the treatment and BW0 is the mean BW on the 1st day of treatment.

A total of 4 groups were used as summarized in the scheme below. Each group initially included 10 mice.

| Gr. | Nb of included mice | Test Item | Mean (mm$^3$) | Median (mm$^3$) | SEM (mm$^3$) |
|---|---|---|---|---|---|
| 1 | 10 | Vehicle MCLA-128 | 126.9 | 117.0 | 16.52 |
| 2 | 10 | MCLA-128 25 mg/kg | 124.4 | 117.0 | 13.31 |
| 3 | 10 | Letrozole 2.5 mg/kg | 126.9 | 117.0 | 16.92 |
| 4 | 10 | MCLA-128 25 mg/kg Letrozole 2.5 mg/kg | 123.1 | 126.0 | 19.72 |

In group 1, vehicle MCLA-128 and vehicle Letrozole were dosed at 10 ml/kg, i.p. D0, D3, D7, D10, D14, D17, D21, D24, D28, D31, D35, D38, D42, D45, D49, D52, D56 and p.o. qdx 57 respectively;

In groups 2 and 4, MCLA-128 was dosed at 25 mg/kg, i.p., D0, D3, D7, D10, D14, D17, D21, D24, D28, D31, D35, D38, D42, D45, D49, D52, D56; In groups 3 and 4, Letrozole was dosed at 2.5 mg/kg, p.o., qdx57.

All treatment doses were body weight adjusted at each injection.

|     |    |            | 1 Drug/Testing Agent |       |                |                                                                                           | 2 Drug/Testing Agent |               |       |                 |          |
| --- | -- | ---------- | -------------------- | ----- | -------------- | ----------------------------------------------------------------------------------------- | -------------------- | ------------- | ----- | --------------- | -------- |
| Gr. | N  | Agent      | Dose mg/kg           | Route | Volume ml/kg   | Schedule                                                                                  | Agent                | Dose mg/kg    | Route | Volume ml/kg    | Schedule |
| 1   | 10 | Vehicle MCLA-128 | —              | IP    | 10             | D 0, D 3, D 7, D 10, D 14, D 17, D 21, D 24, D 28, D 31, D 35, D 38, D 42, D 45, D 49, D 52, D 56 | Vehicle Letrozole ^ | —            | PO    | 10              | qdx57*   |
| 2   | 10 | MCLA-128   | 25                   | IP    | 10             | As above                                                                                  | —                    | —             | —     | —               | —        |
| 3   | 10 | —          | —                    | —     | —              | —                                                                                         | Letrozole            | 2.5           | PO    | 10              | qdx57*   |
| 4   | 10 | MCLA-128   | 25                   | IP    | 10             | As above                                                                                  | Letrozole            | 2.5           | PO    | 10              | qdx57*   |

*qdx57: from D 0 to D 56.
^ Vehicle Letrozole = 0.9% NaCl

Results

Mean percent body weight change during the treatment period are illustrated in FIG. 3.

In group 1, MCLA-128 vehicle given i.p. on D0, D3, D7, D10, D14, D17, D21, D24, D28, D31, D35, D38, D42, D45, D49, D52, D56 and Letrozole vehicle given p.o. qdx57, both administered at 10 ml/kg, were well tolerated with 0.4% of maximum mean body weight loss on day 4 and 3.7% of maximum individual body weight loss on day 49.

In group 2, MCLA-128 given i.p. on D0, D3, D7, D10, D14, D17, D21, D24, D28, D31, D35, D38. D42, D45, D49, D52, D56 at 25 mg/kg, administered at 10 ml/kg, was well tolerated with 0.4% of maximum mean body weight loss on day 25 and 8.3% of maximum individual body weight loss on day 39.

In group 3, Letrozole dosed p.o. at 2.5 mg/kg, administered at 10 ml/kg, qdx57, was well tolerated with no mean body weight loss and 4.1% of maximum individual body weight loss on day 4.

In group 4, MCLA-128, i.p. D0, D3, D7, D10, D14, D17, D21, D24, D28, D31, D35, D38, D42, D45, D49, D52, D56 dosed at 25 mg/kg, i.p. and Letrozole dosed at 2.5 mg/kg, p.o. qdx57, both administered at 10 ml/kg, was well tolerated with 0.7% of maximum mean body weight loss on day 4 and 4.2% of maximum individual body weight loss on day 4.

Tumor growth curves (mean tumor volume over time) are illustrated in FIG. 1. Percent T/C values for each treatment group are indicated in table 1 and illustrated in FIG. 2. Definitions of partial and complete responses are defined in Table 2. Statistical analysis is shown in Table 3 and Table 4. In this study tumors were measured biweekly during the experimental period.

In group 2, MCLA-128, i.p. D0, D3, D7, D10, D14, D17, D21, D24, D28, D31, D35, D38, D42, D45, D49, D52, D56 dosed at 25 mg/kg, i.p. administered at 10 ml/kg did not induce statistically significant tumor growth inhibition with TGDi=0.93, best T/C %=91.14% on day 28; T/C %=101.56% (end of the control group) and best TGI %=31.59% at the end of the control group. However, 1/9 tumor stabilization and 1/9 partial tumor regression were observed.

In group 3, Letrozole dosed at 2.5 mg/kg, administered at 10 ml/kg, p.o. qdx57, induced a statistically significant tumor growth inhibition (p<0.001 compared with the vehicle group, Mann Whitney test and p<0.05 compared to the group control by Dunn's test) with TGDi>1.1, best T/C %=18.68% on day 56 (end of the control group) and best TGI %=145.70% at day 35. Moreover, 7/10 partial tumor regression and 1/10 complete tumor regression were observed.

In group 4, the combination MCLA-128, i.p. D0, D3, D7, D10, D14, D17, D21, D24, D28, D31, D35. D38, D42, D45, D49, D52, D56 dosed at 25 mg/kg, i.p. and Letrozole dosed at 2.5 mg/kg, administered at 10 ml/kg, p.o. qdx57, induced a statistically significant tumor growth inhibition (p<0.001 compared with the vehicle group, Mann Whitney test and Dunn's test) with TGDi>1.1, best T/C %=9.64% on day 56 (end of the control group) and TGI %=169.03% at day 32. Moreover, 5/10 partial tumor regressions and 5/10 complete tumor regressions were observed, with 5/10 tumor-free survivors at the end of the study.

Discussion

Based on body weight data and clinical observations all test compounds as single agent or in combination were well tolerated at the tested doses and schedules.

In the HBCx-34 model, MCLA-128 alone did not induce tumor growth inhibition whereas Letrozole alone induced a statistically significant tumor growth inhibition. Letrozole in combination with MCLA-128 induced a statistically significant synergistic tumor growth inhibition.

Treatment selection for breast cancer patients are guided by three biomarkers: HER2, estrogen (ER) and progesterone (PR) receptors. Patients with HER2 overexpression are eligible for HER2-targeting therapies, such as Trastuzumab and Pertuzumab. ER/PR positive patients will receive antiestrogen therapies or aromatase inhibitors. Antiestrogens (such Tamoxifen and Fulvestrant) modulate ER activity while aromatase inhibitors (AI, such as Letrozole or exemestane) inhibit the conversion of androgens to estrogens, depleting levels of ER stimuli in patients. Antiestrogen and aromatase inhibitors are used in different ER+ breast cancer patient populations, e.g. AI being used as first line treatment in post-menopausal patients. In example 2 it is demonstrated that adding MCLA-128 to either Tamoxifen or Fulvestrant enhances the activity of the antiestrogen treatments.

Example 2

MCLA-128 was evaluated as monotherapy and in combination with the SERM Tamoxifen and SERD Fulvestrant (Faslodex®) for efficacy in a nude mouse xenograft model of estrogen responsive MCF-7 human breast carcinoma. The study design also included tumor collection for downstream analysis.

Treatments began on D1 in mice with established subcutaneous MCF-7 tumors. The study endpoint was intended to be a tumor volume endpoint of 1000 mm3 45 days, whichever came first. The study ended on D39, and treatment outcome was based on percent tumor growth inhibition (% TGI), defined as the percent difference between D25 median tumor volumes (MTVs) of treated and control mice. D25 was chosen for analysis as it was the last day before animals exited the study for tumor progression. Treatment response was determined from an analysis of percent tumor growth inhibition (% TGI), defined as the percent difference between final (D25) median tumor volumes (MTVs) of treated and control groups, with differences between groups deemed statistically significant at P≤0.05 using the Mann-Whitney test. Tumor regressions, mean tumor growth, and treatment tolerability also were considered.

Mice

Female athymic nude mice (Crl:NU(NCr)-Foxn1$^{nu}$, Charles River) were ten weeks old and had a body weight range of 19.2 to 30.5 grams on D1 of the study. The animals were fed ad libitum water (reverse osmosis, 1 ppm Cl) and NIH 31 Modified and Irradiated Lab Diet® consisting of 18.0% crude protein, 6.0% crude fat, and 5.0% crude fiber. The mice were housed on irradiated Enrich-o'Cobs™ Laboratory Animal Bedding in static 85 microisolators on a 12-hour light cycle at 20.22° C. (68-72° F.) and 40-60% humidity.

Tumor Implantation

Three days prior to tumor cell implantation, estrogen pellets (0.36 mg estradiol, 60-day release, Innovative Research of America, Sarasota, FL) were implanted subcutaneously between the scapulae of all test animals using a sterilized trocar.

Xenografts were initiated with cultured MCF-7 human breast carcinoma cells. Tumor cells were grown to mid-log phase in RPMI-1640 medium containing 10% fetal bovine serum, 100 units/mL penicillin G, 100 µg/mL streptomycin sulfate, 2 mM glutamine, 10 mM HEPES, 0.075% sodium bicarbonate and 25 µg/mL gentamicin. On the day of tumor cell implant, the cells were trypsinized, pelleted, and resuspended in phosphate buffered saline (PBS) at a concentration of 1×10e8 cells/mL. Each test mouse received 1×10e7 MCF-7 cells implanted subcutaneously in the right flank, and tumor growth was monitored as their mean volume approached the desired 100 to 150 mm3 range.

Nineteen days after tumor cell implantation, designated as D1 of the study, the mice were placed into six groups of 15 animals and four groups of six animals, Individual tumor volumes ranged from 75 to 196 mm3 and group mean tumor volumes of 134-137 mm3 on D1. Tumor weight was estimated with the assumption that 1 mg is equivalent to 1 mm3 of tumor volume.

Therapeutic Agents

MCLA-128 was stored at 4° C., was provided preformulated at 2.5 mg/mL and ready to dose as 25 mg/kg in a 10 mL/kg dose volume, and was protected from light during storage and handling. Tamoxifen (Sigma-25 Aldrich. Lot No. WXBB5732V) was received as a powder and was stored at 4° C. protected from light. Each week, a 5 mg/mL dose solution was prepared in corn oil, and each mouse received 0.2 mL for a dose of 1 mg/animal. The dose solution was stored at 4° C. Fulvestrant tradename Faslodex® (AstraZeneca, Lot No. LV032, LW466, and LX432) was received as 50 mg/mL stock solution that was stored at 4° C. Each dosing day, the stock was diluted in corn oil to 25 mg/mL, and each mouse received 0.2 mL for a dose of 5 mg/animal.

Treatment

Groups 1 and 7 served as controls for efficacy and sampling, respectively, and received MCLA-128 vehicle intraperitoneally (i.p.) on D1, 4, 8, 11, 15, 18, 22, 25, and 29 and corn oil subcutaneously (s.c.) every other day for fifteen doses (qodx15). Groups 2 and 8 were administered MCLA-128 at 25 mg/kg, i.p., on the same schedule as MCLA-128 vehicle. Groups 3 and 9 were administered Faslodex® at 5.0 mg/animal, s.c., once weekly for five weeks (qwkx5). Group 4 was administered Tamoxifen at 1 mg/animal, s.c., qodx15. Groups 5 and 10 received MCLA-128 and Faslodex®, on the regimens described above. Group 6 received MCLA-128 and Tamoxifen on the regimens described above.

MCLA-128 was administered at a 10 mL/kg dose volume, scaled to the individual body weight of each animal. Faslodex® and Tamoxifen were administered at a fixed volume of 0.2 mL.

Results

FIG. 5 is a scatter plot showing the tumor distribution by group. Figure G shows the group median tumor growth curves for all groups in the study.

Growth of MCF-7 Tumors in Control Mice (Group 1)

Group 1 mice received MCLA-128 vehicle and corn oil as indicated above and served as the control group for calculation of percent TGI and statistical comparisons. The median tumor volume was 600 mm3 with individual tumor volumes on D25 ranging from 288 to 936 mm3 (FIG. 5) in this group. At the time of data analysis, there were two NTRu deaths recorded on D15 and D21, leaving thirteen assessable animals. Additional NTRu deaths were recorded after D25; one on D26 and two on D35. All deaths were due to suspected estrogen-related toxicity.

Response to MCLA-128 (Group 2)

In Group 2, MCLA-128 was administered as indicated above. This treatment resulted in a median tumor volume of 600 mm3, corresponding to a non-significant 0% TGI relative to the control group (P>0.05). At the time of data analysis, there were six NTRu deaths recorded; two each on D17 and D22, and one each on D19 and D20, leaving nine assessable animals. Additional NTRu deaths were recorded after D25; one each on D29 and D36. All deaths were due to suspected estrogen-related toxicity.

Response to Faslodex® (Group 3)

In Group 3, Faslodex® was administered as indicated above. This treatment resulted in a median tumor volume of 288 mm3, corresponding to a significant 52% TGI relative to the control group (P<0.001). There were two NTRu deaths recorded on D20 and D24, leaving thirteen assessable animals. All deaths were due to suspected estrogen-related toxicity.

Response to Tamoxifen (Group 4)

In Group 4, Tamoxifen was administered as indicated above. This treatment resulted in a median tumor volume of 184 mm3, corresponding to a significant 69% TGI relative to the control group (P<0.001). At the time of data analysis, there were three NTRu deaths recorded on D3, D10, and D22, leaving twelve assessable animals. Two deaths were also recorded on D26 which was after the time of data analysis. All deaths were due to suspected estrogen-related toxicity.

Response to MCLA-128 combined with Faslodex® or Tamoxifen (Groups 5 and 6)

In Group 6, MCLA-128 was combined with Faslodex® and administered as indicated above. This treatment resulted in a median tumor volume of 126 mm3 corresponding to a significant 79% TGI. This outcome was significant relative to control and MCLA-128 monotherapy groups (P<0.001) as well as to Faslodex® monotherapy (P<0.05). Three PRs were recorded in this group. One NTRu death was recorded on D17, leaving fourteen assessable animals. This death was due to suspected estrogen-related toxicity.

In Group 6, MCLA-128 was combined with Tamoxifen and administered as indicted. This treatment resulted in a median tumor volume of 108 mm3 corresponding to a significant 82% TGI. This outcome was significant relative to control and MCLA-128 monotherapy (P<0.001) as well as to Tamoxifen monotherapy (P<0.05). Four PRs were recorded in this group. At the time of data analysis, there was one NTRu death recorded on D15, leaving fourteen assessable animals. Three additional deaths were also recorded after the time of data analysis; two on D30 and one on D39. These deaths were due to suspected estrogen-related toxicity.

Discussion

This example evaluated the agent MCLA-128 compared to and combined with Faslodex® and Tamoxifen for efficacy in a nude mouse xenograft model of estrogen responsive MOF-7 human breast carcinoma. Tumors were measured twice per week through D39, and TGI analysis was performed on D25.

On D25, the median tumor volume for the control Group 1 was 600 mm3, with an individual tumor range of 288 to 936 mm3. Groups administered MCLA-128, Faslodex®, or Tamoxifen resulted in median tumors volumes of 600, 288, and 184 mm3, corresponding to TGIs of 0, 52 and 69% TGI. The outcome of MCLA-128 monotherapy was not significant compared to control (P>0.05), but the outcomes for Tamoxifen and Faslodex® were significant compared to control (P<0.001). MCLA-128 treatment in combination with Tamoxifen or Faslodex® resulted in median tumor volumes of 126 and 108 mm3, corresponding to 79 and 82% TGI, respectively. Each of these outcomes was significant compared to control and MCLA-128 monotherapy (P<0.001) as well as to Tamoxifen or Faslodex® respective therapies (P<0.05). Three PRs were recorded in the MCLA-128/Faslodex® group and four PRs were recorded in the MCLA-128/Tamoxifen group. All treatments were well tolerated. Several deaths across all groups were attributed to estrogen toxicity. In summary, MCLA-128 combination therapy with either Faslodex® or Tamoxifen offered significant synergistic survival benefit compared to respective monotherapies in the MCF-7 nude mouse xenograft model. All treatments were acceptably tolerated.

MCLA-128 showed no anti-tumor efficacy as a single agent, while Fulvestrant and Tamoxifen both significantly reduced tumor growth. Towards the end of the treatment period at day 25, MCLA-128 combination therapy with either Fulvestrant or Tamoxifen offered significant survival benefit when compared with the respective monotherapies (FIG. 5). Interestingly, the beneficial anti-tumor effect of combined treatment continued during the treatment-free observation period (FIG. 6). All treatments were acceptably tolerated.

Example 3

Pharmacodynamic Analysis
VeraTag Assay Round 1

All formalin-fixed tumors from example 2 were processed to FFPE blocks. The initial VeraTag assay analysis (round 1) was performed with 3 tumors per group Prior to the VeraTag analysis, tumors were sectioned and stained with hematoxylin-eosin to determine the percentage of tumor content. Microlaser capture was used to grossly remove any non-tumor content. The initial round of analysis included the following five VeraTag assays: total HER2, total HER3, HER2:HER3 dimers, HER3-PI3K complexes and phosphorylated HER3.

Relative to vehicle, MCLA-128 treatment showed no significant effect in any of the assays. A significant difference between the groups was only observed in the HER2:HER3 assay, where treatment with Fulvestrant significantly upregulated the formation of HER2:HER3 dimers and co-treatment with MCLA-128 reversed the levels of HER2:HER3 dimers to the situation in vehicle-treated tumors.

While not statistically significant, a similar trend was observed in the HER2 and HER assays. Since the data included only three tumors per treatment group, more data points were needed in order to confirm whether this trend was an indication of a result similar to that seen for the HER2:HER3 assay. Therefore, the remaining tumors from Table 5 were included in a second round of VeraTag assays for total HER2, total HERE and HER2:HER3 dimers. Since no significant effect of Fulvestrant or the combination with MCLA-128 was observed in the phospho HERS and HER3-PI3K assays, these assays were not included in Round 2.

VeraTag Assay Round 2

The tumors analyzed in Round 1 that had scores close to the average value of the specific assays were included in Round 2 to estimate the inter-assay reproducibility and to ensure the data from the two independent experiments could be combined. The results for those tumors analyzed in both rounds correlated well between assays, with a coefficient of variation (CV) below 20%, except for tumor "Gr.7 An.3", which was excluded from the final analysis (FIG. 7).

Data from both rounds were combined and the results confirmed that Fulvestrant significantly induced HER2:HER3 dimerization compared to vehicle, and that this was reversed by co-administration of MCLA-128 (FIG. 8).

In addition, HER2 expression levels in the Fulvestrant group were significantly higher than in the MCLA-128 single or combined treatment groups. The vehicle group had some variation between the samples and did not show a significant difference with the Fulvestrant group. Finally, HERS expression were not significantly altered between the different treatment groups, although there was a slight increase in HER3 in the Fulvestrant group relative to all other groups.

RPPA Analysis

Tumors from groups 1-6 were collected when they had reached the maximum tolerated volume, or at the end of the experiment at day 39, which was 10 days after the last dose. Per treatment group, six tumors were included in the Reverse phase protein array (RPPA). The selection of tumors was made so that the average tumor size of the 6 specimens was close to that of the whole group. RPPA analysis was performed as follows: tumors were sectioned and placed on immunohistochemistry slides. Stromal and inflammatory content was macrodissected to purify for tumors cells. Protein lysates were prepared and protein content was quantified. Protein samples were then spotted on nitrocellulose slides in quadruplicate at two different concentrations and then incubated with primary antibodies specific for Akt, ERK, HER2 and HER3, in their total or phosphorylated forms. Reverse phase protein array (RPPA) data were analyzed using one-way ANOVA to detect significant differences between the treatment groups and the vehicle group. Total and phosphorylated Akt levels were increased in the Faslodex group, no significant differences were observed in the other groups. Total ERK levels were increased in the single agent groups only, no differences were measured in the other groups or in the phosphorylated ERK analysis. Total HER2 levels, but not phosphorylated HER2, were significantly increased in the Tamoxifen and Faslodex groups. MCLA-128 25 co-treatment with hormonal therapy prevented this induction of HER2 expression.

HER3 total levels were significantly increased in the Faslodex group only and were reduced with co-treatment of MCLA-128.

Discussion

Pharmacodynamic Analysis

A finding of the VeraTag assay analysis was the significantly higher levels of HER2 expression in tumors from mice treated with Fulvestrant. Scores on the VeraTag assay correlate with HER2 positivity as determined by immunohistochemistry (IHC): HER2 VeraTag scores below 10.5 are negative in IHC, scores between 10.5 and 17.8 are equivocal and scores above 17.8 are positive (Huang et al., 2010 Am J Clin Pathol, 134 (2): 303-11). It therefore appears that Fulvestrant treatment can change the HER2 status of a HER2-negative tumor (i.e. scored as 0 or 1+ according to ASCO guidelines. Wolff et al. 2013 J Clin Oncol. 31 (31): 3997-4013), to a HER2 status that is at least equivocal (typically scored as 2+). Most importantly, the VeraTag analysis showed that Fulvestrant treatment induces the formation of HER2:HER3 dimers, which can be reversed by the addition of MCLA-128 to this treatment regimen.

Biomarker Analysis

A finding of this set of experiments—in which we measured levels of a panel of biomarkers using RPPA—was enhanced Akt, HER2 and HER3 expression in hormonal therapy-treated tumors. The fact that this hormonal therapy-induced increase could be reverted by co-administering MCLA-128 suggests that the activation of the Akt signaling pathway is linked to HER2:HER3 dimer activity, which was thus targeted by MCLA-128 in these tumors. This is in line with the data obtained from the VeraTag assay and further substantiates the beneficial effect of co-administering MCLA-128 with hormonal therapy in vivo.

General Considerations

The increase in HER2 protein expression after Fulvestrant treatment in an MCF-7 xenograft is in line with mechanisms of resistance against hormonal therapy that have been observed in patients (Osborne and Schiff 2011 Osborne C K, Schiff R. Annu Rev Med. 62:233-47). Fulvestrant has also been described to upregulate HER3 expression in MCF-7 cells in vitro and in vivo (Morrison et al., 2013 J Clin Invest. 123 (10): 4329-43), which was observed with the RPPA analysis but not the VeraTag analysis. This may be due to different timing for the tumor harvest (at the beginning and end of the treatment period for the VeraTag and RPPA assays, respectively). The synergy between MCLA-128 and Fulvestrant can be explained by the increased HER2:HER3 dimer formation seen in tumors derived from mice treated with this combination. Also the increased phosphorylation of Akt observed in tumors of mice treated with Fulvestrant alone (RPPA analysis).

Example 4: Phase II Study of MCLA-128/Endocrine Therapy in Estrogen Receptor Positive and Low HER2 Expression MBC While the Example describes the administration of MCLA-128 in combination with endocrine therapy, the Example is not intended to be limiting to the use of the specific therapeutic agents set out, and applies to the disclosed ErbB-2 and ErbB-3 binding bispecific antibodies in combination with an endocrine therapy.

OBJECTIVES: Estrogen receptor [ER]-positive/low HER2 expression MBC): MCLA-128+ endocrine therapy Primary Objective:

Evaluate efficacy of MCLA-128 combined with endocrine therapy in terms of clinical benefit rate (CBR) at 24 weeks based on RECIST 1.1 (per investigator review) in ER-positive and low HER2 expression MBC patients who have previously progressed on the same endocrine therapy Secondary Objectives:

Evaluate CBR at 24 weeks based on RECIST 1.1 per central review

Evaluate progression free survival (PFS) (per investigator and central review).

Evaluate objective response rate (ORR) based on RECIST 1.1 (per investigator and central review).

Evaluate the time from response (CR or PR) until progression or death due to underlying cancer (DoR) based on RECIST 1.1 (per investigator and central review)

Evaluate OS

Evaluate safety and tolerability of MCLA-128 combined with endocrine therapy

Characterize PK of MCLA-128 combined with endocrine therapy

Characterize immunogenicity of MCLA-128 combined with endocrine therapy

Exploratory Objective:

Evaluate potential correlations between biomarkers in tumor or blood samples and antitumor activity (including HER2, HER3, HER2:HER3 dimers, bereguline and other potential biomarkers).

Study Design

A phase 2, open-label, multicenter international study is performed to evaluate the efficacy of MCLA-128-based combinations in a metastatic breast cancer (MBC) population, ER-positive/low HER2.

Patients are ER-positive with low HER2 expression metastatic breast cancer (MBC) (immunohistochemistry (IHC) 1+, or IHC 2+ combined with negative fluorescence in situ hybridization (FISH)) who have progressed per RECIST v 1.1 on the last line of prior endocrine therapy (administered for at least 12 weeks) that included an aromatase inhibitor or fulvestrant.

Patients must have received 1 or 2 prior endocrine therapies in the metastatic setting and have progressed (per RECIST v 1.1) on a cyclin-dependent kinase inhibitor (in any line) are eligible.

For enrollment, HER2 and HR status and radiologic documentation of prior progression are based on medical records. Eligibility is confirmed as soon as possible for HER2/HR status by central lab review and for prior disease progression by central imaging review. Patients found to be ineligible retrospectively are not evaluable for the primary objective and may be replaced.

MCLA 128 is administered in combination with the same previous endocrine therapy on which progressive disease is radiologically documented. A total of up to 40 patients evaluable for efficacy is included. See FIG. 12.

Study Population

Inclusion Criteria

Patients must fulfill all of the following requirements to enter the study:
1. Signed informed consent before initiation of any study procedures.
2. Women with histologically or cytologically confirmed breast cancer with evidence of metastatic or locally advanced disease not amenable to any local therapy with curative intent:
    a. Documented hormone receptor positive status (estrogen receptor positive [ER+] and/or progesterone receptor positive [PR+]), including ≥1% positive stained cells, based on analysis on the most recent tumor biopsy.

b. Documented low-level HER2 expression, defined as IHC HER2 1+, or IHC HER2 2+ combined with negative FISH, based on local analysis on a fresh tumor biopsy or an archival biopsy collected within 12 months before screening (preferably metastatic otherwise primary).
c. One or two lines of prior endocrine therapy (aromatase inhibitor or fulvestrant) for metastatic disease, with radiologically documented disease progression on the last line, after at least 12 weeks of therapy.
d. Progression on a cyclin-dependent kinase inhibitor.
e. No more than one previous chemotherapy regimen for advanced/metastatic disease.

Note: Pre/peri-menopausal women can be enrolled if amenable to be treated with the lutenizing hormone-releasing hormone LHRH agonist goserelin. Such patients must have commenced treatment with goserelin or an alternative LHRH agonist at least 4 weeks prior to study entry, and patients who received an alternative LHRH agonist prior to study entry must switch to goserelin for the duration of the trial.

3. Measurable disease as defined by RECIST version 1.1 by radiologic methods on or after the most recent line of therapy. For Cohort 2, imaging must be available for central review.
4. Age ≥18 years at signature of informed consent.
5. Eastern Cooperative Oncology Group (ECOG) performance status of 0 or 1.
6. Life expectancy of ≥12 weeks, as per investigator.
7. Left ventricular ejection fraction (LVEF)≥50% by echocardiogram (ECHO) or multiple gated acquisition scan (MUGA).
8. Adequate organ function:
  a. Absolute neutrophil count (ANC)≥1.5×109/L
  b. Hemoglobin ≥9 g/dL
  c. Platelets ≥100×109/L
  d. Serum calcium within normal ranges (or corrected with supplements)
  e. Alanine aminotransferase (ALT), aspartate aminotransferase (AST)≤ 2.5×upper limit of normal (ULN) and total bilirubin≤1.5×ULN (in cases of liver involvement, ALT/AST≤5×ULN and total bilirubin within normal ranges will be allowed)
  f. Serum creatinine≤1.5×ULN or creatinine clearance ≥60 mL/min calculated according to the Cockroft and Gault formula or modification of diet in renal disease (MDRD) formula for patients aged >65 years (Appendix 19.2)
  g. Serum albumin >3.0 g/dl Investigational and Companion Therapies MCLA-128:750 mg intravenous flat dose over 2 hours, Day 1 every 3 weeks (q3w).

Premedication with paracetamol/acetaminophen, antihistamines and corticosteroids (as per standard practices) is mandatory for every MCLA-128 infusion.

Endocrine therapy: Patients receive the same dose and regimen as that administered under the last line of endocrine therapy prior to study entry on which the patient progressed.

Treatment Regimens

A cycle is 3 weeks (including Cohort 2 which may include q4w fulvestrant dosing). A 6-hour observation period is implemented following infusion start for the initial MCLA-128 administration, and 2 hours for all subsequent administrations.

All patients receive MCLA-128 administration on Day 1 q3w. For endocrine therapy, patients receive the same dose and regimen as that administered under the last line of endocrine therapy prior to study entry and on which the patient progressed.

Fulvestrant is administered on Days 1, 15, 29 and once every 28 days thereafter, or aromatase inhibitor therapy (letrozole, anastrazole and exemestane) is administered daily from Day 1.

Treatment Administration (all Cycles)

See FIG. 13. A 6-hour observation period is implemented following infusion start for the initial MCLA-128 administration, and 2 hours for all subsequent administrations.

Same endocrine therapy under which the patient progressed prior to study entry. Can be administered before, during, or immediately after the MCLA-128 infusion.

Treatment Assignment
  No specific treatment assignment is required.
Treatment Adaptation
  No dose reductions are permitted for MCLA-128 or endocrine therapy agents.
  MCLA-128 infusion will be interrupted in the event of an infusion-related reaction (IRR) and must be stopped definitively for severe IRRs. For mild to moderate events the infusion can be resumed at a 50% infusion rate 35 and infusion duration extended to 4 hours.
  MCLA-128 administration can be delayed for a maximum of 6 weeks between infusions to manage adverse events (AEs), specifically for clinically significant LVEF decreases, signs of congestive heart failure or persistent grade 2 or grade 3-4 diarrhea.
  Hormone therapy drugs are administered according to the summary of product characteristics (SPC) of each drug.

Treatment Duration
  Study treatment is administered until confirmed progressive disease (as per RECIST 1.1), unacceptable toxicity, withdrawal of consent, patient non-compliance, investigator decision (e.g. clinical deterioration), treatment interruption >6 consecutive weeks, withdrawal of any study drug. Patients are followed up for safety for at least 35±5 days following the last study drug administration and until recovery/stabilization of related toxicities, and for disease progression and survival status for 12 months.

Prophylactic and Concomitant Medication
Permitted
  Administration of paracetamol/acetaminophen, antihistamines and corticosteroids is mandatory with every MCLA-128 administration. In the event of an IRR or hypersensitivity, the patient is managed according to local clinical practice, as clinically indicated.
  All medication necessary for the wellbeing of the patient and which is not expected to interfere with evaluation of the study drug, including supportive treatment of symptoms and AEs or standard treatment of concomitant conditions is given at the investigator's discretion.
  Goserelin in pre/peri-menopausal women who started a n (LHRH) agonist >4 weeks prior to study entry.
Prohibited
  Concomitant chronic oral corticosteroids (>10 mg/day prednisone equivalent), TNF-alpha inhibitors, anti-T-cell antibodies (due to risk of immunosuppression).
  Any investigational drugs during the study or 4 weeks prior to the first dose of study treatment.
  Systemic anticancer therapy (other than the last endocrine therapy) during the study or within 3 weeks of the first dose of study treatment.

Safety/Tolerability Assessments
  AEs (CTCAE version 4.03), SAEs
  Lab parameters: hematology, biochemistry, coagulation, urinalysis, cytokines.
  ECG, MUGA/ECHO
  Medical history, vital signs, performance status and physical exam
  Concomitant medications
  Dose modifications (reductions, interruptions, delays), discontinuation due to toxicity Efficacy Assessments Tumor assessment is based on CT/MRI with contrast per RECIST 1.1, every 6 weeks after treatment start. Objective responses are confirmed at least 4 weeks after first observation. Central review of imaging by an independent radiologist(s) is performed for all patients (screening and on-study). Bone scans are performed as clinically indicated for patients with bone metastases at baseline or suspected lesions on study.

Tumor markers (CA15-3, CEA, CA27-29) are assessed on Day 1 every cycle.

Biomarkers

Candidate exploratory biomarkers are evaluated in tumor tissue (screening, optional after 12 weeks and EOT) and blood (pre-dose on Day 1 every 4 cycles and End of Treatment).

Tumor: HER2, HER3, HER2:HER3 dimerization, downstream signaling proteins (eg PIK3CA), heregulin, phosphorylation of HER2, HER3 and proteins in the MAPK and AKT signaling pathway, expression of inhibitors such as PTEN, mutations in cancer-related genes including HER2 and HER3 signaling, heregulin-gene fusions.
  Blood: Fcγ receptor polymorphism, plasma circulating tumor DNA mutations, exploratory serum biomarkers (e.g. soluble HER2, heregulin).

Pharmacokinetics

Blood samples are collected to measure serum MCLA-128. No PK sampling is performed for fulvestrant or aromatase inhibitors.
  PK sampling is performed at the following time points:
  Cycle 1: Day 1, pre-dose, EOI, and at 2, 4, and 22 hours post EOI, then at any time on Day 8:
  Cycle 2, 3, 5: Day 1, pre-dose, EOI
  Every 4 cycles thereafter: pre-dose Immunogenicity Blood samples (5 mL) are collected in all patients to assess serum titers of anti-MCLA-128 antibodies pre-dose on Day 1 pre-dose for Cycles 1, 3, 5, every 4 cycles thereafter, and End of Treatment.

Definitions

All efficacy endpoints will be defined and analyzed based on tumor assessment by RECIST 1.1.

CBR: the proportion of patients with a best overall response of CR, PR or SD ≥24 weeks.

ORR: the proportion of patients with best overall response of CR or PR.

PFS: the time from treatment start until radiologic progression or death due to any cause.

PFS ratio: the ratio of PFS with the previous regimen to PFS on study treatment.

DoR: the time from response (CR or PR) until progression or death due to underlying cancer.

OS: the time from treatment start until death due to any cause.

Endpoints

Primary
  CBR per investigator radiologic review at 24 weeks

Key Secondary
  CBR at 24 weeks per central review, and PFS per investigator and central review Other Secondary
  Safety: Incidence, severity and relationship of AEs, laboratory abnormalities, SAEs, ECG and LVEF measurements and vital signs
  Tolerability: discontinuations due to AEs, dose modifications due to AEs, immunogenicity, and cytokine assessments
  Other efficacy: DoR, PFS ratio, ORR and OS
  Pharmacokinetics: $C_{max}$, $C_{0h}$, AUC, CL, $V_s$, $t_{max}$ and $t_{1/2}$ for MCLA-128

Analysis Populations

Treated population: patients who receive at least one dose of MCLA-128.

Evaluable for efficacy: patients who receive at least 2 complete cycles (6 weeks) of treatment and have undergone baseline assessment and one on-study tumor assessment, or who discontinue early due to disease progression.

Analyses

Patient disposition and demographics are analyzed in the treated population, efficacy will be analyzed in the evaluable for efficacy population, and safety will be analyzed in the treated population.

Quantitative variables will be summarized using descriptive statistics. Continuous variables will be presented as N, mean and/or median, standard deviation, range. Categorical variables will be presented using frequencies and percentage.

Criteria for success primary endpoint: A median PFS of 5 months is assumed as relevant, with the activity threshold for CBR at 24 weeks set to 45%.

CBR and ORR are summarized with accompanying 90% exact binomial CI. For PFS, OS and DoR the survival function is estimated using the Kaplan-Meier product limit method; probability estimates and 90% CI is provided at specified time points; median duration and 90% CI is also be provided. DoR is estimated for responders only. The number and proportion of any patients with a PFS ratio ≥1.3 is tabulated for Cohort 2 with 90% exact CI. AEs are tabulated by the Medical Dictionary for Regulatory Activities (MedDRA®) preferred term and by organ class according to incidence and severity. Severity of AEs is based on Common Terminology for Adverse Events (CTCAE) 4.03.

PK, immunogenicity and biomarkers are analyzed centrally and reported separately.

TABLE 1

Summary of Dunn's Multiple comparison test analysis on relative body weight in the HBCx-34 tumor model, efficacy study XTS-1521

| Dunn's Multiple Comparison Test - Anova test/Kruskal-Wallis text | DAY | | | | | | | | | | | | | | | | |
|---|---|---|---|---|---|---|---|---|---|---|---|---|---|---|---|---|---|
| | 0 | 4 | 7 | 11 | 14 | 18 | 21 | 25 | 28 | 32 | 35 | 39 | 42 | 46 | 49 | 53 | 56 |
| Vehicle MCLA-128 vs MCLA-128 25 | ns | ns | ns | ns | ns | ns | ns | ns | ns | ns | ns | ns | ns | ns | ns | ns | ns |
| Vehicle MCLA-128 vs Letrozole 2.5 | ns | ns | ns | ns | ns | ns | ns | ns | * | ** | ** | ** | ** | ** | ** | ** | ** |
| Vehicle MCLA-128 vs MCLA-128 25/letrozole 2.5 | ns | ns | ns | * | ns | * | ns | ns | * | ** | ** | ** | *** | ** | * | * | * |
| MCLA-128 25 vs Letrozole 2.5 | ns | ns | ns | ns | ns | ns | ns | * | ns | ** | * | ** | ns | ** | ** | ** | ** |
| MCLA-128 25 vs MCLA-128 25/letrozole 2.5 | ns | ns | ns | * | * | ns | * | *** | ns | ** | * | ** | * | ** | * | ns | * |
| Letrozole 2.5 vs MCLA-128 25/letrozole 2.5 | ns | ns | ns | ns | ns | ns | ns | ns | ns | ns | ns | ns | ns | ns | ns | ns | ns |

Table 1 Summary of Dunn's Multiple comparison test analysis on relative body weight in the HBCx-34 tumor model, efficacy study XTS-1521.
Group comparisons were carried out using a Dunn's Multiple comparison test, between treated group and control group:
ns = not significant;
* = P < 0.05;
** = P < 0.01, and
*** = P < 0.001,
Initial group size: 9-10 animals.

TABLE 2

Anti-tumor activity of MCLA-128 at 25 mg/kg, Letrozole 2.5 mg/kg in the HBCx-34 xenograft, efficacy study XTS-1521.

| Gr. | Drug (1) | Dose (mg/kg) | Route | Schedule | Drug (2) | Dose (mg/kg) | Route | Schedule | Mean Tumor Volume at D 0 (mm3) | median TGD × 3 (In days) | TGDI |
|---|---|---|---|---|---|---|---|---|---|---|---|
| G1 | Vehical MCLA-128 | — | IP | D 0, D 3, D 7, D 10, D 14, D 17, D 21, D 24, D 28, D 31, D 35, D 38, D 42, D 45, D 49, D 52, D 56 | Vehical Letrozole | — | PO | pdx57 | 126.9 | 50.93 | / |
| G2 | MCLA-128 | 25 | IP | D 0, D 3, D 7, D 10, D 14, D 17, D 21, D 24, D 28, D 31, D 35, D 38, D 42, D 45, D 49, D 52, D 56 | — | — | — | — | 124.4 | 48.64 | 0.96 |
| G3 | — | — | — | — | Letrozole | 2.5 | PO | qdx57 | 126.9 | >56 | >1.1 |
| G4 | MCLA-128 | 25 | IP | D 0, D 3, D 7, D 10, D 14, D 17, D 21, D 24, D 28, D 31, D 35, D 38, D 42, D 45, D 49, D 52, D 56 | Letrozole | 2.5 | PO | qdx57 | 123.1 | >56 | >1.1 |

| Gr. | T/C % (at control group day end) | Best T/C % | at Day | TGI % (at control group day end) | Best TGE % | at Day | TS | PR | CR | TFS | Mice Nb |
|---|---|---|---|---|---|---|---|---|---|---|---|
| G1 | / | / | / | / | / | / | 5 | 0 | 0 | 0 | 10 |
| G2 | 101.56% | 91.14% | D 28 | 4.87% | 31.59% | D 4 | 1 | 1 | 0 | 0 | 9 |
| G3 | 18.68% | 18.68% | D 56 | 121.97% | 145.70% | D 35 | 1 | 7 | 1 | 1 | 10 |
| G4 | 9.24% | 9.24% | D 56 | 134.67% | 169.03% | D 32 | 0 | 5 | 5 | 5 | 10 |

XenTech T/C = Mean tumor volume of treated mice/Mean tumor volume of control mice × 100 (calculated at the time of first ethical sacrifice in control group);
TGD (Tumor Growth Delay) = time required for the median tumor volume to reach D 0 tumor volume × 5;
TGDI (Tumor Growth Delay Index) = TGD from treated/TGD from control mice;
TS (Tumor Stabilization) = number of mice presenting a constant tumor size during at least 6 consecutive measurements;
PR (partial regression) = number of mice presenting a tumor size lower than initial tumor size during at least 6 consecutive measurements;
CR (complete regression) = number of mice presenting a 0 to 14 mm$^3$ tumor size during at least 3 consecutive measurements;
TFS (Tumor Free Survivor) = number of compete regressions recorded up to Group Day End. Treatments started 36 days post implantation.

TABLE 3

Summary of Mann-Whitney analysis on tumor volume in the HBCx-34 tumor model, efficacy study XTS-1521

| MANN-WHITNEY TEST | DAY | | | | | | | | | | | | | | | | | |
|---|---|---|---|---|---|---|---|---|---|---|---|---|---|---|---|---|---|---|
| | 0 | 4 | 7 | 11 | 14 | 18 | 21 | 25 | 28 | 32 | 35 | 39 | 42 | 46 | 49 | 53 | 56 | STAT |
| Vehicle MCLA-128 - D 0, D 3, D 7, D 10, D 14, D 17, D 21, D 24, D 28, D 31, D 35, D 38, D 42, D 45, D 49, D 52, D 56 Vehicle Letrozole - qdx57 vs MCLA-128 25 D 0, D 3, D 7, D 10, D 14, D 17, D 21, D 24, D 28, D 31, D 35, D 38, D 42, D 45, D 49, D 52, D 56 - - - | ns | ns | ns | ns | ns | ns | ns | ns | ns | ns | ns | ns | ns | ns | ns | ns | ns | ns |
| Vehicle MCLA-128 - D 0, D 3, D 7, D 10, D 14, D 17, D 21, D 24, D 28, D 31, D 35, D 38, D 42, D 45, D 49, D 52, D 56 Vehicle Letrozole - qdx57 vs - - - Letrozole 2.5 qdx57 | ns | ns | ns | ns | ns | ns | ns | * | * | ** | *** | *** | *** | *** | *** | *** | *** | *** |
| Vehicle MCLA-128 - D 0, D 3, D 7, D 10, D 14, D 17, D 21, D 24, D 28, D 31, D 35, D 38, D 42, D 45, D 49, D 52, D 56 Vehicle Letrozole - qdx57 vs MCLA-128 25 D 0, D 3, D 7, D 10, D 14, D 17, D 21, D 24, D 28, D 31, D 35, D 38, D 42, D 45, D 49, D 52, D 56 Letrozole 2.5 qdx57 | ns | ns | ns | ns | ns | * | ** | *** | *** | *** | *** | *** | *** | *** | *** | *** | *** | *** |

Table 3 Summary of Mann-Whitney analysis on tumor volume in the HBCx-34 tumor model, efficacy study XTS-1521.
Group comparisons were carried out. using a Mann-Whitney nonparametric test between treated group and control group:
ns = not significant;
* = $P < 0.05$;
** = $P < 0.01$, and
*** = $P < 0.001$,
Initial group size: 9-10 animals.

TABLE 4

Summary of Dunn's Multiple comparison test analysis on tumor volume in the HBCx-34 tumor model, efficacy study XTS-1521

| Dunn's Multiple Comparison Test - Anova test/Kruskal-Wallis text | DAY | | | | | | | | | | | | | | | | |
|---|---|---|---|---|---|---|---|---|---|---|---|---|---|---|---|---|---|
| | 0 | 4 | 7 | 11 | 14 | 18 | 21 | 25 | 28 | 32 | 35 | 39 | 42 | 46 | 49 | 53 | 56 |
| Vehicle MCLA-128 vs MCLA-128 25 | ns | ns | ns | ns | ns | ns | ns | ns | ns | ns | ns | ns | ns | ns | ns | ns | ns |
| Vehicle MCLA-128 vs Letrozole 2.5 | ns | ns | ns | ns | ns | ns | ns | ns | ns | ns | * | * | * | * | * | * | * |
| Vehicle MCLA-128 vs MCLA-128 25/letrozole 2.5 | ns | ns | ns | ns | ns | ns | * | ** | ** | ** | *** | *** | *** | *** | *** | *** | *** |
| MCLA-128 25 vs Letrozole 2.5 | ns | ns | ns | ns | ns | ns | ns | ns | ns | * | ** | ** | ** | ** | ** | ** | ** |
| MCLA-128 25 vs MCLA-128 25/letrozole 2.5 | ns | ns | ns | ns | ns | ns | ** | ** | ** | *** | *** | *** | *** | *** | *** | *** | *** |
| Letrozole 2.5 vs MCLA-128 25/letrozole 2.5 | ns | ns | ns | ns | ns | ns | ns | ns | ns | ns | ns | ns | ns | ns | ns | ns | ns |

TABLE 5

Weights and volumes of xenograft MCF-7 tumors prepare Charles River for pharmacodynamic analysis. Bolded tumors were included in the first round of VeraTag analysis.

| Sample ID# | Weight (mgs) | Volume (mm³) |
|---|---|---|
| GR.7 AN.1 | 177.2 | 288 |
| GR.7 AN.2 | 198.8 | 365 |
| GR.7 AN.3 | 150 | 256 |
| GR.7 AN.4 | 138.8 | 196 |
| GR.7 AN.5 | 306.6 | 320 |
| GR.7 AN.6 | 283.7 | 405 |
| GR.8 AN.1 | 120.5 | 144 |
| GR.8 AN.2 | 98.2 | 256 |
| GR.8 AN.4 | 135.5 | 221 |
| GR.8 AN.5 | 134 | 288 |
| GR.8 AN.6 | 207.7 | 320 |
| GR.9 AN.1 | 137.9 | 196 |
| GR.9 AN.2 | 140.1 | 172 |
| GR.9 AN.3 | 174.4 | 196 |
| GR.9 AN.5 | 119.7 | 144 |
| GR.9 AN.6 | 117.3 | 196 |
| GR.10 AN.1 | 110.1 | 172 |
| GR.10 AN.2 | 162.2 | 196 |
| GR.10 AN.3 | 190.3 | 320 |
| GR.10 AN.4 | 150.9 | 196 |
| GR.10 AN.6 | 162.3 | 196 |

List of Abbreviations in Example 1 bid: Bidaily
BW: Body Weight
BWL: Body Weight Loss
C: Control mice
CR: Complete tumor Regression
inj: Injection
i.v.: Intravenous
i.p.: Intraperitoneal
IVC: Individually Ventilated Cages
kg: Kilogram
mg: Milligram
ml: Milliliter
mut: Mutated
ns: Not significant
p.o.: Per os, by mouth (gavage)
PR: Partial tumor Regression
PSU: Polysulfone
qd Que die, every day
qwk Once a week
RBW: Relative Body Weight
RTV: Relative Tumor Volume
S: Significant
s.c.: Subcutaneous
sem: Standard error of the mean
SoC: Standard of Care
T: Treated mice
TGD: Tumor Growth Delay
TGDI: Tumor Growth Delay Index
TGI: Tumor Growth Inhibition
TFS: Tumor Free Survivor
TS: Tumor Stabilization
% T/C: Percent tumor volume change treated over control group
μL: Microliter
qd: quotidian List of Abbreviations in Example 2

BW body weight
CR complete tumor regression
D Study Day
i.p. intraperitoneal(ly)
MTD maximum tolerated dose
MTV median tumor volume
NTR non-treatment-related
PR partial tumor regression
qod×15 dosing every other day for fifteen doses
qwk×5 weekly dosing for five weeks
s.c. subcutaneously
TGI tumor growth inhibition
TR treatment-related death List of Abbreviations in Example 4

AEs adverse events
ALT alanine aminotransferase
ANO absolute neutrophil count
AST aspartate aminotransferase
AUC area under the curve
CBR clinical benefit rate
CHF congestive heart failure:
CR complete tumor regression
DoR the time from response (CR or PR) until progression or death due to underlying cancer.
ECHO echocardiogram
ER estrogen receptor
FISH fluorescence in situ hybridization
IHC immunohistochemistry
IRR infusion-related reaction
MBC metastatic breast cancer
MDRD modification of diet in renal disease
MUGA multiple gated acquisition scan
LVD left ventricular dysfunction
LVEF left ventricular ejection fraction
LHRH luteinizing hormone-releasing hormone
PFS progression free survival
PR progesterone receptor or partial remission depending on context
OCOG eastern cooperative oncology group
ORR objective response rate
OS the time from treatment start until death due to any cause.
SPC summary of Product Characteristics
ULN upper limit of normal

The invention claimed is:

1. A method of treating a hormone receptor positive breast cancer in a subject, comprising administering to the subject in need thereof a combination of a therapeutically effective amount of an ErbB-2/ErbB-3 bispecific antibody and a therapeutically effective amount of tamoxifen, fulvestrant, or letrozole, wherein the bispecific antibody is administered at a flat dose of 750 mg, wherein the bispecific antibody has an antigen binding site that can bind an extra-cellular part of ErbB-2 and an antigen binding site that can bind an extra-cellular part of ErbB-3;
   wherein the antigen binding site that can bind an extra-cellular part of ErbB-2 comprises a variable domain with a heavy chain variable region comprising at least the CDR1, CDR2 and CDR3 sequences of SEQ ID NOs: 43, 44, and 45, respectively, and
   wherein the antigen binding site that can bind an extra-cellular part of ErbB-3 comprises a variable domain with a heavy chain variable region comprising at least the CDR1, CDR2 and CDR3 sequences of SEQ ID NOs: 58, 59, and 60, respectively;
   wherein each of the heavy chain variable regions is paired with a light chain variable region (VL) comprising the CDR1, CDR2 and CDR3 sequences according to SEQ ID NO: 169, SEQ ID NO: 170 and SEQ ID NO: 171, respectively.

2. The method of claim 1, wherein the hormone receptor positive breast cancer is an immunohistochemistry ErbB-2+ cancer or an immunohistochemistry ErbB-2++ without ErbB-2 gene amplification cancer.

3. The method of claim 1, wherein the hormone receptor positive breast cancer is ER-positive with low HER2 expression metastatic breast cancer (MBC), wherein the low HER2 expression is defined as IHC 1+, or IHC 2+ combined with negative FISH.

4. The method of claim 1, wherein the bispecific antibody can reduce a ligand-induced receptor function of ErbB-3 on a ErbB-2 and ErbB-3 positive cell.

5. The method of claim 1, wherein each of the heavy chain variable regions is paired with the light chain variable region of the light chain according to SEQ ID NO: 81.

6. The method of claim 1, wherein the antigen binding site that can bind an extra-cellular part of ErbB-2 comprises a variable domain with a heavy chain variable region comprising the amino acid sequence of SEQ ID NO: 42.

7. The method of claim 1, wherein the antigen binding site that can bind an extra-cellular part of ErbB-3 comprises a variable domain with a heavy chain variable region comprising the amino acid sequence of SEQ ID NO: 57.

8. The method of claim 1, wherein the bispecific antibody is administered weekly, biweekly, every 3 weeks, or every 4 weeks.

9. The method of claim 1, wherein the bispecific antibody is administered every 3 weeks.

* * * * *